US007018836B1

(12) United States Patent
Price

(10) Patent No.: US 7,018,836 B1
(45) Date of Patent: Mar. 28, 2006

(54) P-TEFB COMPOSITIONS, METHODS AND SCREENING ASSAYS

(75) Inventor: David H. Price, Iowa City, IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 08/951,188

(22) Filed: Oct. 15, 1997

Related U.S. Application Data

(60) Provisional application No. 60/029,760, filed on Oct. 25, 1996.

(51) Int. Cl.
*C12N 5/00* (2006.01)
*C12N 9/12* (2006.01)
*C07K 1/00* (2006.01)

(52) U.S. Cl. ............... 435/325; 435/419; 435/252.3; 435/254.11; 435/320.1; 435/194; 536/23.2; 536/23.5; 536/24.31; 536/24.33; 530/350

(58) Field of Classification Search ............ 435/194, 435/320.1, 325; 536/23.1, 23.4, 23.2
See application file for complete search history.

(56) References Cited

U.S. PATENT DOCUMENTS 5,453,362 A   9/1995   Lamarco et al. ........... 435/69.1

FOREIGN PATENT DOCUMENTS

| EP | 0 692 488 | 5/1995 |
|---|---|---|
| WO | WO 95/30026 | 11/1995 |
| WO | WO 95/32307 | 11/1995 |
| WO | WO 96/17084 | 6/1996 |
| WO | WO 96/26292 | 8/1996 |

OTHER PUBLICATIONS

Hillier, L. et al., GenBank Database, Accession No. T83219, Mar. 16, 1995.*
Hillier, L. et al., GenBank Database, Accession No. T90767, Mar. 22, 1995.*
Peng et al. (1998) J Biol Chem 273:13855-13860.*
Matsudaira (1990) Methods Enzymol 182:602-613.*
Wozney (1990) Methods Enzymol 182:738-751.*
Ausubel et al. "Current Protocols in Molecular Biology", John Wiley and Sons, Inc., New York, 1997.*
Branden et al. "Introduction to Protein Structure", Garland Publishing Inc., New York, 1991.*
Witkowski et al. (1999) Biochemistry 38:11643-11650.*
Creighton "Protein Structure," Oxford University Press, New York, 1990.*
Watson et al. "Recombinant DNA," 2nd Ed., W.H. Freeman and Company, New York, 1992.*
Akoulitchev, Makela, Weinberg, and Reinberg, "Requirement for TFIIH kinase activity in transcription by RNA polymerase II," *Nature*, 377:557-560, Oct. 12, 1995.

Allison, Wong, Fitzpatrick, Moyle, Ingles, "The C-Terminal Domain of the Largest Subunit of RNA Polymerase II of *Saccharomyces cerevisiae, Drosophila melanogaster,* and Mammals: A Conserved Structure with an Essential Function," *Mol. Cell. Biol.*, 8(1):321-329, Jan. 1988.
Baskaran, Dahmus, Wang, "Tyrosine Phosphorylation of Mammalian RNA Polymerase II Carboxyl-Terminal Domain," *Proc. Natl. Acad. Sci. USA,* 90:11167-11171, Dec. 1993.
Best, Presky, Swerlick, Burns, Chu, "Cloning of a full-length cDNA sequence encoding a cdc2-related protein kinase from human endothelial cells," *Biochem. Biophys. Res. Comm.,* 208(2):562-568, Mar. 17, 1995.
Bullrich, MacLachlan, Sang, Druck, Veronese, Allen, Chiorazzi, Koff, Heubner, Croce et al., "Chromosomal mapping of members of the cdc2 family of protein kinases, cdk3, cdk6, PISSLRE, and PITALRE, and a cdk inhibitor, p27Kip1, to regions involved in human cancer," *Cancer Research,* 55(6):1199-1205, Mar. 15, 1995.
Cadena and Dahmus, "Messenger RNA Synthesis in Mammalian Cells Is Catalyzed by the Phosphorylated Form of RNA Polymerase II*", *J. Biol. Chem.,* 262(26):12468-12474, Sep. 15, 1987.
Chodosh, Fire, Samuels, Sharp, "5,6-Dichloro-1-β-D-Ribofuranosylbenzimidazole Inhibits Transcription Elongation by RNA Polymerase II in Vitro," *J. Biol. Chem.,* 264(4):2250-2257, Feb. 5, 1989.
Cisek and Corden, "Phosphorylation of RNA Polymerase by the Murine Homologue of the Cell-Cycle Control Protein cdc2," *Nature*, 339:679-684, Jun. 29, 1989.
Cujec et al., "The HIV Transactivator TAT Binds to the CDK-Activating Kinase and Activates the Phosphorylation of the Carboxyl-Terminal Domain of RNA Polymerase II," *Genes & Development*, 11(20):2645-2657, 1997.

(Continued)

*Primary Examiner*—David J. Steadman
(74) *Attorney, Agent, or Firm*—Haynes and Boone, LLP; Mark D. Moore

(57) ABSTRACT

Disclosed is the discovery that the transcription elongation factor termed P-TEFb has a central role in transcription elongation control. P-TEFb is herein shown to phosphorylate RNA polymerase II and to control the transition from abortive into productive elongation mode. P-TEFb has also been discovered to interact with the HIV transcriptional transactivating protein, Tat, showing that P-TEFb is the cellular factor necessary for HIV Tat to effect productive viral mRNA elongation. The invention provides genes encoding P-TEFb subunits, including human genes, and related biological components, and also provides assay methods connected with the control of transcription elongation. Particularly useful assays are those concerning the identification of substances that inhibit viral replication at the transcription elongation stage by inhibiting the binding or functional interaction of viral proteins to P-TEFb.

67 Claims, 8 Drawing Sheets

OTHER PUBLICATIONS

Dahmus, "Phosphorylation of the C-terminal domain of RNA polymerase II," *Biochem. Biophys. Acta*, 1261:171-182, 1995.

Dahmus, "The Role of Multisite Phosphorylation in the Regulation of RNA Polymerase II Activity," *Progress in Nucleic Acid Research and Molecular Biology*, 48:143-179, 1994.

Desai, Loewenstein, Green, "Isolation of a cellular protein that binds to the human immunodeficiency virus Tat protein and can potentiate transactivation of the viral promoter," *Proc. Natl. Acad. Sci. USA*, 88:8875-8879, Oct. 1991.

Dubois, Nguyen, Bellier and Bensaude, "Inhibitors of Transcription Such As 5,6-Dichloro-1-β-D-Ribofuranosylbenzimidazole and Isoquinoline Sulfonamide Derivatives (H-8 and H-7*) Promote Dephosphorylation of the Carboxyl-Terminal Domain of RNA Polymerase II Largest Subunit," *The Journal of Biological Chemistry*, 269(18): 13331-13336, May 6, 1994.

Dvir, Peterson, Knuth, Lu, Dynan, "Ku Autoantigen Is the Regulatory Component of a Template-Associated protein Kinase That Phosphorylates RNA Polymerase II," *Proc. Natl. Acad. Sci. USA*, 89:11920-11924, Dec. 1992.

Egyhazi, Ossoinak, Pigon, Holmgren, Lee, Greenleaf, "Phosphorylation Dependence of the Initiation of Productive Transcription of Balbiani Ring 2 Genes In Living Cells," *Chromosoma*, 104:422-433, 1996.

Feaver, Gileadi, Li, Kornberg, "CTD kinase associated with yeast RNA polymerase II initiation factor b," *Cell*, 67:1223-1230, Dec. 20, 1991.

Flores, Lu, Reinberg, "Factors Involved in Specific Transcription by Mammalian RNA Polymerase II," *J. Biol. Chem.*, 267(4):2786-2793, Feb. 5, 1992.

Fraser, Sehgal, Darnell, "Multiple Discrete Sites for Premature RNA Chain Termination Late in Adenovirus-2 Infection: Enhancement by 5,6-Dichloro-1-β-D-Ribofuranosylbenzimidazole," *Proc. Natl. Acad. Sci. USA*, 76(6):2571-2575, Jun. 1979.

Garcia and Gaynor, "T he human immunodeficiency virus type-1 long terminal repeat and its role in gene expression," [Review]. *Progress in Nucleic Acid Research and Molecular Biology*, 49:157-196, 1994.

Grana, De Luca, Sang, Fu, Claudio, Rosenblatt, Morgan, Giordano, "PITALRE, a nuclear CDC2-related protein kinase that phosphorylates the retinoblastoma protein in vitro", *Proc. Natl. Acad. Sci. USA*, 91:3834-3838, Apr. 1994.

Herrmann and Rice, "Lentivirus Tat proteins specifically associate with a cellular protein kinase, TAK, that hyperphosphorylates the carboxyl-terminal domain of the large subunit of RNA polymerase II: Candidate for a Tat cofactor," *J. Virol.*, 69(3):1612-1620, 1995.

Herrmann and Rice, "Specific interaction of the human immunodeficiency virus Tat proteins with a cellular protein kinase," *Virol.*, 197:601-608, 1993.

Hermann, Gold, Rice, "Viral transactivators specifically target distinct cellular protein kinases that phosphorylate the RNA polymerase II C-terminal domain," *Nucl. Acids Res.*, 24(3):501-508, 1996.

Jeang, Chun, Lin, Gatignol, Glabe, Fan, "In vitro and in vivo binding of human immunodeficiency virus Type 1 protein and Sp1 transcription factor," *J. Virol.*, 67(10):6224-6233, 1993.

Jones and Peterlin, "Control of RNA initiation and elongation at the HIV-1 promoter," [Review]. *Annual Review of Biochemistry*, 63:717-743, 1994.

Kang and Dahmus, "RNA polymerases IIA and IIO have distinct roles during transcription from the TATA-less murine dihydrofolate reductase promoter," *J. Biol. Chem.*, 268(33):25033-25040, Nov. 25, 1993.

Kephart, Marshall, Price, "Stability of *Drosophila* RNA polymerase II elongation complexes in vitro," *Mol. Cell. Biol.*, 12(5):2067-2077, May 1992.

Kim and Dahmus, "The Major Late Promoter of Adenovirus-2 Is Accurately Transcribed by RNA Polymerase IIO, IIA, and IIB*," *J. Biol. Chem.*, 264(6): 3169-3176, Feb. 25, 1989.

Koleske and Young, "The RNA Polymerase II Holoenzyme and Its Implications for Gene Regulation," *Trends Biochem. Sci.*, 20:113-116, Mar. 1995.

Laub, Jakobovits, Aloni, "5,6-Dichloro-1-β-D-Ribofuranosylbenzimidazole Enhances Premature Termination of Late Transcription of Simian Virus 40 DNA," *Proc. Natl. Acad. Sci.USA*, 77(6):3297-3301, Jun. 1980.

Lee and Greenleaf, "A Protein Kinase That Phosphorylates the C-Terminal Repeat Domain of the Largest Subunit of RNA Polymerase II," *Proc. Natl. Acad. Sci. USA*, 86:3624-3628, May 1989.

Li and Kornberg, "Interplay of Positive and Negative Effectors in Function of the C-Terminal Repeat Domain of RNA Polymerase II," *Proc. Natl. Acad. Sci. USA*, 91:2362-2366, Mar. 1994.

Liao, Zhang, Jeffery, Koleske, Thompson, Chao, Viljoen, Van Vuuren, Young, "A Kinase-Cyclin Pair in the RNA Polymerase II Holoenzyme," *Nature*, 374:193-196, Mar. 1995.

Lu, Zawel, Fisher, Egly, Reinberg, "Human general transcription factor IIH phosphorylates the C-terminal domain of RNA polymerase II," *Nature*, 358:641-645, Aug. 20, 1992.

Mancebo et al., "P-TEFb Kinase Is Required For HIV Tat Transcriptional Activation in vivo and in vitro," *Genes & Development*, 11(20):2633-2644, 1997.

Marciniak and Sharp, "HIV-1 Tat protein promotes formation of more-processive elongation complexes," *EMBO J.*, 10(13):4189-4196, 1991.

Marshall and Price, "Control of formation of two distinct classes of RNA polymerase II elongation complexes," *Mol. Cell. Biol.*, 12(5):2078-2090, May 1992.

Marshall and Price, "Purification of P-TEFb, a transcription factor required for the transition into productive elongation," *J. Biol. Chem.*, 270(21):12335-12338, May 1995.

Marshall, Peng, Xie, Price, "Control of RNA polymerase II elongation potential by a novel carboxyl-terminal domain kinase," *J. Biol. Chem.*, 271(43):27176-27183, Oct. 1996.

Meulia, Krumm, Groudine, "Distinct properties of *c-myc* transcriptional elongation are revealed in *Xenopus* oocytes and mammalian cells and by template titration, 5,6-dichloro-1-b-D-ribofuranosylbenzimidazole (DRB), and promoter mutagenesis," *Mol. Cell. Biol.*, 13(9):5647-5658, Sep. 1993.

Nelbock, Dillon, Perkins, Rosen, "A cDNA for a protein that interacts with the human immunodeficiency virus tat transactivator," *Science*, 248:1650-1653, Jun. 1990.

Nonet, Sweetser, Young, "Functional Redundancy and Structural Polymorphism in the Large Subunit of RNA Polymerase II," *Cell*, 50:909-915, Sep. 1987.

Payne and Dahmus, "Partial purification and characterization of two distinct protein kinases that differentially phosphorylate the carboxyl-terminal domain of RNA polymerase subunit IIa," *J. Biol. Chem.*, 268(1):80-87, Jan. 1993.

Peterson, Dvir, Anderson, Dynan, "DNA binding provides a signal for phosphorylation of the RNA polymerase II heptapeptide repeats," *Genes Dev.*, 6:426-438, 1992.

Price, Sluder, Greenleaf, "Fractionation of transcription factors for RNA polymerase II from Drosophila $K_c$ cell nuclear extracts," *J. Biol. Chem.*, 262(7):3244-3255, Mar. 1987.

Rasmussen and Lis, "Short Transcripts of the Ternary Complex Provide Insight Into RNA Polymerase II Elongation Pausing," *J. Mol. Biol.*, 252:522-535, 1995.

Roberts and Bentley, "Distinct Modes of Transcription Read Through or Terminate at the *c-myc* Attenuator," *EMBO J.*, 11(3):1085-1093, 1992.

Sehgal, Darnell, Tamm, "The Inhibition by DRB (5,6-Dichloro-1-β-D-Ribofuranosylbenzimidazole) of hnRNA and mRNA Production of HeLa Cells," *Cell*, 9:473-480, Nov. 1976.

Serizawa, Conaway, Conaway, "A carboxyl-terminal-domain kinase associated with RNA polymerase II transcription factor d from rat liver," *Proc. Natl. Acad. Sci. USA*, 89:7476-7480, Aug. 1992.

Shibuya, Irie, Ninomia-Tsuji, Goebl, Taniguchi, Matsumoto, "New human gene encoding a positive modulator of HIV Tat-mediated transactivation," *Nature*, 357:700-702, Jun. 1992.

Stone and Reinberg, "Protein Kinase From *Aspergillus nidulans* That Phosphorylate the Carboxyl-Terminal Domain of the Largest Subunit of RNA Polymerase II*," *J. Biol. Chem.*, 267(6):6353-6360, 1992.

Tamm and Kikuchi, "Early Termination of Heterogeneous Nuclear RNA Transcripts in Mammalian Cells: Accentuation by 5,6-Dichloro-1-β-D-Ribofuranosylbenzimidazole ," *Proc. Natl. Acad. Sci. USA*, 76(11):5750-5754, Nov. 1979.

Tamm, Kikuchi, Darnell, Salditt-Georgeieff, "Short Capped hnRNA Precursor Chains in HeLa Cells: Continued Synthesis in the Presence of 5,6-Dichloro-1-β-D-Ribofuranosylbenzimidazole ," *Biochem.*, 19:2743-2748, 1980.

Thompson, Steinberg, Aronson, Burgess, "Inhibition of in Vivo and in Vitro Transcription by Monoclonal Antibodies Prepared Against Wheat Germ RNA Polymerase II That React With the Heptapeptide Repeat of Eukaryotic RNA Polymerase II,*" *J. Biol. Chem.*, 264(19):11511-11520, Jul. 1989.

Venetianer, Dubois, Nguyen, Bellier, Seo, Bensaude, "Phosphorylation State of the RNA Polymerase II C-Terminal Domain (CTD) in Heat-Shocked Cells Possible Involvement of the Stress-Activated Mitogen-Activated Protein (MAP) Kinases," *Eur. J. Biochem.*, 233:83-92, 1995.

Xie and Price, "*Drosophila* Factor 2, an RNA polymerase II Transcript Release Factor, Has DNA-dependent ATPase Activity," *J. Biol. Chem.*, 272(50):31902-31907, 1997.

Xie and Price, "Purification of an RNA polymerase II transcript release factor from *Drosophila*," *J. Biol. Chem.*, 271(19):11043-11406, May 1996.

Yang, Herrmann, Price, "The human immunodeficiency virus Tat proteins specifically associate with TAK in vivo and require the carboxyl-terminal domain of RNA polymerase II for function," *J. Virol.*, 70(7):4576-4584, Jul. 1996.

Yankulov, Yamashita, Roy, Egly, Bentley, "The transcriptional elongation inhibitor 5,6-dichloro-1-β-D-ribofuranosylbenzimidazole inhibits transcription factor IIH-associated protein kinase," *J. Biol. Chem.*, 270(41):23922-23925, Oct. 1995.

Zandomeni, Zandomeni, Shugar, Weinmann, "Casein Kinase Type II Is Involved in the Inhibition by 5,6-Dichloro-1-β-D-Ribofuranosylbenzimidazole of *Specific RNA Polymerase II Transcription ,"* *J. Biol. Chem.*, 261(7):3414-3419, Mar. 1986.

Zehring, Lee, Weeks, Jokerst, and Greenleaf, "The C-Terminal Repeat Domain of RNA Polymerase II Largest Subunit Is Essential in Vivo But Is Not Required for Accurate Transcription Initiation in Vitro," *Proc. Natl. Acad. Sci. USA*, 85:3698-3702, Jun. 1988.

Zhou and Sharp, "Novel Mechanism and Factor for Regulation by HIV-1 Tat," *EMBO J.*, 14(2):321-328, 1995.

Zhou and Sharp, "Tat-SF1: Cofactor for stimulation of transcriptional elongation by HIV-1 Tat," *Science*, 274:605-610, Oct. 1996.

Zhu et al., "Transcription Elongation Factor P-TEFb Is Required for HIV-1 Tat Transactivation in Vitro," *Genes & Development*, 11(20):2622-2632, 1997.

* cited by examiner

P-TEFB COMPOSITIONS, METHODS AND SCREENING ASSAYS

The present application claims priority to co-pending provisional application Ser. No. 60/029,760, filed Oct. 25, 1996, the entire text and figures of which disclosure are specifically incorporated herein by reference without disclaimer.

The U.S. Government owns rights in the present invention pursuant to grant number R01-GM35500 from the National Institutes of Health.

BACKGROUND OF THE INVENTION

1. Field of the Invention

The present invention relates generally to the fields of cellular biochemistry and viral replication. More particularly, it concerns the discovery that a certain factor, P-TEFb, has a central role in transcription elongation control, that it phosphorylates RNA polymerase II and that it binds to the HIV protein, Tat. The invention provides human genes encoding the P-TEFb subunits, various other biological components, and methods relating to the control of transcription elongation that have particular utility in the identification of substances that inhibit viral replication.

2. Description of Related Art

The production of any functional eukaryotic mRNA requires efficient transcription elongation by RNA polymerase II. Eukaryotic gene expression is controlled in part during the elongation phase of transcription. Shortly after initiation, RNA polymerase II acquires the properties necessary to synthesize full length pre-mRNAs (Spencer and Groudine, 1990b; Kerppola and Kane, 1991; Wright, 1993; Bentley, 1995; Maldonado and Reinberg, 1995). As is frequently found in control processes, there is a negative control mechanism which is manifest as a blockage during early elongation.

Blocks in transcription, usually referred to as premature termination, have been observed during transcription in a number of systems, including mammalian genes such as α-tubulin (Middleton and Morgan, 1990; Hair and Morgan, 1993), and in viruses, such as adenovirus (Kessler et al., 1989), simian virus 40 (SV40) (Kessler et al., 1991), minute virus of mice (Krauskopf et al., 1991) and human immunodeficiency virus (HIV) (Laspia et al., 1989). RNA polymerase II molecules are also found blocked, during elongation, near the promoter on many genes in *Drosophila melanogaster* (Rougvie and Lis, 1988; 1990).

Except for the involvement of the viral Tat protein in HIV gene expression (Marciniak and Sharp, 1991), little is known about the molecular mechanisms involved in elimination of this block. In vivo, HIV transcription is tightly controlled by the viral Tat protein. It is known that Tat acts as a potent transcriptional transactivator by binding to the transactivation response (TAR) region on the nascent RNA and interacting with cellular factors (Garcia and Gaynor, 1994; Jones and Peterlin, 1994). Still, many issues remain to be clarified concerning the interactions and functional regulation of transcriptional elongation and Tat, and further information is needed before effective anti-HIV strategies can be developed based upon intervention connected with Tat activity.

Concerning cellular genes, the transcription of the proto-oncogene, c-myc, is regulated by a block during elongation (Miller et al., 1989; Spencer and Groudine, 1990a; Wright and Bishop, 1989). C-myc expression was studied in *Xenopus* oocytes and isolated HeLa nuclei. The block to elongation in c-myc occurs close to the promoter, termed "promoter-proximal pausing", and only short RNAs are produced (Krumm et al., 1995; Meulia et al., 1993; Strobl and Eick, 1992). A block to elongation at the end of the first exon regulates the levels of c-fos RNA in response to tumor promoters and intracellular calcium levels (Collart et al., 1991; Mechti et al., 1991). Other blocks to elongation occur in the transcription of the proto-oncogenes c-myb (Bender et al., 1987; Reddy and Reddy, 1989) and c-fins (Yue et al., 1993). The RNA levels for the adenosine deaminase genes (ADA) of humans and mice are at least partly controlled by a regulated block to elongation (Ramamurthy et al., 1990; Chinsky et al., 1989; Chen et al., 1990; Chen et al., 1991; Kash et al., 1993). Thus this elongation control process has been implicated in the expression of many genes, yet the mechanism of control is not yet understood.

Studies in human, murine, *Drosophila* and *Xenopus* systems have demonstrated the existence of two classes of elongation complexes differing in their potential to produce full length mRNA sized transcripts. A model for the control of elongation has been described which is based, in part, on results obtained from a *Drosophila* in vitro transcription system (Kephart et al., 1992; Marshall and Price, 1992) and is consistent with data obtained in vitro and in vivo from many studies.

Key features of the elongation control model are that all RNA polymerase II molecules that initiate from a promoter are destined to produce only short transcripts, in a process termed "abortive elongation". Abortive elongation is distinct from abortive initiation because the abortive transcripts are 10 to 20 times longer during abortive elongation and, presumably, the polymerase in the abortive elongation complexes must relocate the promoter after producing an abortive transcript to bring about reinitiation. Escape from this negative control is accomplished through the action of P-TEF (positive transcription elongation factor) which allows productive elongation. Fractionation studies have recently identified three components believed to be required to efficiently generate productive elongation complexes, P-TEFa, P-TEFb and factor 2 (Marshall and Price, 1995). P-TEFb was further purified and was shown to act after initiation (Marshall and Price, 1995), although the protein was not subject to detailed biochemical characterization.

The existence of two classes of transcription complexes differing in their elongation potential has also been demonstrated using the nucleoside analog, 5,6-dichloro-1-β-D-ribofuranosylbenzimidazole (DRB). The addition of DRB to mammalian cells in culture resulted in a 95% inhibition in the production of mature mRNA (Sehgal et al., 1976). Nuclei isolated from cells pre-treated with DRB have increased production of short, capped transcripts while labeling of longer RNAs is decreased (Tamm and Kikuchi, 1979; Tamm et al., 1980). Similarly, the short transcripts generated from viral templates in cells infected with SV40 (Laub et al. 1980) and adenovirus (Fraser et al., 1979) are enhanced, while longer transcripts are suppressed with DRB treatment. DRB also inhibits production of long transcripts but leaves shorter products unaffected in injected *Xenopus* oocytes (Meulia et al., 1993; Roberts and Bentley, 1992).

The carboxyl-terminal domain (CTD) of RNA polymerase II is phosphorylated during the transcription cycle at a time coincident with elongation regulation (Dahmus, 1994; Dahmus, 1995). The CTD can be phosphorylated by the kinase associated with the general transcription factor TFIIH (Lu et al., 1992; Serizawa et al., 1992; Feaver et al., 1991), and a CTD kinase activity is believed to be present in preinitiation complexes at several promoters (Peterson et al., 1992; Kang and Dahmus, 1993). Research has been directed at identifying the CTD kinase, but despite the proposal of various candidate kinases, it appears that the relevant kinase has not yet been identified.

A kinase/cyclin pair (SRB10/11) is part of the holoenzyme form of yeast RNA polymerase II (Liao et al., 1995). A number of other kinases, including casein kinase I and II (Zandomeni et al., 1986; Cadena and Dahmus, 1987), DNA-dependent protein kinase (Dvir et al., 1992), and a murine kinase related to cdc2 and CDC28 (Cisek and Corden, 1989), are capable of phosphorylating the CTD. Also, the kinases CTD-K1 and CTD-K2 purified from HeLa cells (Payne and Dahmus, 1993), CTK1 from yeast (Lee and Greenleaf, 1989), and KI, KII, and KIII from *Aspergillus nidulans* (Stone and Reinberg, 1992) can all phosphorylate the CTD. It has been further suggested that the stress activated MAP kinases are involved in phosphorylating RNA polymerase II during heat shock (Venetianer et al., 1995). While all of the above are serine/threonine kinases, there is one example of a tyrosine kinase, c-abl, that can phosphorylate the CTD (Baskaran et al., 1993).

While phosphorylation of the CTD has been correlated with the elongation phase of transcription, none of the kinases described above have been shown to modify the functional properties of RNA polymerase II during elongation. Therefore, the identity of the kinase that operates in this control process remains unknown. The mechanism by which CTD phosphorylation induces the transition into productive elongation also remains to be determined, as does the role in elongation control of various proteins associated with RNA polymerase II in a holoenzyme complex (Koleske and Young, 1995). Although several models for the involvement of CTD in elongation control have been proposed (Rasmussen and Lis, 1995), including tethering of the polymerase to the promoter by the unphosphorylated CTD, no conclusive evidence for one model is available. Further work is still needed to determine the fate of polymerases that stop early, but do not enter productive elongation (Marshall and Price, 1992), and to define the interaction of RNA polymerases in early elongation complexes with termination factors, including "factor 2" (Xie and Price, 1996).

Thus, the role of termination factors and potential anti-termination factors, and the regulation mechanisms that operate in the elongation control process remain to be clarified. Not only will the identification of these factors and their respective properties be of significant scientific interest, such discoveries would also have practical values beyond an understanding of transcriptional control mechanisms. For example, many viruses produce viral proteins that somehow interact with RNA polymerase II and facilitate the production of elongated viral transcripts, an essential step in the viral 'life cycle'. Therefore, the identification and characterization of protein factors involved in productive elongation will likely yield benefits in the development of anti-viral strategies.

SUMMARY OF THE INVENTION

The present invention provides novel genes, proteins and related biological compositions developed for their ability to interact with RNA polymerase II and to control transcriptional elongation. The compositions of the present invention, which are based upon P-TEFb, are particularly beneficial as they also functionally interact with viral proteins, such as HIV Tat, that have central roles in viral transcription elongation. Methods for identifying substances that alter transcription elongation are also provided by the invention, with particular emphasis on the identification of substances that inhibit the binding or functional interaction of viral proteins and P-TEFb, which substances are candidate anti-viral agents.

The invention was, in part, initially based upon the inventor's surprising discovery that the transcription elongation factor termed P-TEFb phosphorylates RNA polymerase II and controls the transition from abortive to productive transcription elongation. The inventor further discovered that human P-TEFb binds to the HIV transcriptional transactivating protein, Tat, and that P-TEFb is the key host cell component that facilitates Tat-mediated viral mRNA elongation during HIV infection. From the initial findings, the inventor developed screening assays to identify substances that inhibit the interaction of human P-TEFb and viral proteins, such as HIV Tat, and will have utility as anti-viral agents.

Certain of the inventor's findings concern the cloning, for the first time, of each of the subunits that make up the *Drosophila* P-TEFb enzyme complex. The *Drosophila* cloning allowed the inventor to make the breakthrough in cloning the full length human counterpart P-TEFb subunit genes. The small, kinase subunit of human P-TEFb is herein identified as the product of a cDNA for which the nucleic acid sequence was known, but to which no known function had been ascribed. The large, cyclin-like subunit of human P-TEFb has been discovered by the present inventor and is disclosed for the first time in the present application. This invention therefore provides novel human biological components, including genes, proteins and purified holoenzymes, and also new screening methods based upon the use of the human P-TEFb enzyme complex.

P-TEFb is a key regulator of the process controlling the processivity of RNA polymerase II. The inventor has shown that P-TEFb can phosphorylate the CTD of pure RNA polymerase II. Furthermore, P-TEFb can phosphorylate the CTD of RNA polymerase II when the polymerase is in an early elongation complex. Both the function and kinase activity of P-TEFb are blocked by the drugs DRB and H-8. P-TEFb is distinct from TFIIH because the two factors have no subunits in common, P-TEFb is more sensitive to DRB than TFIIH and, most importantly, TFIIH can not substitute functionally for P-TEFb. This invention discloses that phosphorylation of the CTD by P-TEFb controls the transition from abortive into productive elongation mode.

Both the human and the *Drosophila* small, or kinase, subunits are members of the CDC2-family of kinases and are cyclin-dependent kinases. The human small subunit associates with the activation domain of HIV-1 Tat, indicating that human P-TEFb is the Tat-associated kinase (TAK), previously poorly characterized and not purified prior to the present invention. An in vitro transcription assay demonstrates that the effect of Tat on transcription elongation requires P-TEFb and suggests the enhancement of transcriptional processivity by Tat is due to enhanced function of P-TEFb.

The present invention provides DNA segments, vectors and the like comprising at least one isolated gene, DNA segment or coding region that encodes a *Drosophila* P-TEFb kinase or large subunit protein, polypeptide, domain, peptide or any fusion protein thereof. Further provided are at least a first isolated gene, DNA segment or coding region that encodes a human P-TEFb large subunit protein, peptide, domain or derivative.

These aspects of the present invention may be described as follows: a DNA segment comprising an isolated coding region that encodes a substantially full length P-TEFb subunit, wherein the coding region is characterized as:

a) encoding a substantially full length P-TEFb kinase subunit having the amino acid sequence of SEQ ID NO:2; or b) encoding a substantially full length P-TEFb large subunit that includes a contiguous sequence of at least about 7 amino acids from SEQ ID NO:4, SEQ ID NO:45, SEQ ID NO:47 or SEQ ID NO:50; or as a substantially full length coding region that hybridizes to the nucleotide sequence of SEQ ID NO:3, SEQ ID NO:43 or SEQ ID NO:48 under stringent hybridization conditions.

The term "substantially full length" as used herein, means that the genes and coding regions of the invention encode a substantially full length P-TEFb kinase or large subunit protein or polypeptide such that the subunit produced on expression of the gene or coding region includes each of the polypeptide regions or domains necessary to impart functional activity to the expressed product. As disclosed herein, even subunits from the same species may vary in length and yet still have functional activity. For example, variations of the human P-TEFb large subunits are provided by the present invention which have differing lengths and yet still have biological activity. In particular, human large subunits of 696, 729 and 726 amino acids in length are provided hereby. Genes and coding regions that encode a protein of between about 600 and about 750, or preferably of between about 650 and about 750 amino acids in length are thus generally considered to be substantially full length genes or coding regions, although smaller genes and coding regions are by no means excluded from the present invention so long as they encode a protein that has biological activity when expressed.

It will also be understood that more variability in length will likely exist between genes and coding regions encoding P-TEFb subunits from different species. By way of example only, the *Drosophila* P-TEFb large subunits included within the invention encode a protein of about 1097 amino acids in length that has biological activity. A comparison of this protein with the human large subunit proteins disclosed herein reveals that there may be some considerable variability in the full length sequences of active subunits from different species. So long as a gene encodes a protein subunit that has biological activity as disclosed herein, this will be a "substantially full length" gene as this term is presently used.

The P-TEFb kinase subunits provided by and for use in the present invention also exemplify the concept of substantially full length and active proteins that may nonetheless have certain differences in sequence and actual length. The *Drosophila* kinase subunit provided hereby is about 404 amino acids in length, whereas the human subunit for use in the various methods and combined compositions of the invention is about 372 amino acids long. Each of these proteins have biological activity, as disclosed herein.

Although the concept of substantially full length sequences will be readily understood by those of ordinary skill in the art, another means for assessing the substantially full length nature of a gene, coding region or expressed protein of the invention is to analyze the terminal or near-terminal sequences of the biological components and to confirm that they generally correlate with sequences at the termini of the sequences provided herein, or sequences proximal to such termini. By conducting such a comparison, one may identify substantially full length genes or coding regions that express biologically active proteins with even more variation in length.

Such a terminal sequence comparison is contemplated to be an effective means for identifying substantially full length biological components that may have inserted into their sequence additional coding or non-coding sequences (in the context of DNA) or additional polypeptide sequences. Working examples of this phenomenon are also provided herein, as a comparison of the human P-TEFb large subunit of SEQ ID NO:45 and SEQ ID NO:47 reveals that the second encoded subunit contains additional polypeptide sequence that results from translation of an apparent intron in the DNA sequence. Genes encoding such introns and polypeptides including additional amino acid sequences are clearly encompassed within the present invention, and comparison of the substantially terminal sequences is an effective means for confirming the identity of longer sequences that are nonetheless P-TEFb coding regions or protein subunits.

In providing a DNA segment or vector that comprises an isolated gene or coding sequence that encodes a P-TEFb kinase subunit, protein or peptide, particularly a *Drosophila* P-TEFb kinase subunit, protein or peptide, the subunit may be generally characterized as:

a) having an observed molecular weight of between about 42 kD and about 43 kD, generally as measured by gel filtration chromatography and SDS-PAGE (sodium dodecyl sulfate (SDS) polyacrylamide gel electrophoresis PAGE); and having an actual molecular weight of about 47 kD, as calculated from the known protein sequence; and optionally characterized as b) capable of forming a cyclin kinase pair with the P-TEFb large subunit protein, e.g., capable of binding to the *Drosophila* P-TEFb large subunit protein under suitable binding conditions, such as conditions using non-denaturing buffers of non-dissociating ionic strength and non-dissociating pH, which buffers generally approximate in effect to the non-denaturing, non-dissociating cellular or nuclear conditions in which the P-TEFb protein complex exists in the natural state; and optionally characterized as c) being a cyclin-dependent kinase (CDK) that is capable of phosphorylating RNA polymerase II, and capable of phosphorylating RNA polymerase II when operatively combined with a P-TEFb large subunit protein, e.g., the kinase subunit is capable of binding to *Drosophila* RNA polymerase II in a manner and for a period of time effective to catalyze the transfer a phosphate group to RNA polymerase II from an available phosphate group donor molecule, such as adenosine triphosphate (ATP); wherein the RNA polymerase II is preferably phosphorylated on the carboxyl terminal domain (CTD) of the *Drosophila* large subunit of RNA polymerase II;

(i) more preferably, being identified as a DRB-sensitive cyclin-dependent kinase, wherein the phosphorylation of RNA polymerase II by the isolated P-TEFb kinase subunit protein, or the P-TEFb kinase subunit protein within the P-TEFb enzyme complex, is inhibited by an effective amount of DRB, and most preferably, wherein the phosphorylation of RNA polymerase II by the P-TEFb kinase subunit protein is inhibited by an effective amount of DRB and by an effective amount of H-8; and optionally characterized as d) being involved in the control of elongation by RNA polymerase II, and generally being capable of promoting transcription elongation when combined with a P-TEFb large subunit protein, e.g., capable of promoting proper elongation of mRNA transcripts when operatively combined with a P-TEFb large subunit to form a P-TEFb enzyme complex and wherein the P-TEFb enzyme complex is contacted with a functional *Drosophila* RNA polymerase II molecule in the presence of a DNA template and under conditions otherwise appropriate to result in transcription elongation, i.e., in the presence of effective amounts of nucleotides, ATP, other necessary co-factors and the like;
  (i) more preferably, wherein the capacity to promote transcription elongation when operatively combined with a P-TEFb large subunit protein, a functional RNA polymerase II and the necessary transcriptional elongation components, co-factors and precursors, is inhibited by an effective amount of DRB.

The genes and DNA segments preferably encode a substantially full length P-TEFb kinase subunit, protein or polypeptide that includes a contiguous amino acid sequence of at least about 24 amino acids, and more preferably, of at least about, 25, 27, 30, 35, 40, 45, 50, 60, 70, 80, 90, 100, 125, 150, 200 amino acids or so from SEQ ID NO:2, or a biologically functional equivalent thereof. More preferably, the genes and DNA segments will encode a substantially full length P-TEFb kinase subunit having the amino acid sequence of SEQ ID NO:2, or a biologically functional equivalent thereof.

Preferably, the isolated genes and coding regions will include a contiguous nucleic acid sequence of at least about 722 nucleotides, and more preferably, of at least about 725, 750, 800, 825, 850, 900 or so nucleotides from between position 115 and position 1326 or 1327 of SEQ ID NO:1, or a biologically functional equivalent thereof. More preferably, the isolated genes and DNA segments will comprise an isolated coding region having the nucleic acid sequence of the foregoing coding region SEQ ID NO:1, or a biologically functional equivalent thereof.

The human small kinase subunit, SEQ ID NO:6, comprises a single protein called "PITALRE", so called because of the presence of those amino acids in a characteristic location in the kinase subunit, which is encoded by the sequence presented in SEQ ID NO:5. It is a cyclin-dependent kinase of the cell division cycle 2 (CDC2) family of kinases.

In providing new combined compositions and new uses for the DNA segments herein discovered to encode the human P-TEFb kinase subunit protein (particularly combined compositions and uses in connection with DNA segments encoding a P-TEFb large subunit), the human P-TEFb kinase subunit gene is generally characterized as follows:
  a) encoding a human P-TEFb kinase subunit, protein or peptide that includes a contiguous amino acid sequence of at least about 6, 8, 10, 15, 20 or 24 amino acids or so from SEQ ID NO:6, or a biologically functional equivalent thereof; and optionally characterized as
  b) including a contiguous nucleic acid sequence of at least about 20–21 nucleotides or so, and more preferably, of at least about 30, 40, 50, 60, 72 or so nucleotides from the coding region of SEQ ID NO:5, or a biologically functional equivalent thereof.

Preferably, these genes and DNA segments will encode a human P-TEFb kinase subunit comprising, consisting essentially of, or having the contiguous amino acid sequence of SEQ ID NO:6, or a biologically functional equivalent thereof; or the genes and DNA segments will hybridize thereto under stringent hybridization conditions. These isolated genes and coding regions will therefore preferably include a contiguous nucleic acid sequence corresponding to substantially the full length coding region of SEQ ID NO:5, or a biologically functional equivalent thereof; or the genes and DNA segments will hybridize thereto under stringent hybridization conditions. Isolated genes and DNA segments having the nucleic acid sequence of SEQ ID NO:5 are just one example.

In providing new uses for the newly discovered human P-TEFb kinase subunit protein, particularly in combination with other P-TEFb subunits, proteins or peptides such that, for example, a recombinant human P-TEFb holoenzyme, as in Example 5, is provided, the human P-TEFb kinase subunit protein is also generally characterized as follows:
  a) capable of forming a cyclin kinase pair with a human P-TEFb large subunit protein, or other large subunit protein, such that it is capable of binding to a human P-TEFb large subunit protein under suitable binding conditions, such as conditions using non-denaturing buffers of non-dissociating ionic strength and non-dissociating pH, which buffers generally approximate in effect to the non-denaturing, non-dissociating cellular or nuclear conditions in which the P-TEFb protein complex exists in the natural state;
  b) being a cyclin-dependent kinase (CDK) that is capable of phosphorylating human RNA polymerase II, and capable of phosphorylating human RNA polymerase II when operatively combined with a human P-TEFb large subunit protein, i.e., the kinase subunit is capable of binding to RNA polymerase II in a manner and for a period of time effective to catalyze the transfer a phosphate group to RNA polymerase II from an available phosphate group donor molecule, such as ATP; wherein the human RNA polymerase II is preferably phosphorylated on the carboxyl terminal domain (CTD) of the large subunit of RNA polymerase II;
    (i) more preferably, being identified as a DRB-sensitive cyclin-dependent kinase, wherein the phosphorylation of human RNA polymerase II by the isolated human P-TEFb kinase subunit protein, or the P-TEFb kinase subunit protein within the human P-TEFb enzyme complex, is inhibited by an effective amount of DRB, and most preferably, wherein the phosphorylation of RNA polymerase II by the P-TEFb kinase subunit protein is inhibited by an effective amount of DRB and by an effective amount of H-8; and
  c) being involved in the control of elongation by human RNA polymerase II, and generally being capable of promoting transcription elongation when combined with a human P-TEFb large subunit protein, i.e., capable of promoting proper elongation of mRNA transcripts when operatively combined with a human P-TEFb large subunit to form a P-TEFb enzyme complex and wherein the human P-TEFb enzyme complex is contacted with a functional human RNA polymerase II molecule in the presence of a DNA template and under conditions otherwise appropriate to result in transcription elongation, i.e., in the presence of effective amounts of nucleotides, ATP, other necessary co-factors and the like;
    (i) more preferably, wherein the capacity to promote transcription elongation when operatively combined with a human P-TEFb large subunit protein, a functional human RNA polymerase II and the necessary transcriptional elongation components, co-factors and precursors, is inhibited by an effective amount of DRB.

In certain embodiments, the DNA segments and coding regions may encode *Drosophila* and human P-TEFb kinase subunit peptides, for example from about 25 to about 30 or about 50 amino acids in length or so. Preferably, the DNA segments and coding sequences will encode a *Drosophila* P-TEFb kinase subunit protein of about 404 amino acids in length; or a human P-TEFb kinase subunit protein of about 372 amino acids in length, preferably where the human subunit is used in combination with other DNA segments, such that a recombinant human P-TEFb total enzyme is encoded.

The DNA segments and vectors of the present invention may comprise an isolated gene or coding region that encodes a *Drosophila* P-TEFb large subunit, protein or peptide. The *Drosophila* P-TEFb large subunit, protein or peptide may be generally characterized as:

a) having a molecular weight of about 121 kD, generally as measured by gel filtration chromatography and also by calculating the molecular weight from the known protein sequence; and optionally characterized as b) capable of forming a cyclin kinase pair with the *Drosophila* P-TEFb kinase subunit protein, i.e., being capable of binding to the *Drosophila* P-TEFb kinase subunit protein under suitable binding conditions, such as conditions using non-denaturing buffers of non-dissociating ionic strength and non-dissociating pH, which buffers generally approximate to the non-denaturing, non-dissociating cellular or nuclear conditions in which the P-TEFb protein complex exists in the natural state; and optionally characterized as c) having cyclin protein-like sequence characteristics, such as the conserved cyclin box domain; and optionally characterized as d) capable of promoting transcription elongation when combined with a *Drosophila* P-TEFb kinase subunit protein, i.e., capable of promoting proper elongation of mRNA transcripts when operatively combined with a *Drosophila* P-TEFb kinase subunit to form a P-TEFb enzyme complex and wherein the *Drosophila* P-TEFb enzyme complex is contacted with a functional *Drosophila* RNA polymerase II molecule in the presence of a DNA template and under conditions otherwise appropriate to result in transcription elongation, i.e., in the presence of effective amounts of nucleotides, ATP, other necessary co-factors and the like, (i) more preferably, wherein the capacity to promote transcription elongation when operatively combined with a *Drosophila* P-TEFb kinase subunit protein, a functional *Drosophila* RNA polymerase II and the necessary transcriptional elongation components, co-factors and precursors, is inhibited by an effective amount of DRB.

Certain genes and DNA segments preferably encode a substantially full length P-TEFb large subunit, protein or polypeptide that includes a contiguous amino acid sequence of at least about 7 amino acids, or more preferably, of at least about 8, 10, 12, 14, 16, 18, 20, 22 or 25 amino acids or so from SEQ ID NO:4, or a biologically functional equivalent thereof; or the genes and DNA segments will hybridize to such a coding sequence under stringent hybridization conditions. More preferably, the genes encode a P-TEFb large subunit, protein or peptide that includes a contiguous amino acid sequence of at least about 30, 35, 40, 45, 50, 60, 70, 80, 90, 100, 125, 150, 200 amino acids or so from SEQ ID NO:4, or a biologically functional equivalent thereof; or the genes and DNA segments will hybridize to such a coding sequence under stringent hybridization conditions. Most preferably, these genes and DNA segments will encode a P-TEFb large subunit having the amino acid sequence of SEQ ID NO:4, or a biologically functional equivalent thereof; or the genes and DNA segments will hybridize to such a coding sequence under stringent hybridization conditions.

These isolated genes and coding regions may include a contiguous nucleic acid sequence of at least about 20–21 nucleotides or so, and more preferably, of at least about 30, 40, 50, 60 or 72 or so nucleotides from between position 716 and position 4054 of SEQ ID NO:3, or a biologically functionally equivalent thereof; or the genes and DNA segments will hybridize to such a coding sequence under stringent hybridization conditions. Preferably, these isolated genes and DNA segments will comprise an isolated coding region having the nucleic acid sequence of SEQ ID NO:3, or a biologically functional equivalent thereof; or the genes and DNA segments will hybridize to such a coding sequence under stringent hybridization conditions.

Exemplary genes and DNA segments may also be characterized as encoding a substantially full length P-TEFb large subunit including a contiguous amino acid sequence of at least about 7 amino acids, or more preferably, of at least about 8, 10, 12, 14, 16, 18, 20, 22 or 25 amino acids or so from SEQ ID NO:4, or a biologically functional equivalent thereof, and as hybridizing to the nucleic acid sequence of SEQ ID NO:3 under stringent hybridization conditions.

In certain embodiments, the isolated DNA segments and coding regions may encode a P-TEFb large subunit peptide of from about 15 to about 30 or about 50 amino acids in length or so. Preferably, the DNA segments and coding regions encode a *Drosophila* P-TEFb large subunit protein of about 1113 amino acids in length.

The present invention provides several human P-TEFb large subunit genes, proteins and compositions. Methods of using the various compositions, for example, in the diagnosis and treatment of a viral infection, such as HIV, or cancer are also provided. Human P-TEFb large subunit proteins and peptides are generally characterized as:

a) capable of forming a cyclin kinase pair with the human P-TEFb kinase subunit protein, i.e., being capable of binding to the human P-TEFb kinase subunit protein of SEQ ID NO:6 under suitable binding conditions, such as conditions using non-denaturing buffers of non-dissociating ionic strength and non-dissociating pH, which buffers generally approximate to the non-denaturing, non-dissociating cellular or nuclear conditions in which the P-TEFb protein complex exists in the natural state; and b) having cyclin protein-like sequence characteristics, such as the conserved cyclin box domain; and c) being capable of promoting transcription elongation when combined with a human P-TEFb kinase subunit protein, i.e., capable of promoting proper elongation of mRNA transcripts when operatively combined with a human P-TEFb kinase subunit to form a human P-TEFb enzyme complex and wherein the P-TEFb enzyme complex is contacted with a functional human RNA polymerase II molecule in the presence of a DNA template and under conditions otherwise appropriate to result in transcription elongation, i.e., in the presence of effective amounts of nucleotides, ATP, other necessary co-factors and the like, (i) more preferably, wherein the capacity to promote transcription elongation when operatively combined with a human P-TEFb kinase subunit protein, a functional human RNA polymerase II and the necessary transcriptional elongation components, cofactors and precursors, is inhibited by an effective amount of DRB.

The human genes and DNA segments preferably encode a substantially full length human P-TEFb large subunit, protein or polypeptide that includes a contiguous amino acid sequence of at least about 6 or 7 amino acids or so, or more preferably, of at least about 8, 10, 12, 14, 16, 18, 20, 22 or 25 amino acids or so from SEQ ID NO:45, SEQ ID NO:47 or SEQ ID NO:50, or a biologically functional equivalent thereof; or the genes and DNA segments will hybridize to such a coding sequence under stringent hybridization conditions. More preferably, the genes encode a P-TEFb large subunit, protein or peptide that includes a contiguous amino acid sequence of at least about 30, 35, 40, 45, 50, 60, 70, 80, 90, 100, 125, 150, 200 amino acids or so from SEQ ID NO:45, SEQ ID NO:47 or SEQ ID NO:50, or a biologically functional equivalent thereof; or the genes and DNA segments will hybridize to such a coding sequence under stringent hybridization conditions.

In certain preferred aspects, the human genes and DNA segments of the present invention will encode a P-TEFb large subunit having the amino acid sequence of SEQ ID NO:45, SEQ ID NO:47 or SEQ ID NO:50, or a biologically functional equivalent thereof; or the genes and DNA segments will hybridize to such a nucleic acid segment under stringent hybridization conditions.

The isolated human genes and coding regions may include a contiguous nucleic acid sequence of at least about 20–21 nucleotides or so, and more preferably, of at least about 30, 40, 50, 60 or 72 or so nucleotides from the coding region of SEQ ID NO:43 or SEQ ID NO:48, or a biologically functionally equivalent thereof; or the genes and DNA segments will hybridize to such a coding sequence under stringent hybridization conditions. Preferably, the isolated genes and DNA segments will comprise an isolated coding region having the nucleic acid sequence of SEQ ID NO:44, SEQ ID NO:46 or SEQ ID NO:49, or a biologically functional equivalent thereof; or the genes and DNA segments will hybridize thereto under stringent hybridization conditions.

Exemplary human genes and DNA segments may also be characterized as encoding a substantially full length P-TEFb large subunit including a contiguous amino acid sequence of at least about 7 amino acids, or more preferably, of at least about 8, 10, 12, 14, 16, 18, 20, 22 or 25 amino acids or so from SEQ ID NO:45, SEQ ID NO:47 or SEQ ID NO:50, or a biologically functional equivalent thereof, and as hybridizing to the nucleic acid sequence of SEQ ID NO:43 or SEQ ID NO:48 under stringent hybridization conditions.

The present invention also provides DNA segments comprising a first isolated gene or coding region that encodes a *Drosophila* or human P-TEFb kinase subunit, protein or polypeptide and a second isolated gene or coding region that encodes a corresponding *Drosophila* or human P-TEFb large subunit, protein or peptide.

As such, the present invention provides an expression system comprising:

a) a first expression unit comprising, under the transcriptional control of a promoter, a first coding region that encodes a substantially full length P-TEFb kinase subunit that includes a contiguous sequence of at least about 7 amino acids from SEQ ID NO:2 or SEQ ID NO:6 and b) a second expression unit comprising, under the transcriptional control of a promoter, a second coding region that encodes a substantially full length P-TEFb large subunit that includes a contiguous sequence of at least about 7 amino acids from SEQ ID NO:4, SEQ ID NO:45, SEQ ID NO:47 or SEQ ID NO:50.

Such expression systems may comprise a first and second expression unit on a single expression vector; or a first and second expression unit on two distinct expression vectors. The expression systems may be advantageously comprised within a recombinant host cell.

Such host cells will generally express a substantially full length P-TEFb kinase subunit and a substantially full length P-TEFb large subunit. These cells will therefore produce P-TEFb enzyme complexes comprising subunits generally of the same species. However, cross-species P-TEFb enzyme complexes, e.g., those that comprise one *Drosophila* subunit and one human subunit, are also contemplated.

Isolated, functional P-TEFb enzyme complexes thus form another aspect of the present invention. The *Drosophila* P-TEFb enzyme complex is generally characterized as:

a) comprising at least two subunits in operative association, a first, kinase subunit having a molecular weight of about 42 kD, and a second, large subunit (or cyclin-related subunit) having a molecular weight of about 121 kD;

b) being naturally localized to the cell nucleus and capable of interacting with and phosphorylating *Drosophila* RNA polymerase II present in an early elongation complex under suitable cellular conditions, or under suitable in vitro binding conditions that effectively duplicate the non-denaturing, non-dissociating cellular transcription elongation conditions;

c) being capable of phosphorylating *Drosophila* RNA polymerase II; and preferably, capable of phosphorylating *Drosophila* RNA polymerase II on the carboxyl terminal domain (CTD) of the large subunit of RNA polymerase II; and more preferably, wherein the capacity to phosphorylate *Drosophila* RNA polymerase II is inhibited by an effective amount of DRB; and d) being capable of promoting transcriptional elongation, which is also termed promoting the transition from an abortive to a productive elongation mode, i.e., being capable of promoting proper or productive elongation of mRNA transcripts (rather than abortive elongation) when operatively combined with a functional *Drosophila* RNA polymerase II molecule in the presence of a DNA template and under conditions otherwise appropriate to result in transcription elongation, i.e., in the presence of effective amounts of nucleotides, ATP, other necessary co-factors and the like; and preferably, wherein the capacity to promote transcriptional elongation is inhibited by an effective amount of DRB. The human P-TEFb enzyme complex is generally characterized as:

a) comprising at least two subunits in operative association, a first, kinase subunit preferably comprising the sequence of SEQ ID NO:6, and a second, large or cyclin-related subunit preferably comprising the sequence of SEQ ID NO:45, SEQ ID NO:47 or SEQ ID NO:50;

b) being naturally localized to the human cell nucleus and capable of interacting with and phosphorylating human RNA polymerase II present in an early elongation complex under suitable cellular conditions, or under suitable in vitro binding conditions that effectively duplicate the non-denaturing, non-dissociating cellular transcription elongation conditions;

c) being capable of phosphorylating human RNA polymerase II; and preferably, capable of phosphorylating human RNA polymerase II on the carboxyl terminal domain (CTD) of the large subunit of RNA polymerase II; and more preferably, wherein the capacity to phosphorylate human RNA polymerase II is inhibited by an effective amount of DRB; and d) being capable of promoting transcriptional elongation, which is also termed promoting the transition from an abortive to a productive elongation mode, i.e., being capable of promoting proper or productive elongation of mRNA transcripts (rather than abortive elongation) when operatively combined with a functional human RNA polymerase II molecule in the presence of a DNA template and under conditions otherwise appropriate to result in transcription elongation, i.e., in the presence of effective amounts of nucleotides, ATP, other necessary co-factors and the like; and preferably, wherein the capacity to promote transcriptional elongation is inhibited by an effective amount of DRB.

DNA segments and isolated genes may also be manipulated to encode a P-TEFb subunit fusion protein or polypeptide construct in which at least one P-TEFb subunit, protein, polypeptide or even peptide is operatively attached to a second coding region that encodes a selected peptide or protein sequence. The combination of P-TEFb subunit sequences, including human subunits, with selected antigenic amino acid sequences; selected non-antigenic carrier amino acid sequences, for use in immunization; selected adjuvant sequences; amino acid sequences with specific binding affinity for a selected molecule; amino acid sequences that form an active DNA binding or transactivation domain are particularly contemplated. Certain fusion proteins may be linked together via a protease-sensitive peptide linker, allowing subsequent easy separation.

The DNA segments intended for use in expression will be operatively positioned under the control of, i.e., downstream from, a promoter that directs expression of a P-TEFb subunit, protein or polypeptide in a desired host cell, such as *E. coli*, or in certain other preferred embodiments in an insect, mammalian or human cell. The promoter may be a recombinant promoter, or a promoter naturally associated with P-TEFb. Recombinant vectors, including baculoviral vectors, thus form another aspect of the present invention. The recombinant vectors may express a *Drosophila* P-TEFb kinase subunit, protein or polypeptide and a *Drosophila* P-TEFb large subunit, protein or polypeptide. Recombinant vectors expressing human P-TEFb large subunit proteins or polypeptides, human P-TEFb kinase subunits in combination with large subunits or even human kinase subunits for various uses are also provided.

Although sequences encoding substantially full length subunits are preferred, the invention further provides nucleic acid probes and primers and other nucleic acid segments, including those characterized as including:

a) comprising a sequence region that consists of at least about 120, 150, 200 or so contiguous nucleotides that have the same sequence as, or are complementary to, about 120, 150, 200 or so contiguous nucleotides selected from any region of SEQ ID NO:3; or b) a nucleic acid segment of from about 120, 150, 200 or so to about 20,000 nucleotides in length that hybridizes to any region of the nucleic acid segment of SEQ ID NO:3, or the complement thereof under standard hybridization conditions, and particularly under hybridization conditions in which the *Drosophila* sequence will not bind to the human kinase subunit sequence.

However, in defined regions of the sequence, e.g., those with less conservation, segments of each of SEQ ID NO:3 or the complement thereof, may variously be about 20, 25, 30, 50, 100, 200, 500, or 1000 or so nucleotides in length, up to and including full length sequences, or even longer, as may be achieved by duplication of certain regions. Where the sequence of SEQ ID NO:3 is concerned, sequences of at least about 2000, 3000, 4000 nucleotides of SEQ ID NO:3, or complements thereof are provided, up to and including the full length sequence of 4328 contiguous nucleotides of SEQ ID NO:3, or the complement thereof.

In addition, the invention provides nucleic acid probes and primers and other nucleic acid segments, including those characterized as including:

a) comprising a sequence region that consists of at least about 360, 400, 450 or so contiguous nucleotides that have the same sequence as, or are complementary to, about 360, 400, 450 or so contiguous nucleotides selected from any region of SEQ ID NO:43, SEQ ID NO:46 or SEQ ID NO:48; or b) a nucleic acid segment of from about 360, 400, 450 or so to about 20,000 nucleotides in length that hybridizes to any region of the nucleic acid segment of SEQ ID NO:43, SEQ ID NO:46 or SEQ ID NO:48, or the complement thereof under standard hybridization conditions.

Again, in certain defined regions of the sequences, e.g. those with less conservation as defined herein, segments of each of SEQ ID NO:43, SEQ ID NO:46 or SEQ ID NO:48, or the complements thereof, may variously be about 20, 25, 30, 50, 100, 200, 500, or 1000 or so nucleotides in length, up to and including full length sequences, or even longer, as may be achieved by duplication of certain regions.

It will be readily understood that what is meant by "defined regions of the sequence, e.g., those with less conservation" are contiguous stretches of at least about 20 nucleotides that are not identical or complimentary to known nucleic acid sequences. Such defined regions include, for example, positions 1–258, 320–345 and 1244–1457 of SEQ ID NO:1; positions 587–964, 1156–1711, 1764–3287, 3460–3775 and 3800–4328 of SEQ ID NO:3; and preferably, positions 1–244, 297–546, 867–1142, 1895–2331, 2821–2890, 3341–3442, 3953–3860 and 4491–4528 of SEQ ID NO:43; and positions 1–209, 418–667, 919–1031, 2045–2164 and 2219–23 60 of SEQ ID NO:48.

Where the sequence of SEQ ID NO:43, SEQ ID NO:46 or SEQ ID NO:48 is concerned, sequences of at least about 2000, 3000, 4000 nucleotides of SEQ ID NO:3, or complements thereof are provided, up to and including the full length sequence of 4528 contiguous nucleotides of SEQ ID NO:43, including the full length sequence of 2190 contiguous nucleotides of SEQ ID NO:46 or including the full length sequence of 2360 contiguous nucleotides of SEQ ID NO:48, or the complement thereof.

Any segment may be combined into a DNA segment or vector of up to about 30,000, about 20,000, or about 15,000 base pairs in length. Segments of up to about 20,000, 15,000, and 10,000 basepairs in length will generally be preferred, and segments of up to about 5,000 basepairs in length are also provided.

The nucleic acids of the present invention may also be DNA segments or RNA segments. Nucleic acid detection kits are also provided.

The present invention further provides recombinant host cells comprising at least one DNA segment or vector that comprises an isolated gene or coding region that encodes a *Drosophila* or human P-TEFb subunit protein, polypeptide, domain or any fusion protein thereof. Prokaryotic host cells, such as *E. coli*, are provided, as are eukaryotic host cells, such as insect cells and mammalian cells.

The recombinant host cells may further comprises an operative HIV Tat protein or active fragment thereof. Such recombinant host cells may be provided with the HIV Tat protein or peptide in vitro, for example, to test P-TEFb subunit protein and HIV Tat interactions, or may naturally express HIV Tat, including cells provided with P-TEFb subunit proteins, peptides or domains in vivo and in vitro.

The recombinant host cells of the present invention preferably have one or more DNA segments introduced into them by means of a recombinant vector, and preferably express the DNA segment to produce the encoded P-TEFb subunit, protein or polypeptide. The recombinant host cells may express a P-TEFb subunit, protein or polypeptide including a contiguous amino acid sequence of at least about 7 amino acids from SEQ ID NO:2 or SEQ ID NO:4, and preferably express a P-TEFb subunit, protein or polypeptide having the amino acid sequence of SEQ ID NO:2 or SEQ ID NO:4.

More preferably, the recombinant host cells will express human P-TEFb large subunits, proteins or peptides that include a contiguous amino acid sequence of at least about 7 amino acids from SEQ ID NO:45, SEQ ID NO:47 or SEQ ID NO:50, and preferably express P-TEFb subunits having the amino acid sequence of SEQ ID NO:45, SEQ ID NO:47 or SEQ ID NO:50. Cells expressing any of the foregoing large subunits in combination with human P-TEFb kinase subunits, proteins or peptides, preferably those that include a contiguous amino acid sequence from SEQ ID NO:6, are also provided.

The recombinant host cells of the present invention may express a P-TEFb subunit, protein or polypeptide fusion protein in which a contiguous P-TEFb subunit amino acid sequence is operatively attached to a selected peptide or protein sequence. Also provided are recombinant host cells that express a *Drosophila* or human P-TEFb kinase subunit and a *Drosophila* or human P-TEFb large subunit. Cells that allow the production of human holoenzymes are preferred.

Methods for detecting P-TEFb nucleic acids in cells or samples are also provided, and generally comprise obtaining sample nucleic acids from a sample suspected of containing P-TEFb nucleic acids, contacting the sample nucleic acids with a nucleic acid segment that encodes a P-TEFb subunit, protein or polypeptide, preferably a human P-TEFb subunit, protein or polypeptide, under conditions effective to allow hybridization of substantially complementary nucleic acids, and detecting the hybridized complementary nucleic acids thus formed. Use of nucleic acid segments that comprise a discriminating contiguous sequence from the sequence of SEQ ID NO:1, SEQ ID NO:3, SEQ ID NO:5, SEQ ID NO:43, SEQ ID NO:48, SEQ ID NO:44, SEQ ID NO:46 or SEQ ID NO:49 are preferred, with discriminating nucleic acid sequences from the sequence of SEQ ID NO:43, SEQ ID NO:48, SEQ ID NO:44, SEQ ID NO:46 or SEQ ID NO:49 being more preferred.

As the P-TEFb enzyme complex is herein shown to be essential to the transcription elongation process in eukaryotic, mammalian and human cells, it is envisioned that the levels of P-TEFb may correlate with various diseases, such as cancer. Accordingly, the present invention further provides methods of determining the levels of P-TEFb in cells or tissue samples, including tumor cells and samples, which generally comprise obtaining a biological sample suspected of containing P-TEFb; contacting the sample with a biological reagent that detects P-TEFb, under conditions effective to allow detection; and determining the level of P-TEFb detected. The "biological reagent that detects P-TEFb" may be a nucleic acid segment that encodes a human P-TEFb subunit, protein or polypeptide or it may be an antibody that has specific binding affinity for a human P-TEFb subunit, protein or polypeptide.

It is also contemplated that the "type" of P-TEFb, i.e., the presence of one or more P-TEFb proteins or mutants thereof, may correlate with diseases, such as cancer. Accordingly, the invention even further provides methods of determining whether P-TEFb mutants or one or more different P-TEFb proteins are present in cells or tissue samples. The methods generally comprise obtaining a biological sample suspected of containing a mutant P-TEFb or different P-TEFb protein; contacting the sample with a biological reagent capable of detecting a mutant, distinct from a wild type, P-TEFb or a different, or second, P-TEFb protein, under conditions effective to allow differential detection; and determining whether another P-TEFb protein or a P-TEFb mutant is present.

The "biological reagent that detects mutant P-TEFb" will generally be a nucleic acid segment or gene, or an antibody, that has specificity for the mutant sequence or protein in preference to the wild type sequence or protein, allowing effective differentiation between the two, as may be used in diagnostic tests for cancer cells or patients.

The "biological reagent that detects different P-TEFb" will generally be a nucleic acid segment or gene, or an antibody, that has specificity for another wild type sequence or protein in preference to the first wild type sequence or protein, allowing effective differentiation between the two, as may be used in diagnostic tests for cancer cells or patients. The use of nucleic acid segments, probes or primers that differentiate between the three different human P-TEFb large subunit proteins provided herein, i.e., proteins having the amino acid sequence of SEQ ID NO:45, SEQ ID NO:47 or SEQ ID NO:50, is particularly contemplated.

The invention therefore also includes the provision of DNA segments, vectors, genes and coding sequence regions that encode *Drosophila* or human P-TEFb proteins, polypeptides, domains, peptides or any fusion protein thereof, where the P-TEFb protein element comprises at least one mutation in comparison to the wild type sequence. The mutation may be deliberately introduced by the hand of man, for example, in order to test the function of the changed amino acid, e.g., in Tat or RNA polymerase II binding, and/or other functions. The mutation may be also be discovered in the natural population, as may be connected with dysfunction or disease.

Once a correlation between the levels of P-TEFb and a disease, such as cancer, has been confirmed, the present invention further provides methods for diagnosing said disease in other patients. Diagnostically, the present invention then provides methods for identifying a patient having or at risk for developing, for example, cancer; the methods comprising determining the type or amount of P-TEFb present within a biological sample from the patient, wherein the presence of a type or amount of P-TEFb different to the type or amount of P-TEFb present in a corresponding sample from a normal subject, is indicative of a patient having or at risk for developing the disease.

Methods of using DNA segments that include an isolated P-TEFb subunit gene or coding region, including human DNA segments, are provided, wherein the methods comprise expressing a P-TEFb subunit DNA segment in a recombinant host cell and collecting the P-TEFb subunit protein, polypeptide, domain or fusion protein expressed by the cell. This method may be represented by the steps of:
a) preparing a recombinant vector in which a P-TEFb subunit-encoding DNA segment, preferably a human DNA segment, is positioned under the control of a promoter;
b) introducing the recombinant vector into a recombinant host cell;
c) culturing the recombinant host cell under conditions effective to allow expression of an encoded P-TEFb subunit protein, polypeptide, domain or fusion protein; and
d) collecting the expressed P-TEFb subunit protein, polypeptide, domain or fusion protein.

The invention further provides recombinant P-TEFb subunit polypeptides, proteins and fusion proteins, preferably of human origin, prepared at levels that could not previously be obtained prior to the present invention. The methods comprise expressing a gene encoding a P-TEFb subunit polypeptide, protein or fusion protein in a recombinant host cell and purifying the expressed polypeptide, protein or fusion protein away from total recombinant host cell components to prepare between about 100 µg and about 1000 mg of a recombinant P-TEFb subunit polypeptide, protein or fusion protein. With scale up, the inventor contemplates that 10-fold increases can be achieved yielding up to about 10 g of recombinant P-TEFb proteins. The invention also provides compositions comprising isolated P-TEFb subunit peptides, proteins or fusion proteins in all amounts between about 100 µg and about 1000 mg, such as between about 500 µg and about 100 mg.

P-TEFb fusion proteins or constructs including P-TEFb subunit, protein or polypeptide sequences operatively attached to distinct, selected amino acid sequences, such as selected antigenic amino acid sequences, amino acid sequences with selected binding affinity, and DNA binding or transactivation amino acid sequences, are also encompassed within the invention. Particularly, P-TEFb subunit, protein or polypeptide sequences operatively attached to glutathione-S-transferase amino acid sequences are provided. Fusion proteins with selectably-cleavable bonds are also provided.

Compositions comprising isolated and purified P-TEFb kinase subunit proteins, polypeptides or fusion proteins that include a contiguous amino acid sequence of at least about 24 amino acids, and more preferably, of at least about, 25, 27, 30, 35, 40, 45, 50, 60, 70, 80, 90, 100, 125, 150, 200 amino acids or so from SEQ ID NO:2, or a biologically functional equivalent thereof, are also provided. P-TEFb kinase subunit proteins, polypeptides or fusion proteins having the amino acid sequence of SEQ ID NO:2 or a biologically functional equivalent thereof are preferred.

Also provided are isolated and purified P-TEFb large subunit proteins, polypeptides or fusion proteins that include a contiguous amino acid sequence of at least about 6 or 7 or so amino acids, and more preferably, of at least about, 8, 10, 12, 14, 16, 18, 20, 25, 30, 35, 40, 45, 50, 60, 70, 80, 90, 100, 125, 150 or 200 amino acids or so from SEQ ID NO:4, or a biologically functional equivalent thereof. P-TEFb large subunit proteins, polypeptides or fusion proteins having the amino acid sequence of SEQ ID NO:4 or a biologically functional equivalent thereof are more preferred.

Still more preferred aspects of this invention are isolated and purified human P-TEFb large subunit proteins, polypeptides or fusion proteins. These components generally include a contiguous amino acid sequence of at least about 6 or 7 or so amino acids, and more preferably, of at least about, 8, 10, 12, 14, 16, 18, 20, 25, 30, 35, 40, 45, 50, 60, 70, 80, 90, 100, 125, 150 or 200 amino acids or so from SEQ ID NO:45, SEQ ID NO:47 or SEQ ID NO:50, or a biologically functional equivalent thereof. P-TEFb large subunit proteins, polypeptides or fusion proteins having the amino acid sequence of SEQ ID NO:45, SEQ ID NO:47 or SEQ ID NO:50, or a biologically functional equivalent thereof, are even more preferred still.

Further provided are compositions comprising isolated and purified active *Drosophila* P-TEFb enzyme complexes comprising P-TEFb kinase subunits in operative association with P-TEFb large subunits, preferably at levels that could not be previously obtained. Further provided are compositions comprising isolated and purified active human P-TEFb enzyme complexes comprising P-TEFb kinase subunits in operative association with P-TEFb large subunits, preferably at levels that could not be previously obtained.

The invention further provides compositions comprising an HIV Tat protein in combination with an active P-TEFb enzyme complex comprising P-TEFb kinase subunits in operative association with P-TEFb large subunits. The complex is preferably a human complex.

The present invention provides P-TEFb immunodetection reagents. The immunodetection reagents may be characterized as:
a) an antibody that has immunospecificity for a *Drosophila* P-TEFb kinase subunit protein, preferably a protein of at least about 7 amino acids from SEQ ID NO:2, or more preferably, a protein of SEQ ID NO:2; an antibody that has immunospecificity for a *Drosophila* P-TEFb large subunit protein, preferably a protein of at least about 7 amino acids from SEQ ID NO:4, or more preferably, a protein of SEQ ID NO:4; or an antibody that has immunospecificity for a human P-TEFb large subunit protein, preferably a protein of at least about 7 amino acids from SEQ ID NO:45, SEQ ID NO:47 or SEQ ID NO:50, or more preferably, a protein of SEQ ID NO:45, SEQ ID NO:47 or SEQ ID NO:50; any of which antibodies may be operatively attached to a detectable label; or
b) an antibody that has immunospecificity for a human P-TEFb kinase subunit protein, preferably a protein of SEQ ID NO:6, wherein the antibody is operatively attached to a detectable label.

The immunodetection reagent comprising an antibody that has immunospecificity for a human P-TEFb large subunit protein, may further be attached to a detectable label. The detectable labels for use in the present invention may be a radioactive label, a fluorescent label, biotin, avidin or an enzyme that will generate a detectable product upon contact with a appropriate substrate, which is preferably a colored product. The antibodies for use in the immunodetection reagents of the present invention are preferably monoclonal antibodies.

The present invention provides immunodetection kits, certain of which may be described as comprising:
a) a Tat composition comprising a purified HIV Tat protein;
b) a P-TEFb composition comprising a purified human P-TEFb subunit; and
c) an immunodetection means.

The P-TEFb composition may comprise a purified human P-TEFb kinase subunit, a purified human P-TEFb large subunit, or a purified human P-TEFb enzyme complex comprising a P-TEFb kinase subunit bound to a P-TEFb large subunit.

The immunodetection kits of the present invention provide a variety of immunodetection means. The immunodetection means may be a detectable label that is operatively attached to the HIV Tat protein. In other kits, the immunodetection means may be a first anti-Tat antibody that binds to the HIV Tat protein, preferably wherein the first anti-Tat antibody is operatively attached to a detectable label. Additionally, the immunodetection means may be a detectable label that is operatively attached to the human P-TEFb subunit.

Alternatively, the immunodetection means may be a first anti-P-TEFb antibody that binds to a human P-TEFb subunit. The invention further provides kits wherein the first anti-P-TEFb human P-TEFb enzyme complexes. Further, the first anti-P-TEFb antibody may be operatively attached to a detectable label.

Certain other kits may comprise a first anti-Tat antibody or a first anti-P-TEFb antibody, wherein the immunodetection means is a detectable label that is operatively attached to a second antibody that has binding affinity for the first antibody. In such kits, the HIV Tat protein or the human P-TEFb subunit may be bound to a solid support.

The present invention further advantageously provides methods for identifying genes that encode P-TEFb subunit proteins from a desired species based upon the "two hybrid screening system". The methods rely on the use of one defined subunit to clone a matching subunit of the desired species, such that one of the binding pair (kinase or large subunit) is known and the other is identified by practicing the method. Accordingly, where one desires to clone a P-TEFb large subunit protein one uses the "complementary" P-TEFb kinase subunit protein in the screen. That is the meaning of "complementary" as used in the following methodological description. The methods may thus be characterized as comprising the steps of:
  a) obtaining a first DNA segment comprising a candidate P-TEFb subunit gene from a desired species; the first DNA segment expressing a first fusion protein comprising a transcriptional transactivating domain operatively attached to the candidate P-TEFb subunit protein encoded by the candidate gene;
  b) obtaining a second DNA segment that expresses a second fusion protein comprising the complementary P-TEFb subunit protein operatively attached to a DNA binding domain that binds to a defined nucleic acid sequence;
  c) providing the first and second DNA segments to a eukaryotic host cell that comprises a marker gene operatively positioned downstream of the defined nucleic acid sequence; and
  d) identifying a eukaryotic host cell that expresses the marker gene, thereby identifying the candidate gene as a gene of the desired species that encodes a P-TEFb subunit protein.

The methods generally further comprise isolating the identified candidate P-TEFb subunit gene from the first DNA segment within the eukaryotic host cell. U.S. Pat. No. 5,667,973 is specifically incorporated herein by reference for the purposes of providing further details concerning the execution of screening methods based upon this general technique.

The transcriptional transactivating domains used in the present invention may be the GAL4 or VP16 transcriptional transactivating domain. The fusion protein may comprise a GAL4 DNA binding domain, wherein the defined nucleic acid sequence comprises a GAL4 binding domain recognition sequence, or a lexA DNA binding domain, wherein the defined nucleic acid sequence comprises a lexO binding site sequence. In the methods, the eukaryotic host cell may be a yeast host cell (yeast two hybrid system) or a mammalian host cell.

In the two hybrid system methods of the present invention, marker genes preferred for use are chloramphenicol acetyltransferase, β-galactosidase, green fluorescent protein, β-glucuronidase or the luciferase gene, preferably the β-galactosidase gene.

A further explanation of the two hybrid system cloning method for identifying a gene of a desired species that encodes a P-TEFb subunit protein is that it generally operatively comprises the steps of:
  a) obtaining a plurality of first DNA segments comprising a plurality of candidate genes of the desired species;
  b) obtaining multiple copies of the second DNA segment;
  c) providing the plurality of first DNA segments and multiple copies of the second DNA segments to a population of eukaryotic host cells in an amount sufficient to provide about one first DNA segment and at least about one second DNA segment to each host cell in the population;
  d) culturing the population of cells under conditions and for a period of time effective to allow marker gene expression; and
  e) detecting a host cell from the population that expresses the marker gene, thereby identifying the presence in the cell of a first DNA segment that comprises a candidate gene of the desired species that encodes a P-TEFb subunit protein.

The method also generally further comprises isolating the detected cell of step (e) free from the population of cells, and isolating the candidate gene of the desired species from the first DNA segment within the cell.

Although human P-TEFb-encoding nucleic acids are directly provided by the present invention, the invention also enables the identification and use of additional P-TEFb-encoding nucleic acid segments of any defined species. Methods for obtaining such sequences generally comprise the steps of:
  a) obtaining at least one isolated nucleic acid segment designed to hybridize to a P-TEFb subunit gene of the desired species;
  b) contacting a population of nucleic acids of the desired species with the isolated nucleic acid segment under conditions effective to allow hybridization of the isolated nucleic acid segment to P-TEFb subunit nucleic acids within the population of nucleic acids of the desired species; and
  c) identifying a nucleic acid segment of the desired species that hybridizes to the isolated nucleic acid segment, preferably free from the population of nucleic acids of the desired species.

The methods of identifying nucleic acids of defined species that encode P-TEFb subunit proteins may utilize a single isolated nucleic acid segment designed to hybridize to a P-TEFb subunit gene of the desired species, wherein the population of nucleic acids of the desired species are contacted with the single isolated nucleic acid segment under conditions in which the single isolated nucleic acid segment sequence will bind to the large subunit sequence from the desired species. The single isolated nucleic acid segment may be designed from knowledge of the *Drosophila* or human genes provided by the present invention, or may be a probe sequence designed from a peptide purified from the desired species.

The methods of identifying P-TEFb subunit-encoding nucleic acids of a desired species may also utilize a pair of isolated nucleic acid segments or probes designed to hybridize to spatially distant sequences from a P-TEFb subunit gene of the desired species, wherein a polymerase chain reaction is conducted to amplify the P-TEFb subunit gene located between the spatially distant sequences, using protocols that are known to those of skill in the art. The probes may again be designed from the *Drosophila* and human sequences of the present invention or may be designed from peptide sequences of the desired species.

The present invention also provides methods of identifying a nucleic acid segment of a desired species that comprises an isolated coding region that encodes a P-TEFb subunit, protein or peptide wherein the isolated nucleic acid segment is designed from an analysis of at least one peptide sequence obtained from a P-TEFb subunit protein of the desired species. The peptide sequence may be an N-terminal or internal peptide sequence. In certain aspects of the present invention, the peptide sequence may be obtained by hydrolyzing a purified P-TEFb subunit protein from the desired species to form peptides and sequencing a peptide there formed. The method of obtaining the peptide sequence may comprise the steps of:

a) purifying a P-TEFb subunit protein from the desired species, preferably by fractionating a cellular extract comprising a P-TEFb subunit protein of the desired species and obtaining a fraction enriched for the subunit;

b) hydrolyzing the purified P-TEFb subunit protein to form a population of peptides;

c) isolating a single peptide from the population of peptides; and d) sequencing the isolated peptide.

The present invention further provides methods for preparing purified P-TEFb subunit proteins of a desired species comprising the steps of:

a) obtaining a nuclear extract from a cell of the desired species;

b) subjecting the extract to fractionation via column chromatography, using a series of chromatography columns, such as phosphocellulose (P-11), DEAE cellulose, Phenyl Sepharose™, hydroxylapatite, Mono Q, Mono S™ and the like; and preferably, subjecting the extract to fractionation via column chromatography using, in sequence, a phosphocellulose, Phenyl Sepharose™ affinity chromatography medium (GE Healthcare, Waukesha, Wis.), hydroxylapatite, Mono Q™ and Mono S™ columns (GE Healthcare, Waukesha, Wis.); and c) obtaining a fraction comprising the P-TEFb subunit protein substantially free from other protein components.

The invention also provides methods of preparing purified P-TEFb subunit proteins of a desired species that comprise the steps of:

a) obtaining a nuclear extract from the desired species;

b) subjecting the extract to fractionation using an antibody that binds to a known P-TEFb subunit protein;

c) purifying a fraction comprising the desired P-TEFb subunit protein in combination with the known P-TEFb subunit protein; and d) separating the desired P-TEFb subunit protein free from the known P-TEFb subunit protein.

The antibodies used for preparing purified P-TEFb subunit proteins may be immobilized on a solid support, with the extract fractionated by applying the extract to the solid support. More preferably, the antibodies are monoclonal antibodies. These antibodies may be prepared by immunizing an animal with a P-TEFb subunit, protein or peptide, and collecting the resultant antibodies.

The present invention thus provides nucleic acid segments of any desired species that comprise an isolated coding region or gene that encodes a P-TEFb subunit protein of the desired species. These nucleic acid segments may also be comprised within a recombinant vector, which may be comprised within a recombinant host cell.

Compositions comprising purified P-TEFb subunit proteins of any desired species are further provided. The compositions may be obtained from cells that naturally express the P-TEFb subunits, or obtained from a recombinant cell that has been engineered to express the P-TEFb subunit of the desired species. The compositions may be prepared by fractionating a cell extract comprising a P-TEFb subunit protein and purifying the subunit protein away from total cell components. The fractionation may comprise column chromatography, preferably affinity column chromatography, and more preferably immunoaffinity column chromatography using a column comprising an antibody that binds to the P-TEFb subunit protein of the desired species.

The compositions comprising purified P-TEFb subunit proteins of a desired species may further comprise the other P-TEFb subunit protein of the binding pair, and may still further comprise a viral protein, such as a species-specific protein equivalent of the HIV Tat protein.

In particularly useful embodiments, this invention also provides methods of assaying for P-TEFb. One of the methods comprises testing a composition suspected of containing P-TEFb for the ability to phosphorylate RNA polymerase II, wherein phosphorylation is indicative of a composition comprising at least a P-TEFb kinase subunit, and preferably is indicative of a composition comprising a functional P-TEFb holoenzyme. The method may be described as comprising the steps of:

a) admixing (i) a test composition suspected of containing P-TEFb, (ii) a composition comprising at least the carboxyl terminal domain (CTD) of the large subunit of RNA polymerase II, and (iii) an effective phosphate donor compound comprising a labeled phosphate group; and b) determining the ability of the test composition to catalyze the transfer of the labeled phosphate group to the carboxyl terminal domain (CTD) of RNA polymerase II.

The effective phosphate donor compound is preferably ATP that comprises a $^{32}$P- or $^{33}$P-labeled terminal phosphate group, although GTP also functions in this regard.

The invention also provides a phosphorylation-based method for identifying a candidate transcriptional inhibitor, comprising preparing a P-TEFb composition comprising at least a P-TEFb kinase subunit, and preferably comprising a functional P-TEFb holoenzyme, and testing the candidate inhibitor for the ability to inhibit P-TEFb-mediated phosphorylation of RNA polymerase II, wherein inhibition of phosphorylation is indicative of a candidate transcriptional inhibitor. The method may be described as comprising the steps of:

a) obtaining a P-TEFb composition comprising at least a P-TEFb kinase subunit, and preferably comprising a functional P-TEFb holoenzyme;
b) obtaining an RNA polymerase II composition comprising at least the carboxyl terminal domain (CTD) of the large subunit of RNA polymerase II;
c) admixing the P-TEFb composition with the RNA polymerase II composition and an effective phosphate donor compound comprising a labeled phosphate group; and
d) determining the ability of the P-TEFb composition to transfer the labeled phosphate group to the RNA polymerase II composition in the presence of the candidate transcriptional inhibitor and in the absence of the candidate transcriptional inhibitor, wherein a reduction in the amount of labeled phosphate transferred to RNA polymerase II in the presence of the candidate is indicative of a positive candidate transcriptional inhibitor.

The P-TEFb composition may comprise a *Drosophila* P-TEFb composition or a human P-TEFb composition. The P-TEFb composition will preferably comprise a P-TEFb enzyme complex that has transcription elongation promoting activity. The terms "a P-TEFb enzyme complex that has transcription elongation promoting activity", or "a transcriptionally active P-TEFb enzyme complex" is a complex, generally comprising at least a kinase subunit and a large, cyclin-like subunit, which facilitates transcriptional elongation by RNA polymerase II, or removes a previous 'block' that was preventing proper transcriptional elongation, when admixed with an otherwise transcriptionally capable or competent composition. The P-TEFb enzyme complex may also be termed "transcriptionally active" or "elongationally active".

The methods for identifying a candidate transcriptional inhibitor may further comprise testing the candidate transcriptional inhibitor so identified in a transcription elongation assay, wherein inhibition of transcription elongation confirms the identification of a transcriptional inhibitor. The transcription elongation assay may be described as comprising the steps of:
a) preparing a transcriptionally competent composition capable of generating elongated RNA transcripts and comprising effective amounts of DNA template, P-TEFb enzyme complex, RNA polymerase II, each four nucleotides and ATP; and
b) determining the ability of the transcriptionally competent composition to generate elongated RNA transcripts in the presence of the candidate transcriptional inhibitor and in the absence of the candidate transcriptional inhibitor, wherein a reduction in the amount of elongated RNA or mRNA transcripts in the presence of the candidate is indicative of the identification or confirmation of a transcriptional inhibitor.

The invention thus provides transcriptional inhibitors, prepared by a process comprising testing a candidate transcriptional inhibitor substance for the ability to inhibit P-TEFb-mediated phosphorylation of RNA polymerase II and identifying a transcriptional inhibitor as a candidate substance that inhibits the phosphorylation.

The invention also provides methods for identifying an HIV Tat protein, comprising contacting a composition suspected of containing an HIV Tat protein with a human P-TEFb composition under conditions effective to allow the formation of bound protein complexes and detecting the bound protein complexes so formed. The human P-TEFb composition may comprise a human P-TEFb kinase subunit, preferably comprising the amino acid sequence of SEQ ID NO:6. Alternatively, the human P-TEFb composition may comprise a human P-TEFb large subunit, preferably comprising the amino acid sequence of SEQ ID NO:45, SEQ ID NO:47 or SEQ ID NO:50. The human P-TEFb composition may also comprise a human P-TEFb complex comprising a P-TEFb kinase subunit and a P-TEFb large subunit.

Given that the studies of the present inventor demonstrate the general importance of human P-TEFb in viral transcription, and show binding to VP16, the invention further provides methods for identifying other transcriptional activator proteins, comprising contacting a composition suspected of containing a transcriptional activator protein with a human P-TEFb composition under conditions effective to allow the formation of bound protein complexes and detecting the bound protein complexes so formed. The detection of a protein that binds to the human P-TEFb composition is indicative of the identification of a transcriptional activator protein.

Also provided in the present invention is a method for identifying a candidate viral transcription inhibitor, comprising testing a candidate substance for the ability to inhibit the binding of a viral transcriptional transactivator protein to a P-TEFb composition comprising a human P-TEFb subunit under effective binding conditions, wherein inhibition of binding is indicative of a positive candidate viral transcription inhibitor. The viral transcriptional transactivator protein may be attached to a solid support, as can the P-TEFb composition. The viral transcriptional transactivator protein may be an HIV Tat protein, or an adenoviral E1A protein or a herpes virus VP16 protein.

The P-TEFb composition may comprise a human P-TEFb kinase subunit, preferably comprising the amino acid sequence of SEQ ID NO:6. Alternatively, the P-TEFb composition may comprise a human P-TEFb large subunit, preferably comprising the amino acid sequence of SEQ ID NO:45, SEQ ID NO:47 or SEQ ID NO:50. In other aspects of the present invention, the P-TEFb composition comprises a human P-TEFb complex comprising a P-TEFb kinase subunit and a P-TEFb large subunit.

Such assays are in effect "ELISA type" assays. Accordingly, the effective binding conditions are binding and washing conditions, as may be determined by contacting a composition comprising the viral transcriptional transactivator protein with the P-TEFb composition under conditions effective to allow the formation of bound protein complexes and detecting the bound protein complexes so formed after removing the non-specifically bound protein species. The bound protein complexes may be detected by means of a detectable label that is operatively attached to the viral transcriptional transactivator protein, or alternatively by means of a first anti-viral antibody that binds to the viral transcriptional transactivator protein, preferably wherein the first anti-viral antibody is operatively attached to a detectable label. Also, the bound protein complexes may be detected by means of a detectable label that is operatively attached to the human P-TEFb subunit.

In other aspects, the bound protein complexes may be detected by means of a first anti-P-TEFb antibody that binds to the human P-TEFb subunit, either the human P-TEFb kinase subunit, the human P-TEFb large subunit or an intact human P-TEFb enzyme complex, preferably wherein the first anti-P-TEFb antibody is operatively attached to a detectable label.

In still further aspects of the present invention, the bound protein complexes may be detected by means of a first anti-viral or anti-P-TEFb antibody in combination with a second antibody, the second antibody having binding affinity for the first antibody and being operatively attached to a detectable label. The effective binding conditions may further comprise admixing a human cell nuclear extract with the viral transcriptional transactivator protein and the P-TEFb composition.

The invention provides extended methods of confirming the identification of a candidate viral transcription inhibitor, which further comprise testing the positive candidate viral transcription inhibitor identified in a viral transcription elongation assay, wherein inhibition of viral transcription elongation is indicative of an active candidate viral transcription inhibitor. The viral transcription elongation assay may be described as comprising the steps of:
  a) preparing a transcriptionally competent composition capable of generating elongated viral RNA transcripts and comprising effective amounts of viral nucleic acid template, viral transcriptional transactivator protein, most preferably from the corresponding virus, P-TEFb enzyme complex, RNA polymerase II, each of the four nucleotides and ATP; and
  b) determining the ability of the transcriptionally competent composition to generate elongated viral RNA transcripts in the presence of the positive candidate viral transcription inhibitor and in the absence of the positive candidate inhibitor candidate, wherein a reduction in the amount of elongated viral RNA or viral mRNA transcripts in the presence of the candidate is indicative of the identification or confirmation of an active candidate viral transcriptional inhibitor.

In certain aspects, the method may further comprise testing the active candidate viral transcription inhibitor identified in a dual transcription elongation assay, wherein inhibition of viral transcription elongation only in the presence of the viral transcriptional transactivator protein confirms the identification of a viral transcription inhibitor. The dual transcription elongation assay may be described as comprising the steps of:
  a) preparing a first transcriptionally competent composition capable of generating elongated human RNA transcripts, the composition comprising effective amounts of human nucleic acid template, P-TEFb enzyme complex, RNA polymerase II, each of the four nucleotides and ATP;
  b) preparing a second transcriptionally competent composition capable of generating elongated viral RNA transcripts, the composition comprising effective amounts of viral nucleic acid template, viral transcriptional transactivator protein, most preferably from the corresponding virus, P-TEFb enzyme complex, RNA polymerase II, each of the four nucleotides and ATP; and
  c) identifying an active candidate viral transcription inhibitor that inhibits the generation of the elongated viral RNA transcripts by the second transcriptionally competent composition and that does not inhibit the generation of the elongated human RNA transcripts by the first transcriptionally competent composition.

The second transcriptionally competent composition may alternatively comprise any viral template any corresponding viral protein, as exemplified by an adenovirus or a herpes virus nucleic acid template and the transcriptional transactivator proteins, adenovirus E1A or herpes virus VP16.

Although the pre-testing or pre-screening for effective candidate inhibitors, using one or more of the binding assays described above, is believed to be an effective strategy, there is no need that such binding assays be first conducted in order to identify a candidate viral transcription inhibitor. Accordingly, the present invention further provides a method for identifying a candidate viral transcription inhibitor, comprising testing a candidate substance for the ability to inhibit viral RNA elongation in a functional viral transcription elongation assay, wherein inhibition of viral RNA elongation is indicative of an active candidate viral transcription inhibitor.

Preferably, anti-viral screening methods comprise testing the active candidate viral transcription inhibitors in parallel human and viral transcription elongation assays, wherein the presence of the active candidate inhibitor reduces viral, but not human, transcription elongation in the parallel assays.

Thus, the present invention provides viral transcription inhibitors, prepared by a process comprising testing a candidate viral transcription inhibitor substance for the ability to inhibit the binding of a viral transcriptional transactivator protein to a human P-TEFb composition and identifying a viral transcriptional inhibitor as a candidate substance that inhibits the binding under otherwise effective binding conditions. The inhibitors may be dispersed in a pharmaceutically acceptable medium, or admixed with a pharmaceutically acceptable diluent or excipient.

The invention additionally provides an HIV inhibitor, or pharmaceutical formulation thereof, which may be prepared by a process that comprises the steps of:
  a) preparing a first transcriptionally competent composition capable of generating elongated human RNA transcripts, the composition comprising effective amounts of human nucleic acid template, P-TEFb enzyme complex, RNA polymerase II, each of the four nucleotides and ATP;
  b) preparing a second transcriptionally competent composition capable of generating elongated HIV RNA transcripts, the composition comprising effective amounts of HIV nucleic acid template, HIV Tat protein, P-TEFb enzyme complex, RNA polymerase II, each of the four nucleotides and ATP; and
  c) identifying an HIV inhibitor that inhibits the generation of elongated HIV RNA transcripts by the second transcriptionally competent composition but that does not inhibit the generation of elongated human RNA transcripts by the first transcriptionally competent composition.

Also provided by the present invention are methods of inhibiting viral replication, as exemplified by HIV replication, comprising contacting a cell suspected of being infected with a virus, such as HIV, with an amount of the instant inhibitors effective to inhibit viral, or HIV, RNA elongation in the cell. The cell may be located within an animal, when a therapeutically effective amount of the inhibitor is administered to the animal.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 7A) Transcription of HIV LTR template (633-nt runoff). (FIG. 7B) CTD kinase assay using immunoprecipitated human P-TEFb and Drosophila RNA polymerase II as substrate described by Price (Price et al., 1987; Price 1995).

SEQUENCE SUMMARY

Figure 1:
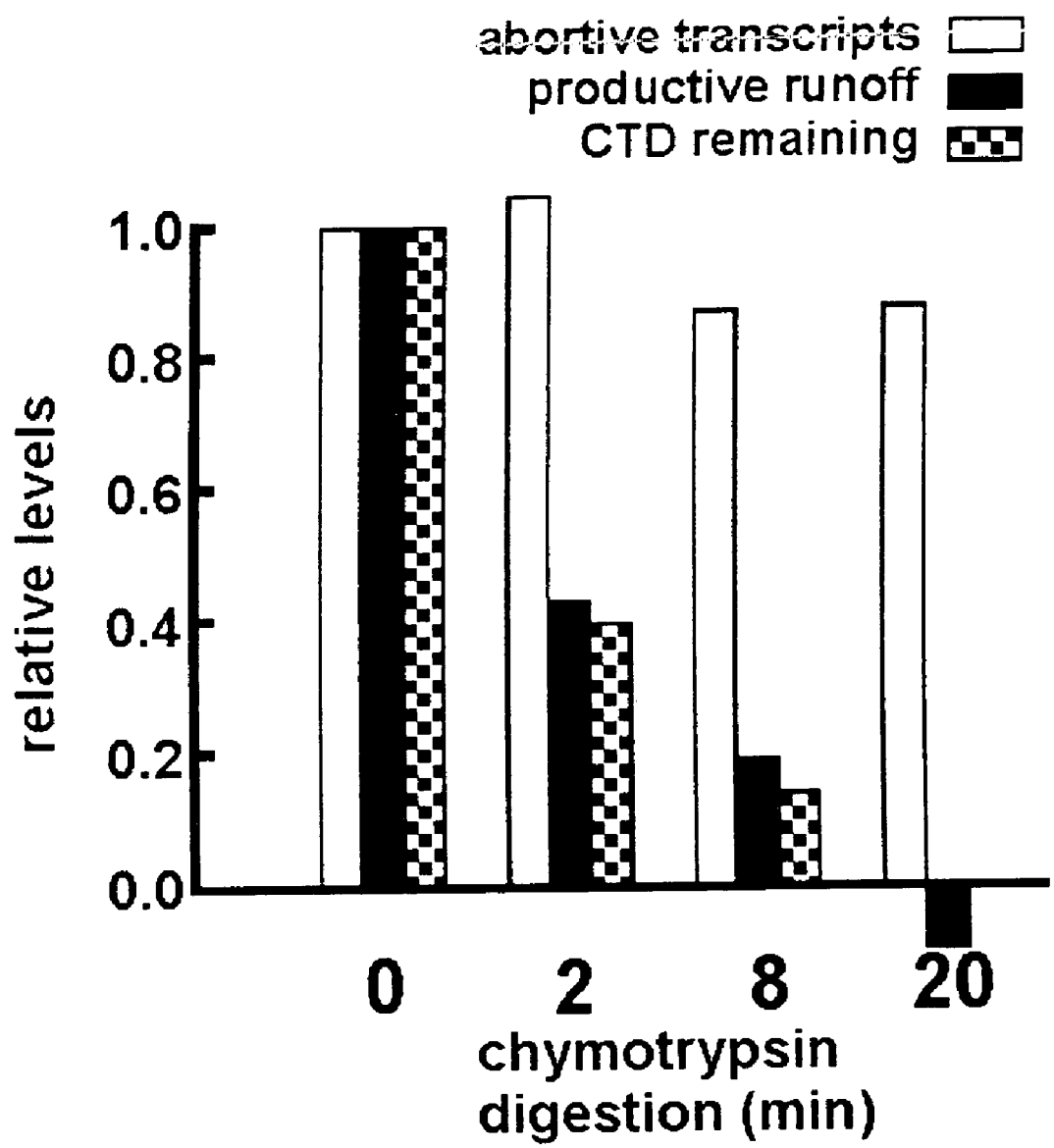
FIG. 1. Requirement of the CTD for productive elongation. Quantitation of transcription by RNA polymerase II treated with chymotrypsin for the indicated times. Transcripts were loaded onto a silver stained 6–15% SDS polyacrylamide gel and autoradiographed. Autoradiographs were scanned using a BIO-RAD Model GS-670 Imaging Densitometer. Areas of the silver stained gel corresponding to subunit Ia, indicative of the intact largest polymerase subunit, were quantitated, normalized to the zero (0) digestion time and plotted as CTD remaining. The portions of the autoradiograph indicated as runoff and abortive (520 nucleotide runoff from the actin promoter) transcripts were quantitated and plotted in parallel.

SEQ ID NO:1 full length cDNA of the Drosophila P-TEFb small (kinase) subunit
SEQ ID NO:2 amino acid sequence of the Drosophila P-TEFb small subunit
SEQ ID NO:3 full length cDNA of the Drosophila P-TEFb large subunit
SEQ ID NO:4 amino acid sequence of the Drosophila P-TEFb large subunit
SEQ ID NO:5 discovered to be the cDNA sequence of human small subunit
SEQ ID NO:6 discovered to be the amino acid sequence of human small subunit
SEQ ID NO:7 primer for Drosophila RNA polymerase II large subunit
SEQ ID NO:8 primer for Drosophila RNA polymerase II large subunit
SEQ ID NO:9 degenerate primer for the Drosophila P-TEFb small (kinase) subunit
SEQ ID NO:10 degenerate primer for the Drosophila P-TEFb small (kinase) subunit
SEQ ID NO:11 primer for the Drosophila P-TEFb small subunit
SEQ ID NO:12 primer for the Drosophila P-TEFb small subunit
SEQ ID NO:13 primer for the Drosophila P-TEFb small subunit
SEQ ID NO:14 primer for the Drosophila P-TEFb small subunit
SEQ ID NO:15 primer for the Drosophila P-TEFb small subunit
SEQ ID NO:16 primer for the Drosophila P-TEFb small subunit
SEQ ID NO:17 primer for the Drosophila P-TEFb small subunit
SEQ ID NO:18 primer for the Drosophila P-TEFb small subunit
SEQ ID NO:19 degenerate primer for the Drosophila P-TEFb large subunit
SEQ ID NO:20 degenerate primer for the Drosophila P-TEFb large subunit
SEQ ID NO:21 degenerate primer for the Drosophila P-TEFb large subunit
SEQ ID NO:22 primer for the Drosophila P-TEFb large subunit
SEQ ID NO:23 primer for the Drosophila P-TEFb large subunit
SEQ ID NO:24 primer for the Drosophila P-TEFb large subunit
SEQ ID NO:25 primer for the Drosophila P-TEFb large subunit
SEQ ID NO:26 primer for the Drosophila P-TEFb large subunit
SEQ ID NO:27 primer for the Drosophila P-TEFb large subunit
SEQ ID NO:28 primer for the Drosophila P-TEFb large subunit
SEQ ID NO:29 primer for the Drosophila P-TEFb large subunit
SEQ ID NO:30 primer for the Drosophila P-TEFb large subunit
SEQ ID NO:31 peptide sequence for part of the Drosophila P-TEFb small subunit
SEQ ID NO:32 peptide sequence for part of the Drosophila P-TEFb small subunit
SEQ ID NO:33 peptide sequence for part of the Drosophila P-TEFb small subunit
SEQ ID NO:34 peptide sequence for part of the Drosophila P-TEFb small subunit
SEQ ID NO:35 peptide sequence for part of the Drosophila P-TEFb large subunit
SEQ ID NO:36 peptide sequence for part of the Drosophila P-TEFb large subunit
SEQ ID NO:37 peptide sequence for part of the Drosophila P-TEFb large subunit
SEQ ID NO:38 peptide sequence for part of the Drosophila P-TEFb large subunit
SEQ ID NO:39 peptide sequence for part of the Drosophila P-TEFb large subunit
SEQ ID NO:40 peptide sequence for part of the Drosophila P-TEFb large subunit
SEQ ID NO:41 primer for the human P-TEFb small subunit cDNA
SEQ ID NO:42 primer for the human P-TEFb small subunit cDNA
SEQ ID NO:43 full length cDNA of the human P-TEFb large subunit HBL1
SEQ ID NO:44 coding sequence of human P-TEFb large subunit clone HBL1-1
SEQ ID NO:45 amino acid sequence of human P-TEFb large subunit clone HBL1-1
SEQ ID NO:46 coding sequence of human P-TEFb large subunit clone HBL1-2
SEQ ID NO:47 amino acid sequence of human P-TEFb large subunit clone HBL1-2
SEQ ID NO:48 full length cDNA of human P-TEFb large subunit clone HBL3

-continued

SEQUENCE SUMMARY

SEQ ID NO:49 coding sequence of human P-TEFb large subunit clone HBL3
SEQ ID NO:50 amino acid sequence of human P-TEFb large subunit clone HBL3

DESCRIPTION OF ILLUSTRATIVE EMBODIMENTS

The present invention addresses one or more shortcomings in the prior art through the cloning and further characterization of various subunits of the enzyme, termed positive transcription elongation factor b (P-TEFb), involved in the regulation of RNA elongation. It is herein shown that viral processing, through the joint binding of viral proteins and the carboxyl terminal domain (CTD) of RNA polymerase II and via the transfer of phosphate groups to RNA polymerase II, is P-TEFb dependent. The invention relates particularly to the molecular cloning of P-TEFb subunits, including human subunits, to the purification of the recombinant enzyme, to compounds that are capable of inhibiting xenobiotic activators, in particular viral activators, of RNA elongation, and to methods for the identification and use of further inhibitory compounds.

A certain object of the present invention is therefore to provide methods for obtaining P-TEFb enzymes, by purification of the recombinant enzyme from host cells engineered to express the constituent subunits, which methods are proposed to be generally applicable to the purification of all species of P-TEFb.

It is an additional objective of the invention to provide methods for obtaining these enzymes in a relatively purified form, allowing their use in predictive assays for identifying compounds having the ability to reduce the activity of or inhibit viral-driven RNA elongation activity, particularly in the context of retroviruses, such as HIV, and even adenoviruses.

It is a still further object of the invention to identify classes of compounds which demonstrate inhibition of xenobiotic activators of RNA elongation along with a potential application of these compounds in the treatment of diseases connected with human immunodeficiency virus (HIV), herpes simplex virus (HSV) and other viruses and retroviruses.

I. P-TEFb Functions

The claimed invention provides a surprising link between the process of productive elongation and phosphorylation of the CTD of RNA polymerase II. The inventor found that removal of the CTD by limited proteolysis prohibits the transition into productive elongation. In correlation with this, the inventor found that a factor required for the transition into productive elongation, P-TEFb, is a CTD kinase that, in contrast to earlier candidates, is relevant in intact elongation systems.

P-TEFb is an essential component of the positive transcription elongation system which regulates the production of long transcripts in vitro (Marshall and Price, 1992). The subunit composition and activity of P-TEFb does not match that of any published Drosophila or human transcription factor. In particular, P-TEFb is unlike the elongation factors TFIIF (factor 5) or DmS-II because it does not stimulate the elongation rate of purified RNA polymerase on dC-tailed templates. P-TEFb was shown to be distinct from Drosophila TFIIH by its function in in vitro transcription, CTD kinase activity and polypeptide composition. Yankulov et al. (1995) proposed that the effect of DRB and H-8 on transcription was due to inhibition of the kinase activity of TFIIH and suggested that the TFIIH associated kinase controlled elongation by RNA polymerase II. The possibility of TFIIH playing a role in elongation control remains, but the present invention directly demonstrates that P-TEFb functions to control elongation and that TFIIH cannot substitute for P-TEFb.

The conclusions of Yankulov et al. (1995) were based on the observation that DRB or H-8 inhibited the TFIIH kinase and the appearance of runoff transcripts during transcription with similar dose-response curves. The reported kinase assays were performed at 7.5 µM ATP and the transcription assays were performed at 500 µM NTPs. Because different triphosphate conditions were used in the two assays a valid comparison of inhibition curves cannot be made. It is likely that the DRB-sensitivity detected during transcription was due to inhibition of P-TEFb rather than TFIIH, although this conclusion could only be deduced after the discoveries of the present invention.

A slight stimulation of the elongation rate of RNA polymerase II in a dC-tailed template assay was seen with some P-TEFb containing fractions, but the activity did not correlate with P-TEFb activity. This activity was chromatographically separated from P-TEFb. Based on chromatographic properties, the factor identified by Chodosh et al. (1989) in crude fractions from HeLa nuclear extract was not P-TEFb, but possibly the human equivalent of factor 2.

Factor 6 was described as a dispensable factor that gave a quantitative stimulation of the amount of runoff transcript seen in reconstructions of transcription initiation (Price et al., 1987). Factor 6 was a DEAE flowthrough fraction from a 0.75 M HGKEDP (buffer comprising 25 mM HEPES, 15% glycerol, gradient concentrations of KCl, 0.1 mM EDTA, 1 mM DTT, 0.1% of a saturated solution of phenylmethylsulfonyl fluoride in isopropanol) step of the phosphocellulose column. The fraction containing factor 6 contained 10–15% of the proteins in the nuclear extract and was, therefore, very crude. Another stimulatory activity, factor 7 was also found in the 0.75 M HGKEDP phosphocellulose fraction and this factor bound to the DEAE (Price et al., 1987).

Neither of the factors could be further purified at the time because they only had small stimulatory effects and they could not be found during elution of further chromatographic steps. Because both factor 6 and 7 had only small stimulatory effects to RNA elongation, it is unlikely that either factor is P-TEFb, but given that a crude column extract was examined, it is reasonable to surmise that, even though P-TEFb was not detected, it was present in the crude extract as were potentially hundreds of other proteins.

The particular chromatographic properties of P-TEFb and the subunit composition of P-TEFb distinguish it from any of the known basal initiation factors with the possible exception of TFIIJ (Flores et al., 1992). At least one form of IIJ elutes from P-11 above 0.5 M KCl and the purified factor has two subunits of 33 and 95 kDa. Whereas, P-TEFb elutes from P-11 below 0.5 M KCl and the subunits of P-TEFb are 46.8 kDa and 121 kDa, respectively, as calculated by computer analysis with the genetic analysis program GeneRunner®. A HeLa ss-DNA agarose column fraction that contains both IIA and IIJ does not substitute for P-TEFb.

P-TEFb or a similar protein may play a role in HIV-1 transcription since productive elongation is similar to the stimulation of highly processive elongation complexes by Tat (Marciniak and Sharp, 1991). Recently, Tat-SF was identified as a factor required for Tat activation of HIV transcription (Zhou and Sharp, 1995). The chromatography of this protein on anion exchange resins is most similar to factor 2 or P-TEFa, not P-TEFb. The relation of Tat-SF to P-TEFb is unclear. Recently, a kinase that can associate with the HIV-1 Tat protein was shown to have DRB-sensitive CTD kinase activity (Herrmann and Rice, 1995), but the protein was not purified or characterized.

A specific interaction between HIV-1 and HIV-2 Tat proteins with a HeLa cell protein kinase, termed Tat-associated kinase (TAK), has been demonstrated (Herrmann and Rice, 1993). Tat is a viral protein that acts as a activator of transcription of the HIV viral transcription unit. It binds to short nascent HIV transcripts and causes RNA polymerase II to synthesize mRNA sized transcripts. It has been suggested that a CTD kinase associates with Tat in vivo. It has been shown that human cell extracts contain a protein that is able to phosphorylate the CTD of the large subunit of RNA polymerase II (Herrmann and Rice, 1995), but this is a long way from the molecular characterization of "TAK". The TAK activity was inhibited by DRB, which has been shown to selectively inhibit Tat function in vivo and in vitro (Herrmann and Rice, 1995; Marciniak and Sharp, 1991).

Recent work by Yang et al. (1996) has shown that Tat proteins specifically associate with TAK activity in vivo and require the CTD of RNA polymerase II for function. An unidentified 42 kDa protein (SEQ ID NO:6) was found to cochromatograph with the TAK activity. They speculated that this protein may be a subunit of TAK. The small subunit of P-TEFb has a similar size to this unidentified protein (Marshall and Price, 1995). Surprisingly, the inventor's comparison of the cDNA sequence of the small subunit of P-TEFb (SEQ ID NO:1) with the cDNA sequence SEQ ID NO:5 of the 42 kDa protein showed an unexpected 71% identity and 82% conserved similarity between the two proteins, suggesting to the inventor that the two proteins are homologous to each other and that P-TEFb is homologous to TAK.

The present invention demonstrates that the human homolog of the small subunit of Drosophila P-TEFb binds to a GST-Tat fusion protein, (GST-Tat 1 86R), but not to a GST-Tat transactivation defective protein, (GST-Tat 1 86R P18IS) as described in the Examples herein. The GST-Tat 1 86R/P-TEFb protein complex can phosphorylate the CTD of RNA polymerase II, corroborating the conclusion that TAK is the human homolog of P-TEFb.

Phosphorylation of the CTD of the large subunit of RNA polymerase II normally occurs during the late stages of initiation or early during elongation (Dahmus, 1994; Dahmus, 1995). An intact CTD is required for Drosophila elongation complexes to escape early blocks to elongation and enter productive elongation. The serine and threonine rich CTD is a substrate for a large number of kinases (Dahmus, 1994). However, those working in this field were, prior to the present invention, unable to determine which kinase(s) actually phosphorylates the CTD in vivo with functional consequences.

Recently, Tat-SF was proposed as a factor required for Tat activation of HIV transcription (Zhou and Sharp, 1995). Based on the chromatographic analysis of Tat-SF, it appears to be most similar to factor 2 or P-TEFa, two factors which stimulate RNA elongation but do not appear to be essential for RNA elongation to occur. The present invention is therefore surprising in that it clarifies the confusion in the prior art by providing a purified kinase which is essential for the transition into productive RNA elongation. This protein, named P-TEFb, has some homology to cyclin proteins although this similarity could not have been predicted prior to cloning and phosphorylating the CTD of RNA polymerase II.

The present invention shows that P-TEFb is distinct from a number of CTD kinases and in vivo studies of the present inventor demonstrate that the transition into productive elongation is controlled by P-TEFb-dependent phosphorylation of the CTD. Subunit composition, DRB sensitivity and functional properties distinguish P-TEFb from TFIIH or the TFIIH associated kinase. P-TEFb functions during elongation and is not stably associated with the transcription complex at any time (Kephart et al., 1992; Marshall and Price, 1992; Marshall and Price, 1995). This further discriminates between P-TEFb and TFIIH as well as the kinase associated with the SRB complex and DNA PK which are part of the initiation complex or otherwise bound to the template. The subunit composition and chromatographic properties of P-TEFb are not similar to any known kinase. Anti-phosphotyrosine antibodies failed to react with RNA polymerase II phosphorylated by P-TEFb, indicating that P-TEFb is a serine/threonine kinase.

The CTD is required for transcription in vivo (Zehring et al., 1988; Nonet et al., 1987; Bartolomei et al., 1988; Allison et al., 1988; Brickey and Greenleaf, 1995), but demonstrating a general requirement for the CTD in vitro requires the use of crude extracts (Li and Kornberg, 1994) or a more purified system which includes specific elongation control factors (Marshall and Price, 1995). However, in more purified systems lacking the elongation control factors some promoters still demonstrate a requirement for the CTD. The CTD is not required for transcription from the Drosophila actin 5C promoter in a Drosophila system (Zehring et al., 1988) or from the Ad-2 ML promoter in a HeLa system (Kim and Dahmus, 1989). The CTD is required for transcription from the murine DHFR promoter in a HeLa system (Kang and Dahmus, 1993; Thompson et al., 1989; Akoulitchev et al., 1995). Akoulitchev et al. (1995), showed that an early step in initiation from the DHFR promoter (formation of the first phosphodiester bond) required the CTD.

A model for the control of elongation has been described which is based on results obtained from a Drosophila in vitro transcription system (Kephart et al., 1992; Marshall and Price, 1992) and is consistent with data obtained in vitro and in vivo from many studies. Key features of the model are that all RNA polymerase II molecules that initiate from a promoter are destined to produce only short transcripts in a process termed abortive elongation. Abortive elongation is distinct from abortive initiation because the abortive transcripts are 10 to 20 times longer during abortive elongation and presumably the polymerase in the abortive elongation complexes must relocate the promoter after producing an abortive transcript to bring about reinitiation. Escape from this negative control is accomplished through the action of the positive transcription elongation system which allows productive elongation.

Elongation control can be divided into two temporally differentiated stages during which specific elongation factors function. The transition into productive elongation occurs during the first stage. Negative transcription elongation factors (N-TEF) influence RNA polymerase II molecules that have initiated from a promoter causing them to enter abortive elongation which is characterized by the generation of short transcripts (Kephart et al., 1992; Marshall and Price, 1992). Some of the components of N-TEF seem to be associated with the preinitiation complex (Marshall and Price, 1992), but one component, factor 2, acts after initiation as an RNA polymerase II transcript release factor (Xie and Price, 1996). The generation of highly processive elongation complexes involves several P-TEFs (Marshall and Price, 1995).

The second stage of the elongation control process occurs after RNA polymerase II has entered productive elongation at which point the polymerase may be further affected by other factors. The first factor identified, S-II, suppresses pausing by RNA polymerase II at specific sites (Reinberg and Roeder, 1987; SivaRaman et al., 1990; Sluder et al., 1989) through a transcript cleavage mechanism (Guo and Price, 1993; Izban and Luse, 1993; Reines, 1992). The required initiation factor TFIIF (*Drosophila* factor 5 or RAP 30/74), also stimulates the elongation rate of RNA polymerase II (Bengal et al., 1991; Burton et al., 1988; Flores et al., 1989; Kephart et al., 1994; Price et al., 1989). Other factors, TFIIX (Bengal et al., 1991), S-III (Bradsher et al., 1993a; Bradsher et al., 1993b), and ELL (Shilatifard et al., 1996) stimulate elongation in a manner similar to TFIIF.

A number of *Drosophila* genes including HSP70 have early blocked polymerases in the IIA form, while downstream elongating polymerases are highly phosphorylated (O'Brien et al., 1994). In injected *Xenopus* oocytes, GAL4 based activators stimulated elongation in a DRB-sensitive manner (Yankulov et al., 1994). It is possible that transcriptional activators work with or through P-TEFb. Dubois et al. (1994) found that addition of DRB or H-8 to HeLa cells caused a rapid decrease in the amount of RNA polymerase IIo. Egyhazi et al. (1996) recently showed that DRB inhibited the phosphorylation of RNA polymerase II to the IIo form in *Chironomus tentans*. Their results indicated that addition of DRB immediately stopped the incorporation of phosphate into the polymerase, but that polymerases in productive elongation complexes maintained their hyperphosphorylated states until they completed their current round of transcription.

The substrate specificity of P-TEFb and the kinetics of P-TEFb to phosphorylate CTD were determined under a variety of conditions as described herein in the Examples. The nucleotide requirements of P-TEFb CTD kinase were similar to those reported for HeLa TFIIH (Lu et al., 1992), CTD-K1 (Payne and Dahmus, 1993), and rat liver 6 (Serizawa et al., 1992), but were different from those for yeast factor b (Feaver et al., 1991) and CTD-K2 (Payne and Dahmus, 1993). The kinetics of phosphorylation using different concentrations of kinase is not consistent with processive P-TEFb action during the phosphorylation of purified RNA polymerase II. P-TEFb does prefer to phosphorylate a CTD that has already been phosphorylated which may have implications for its function after initiation.

II. P-TEFb Genes and Expression

A. DNA Segments

Important aspects of the present invention concern isolated DNA segments and recombinant vectors encoding P-TEFb, and the creation and use of recombinant host cells through the application of DNA technology, that express P-TEFb. DNA segments, recombinant vectors, recombinant host cells and expression methods using sequences of the P-TEFb small subunit and large subunit are also provided.

Each of the foregoing genes are included within all aspects of the following description. The present invention concerns DNA segments, isolatable from insect, mammalian and human cells, that are free from total genomic DNA and that are capable of expressing a P-TEFb protein or polypeptide subunit that has kinase activity, or that has similarity to cyclin proteins, both of which subunits are essential for productive RNA elongation. Such proteins will herein be termed "P-TEFb proteins".

As used herein, the term "DNA segment" refers to a DNA molecule that has been isolated free of total genomic DNA of a particular species. Therefore, a DNA segment encoding a P-TEFb subunit refers to a DNA segment that contains P-TEFb coding sequences yet is isolated away from, or purified free from, total mammalian or human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified P-TEFb kinase or large subunit protein gene refers to a DNA segment including P-TEFb kinase or large subunit protein coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, complementary DNA (cDNA) sequences and smaller engineered gene segments that express, or may be adapted to express, P-TEFb proteins, polypeptides, domains, peptides, fusion proteins and mutants.

"Isolated substantially away from other coding sequences" means that the gene of interest, in this case a P-TEFb kinase or large subunit protein gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, as described in detail in the foregoing 'Summary' section, the invention concerns isolated DNA segments and recombinant vectors that encode substantially full length P-TEFb kinase subunit proteins or polypeptide that include a contiguous amino acid sequence of at least about 24 amino acids, and more preferably, of at least about, 25, 27, 30, 35, 40, 45, 50, 60, 70, 80, 90, 100, 125, 150, 200 amino acids or so from SEQ ID NO:2, or a biologically functional equivalent thereof. Even more preferably, the genes encode a protein with a sequence essentially as set forth in SEQ ID NO:2.

Substantially full length P-TEFb kinase subunit genes preferably include a contiguous nucleic acid sequence of at least about 722 nucleotides, and more preferably, of at least about 725, 750, 800, 825, 850, 900 or so nucleotides from between position 115 and position 1326 or 1327 of SEQ ID NO:1, or a biologically functional equivalent thereof. More preferably, the isolated genes and DNA segments have a nucleic acid sequence essentially as set forth in SEQ ID NO:1.

The substantially full length P-TEFb large subunit genes of the invention generally encode a protein or polypeptide that includes a contiguous amino acid sequence of at least about 6 or 7 amino acids or so, or more preferably, of at least about 8, 10, 12, 14, 16, 18, 20, 22 or 25 amino acids or so from SEQ ID NO:4, SEQ ID NO:45, SEQ ID NO:47 or SEQ ID NO:50, or a biologically functional equivalent thereof; or the genes and DNA segments hybridize to such a coding sequence under stringent hybridization conditions.

More preferably, the substantially full length P-TEFb large subunit genes encode a P-TEFb large subunit protein that includes a contiguous amino acid sequence of at least about 30, 35, 40, 45, 50, 60, 70, 80, 90, 100, 125, 150, 200 amino acids or so from SEQ ID NO:4, SEQ ID NO:45, SEQ ID NO:47 or SEQ ID NO:50, or a biologically functional equivalent thereof; or hybridize to such a coding sequence under stringent hybridization conditions. Most preferably, the substantially full length P-TEFb large subunit genes encode a P-TEFb large subunit having a sequence essentially as set forth in the amino acid sequence of SEQ ID NO:4, SEQ ID NO:45, SEQ ID NO:47 or SEQ ID NO:50, or a biologically functional equivalent thereof; or hybridize to such a coding sequence under stringent hybridization conditions.

In certain embodiments, the substantially full length P-TEFb large subunit genes include a contiguous nucleic acid sequence of at least about 120, 150 or 200 or so nucleotides from between position 716 and position 4006 of SEQ ID NO:3, or include a contiguous nucleic acid sequence of at least about 360, 400, 450 or 500 or so nucleotides from a coding region from SEQ ID NO:43 or SEQ ID NO:48 (e.g., SEQ ID NO:44, SEQ ID NO:46 or SEQ ID NO:49); or a biologically functionally equivalent thereof; or will hybridize to such a coding sequence under stringent hybridization conditions.

Most preferably, the substantially full length P-TEFb large subunit genes comprise an isolated coding region having a nucleic acid sequence essentially as set forth in SEQ ID NO:3, SEQ ID NO:44. SEQ ID NO:46 or SEQ ID NO:49, or a biologically functional equivalent thereof; or will hybridize to such a coding sequence under stringent hybridization conditions.

The term "a sequence essentially as set forth in SEQ ID NO:2, SEQ ID NO:4, SEQ ID NO:45, SEQ ID NO:47 or SEQ ID NO:50" means that the sequence substantially corresponds to a portion of SEQ ID NO:2, SEQ ID NO:4, SEQ ID NO:45, SEQ ID NO:47 or SEQ ID NO:50 and has relatively few amino acids that are not identical to, or a biologically functional equivalent of, the amino acids of SEQ ID NO:2, SEQ ID NO:4, SEQ ID NO:45, SEQ ID NO:47 or SEQ ID NO:50. The term "biologically functional equivalent" is well understood in the art and is further defined in detail herein. Accordingly, sequences that have between about 85% and about 90%; or more preferably, between about 91% and about 95%; or even more preferably, between about 96% and about 99%; of amino acids that are identical or functionally equivalent to the amino acids of SEQ ID NO:2, SEQ ID NO:4, SEQ ID NO:45, SEQ ID NO:47 or SEQ ID NO:50 will be sequences that are "essentially as set forth in SEQ ID NO:2, SEQ ID NO:4, SEQ ID NO:45, SEQ ID NO:47 or SEQ ID NO:50", provided the biological activity of the protein is maintained.

In certain other embodiments, the invention concerns isolated DNA segments and recombinant vectors that include within their sequence a nucleic acid sequence essentially as set forth in SEQ ID NO:1, SEQ ID NO:3, SEQ ID NO:43, SEQ ID NO:46 or SEQ ID NO:48. The term "essentially as set forth in SEQ ID NO:1, SEQ ID NO:3, SEQ ID NO:43, SEQ ID NO:46 or SEQ ID NO:48" is used in the same sense as described above and means that the nucleic acid sequence substantially corresponds to a portion of SEQ ID NO:1, SEQ ID NO:3, SEQ ID NO:43, SEQ ID NO:46 or SEQ ID NO:48 and has relatively few codons that are not identical, or functionally equivalent, to the codons of SEQ ID NO:1, SEQ ID NO:3, SEQ ID NO:43, SEQ ID NO:46 or SEQ ID NO:48. Again, DNA segments that encode proteins exhibiting kinase activity or large functional subunits will be most preferred.

The term "functionally equivalent codon" is used herein to refer to codons that encode the same amino acid, such as the six codons for arginine or serine, and also refers to codons that encode biologically equivalent amino acids (see Codon Table, below).

| CODON TABLE | | | |
|---|---|---|---|
| Amino Acids | | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 75% and about 79%; or more preferably, between about 80% and about 89%; or even more preferably, between about 90% and about 99%; of nucleotides that are identical to the nucleotides of SEQ ID NO:1, SEQ ID NO:3, SEQ ID NO:43, SEQ ID NO:46 or SEQ ID NO:48 will be sequences that are "essentially as set forth in SEQ ID NO:1, SEQ ID NO:3, SEQ ID NO:43, SEQ ID NO:46 or SEQ ID NO:48".

Sequences that are essentially the same as those set forth in SEQ ID NO:1, SEQ ID NO:3, SEQ ID NO:43, SEQ ID NO:46 or SEQ ID NO:48 may also be functionally defined as sequences that are capable of hybridizing to a nucleic acid segment containing the complement of SEQ ID NO:1, SEQ ID NO:3, SEQ ID NO:43, SEQ ID NO:46 or SEQ ID NO:48 under relatively stringent conditions. Suitable relatively stringent hybridization conditions will be well known to those of skill in the art.

Suitable standard hybridization conditions for the present invention include, for example, hybridization in 50% formamide, 5× Denhardts' solution, 5×SSC, 25 mM sodium phosphate, 0.1% SDS and 100 μg/ml of denatured salmon sperm DNA at 42° C. for 16 h followed by 1 h sequential washes with 0.1×SSC, 0.1% SDS solution at 60° C. to remove the desired amount of background signal. Lower stringency hybridization conditions for the present invention include, for example, hybridization in 35% formamide, 5× Denhardts' solution, 5×SSC, 25 mM sodium phosphate, 0.1% SDS and 100 µg/ml denatured salmon sperm DNA or *E. coli* DNA at 42° C. for 16 h followed by sequential washes with 0.8×SSC, 0.1% SDS at 55° C. Those of skill in the art will recognize that conditions can be readily adjusted to obtain the desired level of stringency.

Naturally, the present invention also encompasses DNA segments that are complementary, or essentially complementary, to the sequence set forth in SEQ ID NO:1, SEQ ID NO:3, SEQ ID NO:43, SEQ ID NO:46 or SEQ ID NO:48. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1, SEQ ID NO:3, SEQ ID NO:43, SEQ ID NO:46 or SEQ ID NO:48 under relatively stringent conditions such as those described immediately above.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared from any region of the presently disclosed sequences that include contiguous sequences characterized as follows: about 117–125 or about 126–135 nucleotides of SEQ ID NO:3; about 315–320 or about 321–330 nucleotides of SEQ ID NO:48; about 360–370 or about 371–380 nucleotides of either SEQ ID NO:43 or SEQ ID NO:46. The sequences may be up to about 30,000 or 20,000, or about 10,000, or about 5,000 base pairs in length, with segments of about 3,000 being preferred in certain cases.

DNA segments with total lengths of about 1,000, about 500, about 300, about 200, and about 150 base pairs in length (including all intermediate lengths) are also contemplated to be useful for certain sequences as described above. For the smaller fragments, probes and primers the sequences will generally be selected from the following defined regions: between positions 1–258, 320–345 and 1244–1457 of SEQ ID NO:1; positions 587–964, 1156–1711, 1764–3287, 3460–3775 and 3800–4328 of SEQ ID NO:3; and preferably positions, 1–244, 297–546, 867–1142, 1895–2331, 2821–2890, 3341–3442, 3953–3860 and 4491–4528 of SEQ ID NO:43; and positions 1–209, 418–667, 919–1031, 2045–2164 and 2219–2360 of SEQ ID NO:48.

It will be readily understood that "intermediate lengths", in these contexts, means any length between the quoted ranges, bearing in mind that the stated constraints on ht elengths and regions of complementarity. For example, 19, 20, 21, etc.; 24, 25, 26, etc.; 29, 30, 31, etc.; 48, 49, 50, 51, etc.; 75, 76, 77, 78, 79, 80 etc.; 100, 101, 102, 103 etc.; 118, 119, 120, 121 etc.; 127, 128, 129, 130, 131, etc.; 316, 317, 318, 319, etc.; 322, 323, 324, 325, 326, etc.; 361, 362, 363, 364, etc.; 372, 373, 374, 375, etc.; including all integers through the 400–500; 500–1,000; 1,000–2,000; 2,000–3,000; 3,000–5,000; 5,000–10,000 ranges, up to and including sequences of about 12,001, 12,002, 13,001, 13,002, 15,000, 20,000, 30,000 and the like as is appropriate for each sequence.

The various probes and primers designed around the disclosed nucleotide sequences of the present invention may be of any length. By assigning numeric values to a sequence, for example, the first residue is 1, the second residue is 2, etc., an algorithm defining all primers can be proposed:

$$n \text{ to } n+y$$

where n is an integer from 1 to the last number of the sequence and y is the length of the primer minus one, where n+y does not exceed the last number of the sequence. Thus, for a 125-mer, the probes correspond to bases 1 to 125, 2 to 126, 3 to 127 . . . and so on. For a 315-mer, the probes correspond to bases 1 to 315, 2 to 316, 3 to 317 . . . and so on. For a 360-mer, the probes correspond to bases 1 to 360, 2 to 361, 3 to 362 . . . and so on.

It will also be understood that this invention is not limited to the particular nucleic acid and amino acid sequences of SEQ ID NO:1, SEQ ID NO:3, SEQ ID NO:43, SEQ ID NO:46 or SEQ ID NO:48. Recombinant vectors and isolated DNA segments may therefore variously include these coding regions themselves, coding regions bearing selected alterations or modifications in the basic coding region, or they may encode larger polypeptides that nevertheless include such coding regions or may encode biologically functional equivalent proteins or peptides that have variant amino acids sequences.

The DNA segments of the present invention encompass biologically functional equivalent P-TEFb and kinase proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine transcription, elongation or Tat binding activity at the molecular level.

One may also prepare fusion proteins and peptides, e.g., where the P-TEFb or kinase protein coding regions are aligned within the same expression unit with other proteins or peptides having desired functions, such as for purification or immunodetection purposes (e.g., proteins that may be purified by affinity chromatography and enzyme label coding regions, respectively).

Encompassed by the invention are DNA segments encoding relatively small peptides, such as, for example, peptides of from about 7 to about 50 amino acids in length, and more preferably, of from about 10 to about 30 amino acids in length; and also larger polypeptides up to and including proteins corresponding to the full-length sequences set forth in SEQ ID NO:2, SEQ ID NO:4, SEQ ID NO:45, SEQ ID NO:47 and SEQ ID NO:50.

The DNA segments of the present invention may be employed for a variety of applications. For example, a particularly useful application concerns the recombinant production of the individual subunits or proteins or peptides whose structure is derived from that of the subunits, or in the recombinant production of the holoenzyme following co-expression of the two subunits. Additionally, the P-TEFb-encoding DNA segments of the present invention can also be used in the preparation of nucleic acid probes or primers, which can, for example, be used in the identification and cloning of P-TEFb genes or related genomic sequences, or in the study of subunit(s) expression, and the like.

B. Nucleic Acid Detection

In addition to their use in directing the expression of the PTEF kinase or large subunit protein, the nucleic acid sequences disclosed herein also have a variety of other uses. For example, they also have utility as probes or primers in nucleic acid hybridization embodiments.

1. Hybridization

The use of a hybridization probe, e.g., of about 14–20, 25–30, 50, 75, 100, 120, 150, 200, 250, 300 or 360 or so nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. In using sequences from any region of those disclosed herein, one may generally prefer to design nucleic acid molecules having stretches of 120 to 360 nucleotides, or even longer where desired. By choosing from more unique regions, as already disclosed herein, those of skill in the art will appreciate that smaller probess and primers may be designed and utilized, e.g., of between about 14–20, 25, 30, 35 or so nucleotides in length.

All fragments may be readily prepared by, for example, directly synthesizing the fragment by chemical means or by introducing selected sequences into recombinant vectors for recombinant production. These chemical means can include PCR™ technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, low stringency hybridization conditions for the present invention provide hybridization in 35% formamide, 5× Denhardts' solution, 5×SSC, 25 mM sodium phosphate, 0.1% SDS and 100 µg/ml denatured salmon sperm DNA or *E. coli* DNA at 42° C. for 16 hours followed by sequential washes with 0.8×SSC, 0.1% SDS at 55° C. and allows for cross-species hybridization to homologous proteins to occur. For example, under these conditions the *Drosophila* P-TEFb small subunit cDNA (SEQ ID NO:1) cross hybridizes to the human 42 kDa protein of SEQ ID NO:6. Thus, hybridization conditions can be readily manipulated depending on the desired results. Alternative hybridization conditions which are useful are given in Examples 3 and 4. Of course, the hybridization conditions chosen are dependent upon the objective that is to be achieved.

In other embodiments, more stringent hybridization may be achieved under conditions of, for example, 50% formamide, 5× Denhardts' solution, 5×SSC, 25 mM sodium phosphate, 0.1% SDS and 100 µg/ml of denatured salmon sperm DNA at 42° C. for 16 h followed by 1 hour sequential washes with 0.1×SSC, 0.1% SDS solution at 60° C. to remove the desired amount of background signal.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

2. Amplification and PCR™

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a cDNA.

Pairs of primers that selectively hybridize to nucleic acids corresponding to P-TEFb, kinase protein or a mutant thereof are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ (RT-PCR™) amplification procedure may be performed in order to quantify the amount of mRNA amplified or to prepare cDNA from the desired mRNA. Methods of reverse transcribing RNA into cDNA are well known and described in Sambrook et al., 1989. Alternative methods for reverse transcription utilize thermostable. RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio] triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (ds-DNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("ds-DNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

All the essential materials and reagents required for detecting P-TEFb or kinase protein markers in a biological sample may be assembled together in a kit. This generally will comprise preselected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences specified in SEQ ID NO:1 or SEQ ID NO:3 or SEQ ID NO:43 or SEQ ID NO:46 or SEQ ID NO:48 such that, for example, nucleic acid fragments are prepared that include a contiguous stretch of nucleotides identical to for example about 14–20, 25, 30, 35, etc.; 48, 49, 50, 51, etc.; 75, 76, 77, 78, 79, 80 etc.; 100, 101, 102, 103 etc.; 118, 119, 120, 121 etc.; 127, 128, 129, 130, 131, etc.; 316, 317, 318, 319, etc.; 322, 323, 324, 325, 326, etc.; 361, 362, 363, 364, etc.; 372, 373, 374, 375, etc. of SEQ ID NO:3, SEQ ID NO:48, SEQ ID NO:43 or SEQ ID NO:4, so long as the selected contiguous stretches are from spatially distinct regions. Similar fragments may be prepared which are identical or complimentary to SEQ ID NO:1 such that the fragments do not hybridize to SEQ ID NO:5.

In another embodiment, such kits will comprise hybridization probes specific for P-TEFb large or kinase proteins chosen from a group including nucleic acids corresponding to the sequences specified in SEQ ID NO:1 or SEQ ID NO:3 or SEQ ID NO:43 or SEQ ID NO:46 or SEQ ID NO:48 or to intermediate lengths of the sequences specified. Such kits generally will comprise, in suitable means, distinct containers for each individual reagent and enzyme as well as for each marker hybridization probe.

3. Other Assays

Other methods for genetic screening to accurately detect genetic changes which may be caused by disease, such as cancers, viral or parasitic infections that alter normal cellular production and processing, in genomic DNA, cDNA or RNA samples may be employed, depending on the specific situation.

For example, one method of screening for genetic variation is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as +.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild type sequences, are hybridized to complementary target regions derived from test samples. The test target generally comprises DNA (either genomic DNA or DNA amplified by cloning in plasmids or by PCR™), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

C. Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

D. Recombinant Vectors, Host Cells and Expression

Recombinant vectors form important further aspects of the present invention. The term "expression vector or construct" means any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

Particularly useful vectors are contemplated to be those vectors in which the coding portion of the DNA segment, whether encoding a full length protein or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid to control RNA polymerase initiation and expression of the gene.

The promoter may be in the form of the promoter that is naturally associated with a P-TEFb or kinase protein gene, as may be obtained by isolating the 5' non-coding sequences located upstream of the coding segment or exon, for example, using recombinant cloning and/or PCR™ technology, in connection with the compositions disclosed herein (PCR™ technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a P-TEFb or a kinase protein gene in its natural environment. Such promoters may include promoters normally associated with other genes, and/or promoters isolated from any other bacterial, viral, eukaryotic, or mammalian cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment, such as is advantageous in the large-scale production of recombinant proteins or peptides.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Preferred promoters include those derived from HSV, including the HNF1α promoter. Another preferred embodiment is the tetracycline controlled promoter.

In various other embodiments, the human cytomegalovirus (CMV) immediate early gene promoter, the Simian virus 40 (SV40) early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. The following tables list several elements/promoters which may be employed, in the context of the present invention, to regulate the expression of P-TEFb or a kinase protein gene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

PROMOTER TABLE

| PROMOTER | REFERENCES |
| --- | --- |
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |

-continued

PROMOTER TABLE

| PROMOTER | REFERENCES |
|---|---|
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988; Campere and Tilghman, 1989 |
| τ-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $\alpha_{1\text{-Antitrypain}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

ENHANCER TABLE

| | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |

-continued

ENHANCER TABLE

| | Inducer | References |
|---|---|---|
| B-Interferon | poly(rl)X poly(rc) | Tavernier et al., 1983 |
| Adenovirus 5 E2 | Ela | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2kb | Interferon | Blanar et al., 1989 |
| HSP70 | Ela, SV40 Large T Antigen | Taylor et al., 1989; Taylor and Kingston, 1990a,b |
| Proliferin | Phorbol Ester-TPA | Mordacq and Linzer, 1989 |
| Tumor Necrosis Factor | FMA | Hensel et al., 1989 |
| Thyroid Stimulating Hormone α Gene | Thyroid Hormone | Chatterjee et al., 1989 |

Turning to the expression of the P-TEFb or kinase proteins of the present invention, once a suitable clone or clones have been obtained, whether they be cDNA based or genomic, one may proceed to prepare an expression system. The engineering of DNA segment(s) for expression in a prokaryotic or eukaryotic system may be performed by techniques generally known to those of skill in recombinant expression. It is believed that virtually any expression system may be employed in the expression of the proteins of the present invention.

Two in vitro systems that best represent the features of the in vivo situation are nuclear extracts from HeLa and *Drosophila* $K_c$ cells ($K_cN$). In HeLa nuclear extracts transcription initiating at the HIV LTR promoter gives rise to an abundance of transcripts terminated close to the promoter and only very limited amounts of longer transcripts. Addition of HIV Tat protein increases the number of DRB-sensitive elongation complexes that are able to make long transcripts (Marciniak and Sharp, 1991). Using *Drosophila* $K_cN$ extracts only a fraction of RNA polymerase II molecules that initiate generate transcripts longer than several hundred nucleotides (Kephart et al., 1992). The addition of DRB to $K_cN$ extracts selectively inhibits the production of elongation complexes capable of sustained elongation. Two factors P-TEF (positive transcription elongation factor) and N-TEF (negative transcription elongation factor) were proposed to control this behavior (Marshall and Price, 1992).

The inventor has characterized processive elongation complexes in HeLa nuclear extracts that are either DRB-sensitive or -insensitive. The DRB-sensitive processive elongation complexes produce runoff transcripts at a faster rate than DRB-insensitive processive elongation complexes. The immobilized DNA template studies suggest the existence of a HeLa P-TEFb-like activity. The number of DRB-sensitive processive elongation complexes appears to be determined by the amount of P-TEFb activity. The inventor shows that *Drosophila* and HeLa P-TEFb activities are DRB-sensitive and can act cross-species in the transition into productive elongation.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

It is proposed that the small subunit of P-TEFb may be co-expressed with the large subunit of P-TEFb, wherein the proteins may be co-expressed in the same cell or wherein one subunit, for example the small subunit, may be provided to a cell that already has the other subunit, for example the large subunit, of P-TEFb. Co-expression may be achieved by co-transfecting the cell with two distinct recombinant vectors, each bearing a copy of either the respective DNA. Alternatively, a single recombinant vector may be constructed to include the coding regions for both of the subunits, which could then be expressed in cells transfected with the single vector. In either event, the term "co-expression" herein refers to the expression of both of the subunits of P-TEFb in the same recombinant cell.

As used herein, the terms "engineered" and "recombinant" cells are intended to refer to a cell into which an exogenous DNA segment or gene, such as a cDNA or gene encoding a P-TEFb or kinase protein has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant P-TEFb or kinase protein, whether mutant or wild-type, in accordance with the present invention one would prepare an expression vector that comprises a P-TEFb- or kinase protein-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, the like.

Promoters that are most commonly used in recombinant DNA construction include the b-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media, for example, LB. The expression of the recombinant protein may be induced, e.g., by adding IPTG to the media or by switching incubation to a higher temperature. After culturing the bacteria for a further period, generally of between 2 and 24 h, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as 3-mercaptoethanol or DTT (dithiothreitol).

Under some circumstances, it may be advantageous to incubate the protein for several h under conditions suitable for the protein to undergo a refolding process into a conformation which more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

For expression in *Saccharomyces*, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to microorganisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more P-TEFb or kinase protein coding sequences.

In a useful insect system, Autograph californica nuclear polyhidrosis virus (AcNPV) is used as a vector to express foreign genes. The virus grows in *Spodoptera frugiperda* cells. The P-TEFb or kinase protein coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, Smith, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed. To this end, eukaryotic host cells such as 293 cells have already been shown to produce active P-TEFb.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired P-TEFb or kinase protein gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing P-TEFb or kinase proteins in infected hosts.

Specific initiation signals may also be required for efficient translation of P-TEFb or kinase protein coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly-A addition site is placed about 30 to 2000 nucleotides "downstream" of the termination site of the protein at a position prior to transcription termination.

For long-term, high-yield production of recombinant P-TEFb or kinase proteins, stable expression is preferred. For example, cell lines that stably express constructs encoding P-TEFb or kinase proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus (HSV) tk, hypoxanthine-guanine phosphoribosyltransferase (hgprt) and adenine phosphoribosyltransferase genes (aprt), in tk-, hgprt- or aprt-cells, respectively. Also, antimetabolite resistance can be used as the basis of selection for dhfr, that confers resistance to methotrexate; gpt, that confers resistance to mycophenolic acid; neo, that confers resistance to the aminoglycoside G-418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the P-TEFb subunits or proteins of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

III. P-TEFb Proteins and Peptides

The present invention therefore provides purified, and in preferred embodiments, substantially purified, P-TEFb proteins, subunits and peptides. The term "purified P-TEFb protein, subunit or peptide" as used herein, is intended to refer to a P-TEFb proteinaceous composition, isolatable from insect, mammalian, human or recombinant host cells, wherein the P-TEFb protein, subunit or peptide is prepared at levels that could not be previously obtained prior to the cloning of the P-TEFb subunit genes. A purified P-TEFb protein, subunit or peptide therefore also refers to a P-TEFb protein, subunit or peptide free from the environment in which it naturally occurs.

P-TEFb proteins may be full length proteins comprising either a small subunit or large subunit, such as being 404 (SEQ ID NO:2), 1113 (SEQ ID NO:4), 696 (SEQ ID NO:45), 729 (SEQ ID NO:47) or 726 (SEQ ID NO:50) amino acids in length. P-TEFb proteins, polypeptides and peptides may also be less then full length proteins, such as individual domains, regions or even epitopic peptides. Where less than full length P-TEFb proteins are concerned the most preferred will be those containing predicted immunogenic sites and those containing the functional domains identified herein. Preferred P-TEFb kinase domains or fragments will be those sufficient to phosphorylate RNA polymerase II.

Generally, "purified" will refer to a P-TEFb protein, subunit or peptide composition that has been subjected to fractionation to remove various non-P-TEFb protein, subunit or peptide components, and which composition substantially retains its P-TEFb activity, as may be assessed by phosphorylation of RNA polymerase II and inhibition by DRB.

Where the term "substantially purified" is used, this will refer to a composition in which the P-TEFb protein, subunit or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A polypeptide or protein that is "purified to homogeneity," as applied to the present invention, means that the polypeptide or protein has a level of purity where the polypeptide or protein is substantially free from other proteins and biological components. For example, a purified polypeptide or protein will often be sufficiently free of other protein components so that degradative sequencing may be performed successfully.

Various methods for quantifying the degree of purification of P-TEFb proteins, subunits or peptides will be known to those of skill in the art in light of the present disclosure. These include, for example, determining the specific ability to phosphorylate RNA polymerase II of a fraction, or assessing the number of polypeptides within a fraction by gel electrophoresis.

To purify a P-TEFb protein, subunit or peptide a natural or recombinant composition comprising at least some P-TEFb proteins, subunits or peptides will be subjected to fractionation to remove various non-P-TEFb components from the composition. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

A specific example presented herein is the purification of a P-TEFb fusion protein using a specific binding partner.

Such purification methods are routine in the art. As the present invention provides DNA sequences for P-TEFb proteins, any fusion protein purification method can now be practiced. This is currently exemplified by the generation of a P-TEFb-glutathione S-transferase fusion protein, expression in E. coli, and isolation to homogeneity using affinity chromatography on glutathione-agarose.

The exemplary purification method of fractionation via column chromatography, using a series of chromatography columns, such as phosphocellulose (P-11), DEAE cellulose, Phenyl Sepharose™, hydroxylapatite, Mono Q™, Mono S™ and the like, as disclosed herein represents one method to prepare a substantially purified P-TEFb protein, subunit or peptide. This method is preferred as it results in the substantial purification of the P-TEFb protein, subunit or peptide in yields sufficient for further characterization and use. However, given the DNA and proteins provided by the present invention, any purification method can now be employed.

Although preferred for use in certain embodiments, there is no general requirement that the P-TEFb protein, subunit or peptide always be provided in their most purified state. Indeed, it is contemplated that less substantially purified P-TEFb proteins, subunits or peptides, which are nonetheless enriched in P-TEFb compositions, relative to the natural state, will have utility in certain embodiments. These include, for example, phosphorylating RNA polymerase II, as may be used to examine RNA elongation; and antibody generation where subsequent inhibitor screening assays using purified P-TEFb are conducted.

Methods exhibiting a lower degree of relative purification may have advantages in total recovery of protein product, or in maintaining the activity of an expressed protein. Inactive products also have utility in certain embodiments, such as, e.g., in antibody generation.

IV. P-TEFb Antibodies and Immunological Reagents

A. Epitopic Core Sequences

Peptides corresponding to one or more antigenic determinants, or "epitopic core regions", of P-TEFb proteins or subunits of the present invention can also be prepared. Such peptides should generally be at least 7 or 8 amino acid residues in length, will preferably be about 10, 15, 20, 25 or about 30 amino acid residues in length, and may contain up to about 35–50 residues or so.

Synthetic peptides will generally be about, or less than about, 35–36 residues long, which is the approximate upper length limit of automated peptide synthesis machines, such as those available from Applied Biosystems (Foster City, Calif.). Longer peptides may also be prepared, e.g., by recombinant means.

U.S. Pat. No. 4,554,101, (Hopp) incorporated herein by reference, teaches the identification and preparation of epitopes from primary amino acid sequences on the basis of hydrophilicity. Through the methods disclosed in Hopp, one of skill in the art would be able to identify epitopes from within an amino acid sequence such as the P-TEFb sequence disclosed herein (SEQ ID NO:2; SEQ ID NO:4; SEQ ID NO:45, SEQ ID NO:47 or SEQ ID NO:50).

Numerous scientific publications have also been devoted to the prediction of secondary structure, and to the identification of epitopes, from analyses of amino acid sequences (Chou and Fasman, 1974a,b; 1978a,b, 1979). Any of these may be used, if desired, to supplement the teachings of Hopp in U.S. Pat. No. 4,554,101.

Moreover, computer programs are currently available to assist with predicting antigenic portions and eptiopic core regions of proteins. Examples include those programs based upon the Jameson-Wolf analysis (Jameson and Wolf, 1998; Wolf et al., 1988), the program PepPlot® (Brutlag et al., 1990; Weinberger et al., 1985), and other new programs for protein tertiary structure prediction (Fetrow and Bryant, 1993). Further commercially available software capable of carrying out such analyses is termed MacVector® (IBI, New Haven, Conn.).

In further embodiments, major antigenic determinants of a polypeptide may be identified by an empirical approach in which portions of the gene encoding the polypeptide are expressed in a recombinant host, and the resulting proteins tested for their ability to elicit an immune response. For example, PCR™ can be used to prepare a range of peptides lacking successively longer fragments of the C-terminus of the protein. The immunoactivity of each of these peptides is determined to identify those fragments or domains of the polypeptide that are immunodominant. Further studies in which only a small number of amino acids are removed at each iteration then allows the location of the antigenic determinants of the polypeptide to be more precisely determined.

Once one or more such analyses are completed, polypeptides are prepared that contain at least the essential features of one or more antigenic determinants. The peptides are then employed in the generation of antisera against the polypeptide. Minigenes or gene fusions encoding these determinants can also be constructed and inserted into expression vectors by standard methods, for example, using PCR™ cloning methodology.

The use of such small peptides for vaccination typically requires conjugation of the peptide to an immunogenic carrier protein, such as hepatitis B surface antigen, keyhole limpet hemocyanin or bovine serum albumin. Methods for performing this conjugation are well known in the art.

B. Antibody Generation

In certain embodiments, the present invention provides antibodies that bind with high specificity to P-TEFb, and other antibodies that bind to the protein products of the isolated nucleic acid sequences of SEQ ID NO:1, SEQ ID NO:3 SEQ ID NO:43, SEQ ID NO:46 or SEQ ID NO:48. Antibodies specific for the wild type proteins and peptides and those specific for any one of a number of mutants are provided. As detailed above, in addition to antibodies generated against the full length proteins, antibodies may also be generated in response to smaller constructs comprising epitopic core regions, including wild type and mutant epitopes.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Monoclonal antibodies (MAbs) are recognized to have certain advantages, e.g., reproducibility and large-scale production, and their use is generally preferred. The invention thus provides Mabs of the human, murine, monkey, rat, hamster, rabbit and even chicken origin. Due to the ease of preparation and ready availability of reagents, murine Mabs will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's tumor are likewise known and such custom-tailored antibodies are also contemplated.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are well known in the art (See, e.g., Antibodies: A Laboratory Manual, Cold Spring Harbor Laboratory, 1988; incorporated herein by reference).

The methods for generating Mabs generally begin along the same lines as those for preparing polyclonal antibodies. Briefly, a polyclonal antibody is prepared by immunizing an animal with an immunogenic P-TEFb composition in accordance with the present invention and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL-4, IL-7, IL-12, g-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppresser cell activity. Such BRMs include, but are not limited to, Cimetidine (CIM; 1200 mg/d) (Smith/Kline, Pa.); or low-dose Cyclophosphamide (CYP; 300 mg/m$^2$) (Johnson/Mead, N.J.) and Cytokines such as g-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified P-TEFb protein, polypeptide, peptide or domain, be it a wild type or mutant composition. The immunizing composition is administered in a manner effective to stimulate antibody producing cells.

The methods for generating MAbs generally begin along the same lines as those for preparing polyclonal antibodies. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the Mabs of the invention can be obtained from the Mabs so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in E. coli.

C. Antibody Conjugates

The present invention further provides anti-P-TEFb antibodies, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as may be termed "immunotoxins". In the context of the present invention, immunotoxins are generally less preferred.

Antibody conjugates are thus preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging". Again, antibody-directed imaging is less preferred for use with this invention.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$Iodine is often being preferred for use in certain embodiments, and technicium$^{99m}$ and indium$^{111}$ are also often preferred due to their low energy and suitability for long range detection.

Radioactively labeled Mabs of the present invention may be produced according to well-known methods in the art. For instance, Mabs can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$m by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as SNCl$_2$, a buffer solution such as sodium-potassium phthalate solution, and the antibody.

Intermediary functional groups which are often used to bind radioisotopes which exist as metallic ions to antibody are diethylenetriaminepentaacetic acid (DTPA) and ethylene diaminetetracetic acid (EDTA). Fluorescent labels include rhodamine, fluorescein isothiocyanate and renographin.

The much preferred antibody conjugates of the present invention are those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939, 350; 3,996,345; 4,277,437; 4,275,149 and 4,366,241; each incorporated herein by reference.

D. Immunodetection Methods and Kits

In still further embodiments, the present invention concerns immunodetection methods for binding, purifying, removing, quantifying or otherwise generally detecting biological components, such as HIV Tat, that interact with P-TEFb. The binding assays will often be used as a pre-screen to identify agents that inhibit productive RNA elongation, and especially to identify agents that inhibit viral-mediated RNA elongation by disrupting the interaction of viral transactivating proteins, such as Tat, that need to interact with P-TEFb in order to exert their effect on the host cell RNA polymerase II. Subsequent to the identification of components that inhibit the binding of a viral protein to P-TEFb in an immunodetection assay, the compounds will generally be further examined in RNA elongation activity assays to confirm their suitability.

Immunodetection methods may also be employed to identify novel proteins or protein domains that bind to P-TEFb, and/or to identify a new property of a known protein, allowing the definition of that protein as a P-TEFb-binding protein. In any event, the identification of an additional viral protein that binds to P-TEFb will allow the identified protein to become the target of new anti-viral strategies. The first step of such anti-viral approaches will, again, often be based upon a binding assay in which potential anti-viral compounds are tested for their ability to inhibit the binding of the newly discovered protein to P-TEFb.

Accordingly, in the following description of binding assays, the term "viral transactivating protein" is used to refer to any known or discovered viral transactivating protein or domain that binds to P-TEFb and, most preferably, that binds to human P-TEFb. Examples of viral transactivating proteins that are herein discovered to bind to P-TEFb are HIV Tat and VP 16 from herpes virus. E1A from adenovirus is also contemplated to be an appropriate target for use in such a binding assay. Naturally, where the intent of the assay is to identify viral proteins that bind to P-TEFb, the "viral transactivating protein" will more properly be termed a "viral composition comprising a candidate transactivating protein", which is generally exemplified by extracts comprising viral proteins produced during host cell infection.

Antibodies and labeled antibodies against the P-TEFb proteins, subunits or peptides of the present invention may also be employed to purify P-TEFb, as may be used in purification from insect, mammalian or human sources, including recombinant host cells, via immunoaffinity protocols, such as immunoaffinity chromatography. In the purification methods, the antibody removes or purifies the antigenic P-TEFb component from a sample. The antibody will preferably be linked to a solid support, such as in the form of a column matrix, and the sample suspected of containing the P-TEFb antigenic component will be applied to the immobilized antibody. The unwanted components will be washed from the column, leaving the antigen immunocomplexed to the immobilized antibody, which P-TEFb antigen is then collected by removing the P-TEFb from the column.

Antibodies and labeled antibodies against the P-TEFb proteins, subunits or peptides of the invention may even further be employed to detect P-TEFb in samples, including recombinant host cells and clinical samples. Such antibodies may ultimately be employed in diagnostic embodiments to detect increased or decreased levels of P-TEFb or to detect mutant P-TEFb proteins, subunits or peptides in human tissue or fluid samples. As P-TEFb is centrally important to RNA elongation, disturbances in P-TEFb levels or types are likely to be implicated in diseases, such as cancer, in which gene expression is perturbed. Therefore, the use of wild type- and mutant-specific antibodies is contemplated. However, these embodiments also have applications to non-clinical samples, such as in the titering of antigen or antibody samples, in the selection of hybridomas, and the like.

Accordingly, detection of P-TEFb alone is another important aspect of the invention. In general, simple P-TEFb immunobinding methods include obtaining a sample suspected of containing a P-TEFb protein, subunit, peptide, or mutant thereof, and contacting the sample with a first anti-P-TEFb antibody or anti-mutant P-TEFb antibody in accordance with the present invention, under conditions effective to allow the formation of immunocomplexes, and then detecting the immunocomplexes so formed.

In the clinical diagnosis or monitoring of patients with diseases such as cancer, the detection of a P-TEFb mutant, or an alteration in the levels of P-TEFb, in comparison to the levels in a corresponding biological sample from a normal subject will be indicative of a patient with the disease or cancer. However, as is known to those of skill in the art, such a clinical diagnosis would not necessarily be made on the basis of this method in isolation. Those of skill in the art are very familiar with differentiating between significant differences in types or amounts of biomarkers, which represent a positive identification, and low level or background changes of biomarkers. Indeed, background expression levels are often used to form a "cut-off" above which increased detection will be scored as significant or positive.

The P-TEFb-viral protein immunobinding methods of the present invention generally include obtaining a sample suspected of containing a viral transactivating protein, domain, subunit or active peptide, and contacting the sample with a first P-TEFb composition, complex, protein, subunit, domain or binding peptide, in accordance with the present invention, under conditions effective to allow the formation of bound protein complexes, and then detecting the bound protein complexes so formed. The detection of the "bound protein complexes", in the manner described herein, is highly analogous to the techniques of immunocomplex detection, even in embodiments where either the viral transactivating protein or the P-TEFb protein are directly labeled, and all such technology regarding immobilization, specific binding, non-specific binding and washing is applicable.

The steps of various useful immunodetection methods have been described in the scientific literature, such as, e.g., Nakamura et al. (1987), incorporated herein by reference. In terms of detecting or quantifying the amount of viral transactivating proteins, i.e., P-TEFb reactive components in a sample, the methods require the detection or quantification of any bound protein or immune complexes formed during the binding process. Here, one would obtain a sample known or suspected to contain a viral transactivating protein and contact the sample with a P-TEFb protein, subunit or peptide, and then detect or quantify the amount of bound protein complexes formed under the specific conditions.

Contacting the chosen viral transactivating sample with the P-TEFb sample will be effected under conditions effective and for a period of time sufficient to allow the formation of bound protein complexes (primary complexes), which is generally a matter of simply adding the two compositions or samples and incubating the mixture for a period of time long enough for any viral transactivating proteins and P-TEFb proteins present to form bound protein complexes. After this time, the potentially bound protein complexes, as may be present on an ELISA plate, dot blot or such like, will generally be washed to remove any non-specifically bound protein species, allowing only those species specifically bound within the primary complexes to be detected.

In general, the detection of bound protein complexes is analogous to the detection of immunocomplexes, and is well known to those of skill in the art. Detection may be achieved through the application of numerous approaches. These methods are generally based upon the detection of a label or marker, such as any of those radioactive, fluorescent, biological or enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference.

Preferably, in detection, one would find additional advantages through the use of an antibody, or other secondary binding ligand, such as a second biotin/avidin ligand binding arrangement, as is known in the art. The antibody employed in the detection may be an anti-P-TEFb antibody or an anti-viral protein antibody, such as an anti-HIV Tat antibody. Such antibodies would be termed "primary antibodies". The primary antibodies may themselves be linked to a detectable label, wherein one would then simply detect this label, thereby allowing the amount of the bound protein complexes in the composition to be determined.

Alternatively, the first anti-P-TEFb antibody or anti-viral protein antibody (such as anti-HIV Tat) that becomes bound within the protein complexes may be detected by means of a second binding ligand that has binding affinity for the first antibody. In these cases, the second binding ligand may be linked to a detectable label. The second binding ligand is itself often an antibody, which may thus be termed a "secondary" antibody. The primary bound protein-antibody complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected. Further methods including the use of tertiary binding ligands or antibodies linked to a detectable labels are also contemplated, particularly where signal amplification is desired.

1. ELISAs

As detailed above, immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, either P-TEFb or a viral transactivating protein, such as HIV Tat, is immobilized onto a selected surface exhibiting protein affinity, such as a well in a polystyrene microtiter plate. Then, a composition containing the counterpart viral transactivating protein, or P-TEFb, is added to the wells. After binding and washing to remove non-specifically bound complexes, the bound P-TEFb-viral protein complex may be detected. Detection is generally achieved by the addition of an anti-P-TEFb or anti-viral protein antibody that is linked to a detectable label. Detection may also be achieved by the addition of a first anti-P-TEFb or anti-viral protein antibody, followed by a second antibody that has binding affinity for the first antibody, with the second antibody being linked to a detectable label.

Irrespective of the format employed, ELISAs have certain features in common, such as coating, incubating or binding, washing to remove non-specifically bound species, and detecting the bound immune complexes. These are described as follows:

In coating a plate with either P-TEFb or a viral transactivating protein, such as Tat, VP 16 or E1A, one will generally incubate the wells of the plate with a solution of the agent, either overnight or for a specified period of hours. The wells of the plate will then be washed to remove incompletely adsorbed material. Any remaining available surfaces of the wells are then "coated" with a nonspecific protein that is neutral with regard to binding to the biological components. These include bovine serum albumin (BSA), casein and solutions of milk powder. The coating allows for blocking of nonspecific adsorption sites on the immobilizing surface and thus reduces the background caused by nonspecific binding of proteins onto the surface.

In the ELISAs of the present invention it will probably be more customary to use a secondary or tertiary detection means rather than a direct procedure using a labeled P-TEFb or a viral transactivating protein. Thus, after binding of the first protein to the well, coating with a non-reactive material to reduce background, and washing to remove unbound material, the immobilizing surface is contacted with the second biological protein under conditions effective to allow protein complex formation. Detection of the complex then requires a labeled binding ligand or antibody.

"Under conditions effective to allow protein complex formation" means that the conditions preferably include diluting the P-TEFb and viral transactivating proteins, with solutions such as BSA, bovine gamma globulin (BGG) and phosphate buffered saline (PBS)/Tween. These added agents also tend to assist in the reduction of nonspecific background. The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific complexes between the test sample and the originally bound material, and subsequent washing, the occurrence of even minute amounts of bound complexes may be determined.

To provide for detection, a first or second antibody will preferably be provided that has an associated label to allow detection. However, given that the present invention provides highly purified P-TEFb components, and as viral transactivating proteins, such as HIV Tat, are readily available, the P-TEFb or viral protein may also be directly labeled.

Preferably, the label will be an enzyme that will generate color development upon incubating with an appropriate chromogenic substrate. Thus, for example, one will desire to contact and incubate the bound complexes with a urease, glucose oxidase, alkaline phosphatase or hydrogen peroxidase-conjugated antibody for a period of time and under conditions that favor the development of immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

In still further embodiments, the present invention concerns immunodetection kits for use with the immunodetection methods described above. P-TEFb, a viral transactivating protein and, preferably, a labeled antibody to at least one of such components will most generally be included in the kit. However, kits including less than or more than the foregoing components may also be provided. In preferred embodiments of the methods and kits, the antibodies used will be monoclonal antibodies (MAbs).

The immunodetection kits will comprise all the supplied components in suitable container means. In certain embodiments, the kits may comprise a P-TEFb or a viral transactivating protein, that is pre-bound to a solid support, such as a column matrix or well of a microtitre plate.

The immunodetection reagents of the kit may take any one of a variety of forms, including those detectable labels that are associated with or linked to the given P-TEFb or viral transactivating protein. Detectable labels that are associated with or attached to a secondary binding ligands or antibody are generally preferred. As noted above, a number of exemplary labels are known in the art and all such labels may be employed in connection with the present invention.

The kits may further comprise suitably aliquoted compositions of a P-TEFb protein or polypeptide or a viral transactivating protein, whether labeled or unlabeled, as may be used to prepare a standard curve for a detection assay. The kits may also contain protein- or antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the P-TEFb or viral transactivating protein, and other optional components, may be placed, and preferably, suitably aliquoted. Where second and third additional binding components are provided, the kit will also generally contain a second, third or other additional container into which such components may be placed. The kits of the present invention will also typically include a means for containing the reagent containers in close confinement for commercial sale. Such containers may include injection or blow-molded plastic containers into which the desired vials are retained.

V. Biological Functional Equivalents

As will be understood by those of skill in the art, modification and changes may be made in the structure of the P-TEFb kinase and large subunits and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on molecules such as Tat and RNA polymerase II. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated by the inventor that various changes may be made in the sequence of P-TEFb proteins or peptides (or underlying DNA) without appreciable loss of their biological utility or activity.

Equally, the same considerations may be employed to create a P-TEFb protein or peptide with countervailing (e.g., antagonistic) properties. This is relevant to the present invention in which P-TEFb analogues without Tat binding activity are contemplated to be useful in inhibiting the ability of the HIV virus to promote viral RNA elongation by way of inhibiting Tat binding to P-TEFb.

In terms of functional equivalents, it is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where small peptides are concerned, less amino acids may be changed. Of course, a plurality of distinct proteins/peptides with different substitutions may easily be made and used in accordance with the invention.

It is also well understood that where certain residues are shown to be particularly important to the biological or structural properties of a protein or peptide, e.g., residues in the active site of an enzyme, or in the RNA polymerase II binding region, such residues may not generally be exchanged. This is the case in the present invention, where residues in the active site of the kinase subunit should not generally be changed where it is the intention to maintain kinase function.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within +0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented hereinabove for use in such embodiments, as well as for other uses, such as in the design of probes and primers and the like.

VI. Inhibitors and Screening Assays

In still further embodiments, the present invention provides methods for identifying new P-TEFb inhibitory compounds, which may be termed as "candidate substances." It is contemplated that such screening techniques will prove useful in the general identification of any compound that will serve the purpose of inhibiting P-TEFb, and in preferred embodiments, will provide candidate anti-viral compounds.

It is further contemplated that useful compounds in this regard will in no way be limited to proteinaceous or peptidyl compounds. In fact, it may prove to be the case that the most useful pharmacological compounds for identification through application of the screening assays will be non-peptidyl in nature and, e.g., which will serve to inhibit viral RNA elongation through a tight binding or other chemical interaction. Candidate substances may be obtained from libraries of synthetic chemicals, or from natural samples, such as rain forest and marine samples.

A. Inhibition of P-TEFb Phosphorylation

RNA polymerase II is the natural substrate of the P-TEFb kinase and enzyme complex. Although phosphorylation of the CTD of RNA polymerase II is complicated in cellular terms, using phosphorylation of RNA polymerase II as an assay to identify inhibitors of P-TEFb will be straightforward in light of the methods disclosed herein. The inhibitors initially identified in such assays can be used as general transcription elongation inhibitors, or may be modified to prepare second generation compounds for use as specific viral transcription elongation inhibitors.

General transcription elongation inhibitors will have utility in cellular assays, and are also contemplated for therapeutic uses. For example, the ability to generally inhibit transcription elongation is envisioned to be useful in controlling excessive gene transcription/translation and cellular proliferation, as may be used to treat cancer and other diseases associated with aberrant gene expression and/or cellular reproduction and proliferation. It is well understood in the art that many anti-cancer therapeutics, as well as anti-viral therapeutics, can exert certain effects in normal cell types, but such potential side-effects do not generally limit the therapeutic utility of such drugs. Further, the impact of any possible adverse effects can be limited or otherwise controlled by the more specific administration of the inhibitory agent to a disease localized site or area of the body, such as by direct application to a tumor.

To identify a P-TEFb kinase inhibitor and potential transcription elongation inhibitor using a P-TEFb RNA polymerase II phosphorylation assay, one would simply conduct parallel or otherwise comparatively controlled phosphorylation assays and identify a compound that inhibits phosphorylation. The candidate screening assay is quite simple to set up and perform. Thus, after obtaining a relatively purified preparation of the kinase or intact P-TEFb enzyme, either from native or recombinant sources, and either from *Drosophila* or human sources, one will simply admix a candidate substance with the kinase preparation, under conditions that would allow the enzyme to perform its P-TEFb function but for inclusion of an inhibitory substance.

For example, one will typically desire to include within the admixture an amount of a RNA polymerase II, although other phosphate acceptors may be used, such as phosphorable peptides. Potential effectors, such as an HIV Tat protein, may also be included in the assay. In any event, one would measure the ability of the candidate substance to reduce phosphorylation of the RNA polymerase II or phosphate acceptor substrate relatively in the presence of the candidate substance. In general, one will desire to measure or otherwise determine the activity of the relatively purified enzyme in the absence of the added candidate substance relative to the activity in the presence of the candidate substance in order to assess the relative inhibitory capability of the candidate substance.

In terms of optimizing phosphorylation-based inhibitor assays, one should consider the following scientific observations. Each phosphorylation site is unique and may be influenced by phosphorylation of other sites. It is possible to saturate the assay with kinase such that even in the presence of inhibitors, all large subunit molecules are completely shifted to the IIo form. In addition, the exact relationship of the mobility of the large subunit to the number of phosphates added is not known. The levels of phosphorylation required for function during transcription should be determined and the effect that other factors might have on the kinase action in the elongation complex should also be considered.

Therefore, the best correlation between kinase activity and function during transcription can be made by comparing the effects of two inhibitors under the same set of conditions. This does not pose a problem for conducting the P-TEFb phosphorylation-based inhibitor assays of the invention as DRB, and even H-8, are provided as known kinase inhibitors that also inhibit productive transcription elongation. Accordingly, in performing a P-TEFb phosphorylation-based inhibitor assay, one may advantageously compare the effect of a candidate inhibitor with the effect of DRB, or even H-8, under the same set of conditions.

Prior to the present invention, there was continued confusion in the literature concerning the target for the action of the kinase inhibitor, DRB. DRB inhibits the CTD kinase activity of *Drosophila* P-TEFb and its ability to phosphorylate the CTD in EECs. The inventor has shown that under identical conditions the CTD kinase activity of P-TEFb is inhibited by DRB while that of TFIIH is unaffected by the drug. Yankulov et. al. (1996) proposed that the effect of DRB on transcription was due to inhibition of the kinase activity of TFIIH (Yankulov et al., 1995). The Yankulov conclusions were based on the observations that DRB inhibited the TFIIH kinase and the appearance of runoff transcripts during transcription with similar dose-response curves. The Yankulov kinase and transcription assays were performed under conditions that did not allow a valid comparison of inhibition curves to be made. Although recent studies strongly implicate TFIIH in elongation control (Yankulov et al., 1996), results with the *Drosophila* system indicate that TFIIH cannot substitute for the role of P-TEFb in controlling elongation.

The DRB-sensitive process whereby RNA polymerase II escapes abortive elongation and enters a productive mode of elongation is important in controlling transcription. The drugs DRB or H-8 inhibit the transition into productive elongation as well as the CTD kinase activity of P-TEFb. In addition, the present invention discloses that pure P-TEFb can phosphorylate the CTD of RNA polymerase II in early elongation complexes. Post-initiation phosphorylation of the CTD by P-TEFb controls the transition into productive elongation. P-TEFb may remain associated with the complex or it may be released, but the complex is DRB resistant after that point (Kephart et al., 1992).

The present invention further discloses that the concentration of ATP used in phosphorylation assays has a direct effect on the concentration of inhibitor required to achieve 50% inhibition. This should be considered in conducting phosphorylation assays, and in correlating kinase assays, which generally use low ATP concentrations with transcription assays, which have higher levels of all NTPs. Those of ordinary skill in the art will understand that the concentrations of the polymerase and kinase, the time of the reactions and other assay conditions, should be carefully monitored in analyzing the influence of potential inhibitors.

B. Inhibition of P-TEFb-Viral Protein Binding

Potential viral transcription elongation inhibitors can also be identified by conducting a P-TEFb-viral protein binding assay, such as any of the assays described herein. To identify a potential viral transcription elongation inhibitor using a P-TEFb-viral protein binding assay also simply only requires one to conduct parallel or otherwise comparatively controlled binding assays and to identify a compound that inhibits P-TEFb-viral protein binding.

Such candidate inhibitor screening assays are also simple to set up and perform. One will simply admix a candidate substance with the P-TEFb and viral protein combination, under conditions that would normally allow the P-TEFb and viral proteins to bind but for inclusion of an inhibitory substance. One measures the ability of the candidate substance to reduce binding of the P-TEFb and viral proteins relatively in the presence of the candidate substance. In general, one again measures or otherwise determines, e.g., from a known standard curve, the binding of the same amount of the proteins in the absence of the added candidate substance relative to the binding in the presence of the candidate substance in order to assess the relative inhibitory capability of the candidate substance.

C. Inhibition of P-TEFb-Viral-Mediated Transcription Elongation

The invention next provides methods for assaying for, or for confirming the identification of, candidate viral transcription inhibitors, based upon the use of viral transcription elongation assays. To identify a viral transcription elongation inhibitor in this manner, one would again conduct parallel or otherwise comparatively controlled transcription elongation assays and identify a compound that inhibits transcription elongation, and preferably, that inhibits transcription elongation of viral transcripts and not human transcripts.

In these assays, one would admix a candidate substance with a transcriptionally competent composition under conditions that would normally result in the generation of elongated human and viral RNA transcripts but for inclusion of an inhibitory substance. One would then identify a positive inhibitory substance as one that prevented or significantly reduced the generation of elongated RNA transcripts upon addition to the assay system. Most preferably, one would identify a positive anti-viral inhibitory substance as one that prevented or significantly reduced the generation of elongated viral RNA transcripts, but that did not prevent or significantly reduce the generation of elongated human RNA transcripts, upon addition to the assay system.

Assays of this type are described herein and are generally performed using effective amounts of human and viral nucleic acid templates, viral transcriptional transactivator proteins, P-TEFb enzyme complex, RNA polymerase II, each four nucleotides, which of course, includes ATP that provides the energy. Preferably, other partially purified nuclear components are included in the assay, as disclosed herein in the Detailed Examples. The productive viral RNA elongation is measured relatively in the presence of the candidate substance, generally after establishing the basal levels of productive viral RNA elongation in the absence of the candidate substance. In this manner, one can assess the relative inhibitory capability of the candidate substance.

D. Second Generation Inhibitors

In addition to the inhibitory compounds initially identified, the inventor also contemplates that other sterically similar compounds may be formulated to mimic the key portions of the structure of the inhibitors. Such compounds, which may include peptidomimetics of peptide inhibitors, may be used in the same manner as the initial inhibitors.

Certain mimetics that mimic elements of protein secondary structure are designed using the rationale that the peptide backbone of proteins exists chiefly to orientate amino acid side chains in such a way as to facilitate molecular interactions. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of computer-based chemical modeling is now well known. Using such methods, a chemical that specifically inhibits viral transcription elongation can be designed, and then synthesized, following the initial identification of a compound that inhibits RNA elongation, but that is not specific or sufficiently specific to inhibit viral RNA elongation in preference to human RNA elongation. It will be understood that all such sterically similar constructs and second generation molecules fall within the scope of the present invention.

E. Methods of Inhibiting P-TEFb

In still further embodiments, the present invention is concerned with methods of inhibiting productive RNA elongation, and preferably, with preferentially inhibiting productive viral RNA elongation. These methods generally comprise exposing an RNA elongation complex to an effective concentration of a P-TEFb or elongation inhibitor identified in accordance with the candidate screening assay embodiments of the present invention. Where productive viral RNA elongation is to be inhibited, the RNA elongation complex is a complex that comprises viral nucleic acids and transcriptional transactivator proteins, which complex is often located within a virally infected cell.

This aspect of the invention is intended for use in inhibiting the P-TEFb-mediated viral transcription that occurs in various retroviral and other viral infections, such as HIV and HSV infections, and even in adenoviral infections. It is contemplated that the use of such inhibitors to block the transactivating functions of the Tat protein in infected cells of patients suffering with AIDS or HIV-infected states will be useful in itself and/or in conjunction with other anti-viral therapies. Inhibitors designed from dual viral inhibition assay will be particularly useful in the treatment of AIDS because the normal cellular function of P-TEFb should not be influenced.

It is also contemplated that P-TEFb will be involved in controlling cellular proliferation. A number of oncogenes are controlled at the elongation phase of transcription and P-TEFb is a key player in this control. The small subunit of human P-TEFb has been localized to a region of a human chromosome that contains a gene involved in cancer. The inventor has also found that P-TEFb levels correlate with the growth rate of cells. Mutations in either subunit of P-TEFb could have profound effects on the cellular proliferation. Gene therapy is therefore contemplated for treatment of conditions that result from P-TEFb mutations. Drugs that affect the cellular function of P-TEFb are contemplated in the treatment of certain types of cancer, irrespective of their specificity for inhibiting certain transcript formation.

VII. Pharmaceutical Compositions

A. Pharmaceutically Acceptable Carriers Aqueous compositions of the present invention comprise an effective amount of one or more of the inhibitors of the invention dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes.

The preparation of an aqueous composition that contains an RNA elongation transcription inhibitor agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the inhibitory compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An inhibitor or antagonist of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifingal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active inhibitory compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In terms of using peptide inhibitors as active ingredients, the technology of U.S. Pat. Nos. 4,608,251; 4,601,903; 4,599,231; 4,599,230; 4,596,792; and 4,578,770, each incorporated herein by reference, may be used. The preparation of more, or highly, concentrated solutions for direct injection is also contemplated, where the use of DMSO as solvent is envisioned to result in extremely rapid penetration, delivering high concentrations of the active agents to a small body area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active inhibitors or agents may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

Additional formulations which are suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

It will naturally be understood that suppositories, for example, will not generally be contemplated for use in treating all viral infections. However, in the event that the inhibitors of the invention, or those identified by the screening methods of the present invention, are confirmed as being useful in connection with a particular viral infection of a given tissue or organ, then other routes of administration and pharmaceutical compositions will be more relevant. As such, inhalants, tablets, opthalmic solutions and other formulations will be appropriate.

B. Liposomes and Nanocapsules

In certain embodiments, the use of liposomes and/or nanoparticles is contemplated for the introduction of the inhibitors of the invention into host cells. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

C. Kits

Therapeutic kits of the present invention are kits comprising an inhibitor of RNA or viral RNA productive RNA elongation. Such kits will generally contain, in suitable container means, a pharmaceutically acceptable formulation of an inhibitor, or even a gene expressing an inhibitor of a xenobiotic activator of productive RNA elongation in a pharmaceutically acceptable formulation, optionally comprising other anti-viral agents. The kit may have a single container means, or it may have distinct container means for each compound.

When the components of the kit are provided in one or more liquid solutions, the liquid solution is an aqueous solution, with a sterile aqueous solution being particularly preferred. The inhibitors of viral and other xenobiotic activators of productive RNA elongation compositions may also be formulated into a syringeable composition. In which case, the container means may itself be a syringe, pipette, or other such like apparatus, from which the formulation may be applied to an infected area of the body, injected into an animal, or even applied to and mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the inhibitor of viral and other xenobiotic activators of productive RNA elongation are placed, preferably, suitably allocated. Where a second anti-viral therapeutic is provided, the kit will also generally contain a second vial or other container into which this agent may be placed. The kits may also comprise a second/third container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained.

Irrespective of the number or type of containers, the kits of the invention may also comprise, or be packaged with, an instrument for assisting with the injection/administration or placement of the ultimate inhibitor composition within the body of an animal. Such an instrument may be a syringe, pipette, forceps, or any such medically approved delivery vehicle.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Purification of P-TEFb, the Limiting Factor in RNA Elongation

The reconstruction of DRB-sensitive transcription involves three chromatographically distinct protein fractions, P-TEFa and P-TEFb and factor 2. The present example shows the purification of P-TEFb to near homogeneity and demonstrates that P-TEFb is the only factor strictly required for the transition into productive elongation using an accepted partially fractionated transcription system.

A. Materials and Methods:

1. Materials

[$\alpha$-$^{32}$P]CTP (3000 Ci/mmol) was obtained from ICN (Irvine, Calif.). Ribonucleoside triphosphates were obtained from Pharmacia-LKB Biotechnology (Piscataway, N.J.). DRB (Sigma, St. Louis, Mo.) was dissolved in ethanol to 20 mM and stored at −80° C. Phosphocellulose (P-11) and DEAE cellulose (DE-52) were obtained from Whatman (Hillsboro, Oreg.) and prepared according to Price et al. (1987). Phenyl Sepharose (Pharmacia) was prepared according to manufacturer's instructions. All other chemicals were reagent grade.

2. Chromatography Methods and Initial Fractionation

All chromatography was carried out at 2–4° C. The conductivity of extracts and column fractions were determined with a conductivity meter. A standard curve of conductivity versus mM KCl in HGKEDP (25 mM HEPES, 15% glycerol, indicated concentration of KCl, 0.1 mM EDTA, 1 mM DTT, 0.1% of a saturated solution of phenylmethylsulfonyl fluoride in isopropanol) was used to convert the conductivity measurements into KCl concentration equivalents. Phosphocellulose was obtained from Whatman and was prepared according to the manufacturer's instructions except that the volumes of base and acid washes were reduced from 25 volumes of resin to 5 volumes. Before the resin was stored the KCl concentration was adjusted to 100 mM and the pH was adjusted to 7.6 as measured by a pH meter.

All columns were run in HGKEDP. The $K_c$ cell extract (100 ml at 50 mg/ml protein, see Example 3, Methods, Section A.4 for the preparation of $K_c$ cell extracts) was loaded onto a 500 ml phosphocellulose column at 0.25 column volumes per h. After washing the column with 2 column volumes of 100 mM HGKEDP the column was eluted successively with two column volumes each of HGKEDP containing 0.3, 0.4 and 0.75 M HGKEDP. The 0.1 M HGKEDP phosphocellulose flowthrough was brought to 0.3 M and passed through DEAE-cellulose to remove the majority of nucleic acid content before further fractionation.

The DEAE flowthrough was loaded onto an 8 ml FPLC Mono Q™ column (Pharmacia) and the proteins were eluted with a 20 column volume gradient from 0.1 to 0.5 M HGKEDP.

The DNase inhibitor, an activity necessary for in vitro transcription (Biochimie 69:1199–1205, 1987), eluted between 0.29 and 0.31 M HGKEDP and P-TEFa eluted between 0.35 and 0.4 M HGKEDP. The 0.3 M HGKEDP step from phosphocellulose was dialyzed to 0.1 M HGKEDP and loaded onto a 100 ml DEAE cellulose column. A gradient elution from 0.1 to 0.5 M HGKEDP was performed. TFIIE eluted at 0.12 to 0.15 M HGKEDP, RNA polymerase II at 0.25 to 0.37 HGKEDP, and factor 2 at 0.18 to 0.22 M HGKEDP. The 0.4 M HGKEDP step from phosphocellulose was concentrated using Centricon-30™ centrifugal filter unit concentrators (Millipore Corporation, Billerica, Mass.) and then dialyzed versus 75 mM HGKEDP for 2 h. The 0.75 M HGKEDP step from phosphocellulose was dialyzed to 0.15 M HGKEDP, and passed through a 100 ml DEAE-cellulose column. This DEAE flowthrough was loaded onto an 8 ml FPLC Mono S™ column equilibrated in 0.15 M HGKEDP. The Mono S™ column was subjected to a gradient elution from 0.15 to 0.5 M HGKEDP. P-TEFb eluted between 0.25 and 0.29 M HGKEDP.

3. Purification of P-TEFb

The purification of P-TEFb was carried out twice from 70 to 90 ml of $K_c$N and once from 155 ml of P-11 0.75 M HGKEDP step generated during the fractionation of Drosophila embryonic nuclear extract (obtained from W. Zehring, Wayne State University). Although the exact chromatography steps (described below) differed during the three fractionations, the behavior of the P-TEFb activity from both sources was nearly identical. Two schemes used to purify the P-TEFb used in this work are summarized below.

Scheme 1: P-TEFb was purified from 90 ml of $K_c$N (approximately 3.0 g protein). P-TEFb eluted between 0.55 and 0.65 M HGKEDP during gradient elution of a 500 ml P-11 column from 0.15 M to 1.0 M HGKEDP. P-TEFb containing P-11 fractions (250 ml) were adjusted to 0.5 M HGAEDP (HGKEDP with ammonium (NH4)$_2$SO$_4$ substituted for KCl) followed by loading onto a 26 ml Phenyl Sepharose™ column which was eluted with a gradient from 0.5 M to 0 M HGAEDP. P-TEFb eluted from Phenyl Sepharose™ between 0.12 M and 0 M HGAEDP. P-TEFb containing fractions (23 ml) at 0.06 M HGAEDP (equivalent to 150 mM HGKEDP by conductivity) were pooled and allowed to flow through an 8 ml Mono Q™ equilibrated in 0.15 M HGKEDP directly onto a 1 ml Mono S™ column. The Mono S™ column was then eluted with a gradient from 0.15 M to 0.45 M HGKEDP during which P-TEFb eluted in 2.5 ml (50 mg protein) between 0.25 M and 0.29 M HGKEDP. A 200 µl sample from Mono S™ fraction 30 was loaded onto a 4.25 ml, 18%–35% glycerol gradient with a 500 ml 1M HGKE overlay and centrifuged at 55,000 rpm (287,000 g$_{av}$) in a Beckman SW 55 Ti rotor at 1° C. for 44 h.

Scheme 2: P-TEFb was purified from 155 ml (265 mg protein) of P11 0.4M to 0.75 M step from embryonic nuclear extract. The initial P-11 step fraction was adjusted to 0.75 M HGAEDP before loading onto a 26 ml Phenyl Sepharose™ which was then gradient eluted from 0.5 M to 0 M HGAEDP. P-TEFb activity eluted between 0.12 M and 0 M HGAEDP in 17 ml and was then dialyzed to 175 mM HGKEDP before being passed through a 5.0 ml DE-52 column. The DE-52 flowthrough (19 ml, 3.4 mg protein) was loaded directly onto a 1 ml Mono S™ column which was gradient eluted from 175 mM to 500 mM HGKEDP.

P-TEFb activity eluting between 0.25 M and 0.29 M HGKEDP was dialyzed and loaded onto a 1 ml Mono Q™ column at 50 mM HGKEDP, followed by gradient elution from 50 mM to 450 mM HGKEDP. P-TEFb activity was found in both the column flowthrough and early gradient fractions. Both pools of P-TEFb activity were combined and rechromatographed over a 1 ml Mono S™ column loaded at 75 mM and step eluted at 400 mM HGKEDP. P-TEFb eluted in two 0.2 ml fractions. A 125 μl sample from one 0.2 ml fraction was loaded onto a 5 ml, 15%–35% glycerol gradient and centrifuged at 55,000 rpm (287,000 $g_{av}$) in a Beckman SW 55 Ti rotor at 1° C. for 40.5 h.

4. In Vitro Transcription

Two general types of transcription reactions were performed both using the actin Act5C template (Kephart et al., 1992) linearized with Hpa I. Pulse-chase reactions were generally as described previously (Marshall and Price, 1992) and began with a 10 min preincubation (6 ml/reaction) containing 20 mM HEPES, 5 mM $MgCl_2$, 45–50 mM HGKEDP, 33 mg/ml DNA template and extract or $K_c$-FT (as described in Example 1, Section B.4). Transcription was initiated by the addition of 2 ml of pulse solution which contained 5 mCi [α-$^{32}$P]CTP and brought the reaction to 600 mM in GTP, ATP, and UTP. The true specific activity of the pulse is determined by the contamination of CTP in the other NTPs which the inventor has estimated to be 1 mM. The pulse was continued for 15 seconds after which the reaction was brought to 1.2 mM CTP by the addition of 12 ml of chase solution. The reactions were stopped by the addition of 200 ml of a Sarkosyl solution (1% Sarkosyl, 100 mM NaCl, 100 mM Tris pH 8, 10 mM EDTA and 100 mg/ml tRNA). Sample workup and analysis of labeled transcripts in denaturing gels was as described previously (Price et al., 1987). Briefly, samples were phenol extracted with an equal volume of water saturated phenol. The aqueous phase was precipitated for 10 min at −80° C. after addition of 3 volumes of 95% ethanol containing 3 M ammonium acetate. The samples were spun at 15,000 rpm in a microfuge for 10 min. The supernatant was removed and discarded. The pellet and tube were washed with 200 ul of 70% ethanol and spun at 15,000 rpm for 3 min. The pellet was then dried, under vacuum, before being dissolved in gel loading buffer (0.25× TBE, 8 M urea, with bromophenol blue and xylene cyanol). After heating the samples for 3–5 min at 80° C., they were loaded onto a 6% (or other concentration as desired) polyacrylamide gel cast in 1×TBE, 6 M urea. After running, the gels were soaked in water containing 1 ug/ml ethidium bromide for 15 min before being dried, under vacuum, and exposed to autoradiographic film.

B. Results

1. Requirement of the CTD for Elongation

Transcription reactions to assay P-TEF activity in partially purified fractions were performed using a continuous labeling protocol, basically as described previously (Price et al., 1987). These reactions contained 20 mM HEPES, 5 mM $MgCl_2$, 600 mM each of GTP, ATP and UTP, 30 mM CTP, 55–60 mM KCl, 3–4 mCi [c-$^{32}$P]CTP, 5 mg/ml DNA template, and various protein-containing fractions in a total volume of 12.5 ml. A typical P-TEFb assay contained 0.2 ml of DNase inhibitor (DI), 0.2 ml of RNA Polymerase II, 0.2 ml of dTFIIE, 1.5 ml of concentrated P11-0.4M step fraction, 0.1–0.2 ml of factor 2 and 0.5 ml of P-TEFa. A solution containing buffer, DNA, NTPs and $MgCl_2$ was added last to start the reactions. Reactions were incubated 20 min at 23° C. and stopped as described above.

Using previous work on the chromatography of initiation factors as a guide (Price et al., 1987), the fractionation of $K_c$N and reconstruction of DRB-sensitive transcription was accomplished as described above. Complete reconstruction after the first column using flow through (FT), 0.3 M, 0.4 M and 0.75 M steps gives rise to DRB-sensitive transcription. When these four fractions were subjected to further chromatography, a system that only gave rise to DRB-insensitive transcripts was generated. The reconstruction required four fractions: DNase inhibitor (D.I.), TFIIE, RNA polymerase II and a crude P11-0.4 M step. The P11-0.4 M step fraction includes at least TFIIB and TFIIF and probably TFIID and TFIIH.

2. DRB-Sensitive Transcription Requires Three Protein Fractions

Besides the fractions required for efficient initiation, three additional fractions are required to reconstruct efficient DRB-sensitive transcription. Two of these fractions contain P-TEFa and P-TEFb. The third is an activity previously described as factor 2 (Price et al., 1987). Using partially purified factors, P-TEFb is the only fraction that is essentially required for elongation. P-TEFa and factor 2 both lead to stimulations in the level of runoff transcript. P-TEFb alone was able to support a very low, but detectable level of DRB-sensitive transcription.

3. P-TEFb has Two Subunits

Analysis of the final two stages of the purification, chromatography on Mono S™ and glycerol gradient sedimentation, indicate that P-TEFb activity correlates with fractions containing two polypeptides with apparent molecular weights of 124 and 43 kDa. P-TEFb was purified to near homogeneity three times, twice from $K_c$N and once from *Drosophila* embryonic nuclear extract with nearly identical results. Glycerol gradient analysis of P-TEFb purified using scheme 1 gave nearly identical results. Comparison of the sedimentation of known proteins to that of P-TEFb indicates that the factor is a heterodimer.

4. P-TEFb Acts After Initiation

After purification of P-TEFb a transcription competent nuclear extract depleted of P-TEFb activity was generated. $K_c$N was passed through P-11 at 0.4 M KCl. The resulting $K_c$-FT was capable of initiating transcription as efficiently as whole $K_c$N, but produced only 10% of the DRB-sensitive transcripts (compare $K_c$N with $K_c$-FT alone). Addition of P-TEFb to the $K_c$-FT restored the ability to generate DRB-sensitive runoff transcripts. The level of DRB-sensitive transcription achieved was dependent upon the concentration of P-TEFb added back. Even with the highest levels of P-TEFb added back, the ratio of DRB-sensitive to abortive transcripts remained similar to that seen previously in extract (Marshall and Price, 1992). Importantly, since P-TEFb was added to the reactions during the chase, the factor must have acted after initiation on the early elongation complexes.

P-TEFb is not required for initiation, does not associate strongly with preinitiation complexes (Marshall and Price, 1992) but is shown here to act during elongation. The timing of DRB sensitivity (Marshall and Price, 1992) and P-TEFb action coincide closely. This is consistent with the activity of P-TEFb being inhibited by DRB. Since DRB is canonically a kinase inhibitor, these data suggest that P-TEFb is a cyclin kinase. Likely targets for a transcription factor kinase that acts early during elongation are RNA polymerase II or a basal initiation factor such as TFIIF. The subunit composition of P-TEFb displays no obvious similarity to known kinases involved in transcription regulation.

EXAMPLE 2

Control of RNA Polymerase II Elongation Potential by P-TEFb

A. Material and Methods

1. Materials

[$\alpha$-$^{32}$P]CTP (3000 Ci/mmol) was obtained from ICN. Ribonucleoside triphosphates were obtained from Pharmacia-LKB Biotechnology. DRB (Sigma) was dissolved in ethanol to 10 mM and stored at −80° C. H-8 was obtained from Seikagaku America (Ijamsville, Md.) and was dissolved in 20 mM HEPES, pH 7.6 to 20 mM and stored at 4° C. The magnetic concentrator used was the MPC-E from Dynal. All other chemicals were reagent grade.

2. Proteolysis of RNA Polymerase II

Partially purified RNA polymerase II was treated with 0.27 µg/ml chymotrypsin (Sigma) at 27° C. in HGED (25 mM HEPES pH 7.6, 15% glycerol, 0.1 mM EDTA, 1 mM DTT) plus 110 mM KCl for times ranging from 0 to 20 min. Digestions were terminated by the addition of trypsin inhibitor (Sigma) to 20 µg/ml. The extent of proteolysis of the RNA polymerase II subunits was assayed by SDS-PAGE followed by silver staining.

3. Proteolysis of Early Elongation Complexes

Preinitiation complexes were formed on an immobilized actin template digested with HpaII (780 nt runoff) as described in Marshall and Price (Marshall and Price, 1992). The preinitiation complexes were isolated, washed once with 55 mM HKB (20 mM HEPES, 55 mM KCl and 200 µg/ml BSA) and resuspended into 55 mM HKB. Transcription was initiated by the addition of a pulse solution, which contained 5 µCi of [$\alpha$-$^{32}$P]CTP and brought the reaction mixture to 600 µM in ATP, GTP and UTP and 2 mM MnCl$_2$. MnCl$_2$ increased the rate of initiation of preinitiation complexes, thereby, increasing the number of polymerases in early elongation complexes after a short pulse. After 15 seconds the reaction was stopped by the addition of EDTA to 10 mM.

These early elongation complexes were washed 3 times with 1 M HMKB (20 mM HEPES, 5 mM MgCl$_2$, 1 M KCl and 200 µM BSA) then once with 55 mM HMKB (20 mM HEPES, 5 mM MgCl$_2$, 55 mM KCl and 200 µM BSA). The washed early elongation complexes were resuspended in 55 mM HMKB and incubated with the indicated amount of chymotrypsin for 10 min. Proteolysis was terminated by adding trypsin inhibitor to 0.1 mg/ml. After concentration, digested early elongation complexes were either resuspended into 55 mM HMKB and chased with 600 µM of each NTP for 10 min in the presence or absence of K$_c$ nuclear extract and 0.1 µl P-TEFb, or analyzed by SDS-PAGE followed by immunoblotting with affinity purified RNA polymerase II antibody.

4. Production and Purification of RNA Polymerase II Antibodies

Recombinant GST-rpII1 fusion protein was produced in E. coli using a T7 polymerase-dependent expression system. rpII1 is an amino-terminal portion (Pro117 to Lys 205) of Drosophila RNA polymerase II large subunit. First, a GST coding sequence from pEG(KT) was used to replace the Nde I/Sal I fragment in pET21a to construct a GST-expression plasmid (pET21a-GST). Second, The rpII1 coding sequence was amplified by PCR™ using an upstream primer, 5' ACGAATTCCACACAATCCAAAGATC 3' (SEQ ID NO:7), and a downstream primer, 5' CAGAATTCCTAT-TGCCGATCCCCAGA 3' (SEQ ID NO:8), and subcloned downstream of GST in pET21a-GST. The fusion protein was expressed, purified using a glutathione affinity column according to the Pharmacia protocol, and then used to immunize rabbits (Pocono Rabbit Farm). Antibodies to RNA polymerase II were purified by first passing the crude serum through a GST column and then passing the flowthrough over a GST-rpII1 column. Antibodies were eluted from the affinity column with low pH buffer as described by the manufacturer.

5. In Vitro Transcription

Transcription reactions containing partially purified factors and the actin Act5C template (Kephart et al., 1992) linearized with HpaI were carried out as described in Example 1. In addition to RNA polymerase II, transcription reactions (12.5 µl) contained P1'-FT, factor 2, TFIIE (factor 3), P11-0.4M step and P-TEFb all derived from Drosophila K$_c$ cell nuclear extract (K$_c$N) (Price et al., 1987). Transcription reactions using K$_c$N (Marshall and Price, 1992) or K$_c$-FT (see Example 1; Marshall and Price, 1995) were carried out as described previously. H-8 and DRB were incubated with K$_c$N for approximately 3 min at 22° C. prior to the addition of template and NTPs.

6. Purification of P-TEFb

P-TEFb used in FIG. 1 was purified from K$_c$N as described in Example 1. Phosphocellulose, Phenyl-Sepharose, Mono Q™ and Mono S™ columns were used. A sample of the Mono S™ purified material was analyzed on a glycerol gradient as described in Example 1. The P-TEFb used in FIG. 2A, FIG. 2B and FIG. 3 was purified from Drosophila embryonic nuclear extract as described in Example 1 with one addition. Material eluting from the Phenyl-Sepharose column was loaded directly onto a 10.0 ml ceramic Hydroxyl-apatite column (Bio-Rad CHT10). The column was then eluted with a linear gradient of potassium phosphate from 10 mM to 750 mM in 25 mM HEPES, pH 7.6, 15% glycerol. P-TEFb eluted between 400 mM and 500 mM phosphate. Pooled fractions containing P-TEFb were then dialyzed and chromatographed on Mono S™. P-TEFb eluting from Mono S™ still had significant nucleic acid contamination so the material was subjected to chromatography on Mono Q™ followed by Mono S™ for re-concentration. The peak fraction from the final Mono S™ column contained about 0.5 mg/ml P-TEFb.

7. CTD Kinase Assay 0.4 µl of purified RNA polymerase II and various protein samples were mixed in 18 µl of 55 mM HMK. The reaction was then initiated by the addition of 2 µl of a solution containing 2 µCi of [$\gamma$-$^{32}$P]ATP (ICN) and unlabeled ATP at 10 µM, or only unlabeled ATP at concentrations from 1 to 100 µM or other NTPs or dNTPs at concentrations of 1 to 100 µM. Reactions were incubated for the indicated times at 23° C. and then terminated with SDS loading buffer. Samples were analyzed on a 6–15% SDS polyacrylamide gel which was silver stained, dried and subjected to autoradiography if the assay contained label.

B. Results

1. Productive Elongation Requires the CTD

Drosophila RNA polymerase II was treated with chymotrypsin for increasing times to gradually remove the CTD (FIG. 1). Trypsin inhibitor was added to aliquots of the digestion reaction after 0, 2, 8, or 20 min. When trypsin inhibitor was added to a similar reaction before the chymotrypsin, no digestion took place during a subsequent 20 min incubation indicating that the protease was inactivated. Intact or truncated forms of the polymerase were then used to drive transcription from the Act5C promoter using fractions derived from *Drosophila* $K_c$ cell nuclear extract containing factors needed for initiation and productive elongation.

Most of the RNA polymerase II was removed by the fractionation procedure; however, some runoff transcripts were detected in the absence of added RNA polymerase II. When intact RNA polymerase II was added the runoff signal increased dramatically and was sensitive to DRB. The amount of DRB-sensitive, runoff transcript decreased as the CTD was removed. The amount of shorter, DRB-insensitive, abortive transcripts increased with added RNA polymerase II but did not change in amount as the CTD was removed. Quantitation of the autoradiograph and protein gel showed that the level of runoff transcript was directly related to the amount of polymerase containing the CTD while the generation of abortive transcripts was unaffected by loss of the CTD (FIG. 1).

Earlier findings, using a minimal set of *Drosophila* fractions required for initiation, indicated there was no effect when substituting CTD-less polymerase for intact polymerase (Zehring et al., 1988). These earlier results were obtained using fractions that did not contain factors needed for the generation of DRB-sensitive productive elongation complexes (Marshall and Price, 1995). Therefore, the negative effect of removal of the CTD indicates that the CTD is involved in the transition into productive elongation.

To address the possibility that truncation of the CTD in the previous study had an effect on initiation that resulted in the formation of exclusively DRB-insensitive complexes, a protocol for the truncation of the CTD after initiation was developed. Early elongation complexes were formed on an immobilized template and then washed with buffer containing 1 M KCl which removes uninitiated RNA polymerase II. The proteins found in early elongation complexes were stripped from the beads with SDS and analyzed by SDS-PAGE followed by western blotting. Rabbit anti-*Drosophila* large subunit antibodies to a non-CTD containing domain of the large subunit of RNA polymerase II were generated (see above in Methods, Section 4) and used to probe the western blot.

Treatment with increasing amounts of chymotrypsin resulted in removal of the CTD from RNA polymerase II in early elongation complexes. Essentially complete truncation occurred when 0.2 µg/ml or more of chymotrypsin was used. The protease treatment did not negatively affect the ability of the isolated early elongation complexes to continue elongation during the subsequent chase. Except for the increase in the longest transcripts at the higher protease concentrations, the typical pattern of transcripts seen during abortive elongation on the actin template (Marshall and Price, 1992; Xie and Price, 1996) were detected. The increase in the longest transcripts is due to the removal of the remaining trace amount of factor 2 (Price et al., 1987) which normally exerts a negative effect on elongation (Xie and Price, 1996).

To assess the ability of the polymerase in early elongation complexes to enter productive elongation, nuclear extract was added back with the chase. In this study the extracts were complemented with a constant amount of additional P-TEFb which is normally limiting in the extracts. DRB-sensitive runoff transcripts due to P-TEF action were visible in the western blot lanes using non-proteolyses complexes. As increasing amounts of chymotrypsin were used, the early elongation complexes lost the ability to form long DRB-sensitive transcripts. The long transcripts seen at high protease levels in the early elongation complexes alone were not seen when $K_cN$ was added because of the effect of endogenous factor 2 in the extract (Xie and Price, 1996). These results show that the CTD is required for the generation of long DRB-sensitive transcripts.

2. P-TEFb is a CTD Kinase

The requirement of the CTD for the generation of DRB-sensitive long transcripts and the inhibition of the process by the kinase inhibitor DRB (Marshall and Price, 1992; Marshall and Price, 1995) prompted studies to determine if P-TEFb was a CTD kinase. Studies similar to those in Example 1, and prepared in the same manner, showed that incubation of P-TEFb with intact RNA polymerase II caused the incorporation of phosphate into the large subunit and a shift to the IIo form.

Truncation of the CTD by chymotrypsin resulted in a loss of the ability of P-TEFb to phosphorylate the polymerase. The polymerase that was treated with chymotrypsin for 0, 2, 8, or 20 min followed by addition of trypsin inhibitor, see Section B.1, was used as a substrate for pure *Drosophila* P-TEFb. Using the incorporation of label into the large subunit of RNA polymerase II as an assay (see Methods, Section A.7) the ability of P-TEFb to label the large subunit was directly related to the amount of the CTD remaining on the subunit. The intact polymerase was labeled very efficiently, while the CTD-less polymerase (20 min digestion) was not detectably phosphorylated. Intermediate truncations gave rise to intermediate levels of phosphorylation.

To correlate the CTD kinase activity with P-TEFb function in transcription, fractions from a gradient elution of P-TEFb from a Mono S™ column and a subsequent glycerol gradient were tested in both assays. P-TEFb was about 25% pure in the peak fraction (Peterson et al., 1992) from Mono S™ (Example 1; Marshall and Price, 1995). CTD kinase activity coeluted with the transcription activity of P-TEFb on Mono S™. Fractions from the glycerol gradient analysis of P-TEFb from Mono S™ fraction 30 were analyzed for transcription and CTD kinase activities on a silver-stained 6–15% SDS-polyacrylamide gel (SDS-PAGE). Both activities again co-migrated with each other and with the 124 and 43 kDa subunits of P-TEFb previously identified (Example 1; Marshall and Price, 1995). P-TEFb subunits, transcription function and CTD kinase activity correlated across all columns assayed.

3. Characterization of P-TEFb CTD Kinase

To begin to establish the basic parameters of the CTD kinase activity of P-TEFb, P-TEFb was incubated for 5 min with RNA polymerase II and various cold nucleotides. The products were subjected to SDS-PAGE and silver stained to visualize the RNA polymerase II. The mobility shift from the unphosphorylated IIa form to the highly phosphorylated IIo form of the large subunit was used to ascertain kinase activity. Partial shifts indicated lower levels of incorporation of phosphate. P-TEFb was capable of utilizing the purine nucleotides in rough order of efficiency ATP >>DATP=GTP>dGTP. ATP was used 10–100 times more efficiently than dATP. GTP was used ~2-fold more efficiently than dGTP. P-TEFb was unable to utilize any of the pyrimidine nucleotides at 100 µM. In a similar study it was found that even at high concentration, i.e. 600 µM CTP, 600 µM UTP, 600 µM dCTP, or 600 µM dTTP, other nucleotides were not used as substrates for P-TEFb in the phosphorylation of RNA polymerase II.

4. Kinetics of Phosphorylation

The kinetics of phosphorylation of the CTD were examined with three concentrations of P-TEFb and 10 µM ATP. At all concentrations of P-TEFb intermediates between Ia and IIo were seen at early time points indicating a progressive increase in phosphorylation. At the lowest concentration of P-TEFb ~50% of the large subunit molecules were progressively phosphorylated, even though the molar ratio of P-TEFb to RNA polymerase II was about 1:50. This result indicates that P-TEFb was not stably associated with the polymerase during the addition of all phosphates and, therefore, was not completely processive. As the concentration of P-TEFb was increased the fraction of the large subunit that was shifted to IIo increased to about 90%.

Comparison of the kinetics of the appearance of the intermediate forms indicates that increasing the P-TEFb concentration had a modest but non-linear effect on the rate of the phosphorylation. For example, comparing 1 min with 0.01 μl of P-TEFb to 30 seconds with 0.05 μl indicates that although less large subunit was affected, an equivalent mobility shift was obtained. At all P-TEFb concentrations tested there were at least some polymerase molecules that received no or very few phosphates while others were heavily phosphorylated to the IIo form. These data are consistent with a slow initial phosphorylation event(s) followed by more rapid subsequent phosphate incorporation. The different rates could be due to conformational changes in the polymerase or CTD required for initial kinase action or to increased reactivity of partially phosphorylated CTD.

5. Sensitivity of the Kinase to Inhibitors

The sensitivity of the kinase to both DRB and H-8 under various conditions was observed. At 10 μM ATP (the same concentration of ATP used in the labeling assay), P-TEFb was strongly inhibited by DRB at 10 μM. Under the same conditions, approximately 10 times as much H-8 was required to inhibit the kinase to the same level. This 10-fold difference was seen consistently under all conditions tested. At 100 μM ATP both drugs were less effective. The inhibition by DRB and H-8 was directly related to the concentration of nucleotides used. Because the inhibition by DRB and H-8 was affected by nucleotide levels the relative inhibition between DRB and H-8 can be utilized as a more useful way to compare P-TEFb with other kinases.

Figure 2A:
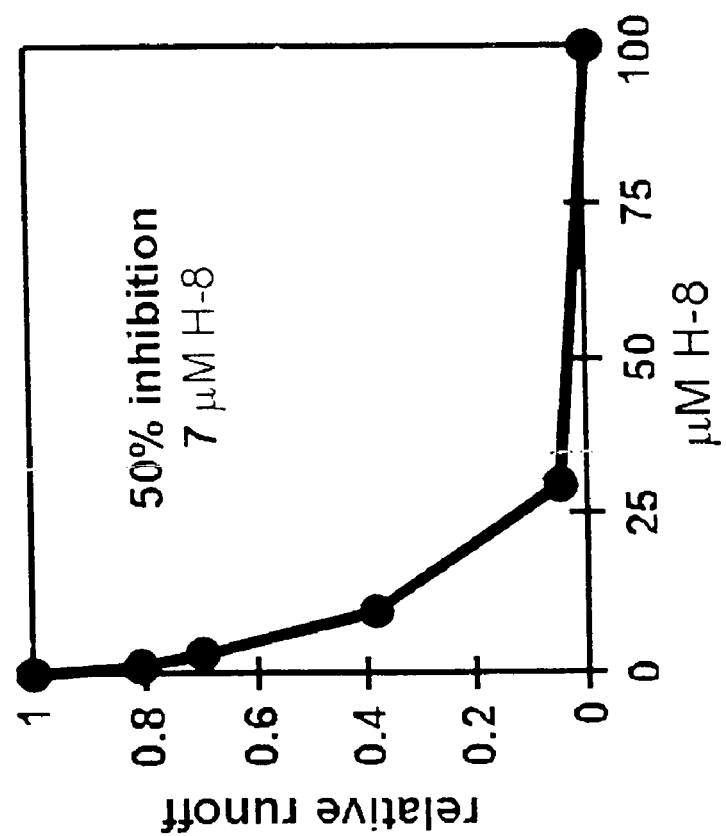
FIG. 2A and FIG. 2B. Inhibition of productive elongation by DRB and H-8. Transcription reactions in $K_cN$ extract were conducted for 20 min in the presence of the either 0.7 μM DRB (FIG. 2A) or 7 μM H-8 (FIG. 2B). Quantitation of levels of runoff transcripts were determined using a Packard InstantImage™. Relative levels of runoff at 50% inhibition are shown.
Figure 2B:
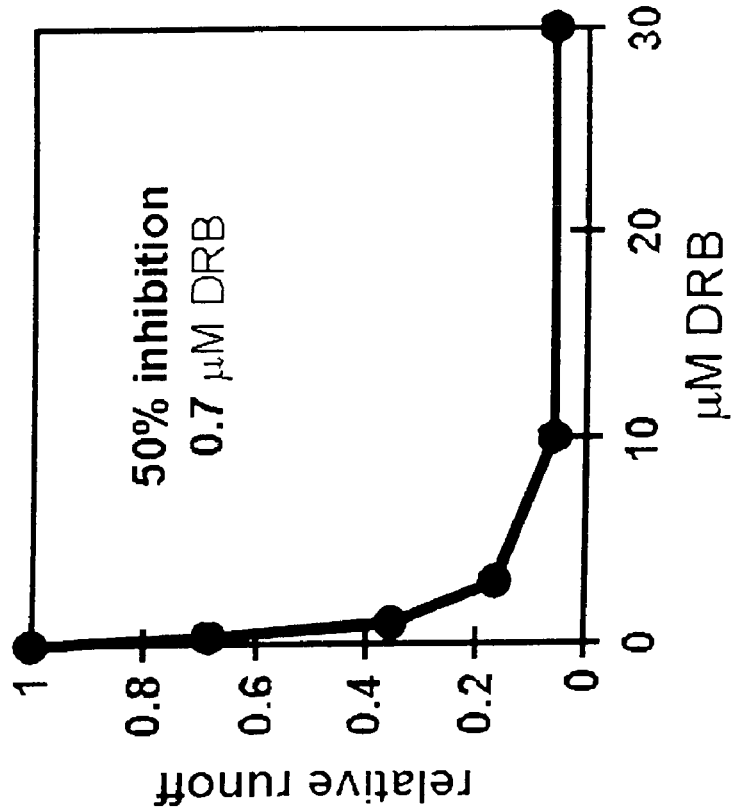

Since the CTD kinase activity of P-TEFb was sensitive to H-8, the effect of the drug during transcription in nuclear extracts was examined. Increasing amounts of DRB or H-8 were included in a continuous labeling assay. As seen earlier runoff transcription was very sensitive to DRB with a 50% inhibition point of 0.7 μM (FIG. 2A). Under identical transcription conditions, H-8 had a 50% inhibition point of 7 μM (FIG. 2B). This 10-fold difference is the same as that seen with the CTD kinase assay. As expected for an inhibitor of productive elongation, initiation and abortive transcription were unaffected by H-8 even at concentrations that severely inhibited the appearance of runoff. These data show that P-TEFb is the target of these kinase inhibitors during transcription.

6. P-TEFb Phosphorylates the CTD of RNA Polymerase II in Early Elongation

The data herein show that an intact CTD is required for productive elongation and that P-TEFb can phosphorylate pure RNA polymerase II. Since P-TEFb acts during elongation (Marshall and Price, 1995), it should phosphorylate the CTD if the polymerase is in an early elongation complex. To determine if the polymerase is in an early elongation complex western blot analysis was used to determine the phosphorylation state of the polymerase in isolated transcription complexes.

Preinitiation complexes were formed on an immobilized actin template as described above in Methods, Section 3. When these complexes were washed with low salt buffer they remained intact and western blot analysis indicated that the large subunit of RNA polymerase II was hypophosphorylated. Incubation of the preinitiation complexes with ATP caused a significant shift of the polymerase to the IIo form. The antibodies used to detect the large subunit of RNA polymerase II reacted more strongly with the Ia form of the large subunit than either the phosphorylated IIo form or the truncated IIb form. This phosphorylation was unaffected by the presence of 20 μM DRB.

This result is consistent with the previous data that P-TEFb is not associated with preinitiation complexes (Marshall and Price, 1992; Marshall and Price, 1995: see Example 1). Essentially all of the RNA polymerase II was removed by washing with buffer containing 1 M KCl. When the preinitiation complexes were incubated under transcription conditions for a short time, a portion of the polymerases initiated and, therefore, remained associated with the template during the high salt wash. The CTD kinase found in the preinitiation complex was no longer associated with the polymerase because incubation with ATP had no effect. However when increasing amounts of P-TEFb were incubated with the high salt washed early elongation complexes, the Ia form of the polymerase decreased and the IIo form increased. The ability of P-TEFb to phosphorylate RNA polymerase II in an early elongation complex was inhibited by 20 μM DRB.

7. TFIIH does not Functionally Substitute for P-TEFb

To determine whether P-TEFb was related to the protein kinase associated with TFIIH (Roy et al., 1994; Feaver et al., 1994; Cismowski et al., 1995; Serizawa et al., 1995; Shiekhattar et al., 1995), P-TEFb was compared with *Drosophila* TFIIH purified from *Drosophila* embryos by the method of Austin and Biggin (1996).

The two proteins did not have any subunits in common when analyzed by SDS-PAGE and silver staining. The large subunit of P-TEFb ran as a doublet which may be due to phosphorylation, since autophosphorylation of both P-TEFb subunits had been previously observed.

Figure 3:
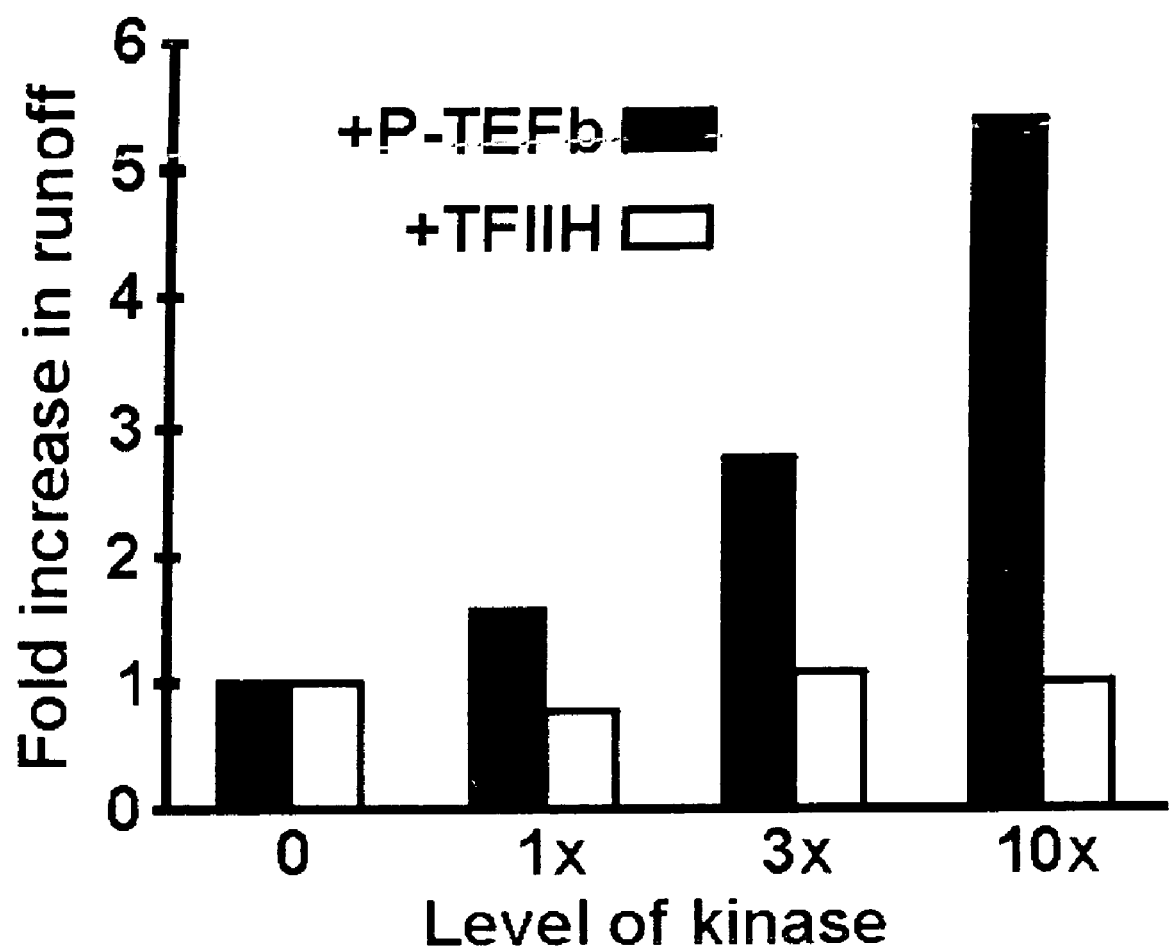
FIG. 3. Comparison of the composition and properties of P-TEFb and TFIIH. Quantitation of continuous labeling $K_c$-FT based transcription assays. Dried silver stained, 6–15% SDS polyacrylamide gels were imaged using the Packard InstantImager™ and the portions of the gel indicated as runoff were quantitated and normalized to the no addition lanes.

To compare the activities of the two factors, both were tested in the CTD kinase assay under identical conditions. Using equal concentrations of the two kinases, as determined by relative protein staining, both were able to incorporate similar amounts of $^{32}PO_4$ into the CTD of RNA polymerase II and cause the shift to the IIo form. The CTD kinase activity of P-TEFb was sensitive to 20 μM DRB while that of TFIIH was unaffected. Since DRB inhibition could be affected by enzyme levels titration studies were used to determine that the levels of P-TEFb and TFIIH were not saturating. To determine if TFIIH could functionally replace P-TEFb similar amounts of both proteins were tested in the P-TEFb-dependent $K_c$-FT (Marshall and Price, 1995; Example 1) transcription assay. As expected, addition of increasing amounts of P-TEFb led to an increase in DRB-sensitive runoff transcripts (FIG. 3). In contrast, addition of even the highest levels of TFIIH had little effect on the amount of runoff even though the added TFIIH had high CTD kinase activity when assayed using purified RNA polymerase II. Therefore, it appears that TFIIH cannot substitute for P-TEFb during the transition into productive elongation.

The 10-fold difference between levels of DRB and H-8 required to achieve equal inhibition of CTD phosphorylation remained constant under all conditions examined. Since a 10-fold difference in the levels of DRB and H-8 was required to inhibit transcription, this indicates that the effect of the drugs in transcription is due to inhibition of the CTD kinase activity of P-TEFb.

After the initial transition into productive elongation has been passed, it may be necessary to maintain the highly phosphorylated state of the polymerase. However, the results of Egyhazi et al. (1996) and Kephart et al. (1992) suggest that if CTD kinases are needed for maintenance of the IIo form during elongation then these kinases are not sensitive to DRB. Therefore, P-TEFb does not appear to be involved in maintenance. Maintenance could be accomplished by the inhibition of CTD phosphatase (Chambers et al., 1995) activity.

EXAMPLE 3

Drosophila P-TEFb Increases the Processivity of Human RNA Polymerase II

A. Materials and Methods

1. Materials

Ribonucleoside triphosphates were obtained from Pharmacia LKB Biotechnology Inc. [α-$^{32}$P]CTP (3000 Ci/mmol) was purchased from ICN pharmaceuticals. Streptavidin-coated paramagnetic beads (Dynabead™ M280) were obtained from Dynal (Great Neck, N.Y.). All other reagents were as described previously (Marshall and Price, 1992).

2. Growth Mediums

| D22 Medium for Growth of $K_c$ cells (for 50 L): | | |
|---|---|---|
| A: | $MgCl_2.6H_2O$ | 50 g |
| | $MgSO_4$ (Anhydr.) | 82 g |
| | $CaCl_2$ (Anhydr.) | 40.5 g |
| | L-glutamic acid | 530 g |
| | Glycine | 270 g |
| B: | Potassium hydroxide (45%) | 152.5 ml |
| | Sodium hydroxide (50%) | 180.5 ml |
| C: | L-malic acid | 30.5 g |
| | Succinic acid | 2.75 g |
| | Glucose | 91 g |
| | Sodium acetate | 0.7 g |
| | Lactalbumin hydrolysate | 682 g |
| | Yeastolate | 68 g |
| D: | Grace's vitamins, 100 ml | |
| E: | Potassium hydroxide (45%) to pH 6.7 | |
| F: | $NaH_2PO_4.H_2O$ (100X) pH 6.7, 500 ml (100X = 3.8 g/100 ml) | |

The ingredients are added in sequential order (A, then B, then C, then D, then E, then F) and brought to a final volume of 50 L. The medium is filter sterilized by starting with a large-pore filter and ending with a 0.22 mm final filter.

| Grace's Vitamins (modified) for 1 liter: | |
|---|---|
| chemical | mg/liter |
| Biotin | 50 |
| D-Ca Pantothenate | 10 |
| Choline Chloride | 1000 |
| Folic Acid | 10 |
| i-Inositol | 100 |
| Niacin | 100 |
| para-aminobenzoic acid | 100 |
| pyridoxine HCl | 10 |
| Riboflavin | 10 |
| Thiamine HCl | 10 |

Add 45% KOH until all material is dissolved. Filter or store at ~200C.

3. Solutions

| HGE | 4 liters | 1 M HGKE | 2 liters |
|---|---|---|---|
| 25 mM HEPES | 23.8 g | 25 mM HEPES | 11.9 g |
| 15% glycerol | 600 ml | 15% glycerol | 300 ml |
| 0.1 mM EDTA | 0.8 ml (0.5 M) | 0.1 mM EDTA | 0.4 ml (0.5 M) |
| (adjust pH to 7.6 with 50% NaOH) | | 1 M KCl | 149.1 g |
| | | (adjust pH to 7.6 with 50% NaOH) | |
| Buffer A | 500 ml | Buffer B | 200 ml |
| 15 mM KCl | 7.5 ml 1 M | 1 M KCl | 14.9 g |
| 10 mM HEPES | 10 ml (0.5 M) | 50 mM HEPES | 20 ml (0.5 M) |
| 2 mM $MgCl_2$ | 1 ml (1 M) | 30 mM $MgCl_2$ | 6 ml (1 M) |
| 0.1 mM EDTA | 0.1 ml (0.5 M) | 0.1 mM EDTA | 0.04 ml (0.5 M) |

Stock solutions: 0.5 M HEPES, pH 7.8; 0.5 M, EDTA, pH 8.3; 1 M $MgCl_2$. Complete the above buffers just before use with: 1 mM DTT from 1 M stock (stored at −80° C.) and 1:1000 dilution of isopropanol saturated with PMSF at room temperature.

Stock solution: 4M $(NH_4)SO_4$, pH 7.9

All buffers are filter sterilized. All glassware is autoclaved.

4. DNA templates

The Drosophila actin A2 (RI/PstI) DNA template has been described (Marshall and Price, 1992). Transcription of this template after digestion with HpaI yields a 520-nucleotide (nt) runoff transcript. The HIV-1 template (pLTR-4/CAT) derived from HIV-SF2, was obtained from P. Luciw (Sanchez-Pescador et al., 1985). It contains the HIV-1 LTR from −153 to +80 and has the CAT gene downstream of the LTR. Transcription of this construct after digestion with NcoI produces a 633 nucleotide runoff transcript. Transcription of the HIV-1 construct after digestion with BamHI produces a 1640 nucleotide runoff and digestion with XbaI produces a 4000 nucleotide runoff transcript. Biotinylated Drosophila A2 DNA templates were made as previously described (Marshall and Price, 1992).

5. $K_c$ Cells and Cell Extracts

Growth of $K_c$ cells and preparation of nuclear extracts are as described (Price et al., 1987).

a. Freezing and Thawing Cells:

Cells are grown in spinner culture to $4 \times 10^6$ cells/ml then gently spun in 50 ml conical tubes in a JS-4.2 rotor (Beckman) at 500 rpm/10 min/4° C. Spun cells are resuspended in 4.5 ml ice-cold fetal calf serum and 0.5 ml DMSO or 1/10 original volume. Aliquots of 1 ml each are placed into cryotubes while on ice, frozen at −20° C. for 1 h and then transferred to −80° C. overnight. Cells can be stored for months at −80° C. or longer in liquid $N_2$ without impairment to function.

Frozen cells are thawed at room temperature and diluted 10–20 fold with D22 media in a 25 ml tissue culture flask. The D22 media is removed and replaced with 6-fold fresh D22 media when cells have attached to the flask (approximately 30 min). Fresh D22 media is added over the next two days until the cells reach the desired density and can be split.

b. Continuation of Line:

The cells should be continued in flasks with care being taken never to allow them to become overgrown, as evidenced by the release of all cells from the bottom of the flask with only gentle tilting. The cells will tolerate lower densities in flasks due to the close proximity of other settled cells, but the cultures should be split at least every 3.5 days or one day before cells become detached by tilting.

c. Growth for Production of Extracts:

Careful control of the conditions of growth of KC cells is critical for the production of high quality extracts for in vitro transcription. The cells must be maintained between $1.5 \times 10^6$ and $8 \times 10^6$ cells/ml in spinner cultures, preferably between $2 \times 10^6$ and $6 \times 10^6$ cells/ml. Cells will double every 16 to 18 h when growing well. Cells that are diluted too much will not grow, and cells that reach densities of over $8 \times 10^6$ cells/ml will not yield good extracts even if their growth rate is good after dilution and further growth. Extracts should be made when cells are between $3 \times 10^6$ and $5 \times 10^6$ cells/ml. Most of the cells in a good culture will be attached to another cell. However, the stirring rate should be increased if many cells are attached in chains of four or longer.

d. Preparation of $K_c$ Cell Nuclear Extract, $K_cN$:

This protocol details the production of a nuclear extract from *Drosophila* $K_c$ cells. It has been described in Price, et al. (1987). A standard preparation starts with 18 liters of cells, but the protocol can be scaled down or up as desired. Provisions are given to save the cytoplasmic portion of the cells which may contain other cellular factors of interest. Phenol extraction of the cytoplasm will produce massive quantities of high quality $K_c$ cell cytoplasmic RNA. This procedure produces extracts that are more active than any other extracts reported. The procedure can also be used on other types of cells including mammalian cells. $K_c$ cells are grown in D22 media to a density of 3 to $5 \times 10^6$ cells/ml. Prepare, at 4° C., solutions A, B and A+1/15B. Add DTT and PMSF just prior to use.

e. Cell Harvesting:

$K_c$ cells are aliquoted into centrifuge tubes, about 65 mls per bottle, and spun in a Beckman JS-4.2 rotor at 4.2K rpm (4000×g) for 7 min. The supernatant is removed and the pelleted cells are retained. 10 ml Buffer A+1/15 B is added to each centrifuge bottle and the cells are resuspended and transferred to four 40 ml polycarbonate tubes. A 10 ml wash of Buffer A+1/15 B is used to wash all of the bottles and the wash is added to the appropriate polycarbonate tube. The cells are spun in the Beckman JS-13.1 swinging bucket rotor for 5 min at 4,000 rpm (4000×g).

The supernatant is discarded and the pelleted cells are gently resuspended the cells in Buffer A (10 ml/tube). Resuspended cells are spun a JS-13.1 rotor for 5 min at 5,000 rpm. The slightly cloudy supernatant is discarded. The pelleted cells are resuspended in Buffer A to 40 ml total volume, transferred to a 40 ml Dounce homogenizer and homogenized until cell lysis is greater than 90%. Cell lysis is normally 95%–98%. 3 mls of Buffer B is added and lyzed cells are briefly homogenized again. Lyzed cells are transferred to a polycarbonate tube.

The lyzed cells are spun in a JS-13.1 rotor for 8 min at 8,000 rpm to pellet nuclei. The supernatant ($K_cC$) is transferred to disposable 50 ml conical tube(s) and placed on ice. 10 mls of Buffer A is added to each tube and nuclei ($K_cN$) are gently mixed until completely resuspended. The volume of the resuspended nuclei is brought to total volume of 40 ml with Buffer A. The nuclei are uniformly resuspended by gentle homogenization.

The nuclear suspension is transferred to 28 ml Oak Ridge Tubes, 20 ml/tube, 2 ml of 4 M $(NH_4)SO_4$ is added to each tube (360 mM $(NH_4)SO_4$ final) and mixed for 30 minutes at 4° C. The resulting suspension is transferred to fresh Oak Ridge tubes. Both the nuclear suspension and the saved supernatant are spun in a Beckman 55.2Ti rotor for 45 min at 45,000 rpm (150,000×g) to pellet the chromatin.

The resulting supernatant from the nuclear suspension is transferred into a fresh Oak Ridge tube containing 5.5 g solid $(NH_4)SO_4$ (0.25 g/ml) and mixed for 20 min at 4° C. The spun $K_cC$ supernatant is frozen at −80° C. The nuclear suspension is precipitated with ammonium sulfate in the Beckman 55.2Ti rotor for 15 min at 45.000 rpm and the supernatant is removed.

f. Pellet Resuspension and Dialysis:

The protein pellet is dissolved in ½ of 1 nuclear volume of HGEDP (HGE+DTT and PMSF) and transferred to a 7 ml Dounce homogenizer and homogenize gently until the protein is completely dissolved. 25 ml HGKE is added to 475 ml HGEDP to make 500 ml HGKEDP. the solubilized protein is dialyzed against 500 ml of 50 mM HGKEDP for 2.5–3.0 h. at 4° C. The final salt concentration should be 120–150 mM KCl. Dialized protein is aliquoted and frozen at −80° C.

6. Preparation of HeLa Cell Nuclear Extract

The growth of HeLa cells and preparation of nuclear extracts (NE's) are essentially as described by Dignam et al. (1983) with some modification as described below. P-TEFb was purified from *Drosophila* embryonic nuclear extract as previously described in Example 1. This protocol details the production of a nuclear extract from mammalian cervical cancer, HeLa, cells. It is very similar to the $K_c$ cell extract described above in Section A.4 and by Price, et al. (1987). Modifications to the cell harvest are described below. All other methods for preparation of HeLa cells are described in Section A.4 above.

a. Cell Harvest:

HeLa cells are grown on plates or in spinner flasks ($5 \times 10^6$–$7.5 \times 10^6$ cells/ml) in DMEM/10% Calf Serum. The HeLa cells are either scraped off of T-150 Plates or cells grown in D22 media are spun down in a Beckman JS-4.2 rotor at 4.2K rpm (4000×g) for 5 min and the pelleted cells are recovered. Cells are resuspended as before in Buffer A+1/15 B except that only ½ of the volume indicated in Section A.4 is used. Volumes of all following isolation and purification steps are modified accordingly.

7. Transcription Reactions

A pulse-chase protocol was used in which the template DNA was preincubated with the extract, 20 mM HEPES, pH 7.6 and 10 mM $MgCl_2$ for 20 min at 30° C. Nucleotides, including [α-$^{32}$P]CTP were added to start the pulse; 2 min later, excess cold CTP was added to initiate the chase. Reactions were stopped after the indicated chase times. During the pulse, 10 µl reaction mixtures contained the following: 20 mM HEPES (pH 7.6), 10 mM $MgCl_2$, 600 µM each GTP, UTP and ATP, 5 µCi of [α-$^{32}$P]CTP (~1 µM CTP), 66 mM KCl, 10–40 µg/ml DNA template, and 3 µl of HeLa nuclear extract. For the chase, unlabeled CTP was added to bring the total concentration of CTP to 1.2 mM and the final reaction volume to 12 µl. Reaction mixtures containing 250 mM KCl, were supplemented with KCl at the beginning of the chase. *Drosophila* P-TEFb was added to the preincubation mixture where indicated. Reactions were stopped by adding 200 µl of stop solution (1% Sarkosyl, 50 mM Tris, pH 8.0, 50 mM EDTA, 100 mM NaCl and 100 µg/ml tRNA). The reaction mixtures were phenol extracted and the nucleic acids were ethanol precipitated, washed with 70% ethanol, dried and analyzed by gel electrophoresis. Transcription reactions with $K_c$ cell NE were as described (Kephart et al., 1992).

8. Gel Electrophoresis

For polyacrylamide gel electrophoresis, samples were resuspended in 7 ml of 0.25×TBE (1×TBE contains 89 mM Tris base, 89 mM Boric acid and 2 mM EDTA) and 8 M urea, heated for 3 min at 85° C. and analyzed in 6% acrylamide-8 M urea-1×TBE gels. Denaturing agarose gel electrophoresis was performed by resuspending samples in 50% formamide-2.2 M formaldehyde-1× morpholinepropanesulfonic acid (MOPS) buffer (20 mM MOPS, pH 7.0; 5 mM sodium acetate, 1 mM EDTA) and heating the mixture at 60° C. for 5 min. Samples were resolved in a 2% agarose gel containing 2.2 M formaldehyde and IX MOPS buffer.

B. Results

Previous results using *Drosophila* DNA templates and KC cell nuclear extract (NE) have shown that two classes of RNA polymerase II elongation complexes are present during transcription, in vitro (Marshall and Price, 1992). These are either elongation complexes that produce short transcripts or productive elongation complexes capable of making long runoff transcripts. P-TEFb, a factor required for the transition into productive elongation (Marshall and Price, 1995), functions via its ability to phosphorylate the CTD of the large subunit of RNA polymerase II in early elongation. Both the function of P-TEFb and its CTD kinase activity are inhibited by low levels of DRB (see Example 2). The present invention demonstrates that a human P-TEFb homolog is involved in controlling elongation in the HeLa transcription system.

1. DRB-Sensitivity of Human RNA Polymerase II Elongation Complexes

To begin to examine elongation control in a HeLa in vitro transcription system, the general properties of human elongation complexes were studied using conditions similar to those used to study *Drosophila* complexes in Example 2.

Using a HeLa NE pulse-chase reactions were performed at either 10 or 40 µg/ml template with or without DRB. After a 2 min pulse under limiting CTP conditions the incomplete transcripts had a distinct pattern. More early elongation complexes (EECs) were formed at the higher template concentration as indicated by the increase in intensity of the transcripts after the pulse. Addition of 50 µM DRB inhibited the formation of the longest transcripts during the pulse. When the EECs formed during the pulse were chased for the indicated times, a very processive, DRB-sensitive elongation complex was identified. Even though more polymerase molecules initiated at the higher template concentration, a similar number ultimately reached runoff and the runoff accumulated more quickly at the lower template concentration.

These results indicate that, as has been seen in a *Drosophila* transcription system, P-TEF was limiting for the generation of DRB-sensitive runoff transcripts (Marshall and Price, 1992). A difference between the properties of the elongation complexes formed in the HeLa system and the *Drosophila* system was that at long time points only 60% (instead of greater than 95%) of the runoff generated was DRB-sensitive.

To determine if the DRB-insensitive elongation complexes that were capable of making long transcripts arose from incomplete inhibition by DRB, DRB was titrated from 10 to 135 µM. Maximum inhibition by DRB occurred at 30 µM. Increasing the DRB concentration to 135 µM did not inhibit the formation of the DRB-insensitive processive elongation complexes. Therefore, 50 µM DRB was used in all subsequent studies. These results show that the HeLa transcription system gave rise to both types of elongation complexes found in the *Drosophila* system and in addition produced a class of DRB-insensitive, processive elongation complexes not seen in the *Drosophila* system.

It was possible that the apparent difference between the two systems was merely due to properties of HeLa RNA polymerase II and that the DRB-insensitive transcripts generated by the human polymerase were just longer than those seen in the *Drosophila* system. If this were so, then longer transcripts would be more sensitive to DRB than shorter ones.

To determine if this were the case, templates that produced longer runoff transcripts were used. Two min pulse-chase time course assays using DNA templates that generate 1640 or 4000 nucleotide runoff were carried out. At longer time points both DRB-sensitive and DRB-insensitive processive elongation complexes generated 1640 and 4000 nucleotide runoff transcripts. Addition of 250 mM KCl to the chase caused the EEC's to elongate at a slower rate, compared to 60 mM KCl in a normal chase.

As was found in the *Drosophila* system (Kephart et al., 1992; Marshall and Price, 1992) high salt suppressed both positive and negative elongation factors. The rate of elongation was slowed when compared to that seen for productive elongation complexes under normal salt conditions. As in the *Drosophila* system (Kephart et al., 1992; Marshall and Price, 1992), early blocks to elongation (promoter proximal pausing) are apparently removed by the high salt treatment. Rous sarcoma virus LTR, adenovirus major late promoter and SV40 promoter constructs were also examined and gave similar results to those seen with the HIV-1 DNA template.

2. Demonstration of P-TEFb-like activity in HeLa nuclear extracts In the *Drosophila* system the DRB-sensitivity of the generation of highly processive elongation complexes is due to the CTD kinase activity of P-TEFb (Marshall and Price, 1995). To examine the similarity of the DRB-sensitive process in HeLa transcription to that of the well characterized *Drosophila* system, the sensitivity of HeLa elongation complexes to both DRB and H-8 were compared.

Figure 4:
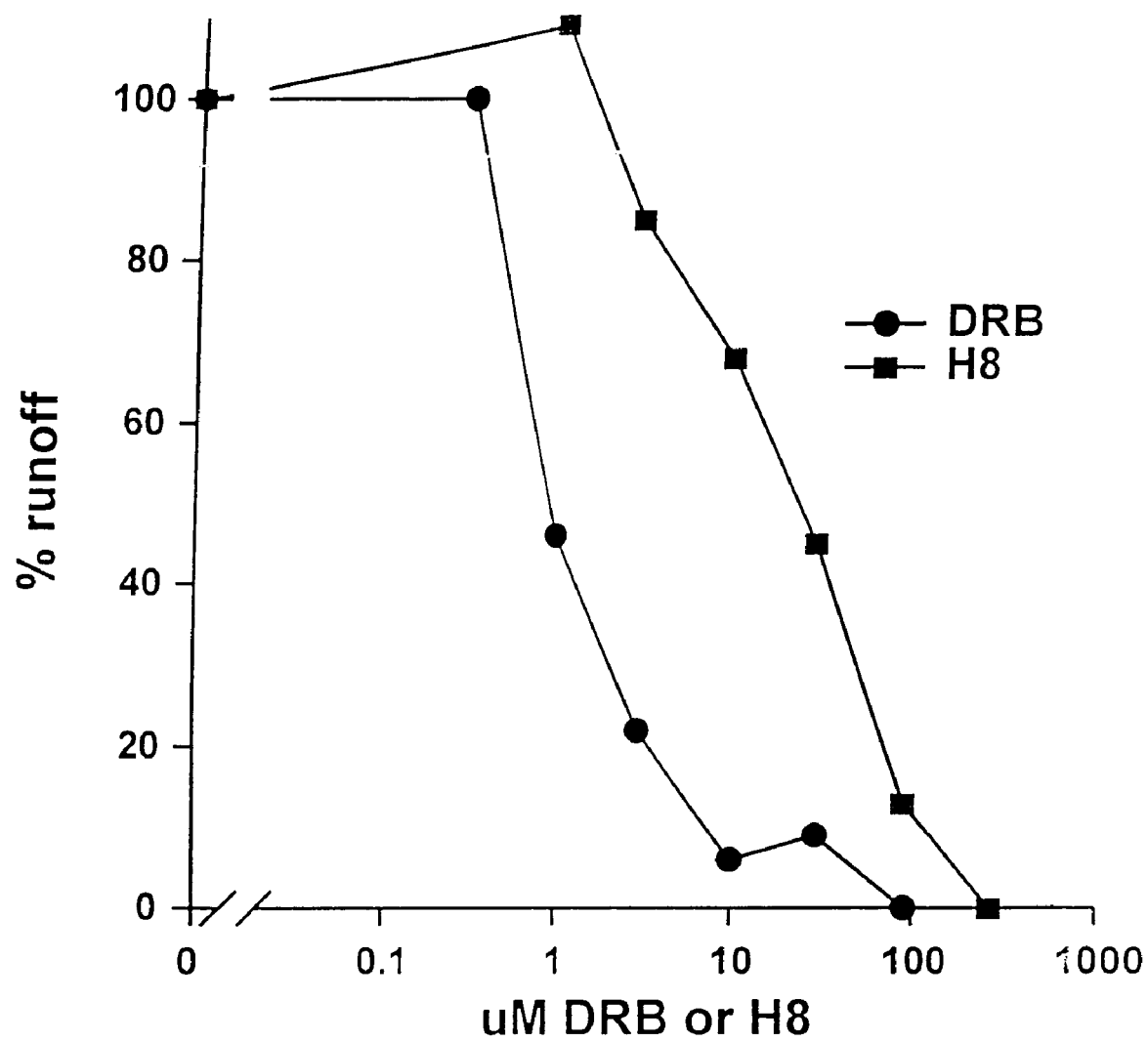
FIG. 4. Inhibition of processive elongation complexes by DRB and H8. The results of a pulse-chase transcription reaction with several DRB and H8 concentrations. The 2 min pulse +/−DRB and H8 was followed by a 45 sec. chase. The reactions were analyzed on a 6%-acylamide-TBE-urea gel. The quantitation of runoff transcripts from dried polyacrylamide gels were imaged using an Packard InstantImage™ and the portion of the gel indicated as runoff was quantitated and expressed as percent (%) of the runoff compared to the control. The values were normalized by subtracting the drug-insensitive runoff found at the highest drug concentrations used.

Two min pulse/45 sec chase transcription assays were performed with variable amounts of DRB or H8. The inhibition of the appearance of runoff was quantitated and plotted versus the concentration of inhibitor (FIG. 4). The 50% inhibition point occurred at 1 µM DRB compared to 20 µM H8 (FIG. 4). Greater sensitivity to DRB was also seen with the *Drosophila* system which was 50% inhibited by 0.7 µM DRB compared to 7 µM H8 (see Example 2). It has been shown that the sensitivity of the CTD kinase activity of P-TEFb is very dependent on the conditions used in the assay (Marshall and Price, 1995; see Example 1). Conditions used here were similar to those used in the *Drosophila* study. These inhibitor studies indicate that there is a HeLa equivalent to *Drosophila* P-TEFb.

Since P-TEF was first identified using an immobilized template assay, the ability of HeLa NE to generate DRB-sensitive elongation complexes when added back to isolated EECs was examined. *Drosophila* actin A2 DNA template and $K_c$ cell NE was used to form EECs containing *Drosophila* RNA polymerase II. An immobilized A2 template was preincubated with $K_c$ cell NE and then pulsed for 30 sec with [$\alpha$-$^{32}$P] CTP. The resulting EECs were isolated, and washed. Only short transcripts were produced during the pulse and the labeled tRNAs were removed by the washing protocol. Addition of only NTPs during the 15 min chase generated a pattern of short and intermediate transcripts that were DRB-insensitive and did not make runoff transcripts. However, addition of $K_c$ cell NE to the chase, allowed some EECs to enter productive elongation and make long DRB-sensitive transcripts. When a HeLa NE that was capable of producing high levels of DRB-sensitive transcription was added to the chase, DRB-sensitive transcripts were also produced.

The HeLa NE used in the other studies in this study was not able to generate an easily detectable level of DRB-sensitive transcripts in the add-back assay, most likely due to the fact that isolated early elongation complexes are not as sensitive to P-TEF as they are when they are formed in the presence of the extract. When α-amanitin was added prior to the chase, elongation by all EECs was inhibited proving that transcripts were produced by RNA polymerase II. When an immobilized HIV-1 DNA template was used to form human EECs both $K_c$ cell and HeLa NE could be added back to form DRB-sensitive transcripts.

3. Effect of Purified *Drosophila* P-TEFb on Transcription

The results presented here show that the HeLa NE used for most studies has limiting amounts of a human P-TEFb-like activity. A number of *Drosophila* basal transcription factors have been shown to be able to replace their human counterparts (Kephart et al., 1994; Wampler and Kadonaga, 1992; Wampler et al., 1990). Purified *Drosophila* P-TEFb was studied to determine if it could function in the human system. Pulse/chase transcription reactions using HeLa NE were carried out. Reactions were chased for either 15 seconds or 1 min and contained either 10 or 40 µg/ml template.

Addition of *Drosophila* P-TEFb increased the level of DRB-sensitive transcripts present at either time point. The largest increase in DRB-sensitive transcripts was obtained with 40 µg/ml template. At either template concentration addition of P-TEFb also reduced the amount of short transcripts. The short transcripts also reappeared upon addition of DRB, demonstrating that P-TEFb acts on complexes that are destined to produce short transcripts in the absence of functional P-TEFb.

These results indicate that the CTD kinase activity of P-TEFb is responsible for its effect on transcription and that a large number of phosphorylation events on an EEC by P-TEFb can cause productive elongation. If human P-TEFb is limiting and multiple phosphorylation events are required for the transition into productive elongation, then increasing the number of EECs in a reaction with a constant amount of P-TEFb would cause a decrease in the DRB-sensitive runoff transcripts because the activity of P-TEFb would be spread over a larger number of complexes and the number of EECs that receive the required number of phosphates would be less.

Figure 5:
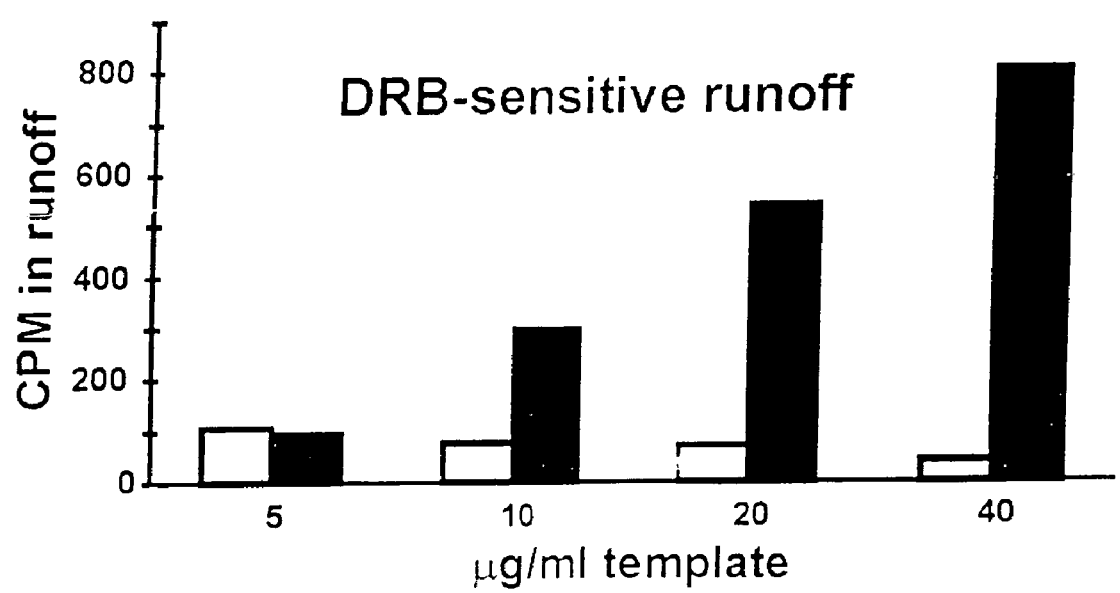
FIG. 5. Effect of Drosophila P-TEFb and DNA titration on transcription. A two min pulse/1 min chase was performed using HeLa nuclear extract and DNA template concentrations of 5, 10, 20, and 40 μg/ml. Templates were preincubated for 20 min at 30° C. in the presence or absence of P-TEFb. The transcripts were analyzed on a 6% acrylamide-TBE-urea gel and quantitation of labeled runoff transcripts, in CPMs, in the presence of DRB was subtracted from the runoff without DRB to obtain DRB-sensitive runoff.

When a template titration from 5 to 40 µg/ml template with a constant amount of HeLa NE was done, the number of EECs increased with the increase in template but the level of DRB-sensitive runoff decreased (FIG. 5). When pure *Drosophila* P-TEFb was added to otherwise identical reactions the level of DRB-sensitive runoff transcripts was dramatically increased. Without additional P-TEFb the level of DRB-sensitive runoff began to decrease above 10 µg/ml, but with additional P-TEFb the level of DRB-sensitive runoff continued to increase at even 40 µg/ml. These results indicate that P-TEFb acts as a CTD kinase that must act multiple times on each EEC.

These results demonstrate that two classes of processive human RNA polymerase II elongation complexes are formed after initiation at a promoter in vitro. The two classes are differentiated by their elongation rates and sensitivities to DRB. DRB-sensitive transcripts were elongated at a faster rate than the DRB-insensitive transcripts. However, both types of complexes were able to transcribe RNAs up to 4000 nucleotide in length. HeLa extracts made using a protocol similar to that used to produce *Drosophila* $K_c$ cell NE generated a much lower fraction of DRB-insensitive long transcripts. These extracts may have more of the negative factors required or less of the DRB-insensitive factor acting like P-TEFb or may have different levels of general elongation factors. Nevertheless, these results of this example clearly demonstrate the functionality of the human cell system.

These results indicate that P-TEFb-like activity is limiting in HeLa nuclear extracts for the generation of DRB-sensitive transcripts. Purified *Drosophila* P-TEFb stimulated the production of DRB-sensitive transcripts up to 10-fold in the HeLa transcription system. Therefore, even if other factors are required to generate DRB-sensitive transcripts, these factors are not limiting. High levels of exogenous P-TEFb did not reduce the formation of DRB-insensitive, processive complexes. If there is another factor which causes the transition into DRB-insensitive productive elongation, it must not be in competition with P-TEFb to modify EECs.

These results provide further evidence for the action of P-TEFb as a CTD kinase. Multiple phosphorylation events are required to cause the shift from the Ia to the IIo form of the polymerase, and P-TEFb is not stably associated with the elongation complex (Marshall and Price, 1992; Marshall and Price, 1995). Therefore, the distributive action of P-TEFb depends on the concentration of the factor and the concentration of its substrate (EECs). The results presented here substantiate this conclusion. As the template concentration was increased in a background of constant low level of P-TEFb found in HeLa NE, the amount of DRB-sensitive runoff decreased as the number of EECs increased. When P-TEFb levels were elevated, the same template titration now gave more DRB-sensitive runoff at every template concentration and now, the number of DRB-sensitive runoff transcripts did not decrease as the number of EECs increased. These results are consistent with the distributive action of P-TEFb such that at low concentrations of the factor and high template concentrations many of the EECs do not receive the required number of phosphates to cause the transition into productive elongation. When the P-TEFb levels were higher more of the EECs were phosphorylated to the level required for the transition to take place.

EXAMPLE 4

Cloning and Expression of *Drosophila* P-TEFb

A. Peptide Sequences from P-TEFb

*Drosophila* P-TEFb was purified as described in Marshall and Price (1995) and Example 1 (Methods, Section 3) from *Drosophila* $K_c$ cell nuclear extract derived from 500 liters of $K_c$ cells (see Example 3, Methods, Section A4 for preparation). About 30 µg of pure P-TEFb was run on a 6–15% gradient SDS-PAGE protein gel. The regions of the gel containing individual subunits were excised and sent to the W.M. Keck Foundation Biotechnology Resource Laboratory (Yale University, New Haven Conn.). Using standard techniques, each protein was subjected to in situ proteolysis and the resulting peptides were separated using reversed phase HPLC. Individual HPLC peaks were analyzed by MALDI mass spectrometry and fractions containing predominately one species were subjected to sequencing. Two or three peptide sequences were obtained from each subunit.

B. Cloning of *Drosophila* P-TEFb Small Subunit

Two peptide sequences, MLQQPSGSTPSNV (SEQ ID NO:31) and ADTALNHDFFWTDPMPS (SEQ ID NO:32), were obtained as described above in Section 1 from sequencing the small subunit fragments. Based on these two peptides, two degenerate primers, 5'-GGAATTCNATGYTNCARCARCC (SEQ ID NO:9) which encoded the region MLQQP (SEQ ID NO:33) of SEQ ID NO:31 and 5'-AACTGCAGTCCARAARAARTCRTGRTT (SEQ ID NO:10) which encoded the region NHDFFWT (SEQ ID NO:34) of SEQ ID NO:32, were designed. The template for the PCR™ reaction was *Drosophila* K$_c$ cell cDNA made through reverse transcription using a 3' RACE™ (Rapid Amplification of cDNA End) kit according to the manufacturer's directions (Gibco, Gaithersburg, Md.). A 1.1 kb cDNA fragment was amplified by PCR™ (30 cycles of 0.5 min at 94° C., 1 min at 55° C. and 1.5 min at 72° C.) using Vent™ DNA polymerase. A 0.7 kb fragment from the 3' portion of the PCR™ product was cloned into the Bluescript SK (Stratagene) after digestion with Pst I (one internal Pst I site in the PCR™ product and one Pst I site designed into the 3' end of the splice site of Bluescript SK (Stratagene).

The 3' region of full length cDNA sequence was obtained using a Gibco 3' RACE™ kit with two specific primers from the 0.7 kb fragment, 5'-TGTCAAGGATCAAACCGGCTGTGAT (SEQ ID NO:11) and

5'-CGAATTCCAAGAAACGCATCGATGC (SEQ ID NO:12).

The 5' region of the full length cDNA was obtained using a Gibco 5' RACE™ kit with three gene specific primers from the 0.7 kb fragment

5'-AGACCTGCCAAATCGTGT (SEQ ID NO:13),

5'-AGAAGGTGGATCTGTAACCATTCGT (SEQ ID NO:14) and

5'-GGAATTCAGATCTCGATCAGATTCA (SEQ ID NO:15).

The coding sequence of the small subunit was cloned by reverse transcription PCR™ (RT-PCR). First, the cDNA of small subunit was generated in a reverse transcription using a primer 5'-TTACTACTCGAGCTACCAAACCCGGTC (SEQ ID NO:16) and *Drosophila* embryonic mRNA as the template. Second, the coding sequence was produced in a 30-cycle PCR™ reaction using VENT DNA polymerase, two primers 5'-TAAGCAAGCTTCTATGGCGCACATGTCC (SEQ ID NO:17) and

5'-TTACTACTCGAGCTACCAAACCCGGTC (SEQ ID NO:18)

and the cDNA as the template. The PCR cycles were performed for 0.5 min at 94° C., 1 min at 55° C. and 3.5 min at 72° C. according to the manufacturer's directions (NEN, Boston, Mass.). Finally, the coding sequence was digested with Hind III and Xho I and cloned into pET-21a vector.

C. Cloning of *Drosophila* P-TEFb Large Subunit:

Three peptide sequences SPEWPDI (SEQ ID NO:35), WYFSNDQLANSPSR (SEQ ID NO:36) and TVHGMPPFEQQLPY (SEQ ID NO:37) of the large subunit that were obtained as described above in Example 4, Section 1. Based on these amino acid sequenced, three degenerate primers, 5'-GGAATTCTGGTAYTTYWSNAAYGA (SEQ ID NO:19) which encoded the region WYFSND (SEQ ID NO:38) of SEQ ID NO:36, 5'-CGGGATCCTGYTCRAANGGNGGCAT (SEQ ID NO:20) which encoded the region MPPFEQ (SEQ ID NO:39) of SEQ ID NO:37, and 5'-CGGGATCCAANGGNGGCATNCCRT (SEQ ID NO:21) which encoded the region HGMPPF (SEQ ID NO:40) of SEQ ID NO:37 were designed.

A 1.6 kb cDNA fragment of the large subunit was cloned through nested PCR™ reactions. First, a 35-cycle PCR™ reaction was performed using Taq DNA polymerase, the degenerate primers, SEQ ID NO:19 and SEQ ID NO:20, and the *Drosophila* embryonic cDNA obtained from Clontech (Palo Alto, Calif.) as the template. The PCR™ cycles were performed for 1 min at 94° C., 1 min at 55° C. and 3 min at 72° C. Second, a 1.6 kb cDNA fragment was amplified in another 35-cycle PCR™ reaction using the total PCR™ products from the first amplification as the template, the primers of SEQ ID NO:19 and SEQ ID NO:21 and the same reaction conditions.

The 1.6 kb fragment of the second round of amplification was digested with EcoRI and BamHI to yield three fragments of 0.9 kb, 0.6 kb and 0.1 kb. The 0.9 kb and 0.6 kb fragments were cloned into Bluescript SK (Stratagene), yielding a 1.5 kb insert, and sequenced using fluorescent automated sequencing at the DNA Facility at the University of Iowa, following manufacturer's recommended protocols.

The 3' region of the full length cDNA sequence was obtained using the 3' RACE kit (Gibco) according to the manufacturer's directions. Three nondegenerate, specific primers,

5'-ATCACGACACCACCAGAGCTGTTA (SEQ ID NO:22),

5'-CGAATTCAGATCGTGAACGGGA (SEQ ID NO:23) and

5'-CGAATTCAGGCGCTAGCAATG (SEQ ID NO:24), were designed based on the 1.5 kb cDNA sequence obtained. The 5' region of cDNA sequence was obtained using a 5' RACE™ kit (Gibco) according to the manufacturer's directions. Three gene specific primers, 5'-GAAAGGCGTAGAACCGA (SEQ ID NO:25),
5'-GCTGACCCATTTCCTGTATCAGATAG (SEQ ID NO:26) and
5'-GGAATTCTTCTGCTTGGCGAAT (SEQ ID NO:27), were designed based on the 1.5 kb sequence and used with the 5' RACE kit (Gibco).

The entire coding sequence of the large subunit was cloned by reverse transcription PCR™ (RT-PCR). First, the cDNA of large subunit was generated in a reverse transcription reaction using the primer, 5'-GGGAATTCGAGGTTCTATACATAT (SEQ ID NO:28) and *Drosophila* embryonic mRNA as the template. Second, a 4 kb cDNA fragment containing the coding sequence was produced in a 35-cycle PCR™ reaction using Expand™ polymerase (Boehringer Mannheim, Indianapolis, Ind.), the two primers 5'-CTGTGTGAATGGAATCTGTGATGTG (SEQ ID NO:29) and
5'-GGGAATTCGAGGTTCTATACATAT (SEQ ID NO:28)

and the *Drosophila* cDNA as the template. The PCR™ cycles were performed according to the following protocol, supplied by the manufacturer:

Amplification reactions were denatured for 2 min at 94° C.; 10 cycles, 10 sec. at 94° C., 30 sec at 58° C., 3 min at 68° C.; 5 cycles, 10 sec at 94° C., 30 sec at 58° C., 4.5 min at 68° C.; 5 cycles, 10 sec at 94° C., 30 sec at 58° C., 6 min at 68° C.; 5 cycles, 10 sec at 94° C., 30 sec at 58° C., 7.5 min at 68° C.; 5 cycles, 10 sec at 94° C., 30 sec at 58° C., 9 min at 68° C.; 1 cycle, 7 min at 68° C.

The resulting amplification product was reamplified in another PCR™ reaction using Vent™ DNA polymerase, the reamplified 4 kb cDNA fragment and the primers 5'-TATCCCGGGTCATATGAGTCTCCTAGCC (SEQ ID NO:30) and
5'-GGGAATTCGAGGTTCTATACATAT (SEQ ID NO:28).

Finally, the coding sequence was digested with Sma I and EcoR I and cloned into pET-21a vector.

D. Characterization of P-TEFb cDNA fragments of P-TEFb large and small subunits were amplified from the total Drosophila embryonic cDNA by using the degenerate primers derived from the peptide sequences, see Sections B and C above. Based on the cDNA fragments, the 5' end and 3' end sequences of P-TEFb cDNAs were obtained from Drosophila $K_c$ cell mRNAs using the RACE technique. The full length small subunit cDNA sequence (SEQ ID NO:1) was 1.45 kb containing an open reading frame of 1.21 kb, beginning at position 115 of SEQ ID NO:1. The large subunit cDNA (SEQ ID NO:3) was 4.33 kb with a coding region of 1.10 kb, beginning at position 716 of SEQ ID NO:3. The encoded small subunit was found to be a cyclin-dependent kinase (CDK) of 46.8 kDa (SEQ ID NO:2), while the large subunit was a cyclin of 121.1 kDa (SEQ ID NO:4). All data derived from the sequences are consistent with the identified properties of P-TEFb.

The amino acid sequence, SEQ ID NO:2, identified the small subunit of Drosophila P-TEFb as a member of the Cdc2-like cyclin dependent kinase family with over 40% identity to S. pombe Cdc2. Thus P-TEFb is a cyclin-dependent kinase (CDK) because the small subunit has all the conserved subdomains found in CDKs and the large subunit has the conserved cyclin box domain. The kinase activity of a CDK is tightly regulated by four conserved mechanisms. A CDK can be activated by the binding of a cyclin subunit and the phosphorylation of a conserved threonine residue at the T-loop in the catalytic subunit. A CDK-cyclin complex can be either inhibited by the phosphorylation of a threonine residue and a tyrosine residue at the ATP-binding site in the catalytic domain, or inactivated by the binding of a family of small proteins termed CKIs (Morgan, 1995).

Whereas the peptide sequences of catalytic subunits are well conserved in the CDK family, the sequences of cyclins are rather divergent. Almost all of the cyclin subunits contain a diverse sequence of about 100 residues called a cyclin box, which is predicted to have a conserved helix-rich secondary structure. Helical fold prediction for the cyclin box is described in Proteins 24, 1–17.

The full length cDNA of the Drosophila large subunit encodeda 1097 amino acid protein (SEQ ID NO:4). As expected the protein contained a canonical cyclin box presumably to allow binding to the small cdk subunit. The carboxyl-terminal two thirds of the protein did not reveal any specific protein motifs, however, the middle third is highly charged and likely to be somewhat unstructured, while the carboxyl-terminal third has high levels of potential helical regions suggesting that it might fold into a specific domain. Attempts to express the cDNA in E. coli, even with the small subunit, only gave insoluble truncated proteins.

However expression of both subunits in a baculovirus expression system gave rise to recombinant proteins with identical mobility to authentic P-TEFb purified from Drosophila $K_c$ cells on a silver stained SDS PAGE gel. Purification of the recombinant protein was aided by the addition of a HIS-tag to the carboxyl-terminus of the small subunit. Both subunits were quantitatively recovered on a nickel column indicating that the subunit interactions were strong. This protein had levels of DRB-sensitive CTD kinase activity indistinguishable from authentic P-TEFb and was able to functionally replace authentic P-TEFb during transcription.

Northern blotting was used to further confirm the presence of the P-TEFb mRNAs in Drosophila $K_c$ cells, embryos and female adults. A probe made from the full length of the small subunit cDNA recognizes a mRNA band around 1.7 kb. Three probes that were generated from the 3', internal, 5' cDNA sequences of the large subunit cDNA recognize an mRNA band approximately 5.3 kb in Drosophila adult females. Final wash stringency was 0.1×SSC at 68° C.

E. Expression of P-TEFb in E. coli

The full length P-TEFb cDNAs were amplified from embryonic mRNA by reverse transcription PCR™ (RT-PCR™) and cloned into a pET21a expression vector in E. coli as described above in Sections B and C. Constructs were made to express (1) the small subunit, (2) a GST-small subunit fusion protein, (3) the large subunit, and (4) the GST-large subunit fusion protein. Two other constructs were used to co-express the small subunit and the large subunit, or the small subunit and the GST-large subunit fusion protein.

Six constructs were made to express P-TEFb in E. coli using a T7 polymerase-dependent expression system. First, a GST coding sequence from pEG(KT) was used to replace the Nde I/Sal I fragment in pET21a (Novagen) to construct a GST-expression plasmid (pET21a-GST). Second, the large subunit coding sequence was digested with SmaI and EcoRI and cloned into pET21a-GST vector to construct a plasmid (pET2 I a-GST-BL) for expression of the GST-large subunit fusion protein. The small subunit coding sequence was digested at the designed Hind III site and Xho I sites and cloned into pET21a-GST vector to construct a plasmid (pET21a-GST-BS) for expression of the GST-small subunit fusion protein. Third, the GST coding sequence was removed from the pET21a-GST-BL and the pET21a-GST-BS by Nde I digestion and the recombinant vectors were religated to construct a plasmid (pET21a-BL) for expression of the large subunit and the other plasmid (pET21a-BS) for expression of the small subunit.

The final constructs were prepared by obtaining the coding region of the GST-large subunit fusion protein via the Xba I digestion of pET21a-GST-BL, and inserted into pET21a-BS to construct a plasmid (pET21a-GST-BL-BS) for the co-expression of the GST-large subunit fusion protein and the small subunit. The coding region of the large subunit was obtained by the Xba I digestion of pET21a-BL, and inserted into pET21a-BS to construct a plasmid (pET21a-BL-BS) for the co-expression of the large subunit and the small subunit.

All constructs gave rise to appropriately sized protein products when transformed into the DE3 host and induced by adding isopropylthio-beta-galactoside (IPTG); P-TEFb small subunit (43 kDa); GST-P-TEFb small subunit (73 kDa); P-TEFb large subunit (124 kDa); GST-P-TEFb large subunit (154 kDa). All proteins were insoluble when expressed alone or in combinations with both large and small subunits.

Two constructs were made to express P-TEFb in the insect cells by using a Baculovirus expression system. First, the coding region of the small subunit was obtained by the Hind III and Xho I double digestion of pET21a-GST-BS, and inserted into pBAC4X-1 (from Novagen) to construct a plasmid (pBAC4X-1-BS) for the expression of the small subunit. Second, the coding region of the large subunit was obtained by the Xma I and EcoR I double digestion of pET21a-GST-BL, and inserted into pBAC4X-1-BS to construct a plasmid (pBAC4X-1-BL-BS) for the co-expression of the large subunit and the small subunit.

The protocol for expression in Sf9 cells is as follows:
1. Linearized BaculoGold DNA and Transfer Vector:
a. DNA templates:
Linearized BaculoGold DNA (2.5 ug/25 ul)
Transfer vector containing large and small subunits of Drosophila P-TEFb pBAC4X-1-BL-BS (1 ug/ul)
b. Buffers (see Example 3, Section A.2):
Buffer A (Grace's Medium with 10% Fetal Calf Serum)
Buffer B (25 mM Hepes pH 7.1, 125 mM $CaCl_2$, 140 mM NaCl)
2. Co-Transfection:

Sf9 cells are cultured in TNM-FH medium (in suspension) to log phase. 2 million cells are placed in an T-25 flask and the cells are allowed to attach to the bottom of the flask for 30 min. The medium is removed from the flasks and 1 ml of Buffer A is added to each flask such that the buffer covers all cells. 4 ug transfer vector pBAC4X-1-BL-BS and 0.5 ug BaculoGold DNA are mixed together in a sterile tube for 5 min. 1 ml of Buffer B is added to each tube containing the DNA mixture. All of the DNA solution (now in Buffer B) is pipetted, drop-by-drop, onto the cells such that the buffer covers all cells. Minor precipitation should be visible in the flask. Cells are left undisturbed at 27° C. for 4 h. After 4 h the incubation medium is changed. The medium is removed from the transfection and control flasks. 3 ml TNM-FH+ 10% FCS is added to each flask and cells are incubate at 27° C. for ~4–5 days.

EXAMPLE 5

Human P-TEFb

A. The Small, Kinase Subunit

The human homolog of the small subunit of Drosophila P-TEFb was first identified by comparing the protein sequence derived from direct protein sequencing of the small subunit of Drosophila P-TEFb with genetic databases accessible via a BLAST genetic analysis search from the National Institutes of Health (NIH). Using the complete sequence of the Drosophila subunit obtained from translation of a full length cDNA, the inventor identified the existence of a human cDNA homologous to the Drosophila P-TEFb small subunit protein. The search of the protein database revealed a human protein, PITALRE, SEQ ID NO:6 (Grana et al., 1994), that exhibits about 72% identity and about 83% similarity to the Drosophila protein, SEQ ID NO:2. The high level of sequence similarity indicated that PITALRE is a potential homologue of the small subunit of Drosophila P-TEFb and, therefore, may be a component of human P-TEFb. Two kinases from S. cerevisiae, SGV1 (Irie et al., 1991) and CTK1 (Sterner et al., 1995), each share 43% identity with PITALRE, SEQ ID NO:6, and the small subunit of Drosophila P-TEFb, SEQ ID NO:2. Although sequence similarity does not allow the prediction of a potential yeast homologue, CTK1 has recently been demonstrated to increase the elongation efficiency of RNA polymerase II (Lee and Greenleaf, 1997).

The human protein identified was first cloned using PCR™ with degenerate oligonucleotides derived from cell division cycle 2 (CDC2) family sequences (Grana et al., 1994). This protein was called "PITALRE" because of the presence of those amino acids in a characteristic location in the kinase subunit. The initial characterization of "PITALRE" included a sequence comparison with other kinases, a northern blot showing ubiquitous expression, an immunoprecipitation study suggesting the association of other proteins with "PITALRE", and a western blot suggesting that the protein was localized in the nucleus. The highest expression of the protein was in the liver and placenta which caused the authors to speculate that "PITALRE" was involved in specialized functions in certain cell types (Grana et al., 1994). Although Grana et al. (1994) investigated the function of the protein "PITALRE" and its interaction with the tumor suppresser gene product pRB, they did not suggest that it may interact with RNA polymerase II. A later paper mapped the chromosomal location of "PITALRE" to a region found to be involved in tumors and breast cancer (Bullrich et al., 1995).

B. The Large, Cyclin-Like Subunit

The inventor realized that human P-TEFb, like the Drosophila protein, is likely to comprise at least two subunits, one a cyclin-dependent kinase (CDK) and the other containing a cyclin box domain. As the amino terminal portion of the large subunit has a cyclin box, the inventor contemplated that this portion of the large subunit interacts with the small kinase subunit. The carboxyl terminal portion of the large subunit is larger than CTDs previously found attached to cyclin boxes, leading the inventor to envision that this portion of the large subunit interacts with other factors, for example the HIV viral protein Tat.

1. Cloning of Human P-TEFb Large Subunits:

Considerable difficulty was encountered in the initial cloning of the cyclin subunits of human P-TEFb, although the ultimate success of the inventor means that this can now be routinely achieved. Intially, searches of protein sequence databases revealed no homologous proteins of the Drosophila P-TEFb large subunit. Only by searching the EST database, with the BLAST genetic analysis (National Institutes of Health), for homologues of the Drosophila P-TEFb large subunit were three, relatively short, human EST sequences, zr91f19.s1, yd48c03.r1 and nc70h05.r1, found that the inventor realized may be part of the human P-TEFb large subunit.

Without having the Drosophila large subunit sequence it would have been impossible to identify any human homologues. The EST database contains very short sequences with numerous errors. For example, high quality sequence for zr91f10.s1 stops at 214 bases; for yd48c03.r1 at 204 bases; and for nc70h05.r1 at 339 bases. Further, the EST clones often contained 5' UTR, 3' UTR or unspliced sequence that could not be compared to the Drosophila sequence. Even when the EST sequences were found to encode protein sequence similar to the Drosophila sequence, errors in the sequence caused the reading frame to be lost. Without the Drosophila sequence it would have been impossible to know whether the sequence was important or not. Each of the EST sequences does represent a human cDNA sequence, but no function was hypothesized for any of the EST sequences. Further clone distribution information for all three EST sequences can be found through either the National Center for Biotechnology Information at the National Institutes of Health of through the I.M.A.G.E. Consortium/LLNL at: www-bio.llnl.gov/bbrp/image/image-.html.

Based on the sequence from zr91f10.s1, three primers, 5'-TTCCCACCAATGCTTTCC-3' SEQ ID NO:51, 5'-CCATCAGTTGATACAGGGATCT-3' SEQ ID NO:52, and 5'-GGAATTCAGAAGGTTGTAAGATGC-3' SEQ ID NO:53 were designed and used to obtain the 5' region of a total cDNA sequence from human brain poly A+ RNA using a 5' RACE kit (Gibco). The 3' region of a total sequence was obtained by using three primers, 5'-ACACACAGATGTG-GTGAAATGTACCCA-3' SEQ ID NO:54, 5'-GCATCTTA-CAACCTTCTG-3' SEQ ID NO:55, and 5'-GGAATTCATG-GAAAGCATTGGTGGGAAT-3' SEQ ID NO:56, a brain Marathon-ready cDNA and a Marathon cDNA Amplification Kit (Clontech). The total cDNA sequence obtained was 4528 bp and termed HBL1, SEQ ID NO:43.

The total cDNA sequence, HBL1, (SEQ ID NO:43) was amplified by RT-PCR using primers 5'-CCTCCACTACTG-GTTTGCCTGG-3' SEQ ID NO:57, 5'-GGACTAG-TATAAATATGGCGTCGGGCCGTG SEQ ID NO:58, and 5'-GGAGATCTTACATGTTCATTCCTTGGG SEQ ID NO:59 and Expand polymerase under the following conditions:

| step 1 | 94° C. | 2 min |
| step 2 | 94° C. | 10 sec |
| step 3 | 65° C. | 30 sec |
| step 4 | 68° C. | 3 min |
| step 5 | Go to step 2 for 9 times | |
| step 6 | 94° C. | 10 sec |
| step 7 | 65° C. | 30 sec |
| step 8 | 68° C. | 4.5 min |
| step 9 | Go to step 6 for 4 times | |
| step 10 | 94° C. | 10 sec |
| step 11 | 65° C. | 30 sec |
| step 12 | 68° C. | 6 min |
| step 13 | Go to step 10 for 4 times | |
| step 14 | 94° C. | 10 sec |
| step 15 | 65° C. | 30 sec |
| step 16 | 68° C. | 7.5 min |
| step 17 | Go to step 14 for 4 times | |
| step 18 | 94° C. | 10 sec |
| step 19 | 65° C. | 30 sec |
| step 20 | 68° C. | 9 min |
| step 21 | Go to step 18 for 4 times | |
| step 22 | 68° C. | 7 min |
| step 23 | stop | |

Two coding sequences were amplified: HBL1-1 (2091 bp), SEQ ID NO:44, and HBL1-2 (2190 bp), SEQ ID NO:46. They were cloned in a plasmid pBAC 4X-1-HBS, which contains human P-TEFb small subunit sequence. These two sequences were also amplified by using HeLa RNA.

Based on the EST sequence of nc70h05.r1, the three primers 5'-GGAGACAAGTATGTGCTACCTTGAT-GACA-3' SEQ ID NO:60, 5'-GGAATTCGGGCTGCTC-CTCCACTTTAG-3' SEQ ID NO:61, and 5'-GGAAT-TCGCTGCTGGAGCCACAGAA-3' SEQ ID NO:62 were used to obtain the 5' region of a total cDNA sequence from human bone marrow Marathon-ready cDNA (Clontech) by using a Marathon cDNA Amplification Kit (Clontech). Using the same cDNA and RACE kit, the 3' region was obtained by using the primers 5'-GTGTCACTGAAA-GAATACCG-3' SEQ ID NO:63 and 5'-GGAATTCAGGTG-GAGATAAAGCTGC-3' SEQ ID NO:64, which were based on the EST sequence of yd48c03.r1. A total cDNA sequence was obtained and designated HBL3 (SEQ ID NO:48). According to the length of the PCR products, the whole HBL3 was 2.8 kb. The first 2.36 kb of the PCR product was sequenced. The rest of the sequence was 3' UTR and was not sequenced.

The total cDNA sequence, HBL3, (SEQ ID NO:48) was then amplified by RT-PCR using the primers 5'-GCTCTA-GATAAATATGGAGGGAGAGAGGAA-3' SEQ ID NO:65, 5'-GGAATTCTTACTTAGGAAGGGGTG-GAAGTG-3' SEQ ID NO:66, and 5'-GGAATTCTTACT-TAGGAAGGGGTGGAAGTGGTGGAGGAGGTT-3' SEQ ID NO:67 from human HeLa cell mRNA. Conditions for amplification of the large subunit using eLONGase (Life technologies) were denaturation for 30 sec at 94° C.; then 35 cycles, 20 sec at 94° C., 30 sec at 55° C., 2.2 min at 68° C.; then 5 min at 68° C. for each reaction.

A single coding sequence for HBL3 (2181 bp), SEQ ID NO:49, was amplified and cloned into a plasmid pBAC 4X-1-HBS as described previously.

2. Analysis of Human P-TEFb Large Subunit cDNAs and Proteins:

The coding sequence HBL1-1 (SEQ ID NO:44) encodes one complete protein (SEQ ID NO:45). Comparison of the cDNA sequences of HBL1 (SEQ ID NO:43) and HBL1-1 shows that the entire coding sequence HBL1-1 is contained within HBL1. The beginning of the start codon (ATG) of the encoded protein corresponds to position 1 of HBL1-1 and position 46 of HBL1, respectively. Thus, the total cDNA sequence of HBL1 includes 45 bp upstream of the start codon and 2392 bp downstream of the stop codon (TAA). Interestingly, HBL1-2 (SEQ ID NO:46) contains an 99 bp intron which is not present in either HBL1 (SEQ ID NO:43) or HBL1-1 (SEQ ID NO:44) but is in-frame and can be translated. This 99 bp intron begins at position 1927 and ends at position 2025 of coding sequence HBL1-2 (SEQ ID NO:46). If the 99 bp intron of HBL1-2 is excluded then HBL1-1 and HBL1-2 are identical.

The coding sequence of HBL3 (SEQ ID NO:49) encodes a different protein which is completely contained with the total cDNA sequence of HBL3 (SEQ ID NO:48). The beginning of the start codon (ATG) of the encoded protein corresponds to position 1 of the coding sequence of HBL3 (SEQ ID NO:49) and position 45 of the total cDNA sequence of HBL3 (SEQ ID NO:48), respectively. Thus, the total cDNA sequence of HBL3 includes 44 bp upstream of the start codon and 135 bp downstream of the stop codon (TAA).

Comparison of the total cDNA sequences, HBL1 (SEQ ID NO:43) and HBL3 (SEQ ID NO:48), revealed that the EST sequence zr91f10.s1 was homologous to a small region of HBL1 and a perfect match to the compliment of positions 603–665 of SEQ ID NO:43. It is noteworthy that only 50 bp of the Drosophila large subunit sequence is homologous to this same EST sequence zr91f10.s1. Whereas, the EST sequences nc70h05.r1 and yd48c03.r1 were homologous to HBL3 and near perfect matches to positions 210–417 and 750–884, respectively, of SEQ ID NO:48.

Comparison of the encoded proteins showed that the proteins encoded by HBL1-1 and HBL1-2, SEQ ID NO:45 and SEQ ID NO:47, respectively, are identical except for a 33 bp contiguous stretch which is encoded by the intron in HBL1-2. Comparison of the protein encoded by HBL1-1, SEQ ID NO:45, and the protein encoded by HBL3, SEQ ID NO:50, shows that the two human proteins share an overall absolute identity of 54% and an overall relative similarity of 70%. Within the region defined as the cyclin box, positions 1–252 of HBL1-1 and positions 1–253 of HBL3, the two proteins share an identity of about 81% to each other.

Downstream of the cyclin box, the two proteins, SEQ ID NO:45 and SEQ ID NO:50, are about 46% identical to each other.

When compared to the Drosophila large subunit protein, SEQ ID NO:4, both human proteins have an identity of about 65% to the Drosophila cyclin domain box (positions 1–280 of SEQ ID NO:4). The two human proteins were 81% similar to each other in this same region. However, downstream of the cyclin box, the two human proteins are only about 25% identical to the Drosophila protein. Overall, the Drosophila large subunit is about 42% identical to the protein encoded by HBL1-1 (SEQ ID NO:45) and 34% identical the protein encoded by HBL3 (SEQ ID NO:50).

As was seen for the Drosophila large subunit the amino-terminal domain contained a cyclin box that was 65% identical to the Drosophila protein. The two human proteins were 81% similar in this region. Both potential human proteins lacked the highly charged, unstructured central region, but had a slight similarity (25% identity) to the carboxyl-terminal domain. Western blotting with antibodies to each of the two proteins that were expressed in E. coli are used to determine the size of both encoded proteins. The two cyclin subunits were co-expressed with a HIS-tagged human kinase subunit (PITALRE) in a baculovirus system. As was found for Drosophila P-TEFb the large subunit was quantitatively recovered after nickel column chromatography indicating that subunit interactions are strong. In contrast to PITALRE alone, both kinase/cyclin pairs (PITALRE/HBL1-1 and PITALRE/HBL3) gave rise to very strong DRB sensitive phosphorylation of the CTD of RNA polymerase II. This clearly indicates that human P-TEFb is a cyclin dependent kinase, since the activity of PITALRE was stimulated approximately 100 fold by the cyclin subunit. The two subunit protein obtained after expressing HBL1-1 large subunit with PITALRE was able to function in transcription when added back to a Drosophila nuclear extract depleted of P-TEFb using anti large subunit antibodies. Although it is not clear if HBL1-1 encodes the proper length protein, HBL3 encodes a protein with identical mobility to the 87 kDa protein found in PITALRE immunoprecipitates. This is confirmed by using antibodies for the human proteins and western blot analysis. It is likely that antibodies against the protein encoded by HBL3 react with the 87 kDa band seen in PITALRE immunoprecipitates.

3. Expression of Human P-TEFb:

The coding regions for HBL1-1, HBL1-2 and HBL3 were individually expressed in a Baculovirus expression system (PharmMingen, San Diego Calif.) along with the HIS-tagged small subunit "PITALRE". A nickel column was used to purify the "PITALRE" from the cytoplasm of infected Sf9 cells. The "PITALRE" was found to associate with each respective putative large subunit protein, and thus indicates that the cyclin domain of each protein can interact with the kinase subunit.

Using the CTD Kinase assay, as previously described in Example 2, Section A.7, both HBL1-1 (SEQ ID NO:45), HBL2(SEQ ID NO:47) and HBL3 (SEQ ID NO:50) were substituted for the large subunit in the Drosophila transcription system. The activity of each recombinant protein is shown in Table 1. Alone "PITARLE" has little kinase activity and no detectable activity in transcription. Thus, these data demonstrate that the proteins encoded by HBL1-1, HBL1-2 and HBL3 can functionally act as the P-TEFb large subunit in Drosophila and likely act in a homologous manner in humans.

TABLE 1

Recombinant proteins expressed in vitro using a kinase assay and a HIS-tagged small subunit.

| Subunits | Complex formed? | Kinase activity | Transcription activity |
| --- | --- | --- | --- |
| DBS | — | very little | none |
| HBS | — | very little | none |
| DBS + DBL | yes | high | high |
| HBS + DBS | no | — | — |
| HBS + HBL1 | yes | high | high |
| HBS + HBL2 | yes | ND | ND |
| HBS + HBL3 | yes | high | ND |

D is Drosophila, H is human, BS is P-TEFb small subunit, BL is P-TEFb large subunit, ND is not determined. If the large subunit was recovered along with the HIS-tagged small subunit from the nickel column it was assumed that a complex was formed. The kinase assay used RNA polymerase II as a substrate and transcription activity was determined by adding the recombinant protein into a Drosophila extract depleted of P-TEFb using antibodies against the large subunit.

4. Tissue Distribution of Expression of Human P-TEFb Subunits.

The expression of mRNAs encoding PITALRE and the two human cyclin subunit clones was examined across a wide variety of human tissues using northern blot analyses. All three were ubiquitously expressed. This is consistent with a general requirement for P-TEFb in all tissues. mRNAs encoding both cyclin subunits were present is all tissues suggesting that a tissue specific role for one of the subunits is not likely.

5. Reconstitution of Tat Transactivation with RecombinantHhuman P-TEFb.

Figure 6:
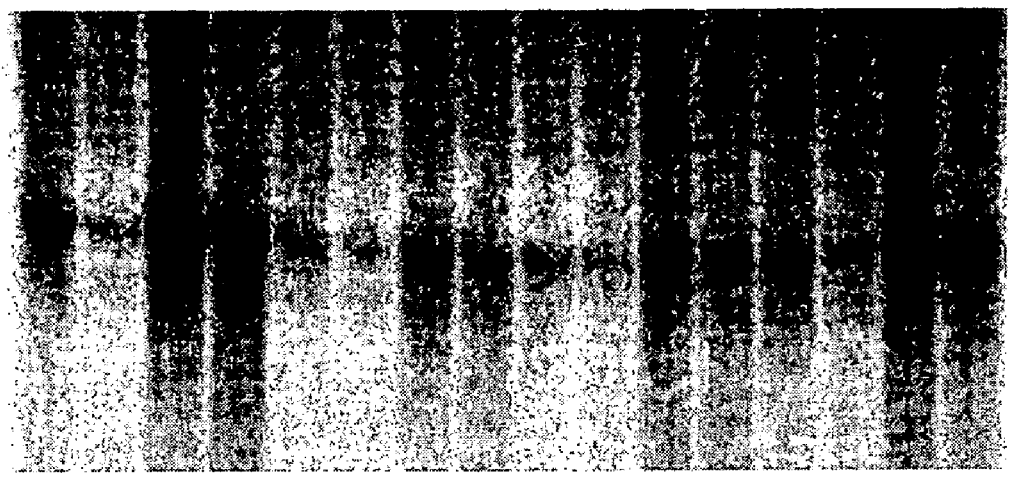
FIG. 6. Transcription reactions utilized either control depleted HeLa nuclear extract (cHNE), or PITALRE depleted extract (dHNE). Baculovirus produced recombinant human P-TEFb comprised of PITALRE and cyclin HBL1-1 (rhP-TEFb) was added to reactions as indicated.

To confirm that the recombinant human P-TEFb comprised of PITALRE and cyclin HBL1-1 could reconstitute Tat transactivation, an add back study was performed on HeLa extracts depleted of PITALRE and, therefore, depleted of P-TEFb. Conditions were as described in Example 6. FIG. 6 shows that Tat was able to stimulate the DRB sensitive runoff transcript from the HIV-LTR.

6. Generation of an Inducible PITALRE Kinase Knockout HeLa Cell Line.

A tetracycline inducible HIS-tagged PITALRE kinase knockout (D167N) expression vector was constructed and stably transfected Tet-on HeLa cells using co-transfection with a hygromycin expression plasmid. Cell lines were selected in the presence of hygromycin, but in the absence of doxycyclin. Several lines were obtained that exhibited doxycyclin induced expression of a protein with slightly lower mobility than PITALRE that reacted with anti-PITALRE antibodies. A time course indicated that after 30 hrs of induction maximal levels of the inactivated PITALRE were produced. The level of the induced PITALRE mutant was equal to the level of endogenous PITALRE as analyzed by SDS PAGE followed by immunoblotting with anti-PITALRE antibodies. A cell line that expressed a great excess of transfected PITALRE was not obtained, suggesting that the levels of PITALRE may be controlled by post-transcriptional mechanisms.

7. Optional Purification of Human P-TEFb:

Purification of human P-TEFb is simplified by the use of antibodies that detect the small subunit of P-TEFb. The inventor has generated rabbit polyclonal antibodies that react with the small subunit of P-TEFb. These antibodies were raised against a recombinant human P-TEFb small subunit. A cDNA encoding the human P-TEFb small subunit was amplified from human cDNA using PCR™ primers designed from the human cDNA sequence found in the database. The cDNA was cloned in a pET expression plasmid and the resulting plasmid was expressed in DE3 cells. The recombinant protein was purified under denaturing conditions and subsequently used to inoculate rabbits. The antibodies were generated using standard techniques (Pocono Rabbit Farm).

On western blots the antibodies strongly recognize the bacterially produced human protein and a 42 kDa protein in HeLa nuclear extracts. The inventor has analyzed HeLa extracts that have functionally different levels of P-TEFb activity and has found that the differences correlate with the level of the 42 kDa protein present in the extracts. Immunoprecipitation and immunodepletion studies are useful in showing that functional human P-TEFb (transcriptional activity and CTD kinase activity) is recognized by the antibodies.

Purification of human P-TEFb from HeLa cell nuclear extract is carried out by using standard methods, essentially as described in Examples 1 and 2 and Marshall and Price (1995). P-TEFb is assayed after each step of the purification using a western blot. Evidence already shows that the purification of human P-TEFb is achievable using methods similar to those used for the purification of the *Drosophila* protein. Chromatography on phosphocellulose was carried out and it was found that P-TEFb eluted in the high salt fractions. The inventor's results are consistent with the existence of more than one chromatographic form of P-TEFb. Further purification is achievable using chromatography on phenyl-sepherose, Mono Q™, Mono S™ and hydroxylapitite.

Although the data is consistent with the existence of multiple forms of the human large subunit, the form or forms isolated in the 42 kDa HeLa extracts correlate with P-TEFb activity.

EXAMPLE 6

P-TEFb is the Tat-Associated Kinase

As P-TEFb is sensitive to DRB which is canonically a kinase inhibitor, it was clear that P-TEFb is a kinase (Marshall and Price, 1995; Example 1). Although likely targets for a transcription factor kinase that acts early during elongation would be RNA polymerase II or a basal initiation factor such as TFIIF, there is no obvious similarity between kinases known to be involved in transcription regulation and the subunit composition of P-TEFb (Marshall and Price, 1995). Therefore it is a surprising discovery that P-TEFb is essential for the HIV viral protein Tat to activate elongation of the viral RNA genome. This finding is particularly surprising in that it was earlier reported that the TAK protein appear to be most similar to factor 2 or P-TEFa, not P-TEFb (Marshall and Price, 1995).

Tat is a viral protein that acts as an activator of transcription of the HIV viral transcription unit. It binds to short nascent HIV transcripts and causes RNA polymerase II to synthesize mRNA sized transcripts. It was hypothesized by several investigators that Tat might enhance the action of RNA polymerase II CTD kinases and that this might have a positive effect on the elongation potential of the polymerase. An interaction between Tat and a CTD kinase has been demonstrated using immobilized Tat and HeLa nuclear extract (Yang, et al., 1996). The human immunodeficiency virus Tat proteins specifically associate with TAK in vivo and require the CTD of RNA polymerase II for function. This TAK protein is sensitive to DRB, but has not been purified or otherwise identified and has not been shown to be required for Tat transactivation.

Similar studies to the immediately preceding were performed using the 48 amino acid transactivation domain of Tat (Tat 48Δ) fused to GST (GST-Tat) and coupled to glutathione beads. HeLa extracts were incubated with the beads and then the beads were extensively washed. The proteins that were bound were eluted with SDS and heat and analyzed on a gradient protein gel. Silver staining indicated that less than 1% of the HeLa proteins bound, but a significant portion of the human P-TEFb was bound as detected by western blotting using antibodies against the small subunit of human P-TEFb.

A. Methods

1. Tat Proteins:

GST-Tat 1 48Δ and GST-Tat 1 48Δ P181S in the pGEX2T vector (Pharmacia) were obtained from the AIDS Research and Reference Reagent Program (NIH) and expressed in *E. coli*. 500 ml cultures were induced and the crude lysates obtained after using the French press were analyzed on silver stained SDSPAGE gels. Roughly equal levels of the 35 kDa proteins were expressed (1 mg/ml of lysate).

2. Binding Assays:

25 µl of glutathione beads were washed 4 times with 200 µl EBC (50 mM Tris, pH 8, 150 mM NaCl, 0.5% NP-40) and then incubated with 100 µl of an *E. coli* lysate containing GST expressed from a pET21 vector (see Example 4). To pre-clear the extract the GST beads were washed 4 times with EBC and then incubated for 3 h. at 4° C. with 100 µl of HeLa nuclear extract that had been spun at 15,000 rpm for 5 min. 5 µl of glutathione beads (10 µl of 50% slurry) was transferred to a yellow pipet tip plugged with glass wool and then washed with 400 µl EBC+5 mM DTT. 5 µl of *E. coli* lysate containing either GST-Tat 1 48A or GST-Tat 1 48Δ P181S (controls were done with no bound protein and with GST alone) and 50 µl EBC+5 mM DTT was allowed to slowly flow over the beads 4 times. The beads were then washed with 200 µl EBC+5 mM DTT+0.075% SDS and then 100 µl EBC+5 mM DTT. 15 µl pre-cleared HeLa nuclear extract was passed over the tip 6 times. The beads were then washed with 900 µl EBC+5 mM DTT+0.03% SDS. 20 µl of protein gel loading buffer was added and the tip boiled for 4 min. 10% of the eluted proteins were analyzed on a 6–15% polyacrylamide SDS protein gel by silver staining and 90% of the sample was run on a similar gel and blotted to nitrocellulose. The blot was probed with a 1:1000 dilution of anti-human P-TEFb antisera followed by 1:20,000 dilution of the secondary antibody. Reacting proteins were detected using a ECL detection kit.

3. In Vitro Transcription Conditions

One preferred method to examine the functional interaction between Tat and P-TEFb is to first develop a P-TEFb-dependent human in vitro transcription system and then examine the function of Tat with and without added purified human P-TEFb. The P-TEFb-dependent system can be obtained in any of three ways.

First since human P-TEFb has similar chromatographic properties to *Drosophila* P-TEFb, it is possible to remove the factor by passing extracts through phosphocellulose at 0.4 M HGKEDP as was done for the *Drosophila* extracts (Marshall and Price, 1995; Example 1). The HeLa-FT (flowthrough) fraction contains much less P-TEFb and is dependent on added P-TEFb to obtain DRB-sensitive transcription.

The second method uses is based on antibody depletion. Purified IgGs from the rabbit anti-P-TEFb serum are covalently coupled to Affigel (BioRad). The IgG beads are washed thoroughly with PBS and then incubated at room temperature with HeLa nuclear extract. The beads are then removed by centrifugation or filtration and the resulting extract is examined for a reduction in DRB-sensitive transcription. The third method uses a more defined in vitro transcription system in which pure or partially pure transcription factors are mixed together. The first two methods result in an extract that has greatly reduced levels of P-TEFb and in the third method one of the required fractions would be P-TEFb.

In all cases the depleted extracts or fractions not containing P-TEFb are examined for their ability to allow Tat transactivation. A pulse-chase or continuous labeling protocol is used in which the template DNA is preincubated with the extract, 20 mM HEPES, pH 7.6 and 7 mM $MgCl_2$ for 20 min at 30° C. For the pulse chase protocol nucleotides, including [$\alpha$-$^{32}$P]CTP, are added to start the pulse; 2 min later, excess cold CTP is added to initiate the chase. Reactions are stopped after various chase times. During the pulse, 10 µl reaction mixtures contain the following:

20 mM HEPES (pH 7.6), 7 mM $MgCl_2$, 600 µM each GTP, UTP and ATP, 5 µCi of [$\alpha$-$^{32}$P]CTP (~1 µM CTP), 66 mM KCl, 10–40 µg/ml DNA template, and 3 µl of HeLa-FT or HeLa nuclear extract as a control.

For the chase, unlabeled CTP was added to bring the total concentration of CTP to 1.2 mM and the final reaction volume to 12 µl. Human P-TEFb and Tat are added to the preincubation mixture where appropriate. For the continuous labeling protocol the pulse mix is supplemented with 30 µM CTP and the reactions are allowed to continue for 20 min with all combinations of inclusion of tat and P-TEFb. Reactions are stopped by adding 200 µl of stop solution (1% Sarkosyl, 50 mM Tris, pH 8.0, 50 mM EDTA, 100 mM NaCl and 100 µg/ml tRNA). The reaction mixtures are phenol extracted and the nucleic acids were ethanol precipitated, washed with 70% ethanol, dried and analyzed by gel electrophoresis.

To correlate the inhibition of binding to the inhibition of Tat transactivation, reactions would be supplemented with increasing concentrations of candidate small compounds or proteins. The inhibition would be quantitated by measuring the amount of runoff transcript or the amount of bound P-TEFb and activity plotted versus the amount of the inhibitor. 50% inhibition points would be determined and compared in the two assays. If inhibition was similar for a given compound in both assays it would be concluded that the compound functioned by inhibiting the interaction of P-TEFb with tat.

B. Results

Control studies indicated that P-TEFb binding was specific. A GST-Tat protein containing a single amino acid change in the activation domain that causes Tat to lose its ability to transactivate in vivo did not bind P-TEFb. Other controls, glutathione beads alone or beads with GST only, also did not bind P-TEFb. These results indicate that P-TEFb is the CTD kinase that binds to Tat. The ability of tat to increase the elongation potential of RNA polymerase II can now be explained through its interaction with P-TEFb.

Further conformation that the Tat/P-TEFb interaction is important is obtained by determining that human P-TEFb is one of the factors required for reconstructing tat transactivation in vitro. A protein blot containing all the required factors is probed with the human P-TEFb small subunit antibodies to determine which fraction contains P-TEFb. Since it is known that the human P-TEFb elutes in the high salt step from phosphocellulose, required factors from that region are likely candidates. Confirmation of the Tat/P-TEFb interaction is obtained by correlating results with inhibitors of the binding assay (microtitre plate assay) with the in vitro transcription assays.

EXAMPLE 7

P-TEFb is Required for HIV-1 Tat Transactivation In Vitro

A. Generation of Antibodies of PITALRE

PITALRE-CT antibodies were affinity-purified rabbit IgG directed to the C-terminal 20 amino acids of PITALRE (Santa Cruz Biotechnology). Antibodies against the whole PITALRE were generated using purified recombinant protein as antigen. First two primers 5'-pGCAGGATCCA-GAATTCCATATGGCAAAGCAGTACGACTCGG-3' (SEQ ID NO:41) and 5'-pCAGTACTCGAGTTATCAGAA-GACGCGCTCAAAC-3' (SEQ ID NO:42) were used in a PCR™ reaction to amplify the cDNA of human P-TEFb small subunit. The human brain cDNA mix (Clontech Co.) was used as template. The PCR™ product was digested with Eco RI and Xho I. The resulting 1.1 kb fragment was purified using Qiagen Gel Extraction Kit™ (Qiagen Co.). pET21a (Novagen Co.) was digested with Eco RI and Xho I. The resulting 5.4 kb fragment was purified using Qiagen Gel Extraction kit™ (Qiagen Co.). The 1.1 kb fragment and 5.4 kb fragment were ligated by using T4 DNA ligase. After amplification, the cloned vector was digested with Nde I and the larger fragment (6.5 kb) was purified using Qiagen Gel Extraction kit™ (Qiagen Co.) and religated. The final vector was amplified and transformed into DE3 (BL21) competent cells for expression of human P-TEFb small subunit.

The transformed DE3 cells were grown to $OD_{600}$=0.6 and induced with 1 mM IPTG. After a 3 hour induction, the cells were collected and lysed by passing through a French press three times. The lysate was subjected to centrifugation at 15,000×g for 30 minutes. The pellet was solubilized in 0.1 M TUS (20 mM Tris, pH7.5, 0.1 M NaCl and 7M Urea) and loaded onto a Mono Q™ column (Pharmacia Co.). The flow through (FT) fraction of the Mono Q™ column was loaded onto a Mono S™ column (Pharmacia Co.). The flow-through fraction of the Mono S™ column was subjected to dialysis against Phosphate buffer (20 mM phosphate, pH7.0). The dialyzed solution was centrifuged at 15,000×g for 30 minutes. The pellet was suspended in Phosphate Buffer (20 mM phosphate, pH7.0) and used to generate rabbit antibodies following standard protocols (Pocono Rabbit Farm and Laboratory, Inc.). Preimmune serum was obtained before injection of antigen (the human P-TEFb small subunit) into the rabbit. Test bleeding was performed 42 days after the first injection of the antigen and antisera were generated monthly after the test bleeding.

B. Immunodepletion of Human P-TEFb

Immunodepletion was performed by passing Protein A Sepharose-precleared HNE (in 20 mM HEPES, pH 7.6, 15% glycerol, 165 mM KCl, 0.1 mM EDTA, 1 mM DTT, 0.1 mM PMSF) through two affinity columns made with Protein A Sepharose beads pre-bound with anti-PITALRE-CT antibodies or control IgGs (affinity-purified rabbit anti-goat IgG. Sigma). For every 50 µl of HNE, 10 µl of protein A beads containing 1 µg of bound IgG was used. After depletion of HNE, the antibody-containing beads were extensively washed with 100 times the bead volume of 20 mM HEPES (pH 7.6), 0.5% NP-40, 1% Triton X-100, and 5 mM DTT, 600 mM or indicated concentration of NaCl, and then washed with 25 times the bead volume of 20 mM HEPES (pH 7.6) and 1 mM DTT. The amounts of the washed beads used for the kinase assays and silver staining were the equivalent of 1 µl and 10 µl of HNE, respectively.

C. CTD Kinase Assay

CTD kinase assays were performed in a 20 µl reaction containing 20 mM HEPES (pH7.6), 10 µM ATP, 5 µCi [γ-$^{32}$P]ATP, 10 ng *Drosophila* RNA polymerase II, 5 mM MgCl$_2$, and purified *Drosophila* P-TEFb or immunoprecipitated human P-TEFb. In the reactions containing DRB it was added to 50 µM unless other indicated amounts were used. The reactions were incubated at 30° C. for 1 hour.

D. TAK Activity Assay

Preparation of Tat fusion proteins and the TAK pull-down assay were conducted as described by Herrmann and Rice (Herrmann and Rice, 1993; 1995) with modifications as described. Nuclear extract, cytoplasmic extract, or fractions containing partially purified TAK were incubated with glutathione-Sepharose beads containing GST-Tat fusion proteins for 1 hour at 4° C. with gentle rocking. DE3 (BL21) bacteria containing the GST-Tat expression vectors were obtained from NIH AIDS Research and Reference Reagent Program. For maximum sensitivity, GST-Tat48Δ was used unless otherwise specified. The beads (30 µl, 50% slurry) were washed 6 to 8 times with 1 ml EBCD buffer (50 mM Tris, pH 8.0, 120 mM NaCl, 0.5% Nonidet P-40, and 5 mM DTT) containing 0.03% SDS, then 2 to 4 times with Tat kinase buffer (TKB/Mg: 50 mM Tris-HCl, pH 7.6, 5 mM DTT, 5 mM MnCl$_2$, and 4 mM MgCl$_2$), and brought to 50 µl with TKB/Mg buffer and kinase assay mix. The final reaction contained 2 µM ATP, 10 µCi γ-$^{32}$P-ATP (ICN, 3000 Ci/mmole), and 50–100 µM of CTD trimer peptide CTD3 (ACSYSPTSPSYSPTSPSYSPTSPSKK, SEQ ID NO:68). Reactions were incubated at 25° C. for 40 minutes, stopped by boiling in Laemmli sample buffer, and resolved by electrophoresis in 15% polyacrylamide: bis-acrylamide (30%:0.15%) gels.

E. Partial Purification of TAK

TAK was partially purified from a HeLa cell cytoplasmic fraction (2.6 gm protein) prepared according to Ausubel et al. (Ausubel et al., 1989) except that dialysis was omitted. Proteins precipitating between 10% and 40% saturation of ammonium sulfate (816 mg) were resuspended in DEAE buffer (25 mM HEPES, pH 7.6, 150 mM KCl, 0.1 mM EDTA, 1 mM DTT, 0.1 mM PMSF, 4 mM MgCl$_2$, protease inhibitors aprotinin, leupeptin, pepstatin A at 1 µg/ml each, and 10% glycerol), dialyzed against the same buffer, and applied to a 230 ml DEAE-Sepharose column equilibrated in DEAE buffer. The flow-through fraction (350 mg protein) was concentrated by 50% ammonium sulfate precipitation. The proteins were resuspended in HE buffer (same as DEAE buffer except 25 mM HEPES, pH 6.9, and 100 mM KCl were used) and loaded onto a perfusion chromatography heparin affinity column (POROS 20 HE; PerSeptive Biosystems). The column was washed with the same buffer and proteins were eluted with a linear gradient of 100–500 mM KCl in 15 column volumes of HE buffer. TAK activity eluted from 200 mM to 250 mM KCl. Active fractions were diluted with an equal volume of the same buffer except that the pH was 8.0 and KCl was omitted, and loaded onto a perfusion chromatography cation exchange column (POROS 20 SP; PerSeptive Biosystems). The column was washed with SP buffer (the same as HE buffer except that the buffer was 25 mM HEPES pH 7.5) and eluted with a linear gradient of 100–500 mM KCl in 15 column volumes of SP buffer. The active fractions (1 mg protein) eluted at ~300 mM KCl.

F. Transcription Assay

The transcription template (Nco I-digested pLTR-4/CAT vector containing the HIV-1 LTR from −153 to +80) was used in a pulse-chase transcription experiment. Reactions (12 µl total; 20 mM HEPES, pH 7.6, 7 mM MgCl$_2$, 20 µg/ml DNA template, 3 µl HNE, 64 mM KCl, with 50 µM DRB or 0.3 µl *Drosophila* P-TEFb (Marshall et al., 1996) as indicated) were pre-incubated for 20 minutes at 30° C., pulsed for 2 minutes by adding ATP, GTP, UTP to 600 µM each and 5 µCi [α-$^{32}$P]CTP (~0.1 mM), and chased for 5 minutes by adding CTP to 1.2 mM. Reactions were stopped, phenol extracted and analyzed on a 6% polyacrylamide gel as described (Marshall and Price, 1995). pLTR-TAR-Luc and pLTR-DTAR-Luc plasmids were digested with Eco RI to generate TAR and DTAR template that were used in the studies. The TAR template contains HIV-1 LTR from −475 to +76, while the DTAR template contains HIV-1 LTR from −475 to +19. Transcription with TAR and DTAR templates generates runoffs of 694 and 646 nucleotides, respectively. The transcription reaction mix contained 20 mM HEPES (pH7.6), 7 mM MgCl$_2$, 60 mM KCl, 0.5 µl HNE (or depHNE as indicated), 20 µg/ml TAR template (or DTAR template as indicated), indicated amount of HIV-1 Tat (86 residue HIV-1 Tat followed by a streptavidin binding tag at its carboxyl terminus) and DRB. The reaction mix was pre-incubated for 15 minutes at 30° C. and the transcription was started by adding nucleotides to final concentrations of 50 µM ATP, 50 µM GTP, 50 µM UTP, 10 µM CTP, and 5 µCi [α-$^{32}$P]CTP (~0.1 mM), and continuously labeled for 20 minutes, or by adding nucleotides to final concentrations of 50 µM ATP, 50 µM GTP, 50 µM UTP, and 5 µCi [α-$^{32}$P]CTP (~0.1 mM), and pulsed for 2 minutes. The reactions were stopped and reaction mix were phenol-extracted. The transcripts were then analyzed on a 6% polyacrylamide gel as described (Marshall and Price, 1995).

G. PITALRE is a Component of Human P-TEFb

According to the present discovery, if PITALRE is the functional homologue of the small subunit of *Drosophila* P-TEFb. Therefore, removal of PITALRE from HeLa nuclear extract (HNE) should eliminate DRB-sensitive run-off transcripts. To confirm this, PITALRE was immunodepleted from HNE with antibodies directed against the last 20 amino acids of PITALRE which are not shared with other known kinases. Western blot analysis indicated that PITALRE was removed by anti-PITALRE antibodies to levels below detection, but not by control antibodies. The depleted HNE was unable to generate DRB-sensitive 633-nt run-off transcripts from an HIV-1 LTR template in a pulse/chase transcription reaction. Addition of pure *Drosophila* P-TEFb to the depleted extract restored DRB-sensitive transcription. These results indicate that depletion of PITALRE abolished human P-TEFb activity, supporting the hypothesis that PITALRE is a component of human P-TEFb.

PITALRE was not previously known to be a CTD kinase. Therefore, the material immunoprecipitated was examined during the depletion of HNE for CTD kinase activity. The antibody-loaded beads containing PITALRE were washed extensively with high salt and subjected to a CTD kinase assay. Similar to *Drosophila* P-TEFb, beads containing PITALRE (together with any other strongly associated proteins) were able to convert the largest subunit of *Drosophila* RNA polymerase II to the hyperphosphorylated IIo form.

Control beads were inactive. As expected, all phosphorylation was sensitive to 50 mM DRB. In the control reaction with Drosophila P-TEFb autophosphorylation of both subunits (43 and 124 kDa) was seen. In the reaction with beads containing PITALRE antibodies, the 40-kDa PITALRE, a band of similar size to the large subunit of Drosophila P-TEFb and several other bands were phosphorylated.

To examine the association of other proteins with PITALRE, immunoprecipitates were washed with buffer containing non-ionic detergents and increasing amounts of salt. The proteins associated with the beads were analyzed by SDS polyacrylamide gel electrophoresis followed by silver staining. When no salt was present many proteins were retained on the beads. Most of these proteins were removed by washing with 200 mM NaCl. No changes occurred in the proteins visible after a wash with buffer containing NaCl higher than 400 mM. Besides immunoglobulin heavy and light chain and PITALRE (40 kDa), proteins with sizes 87, 105, 133, and 140 kDa were found. When rabbit anti-goat IgG control beads were used no other proteins except for the immunoglobulins were seen after high salt washes. The immunoprecipitates were incubated with [$\gamma$-$^{32}$P]-ATP to determine which proteins became phosphorylated. The beads washed without salt carried out extensive phosphorylation of many protein substrates with little DRB-sensitivity. After washing with 400 mM or higher concentration of NaCl, only a few proteins were labeled and all phosphorylation was DRB-sensitive. Of the major proteins associated with PITALRE only the 105 kDa protein was not phosphorylated. At all salt concentrations the partially DRB-sensitive phosphorylation of a 207 kDa protein was observed. Except for PITALRE the identity of the other proteins is unknown. The sizes of these proteins do not correlate with subunits of other known basal transcription factors. The other proteins could be constituents of a larger complex containing P-TEFb or different complexes containing PITALRE.

Figures 7A, 7B:
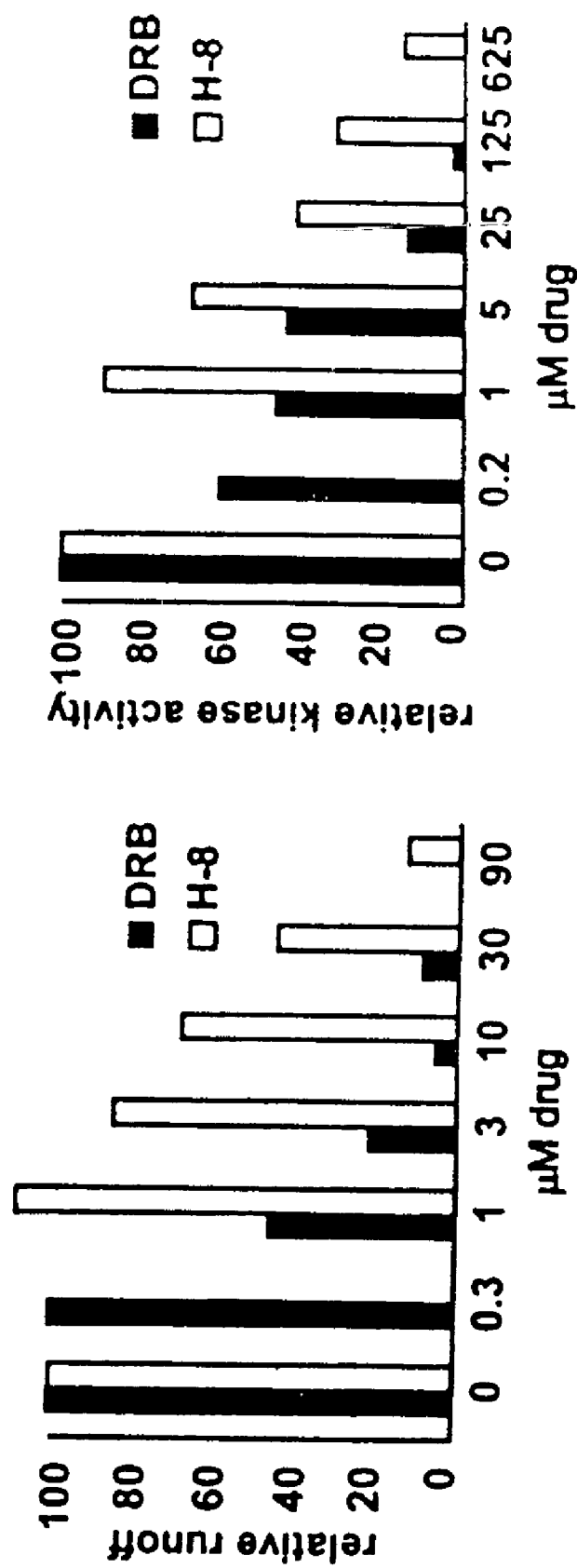
FIG. 7A and FIG. 7B. DRB and H-8 inhibition of transcription and human P-TEFb activity. Plot of radioactivity in runoff or pol IIo after quantitation using a Packard InstantImager and normalization to the starting amount (100).

A distinguishing characteristic of P-TEFb is its sensitivity to the kinase inhibitors DRB and H-8. In vitro transcription and the CTD kinase activity of Drosophila P-TEFb are both inhibited by these two compounds and in both assays DRB is 10 fold more potent than H-8 (Marshall and Price, 1995; Marshall et al., 1996). The effect of DRB and H-8 were determined on transcription in the HNE (FIG. 7A) and on kinase assays using the immunoprecipitated human P-TEFb (FIG. 7B). In both assays DRB was the more effective inhibitor. DRB and H8 compete with ATP for binding to the kinase active site and, therefore, it is inappropriate to compare directly the 50% inhibition points under different conditions, especially if different concentrations of ATP are used (Marshall et al., 1996). However the ratio of 50% points for different compounds under identical conditions can be compared. This ratio is more likely to be independent of assay condition. The ratio of 50% inhibition points (H-8/DRB) was 23 µM/1 µM=23 for the transcription assay and 16 µM/0.65 µM=25 for the CTD kinase assay. These ratios were similar to each other suggesting that the same kinase, namely human P-TEFb, was inhibited in both assays. Considering the sequence similarity between the small subunit of Drosophila P-TEFb and PITALRE, the functional similarity between Drosophila P-TEFb and the activity removed from HNE by PITALRE antibodies, and the presence of other potential subunits in the immunoprecipitates, the inventor concluded that PITALRE is a component of human P-TEFb.

H. P-TEFb Specifically Associates with the Activation Domain of HIV Tat

Several lines of evidence led the inventor to believe that P-TEFb associates with the viral transactivator Tat. Tat transactivation is sensitive to DRB (Braddock et al., 1991; Marciniak and Sharp, 1991) and requires the CTD (Chun and Jeang, 1996; Parada and Roeder, 1996; Yang et al., 1996), and Tat associates with a DRB sensitive CTD kinase (TAK) (Herrmann and Rice, 1993; Herrmann and Rice, 1995; Chun and Jeang, 1996; Yang et al., 1996). The hypothesis was tested by ascertaining if the human P-TEFb kinase associates with Tat during incubation with HeLa extracts. Glutathione beads containing various GST-Tat fusion proteins were incubated with HeLa extract and extensively washed. Proteins associated with Tat constructs containing an intact activation domain (Tat72 and Tat48D) were able to phosphorylate the synthetic peptide, CTD3, as well as RNA polymerase II. GST-Tat fusions containing mutations in the activation domain that abolish Tat-transactivation (Herrmann and Rice, 1995; Rice and Carlotti, 1990) were not able to pull down TAK. The proteins associated with the Tat constructs were probed with anti-PITALRE antibody by western blot analysis. PITALRE was detected only when the constructs contained an intact Tat-transactivation domain. This indicates that P-TEFb is a Tat associated CTD kinase.

When human P-TEFb was depleted from HNE by antibodies to PITALRE, TAK activity (assayed by GST-Tat48A pull-down) was reduced to less than 2% of that found in the intact extract. This strongly suggests that under the conditions used human P-TEFb is the predominant CTD kinase that associates with Tat. Others have shown that TFIIH can associate with Tat (Parada and Roeder, 1996; Garcia-Martinez et al., 1997b), but under the conditions used no p62 subunit of TFIIH was detected as being bound to Tat nor did the inventor detect a reduction in the amount of the subunit in the PITALRE-depleted extract. In addition, when glutathione beads containing TAK were probed with antibodies to all three subunits of CAK (CDK7, cyclin H, MAT1; supplied by D Morgan) no evidence of the TFIIH associated kinase was found.

To further confirm that human P-TEFb can associate with Tat, TAK was partially purified from HeLa cells by sequential chromatography on DEAE, Heparin and SP resins. Fractions eluted from the second and third columns, Heparin and SP, were assayed for TAK activity and probed for human P-TEFb. In the eluate of both columns, TAK activity assayed by GST-Tat48D pull-down correlated with P-TEFb determined by western analysis using two different preparations of PITALRE antibodies. A GST construct with a mutation in the Tat activation domain did not become associated with CTD kinase activity when incubated with the same column fractions. In addition, the drug-sensitivity of TAK and human P-TEFb were compared. As expected, TAK activity was inhibited by DRB and H-8 in a manner similar to P-TEFb.

I. Human P-TEFb is Required for Tat-Stimulated Elongation

Figure 8:
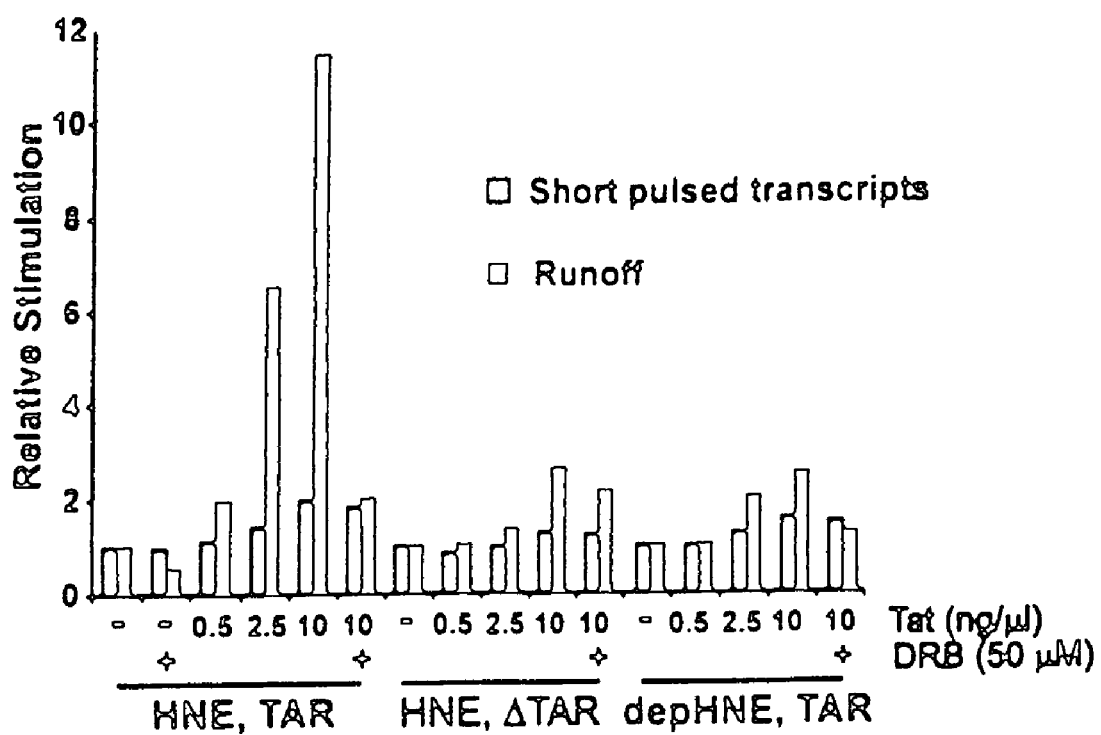
FIG. 8. Quantitation data for in vitro Tat transactivation using a continuous labeling protocol with the indicated templates and extracts and similar reaction mixtures which were subjected to a 2 minute pulse and the short transcripts generated were less than 30 nucleotides. Amount of runoff or short transcripts for each template/extract combination was normalized to the corresponding lane with no DRB or Tat added. Runoff transcripts were analyzed in a 6% TBE/Urea gel.

To investigate the function of P-TEFb in Tat transactivation directly, the effect of Tat on initiation and elongation in whole or PITALRE-depleted extracts were compared (FIG. 8). Two different DNA templates were used. The TAR template contained HIV-1 LTR sequences from −475 to +76 while the DTAR template lacked the sequence encoding TAR and contained HIV-1 LTR sequences from −475 to +19. Using HNE (not depleted) and a continuous labeling protocol, 10 ng/µl Tat stimulated the generation of runoff about 12 fold (filled bars in FIG. 8). This effect of Tat was mostly inhibited by 50 µM DRB and required the TAR sequence. A DRB titration indicated that the DRB sensitivity of Tat-stimulated runoff was similar to that determined for the low level of runoff from the HIV-LTR in the absence of Tat. When PITALRE-depleted extract was used, the majority of the stimulatory effect of Tat was abolished. This result strongly suggests that human P-TEFb is required for efficient transactivation by Tat. Add-back of *Drosophila* P-TEFb to the depleted extract stimulated runoff in the presence or absence of Tat, but did not restore the ability of Tat to specifically enhance elongation. This suggests that other required factors were removed by the depletion of PITALRE or that *Drosophila* P-TEFb lacks appropriate domains required for interaction with Tat or other cofactors. Addition of the high salt washed PITALRE immunoprecipitate had no effect on runoff in the presence or absence of Tat, indicating that immobilization had a negative impact on the function of P-TEFb. Although consistent with an effect on elongation, the experiment did not rule out the possibility that the major effect of Tat was on initiation.

From the autoradiograph and the normalized quantitation data graphed in FIG. 8 (filled bar) it was evident that Tat had a modest effect on transcription (about two fold increase of runoff) in the presence of 50 µM DRB, in the presence of DTAR template, or even in the absence of human P-TEFb. To further analyze the effect of Tat on transcription, a similar sets of studies was performed, except that a pulse-only transcription protocol was used instead of a continuous labeling protocol. Quantitation of the short pulsed transcripts (less than 20 nucleotides in length) gives the efficiency of initiation. Under these conditions it was clear that increasing Tat had the effect of increasing transcription initiation (open bars in FIG. 8). At the highest level of Tat used (10 ng/µl) initiation increased about two fold compared to when no Tat was added. This effect on initiation did not require TAR (FIG. 8). Moreover, the effect of Tat on initiation was not sensitive to DRB and did not require P-TEFb. The effect of Tat on initiation can be used to explain the slight effect of Tat on the generation of runoff in the presence of DRB, DTAR template, or depleted HNE. The two assays taken together indicate that the major effect of Tat is on elongation, although initiation is slightly affected. Most importantly, P-TEFb is required for the effect of Tat on elongation, but not its effect on initiation.

EXAMPLE 8

Determining the Region of P-TEFb Responsible for the Interaction with Tat

Although Example 7 clearly shows that P-TEFb associates with the HIV protein Tat, the interaction of Tat with P-TEFb could be through either subunit. A combination of in vivo and in vitro assays are used to localize the interaction surface. Both subunits are expressed, e.g. in *E. coli*, purified and the recombinant proteins used in vitro to determine which one or both of the subunits bind to Tat or compete for the binding of intact P-TEFb to Tat. The peptide domains are also expressible as GST fusion proteins, and soluble proteins are obtained by removing the GST moiety by specific protease digestion.

In order to identify proteins that bind to P-TEFb, the inventor utilizes the yeast two-hybrid system to identify proteins that associate with P-TEFb in vivo (Fields and Song, 1989; Chien et al., 1991; Durfee et al., 1993; Harper et al., 1993, U.S. Pat. No. 5,667,973, incorporated herein by reference). This system utilizes the yeast GAL4 protein, a well studied eukaryotic transcriptional activator protein. Transcriptional activator proteins are proteins that bind to cognate promoter elements upstream of particular genes, and thereupon activate transcription of the associated gene (Johnston, 1987). This activation function is believed to occur through recruitment of specific proteins which are required, along with RNA polymerase, to effect transcription.

Reports have shown that the DNA binding function and the transcriptional activation function reside in two distinct regions of the GAL4 protein. Further, it has been shown that these regions are able to be localized to relatively short peptide regions, which can function separately (Brent and Ptashne, 1986; Keegan et al., 1986). This ability forms the basis of the two-hybrid system. In the yeast two-hybrid system, the gene encoding the known protein is cloned as a fusion protein with the GAL4 DNA binding domain. Then a gene encoding a protein suspected of interacting with the known protein, or a cDNA library (to assay for the presence of a gene encoding an interacting protein) is cloned as a fusion protein with the transcriptional activation domain. Both constructs are then introduced into individual yeast cells.

Binding in vivo between the two fusion proteins recombines the GAL4 DNA binding domain with the GAL4 transcriptional activation domain, which leads to the transcriptional activation of a marker gene operatively positioned downstream of a GAL4 binding site. The transcriptional activation construct is then recovered from the identified yeast cell, and the interacting protein is identified by DNA sequencing.

The standard yeast two-hybrid system described above is a positive association screening assay. A variation of the two-hybrid assay is the subject of U.S. Pat. No. 5,525,490, by Erickson and Powers, issued Jun. 11, 1996 and incorporated herein by reference. Using this reverse two-hybrid system, inhibitors of protein—protein interaction can be assayed. In this system, the interaction between the fusion proteins represses the transcription of a marker gene. Agents (for example, but not limited to, proteins) which disrupt the association of the fusion proteins are identified by the increase in transcription of the marker gene.

The expressed proteins are included in binding reactions containing GST-Tat immobilized on glutathione beads and P-TEFb. In the event that additional cofactors are required, they are supplied as a crude extract or partially purified fraction. If there are cofactors required for the binding of P-TEFb to Tat, the binding assay with pure P-TEFb can be used as a means to purify the cofactor. The cofactor can then be used as a potential target for drugs that block the function of Tat through the loss of the ability to bind to P-TEFb.

After washing the beads, the binding of P-TEFb is monitored by western analysis by using antibodies to the desired subunit of human P-TEFb. The subunit that inhibits the binding of P-TEFb to Tat is a strong candidate for being the one that contains the domain that interacts between Tat and P-TEFb.

At the same time, the individual proteins are monitored directly for their ability to bind to Tat. The binding of portions of the subunits to Tat are monitored by using antibodies (see Example 5) that recognize the peptides. Antibodies from the crude antisera raised against individual subunits can be used. (Antibodies to the large subunit of P-TEFb can be used similarly.) Alternatively, if the activity of antibodies in the crude antisera is insufficient then antibodies are raised against the portions of the subunits that inhibit P-TEFb binding to Tat. Once direct binding of a peptide containing the interactive domain to Tat is detected, then the identified peptide is useful for screening for drugs that inhibit the binding of P-TEFb to Tat. It is envisioned that these peptides are easy to prepare in large quantities using recombinant DNA technology for use in screening assays for inhibitors of activators of P-TEFb.

A complimentary approach is to utilize a reporter gene assay such as one that utilizes chloramphenicol acetyltransferase (CAT). The use of reporter gene assays are well known to those of skill in the art. Recombinant HeLa cells are prepared such that they express both Tat and the kinase and CTD domains of the subunits of human P-TEFb and are also able to support Tat-transactivation of an HIV promoter driven CAT construct (HIV-CAT). It is envisioned that CAT activity is monitored when HIV-CAT is transiently transfected alone or co-transfected with increasing amounts of different constructs that respectively express the desired domain(s) of the human subunits. A decrease in CAT activity signifies that expression of the specific domain(s) inhibits the function of Tat.

Antibodies to the respective subunit domains of P-TEFb that interact with Tat are generated, using standard methods as modified and described in Example 5, so that expression of the domains can be verified using western blotting. Polyclonal antibodies against the entire large subunit can also be used, but it is envisioned that the individual domains are useful as antigens for the production of more specific antibodies.

These in vivo studies are useful for the identification of regions of P-TEFb that interact with Tat or that directly affect the normal cellular function of P-TEFb. Comparison of the in vivo expression results with the in vitro binding studies generally allows correlation of binding to function and specifically allows the determination of interaction domains that specifically affect Tat-transactivation but not the general function of P-TEFb.

Although it is clear that P-TEFb is essential for elongation to occur, it is possible that the interaction between P-TEFb and Tat is not direct. One or more other proteins may form a bridge between P-TEFb and Tat. The identification of any such proteins would be advantageous for the understanding of Tat-transactivation and the development of drugs that inhibit its interaction. Candidates for Tat/P-TEFb bridging proteins are obtained using the yeast two hybrid system, described above, to select for proteins that bind to P-TEFb.

For example, the bait vector which contains a region or regions of human P-TEFb fused to a DNA binding protein is constructed and transfected into yeast cells along with a human cDNA library fused to transcription activation domain. Yeast are selected based on their ability to activate transcription of the gene downstream of the DNA binding region. The large subunit of P-TEFb is detected if the small subunit of P-TEFb is used as bait. Once constructed, this method is then useful for cloning the large subunit. After the large subunit is cloned, the whole subunit or portions of it are useful as bait to find proteins that interact with P-TEFb. Candidates for bridging proteins are screened for their ability to function in vitro by allowing or enhancing the binding of P-TEFb to Tat.

EXAMPLE 9

Interaction of the Herpes Transactivator VP16 with P-TEFb

The Herpes virus transactivator VP16 increases the ability of RNA polymerase II to synthesize DRB-sensitive runoff transcripts in vitro. Most promoters have sites for activator proteins that are present in cell extracts and can allow for the production of DRB-sensitive long transcripts. But under transcription conditions like those in Marshall and Price (1992), the basal adenovirus E4 promoter contains no activator binding sites except for 5 Gal4 binding sites which give rise to very low levels of DRB-sensitive runoff transcripts in a *Drosophila* $K_c$ cell nuclear extract. Reasonable levels of initiation occur but most of the transcripts (>95%) are short (abortive).

When a protein, containing the N-terminal portion of the VP 16 activation domain (amino acids 413–456) fused to the DNA binding region of Gal4 (amino acids 1–147), was added to the transcription reaction the amount of DRB-sensitive runoff increased 6.2 fold. Only part of the increased production could have been due to increased initiation because only 1.8 times as many polymerases initiated in the presence of Gal4-VP 16 (as determined by quantitating the transcripts generated during a short pulse).

Proteins used to fuse to the DNA binding region were Gal4-VP16 N (wildtype) and Gal4-VP16 N-FA442 (mutant) which has the single amino acid change indicated. The proteins were made by inserting the indicated sequences downstream of the $P_{tac}$ promoter in an expression vector and transforming *E. coli* XA90 cells. 1 liter of cells were grown in LB+Amp to 0.7 $OD_{600}$. After a 3 h. induction with IPTG cells were lysed by sonication in 80 ml of lysis buffer (20 mM HEPES, pH 7.5, 10 µM zinc acetate, 20 mM β-mercaptoethanol and 200 mM NaCl). The proteins were precipitated with 0.25% Polyethyleneimine, spun, and suspended in lysis buffer. The pellet was redissolved in lysis buffer with 750 mM NaCl and spun again. The supernatant was ammonium sulfate precipitated with 40% saturated solution. The pellet was redissolved in 20 ml lysis buffer with 100 mM NaCl and 1 mM DTT instead of β-mercaptoethanol. The supernatant was dialyzed against lysis buffer with 100 mM NaCl.

Transcription conditions were as used in Marshall and Price (1995) and as described in Example 1. If indicated 75 ng of Gal4-VP 16 N or Gal4-VP 16 N-FA442 were added per reaction.

A mutant Gal4-VP 16 that does not activate well in vivo stimulated DRB-sensitive runoff transcripts 2.8 fold and had a slight stimulatory effect on initiation (1.5 fold). Since P-TEFb is responsible for DRB-sensitive runoff transcripts these data strongly indicate that P-TEFb binds to the VP 16 activation domain.

A Packard InstantImager™ was used for the quantitation. After running the products of the transcription reaction on a denaturing gel, the gel was dried and imaged for 30 min in the InstantImager™. Initiation was compared with and without the activator protein by comparing the counts generated by all transcripts during the pulse or by comparing the counts that reached runoff after chasing with 250 mM KCl which has been shown to be directly related to initiation. Both methods gave the same results. Radioactivity in the region of runoff after a normal low salt chase was used to quantitate productive elongation products. DRB-sensitive runoff was calculated by subtracting the runoff in the lane with DRB from the runoff in the lane without DRB. P-TEFb is present in the $K_c$ cell extract used in the reactions. 75 ng of Gal4-VP16 N or N mutant was used in each 12 μl reaction.

These results were extended by removing the upstream region of the *Drosophila* actin template normally used in $K_c$ cell extract transcriptions and inserting the Gal4 binding sites (pBAG1). Transcription of 20 μg/ml pBAG1 using a normal pulse chase conditions gave rise to a low level of DRB-sensitive runoff transcript but inclusion of 75 ng of Gal4-VP16 N increased initiation slightly and significantly stimulated elongation. These are the same results obtained when using the E4 promoter. Therefore, the effect of VP16 is independent of the basal promoter that is used. In addition elongation was stimulated by Gal4-VP16 N from the E4 promoter in HeLa nuclear extract transcriptions.

EXAMPLE 10

Assay for Drugs that Block the Interaction of P-TEFb and Tat

A major goal in medicine today is to find drugs that can inhibit and prevent the occurrence of AIDS and spread of HIV infection. It is envisioned that because P-TEFb has a central role in cell proliferation and interacts with Tat, P-TEFb is useful as a tool in screening immunoassays to find therapeutic drugs that will inhibit or block the proliferation of HIV.

Immunoassays, such as an ELISA, are useful to screen for drugs that inhibit the interaction of Tat with P-TEFb. For example, Tat-coated microtiter plates are incubated with pure P-TEFb or P-TEFb and any other required factors (such as human nuclear extract or fractions derived there from) needed to cause association with Tat. As indicated previously, a requirement for additional cofactors is unlikely, but the existence of needed cofactors does not complicate this assay when HeLa extract is used. As before these cofactors can be supplied by using the crude cellular extract.

As the interaction between components in this assay are interdependent upon the concentration and activity of each other, parameters for each component are established by initially using wide ranges and optimizing the amount of each component as desired. For example, 1–10 μg of Tat can be bound per well initially, and 15 μl of HeLa extract provides sufficient P-TEFb (about 10 ng) to establish binding. Primary anti-P-TEFb small subunit antibodies can initially be in a 1:1000 dilution of antiserum. Secondary antibodies can be initially diluted 1:20,000. Of course, these amounts, as with all other parameters, may be optimized as desired.

It is envisioned that any peptides, proteins or polypeptides derived from P-TEFb and shown to be active towards Tat may be used as a P-TEFb template in an immunoassay. After washing, the plates are incubate with antibodies that have been prepared using standard protocols and methods as exemplified in Example 5 and that recognize either the small or large subunit, intact P-TEFb or peptides derived there from (see Example 8). Following standard methods for immunoassay detection, a label is applied to the plates such that microtiter wells that contain P-TEFb bound to Tat yield a positive signal.

To determine that a candidate drug inhibits the interaction of the P-TEFb with Tat, a competitive assay is performed. It is contemplated that P-TEFb proteins, subunits, polypeptides or peptides can be used. Decreasing or increasing concentrations of candidate drugs are added to microtiter plates which contain constant amount of P-TEFb template and Tat. Disruption of the interaction of P-TEFb with Tat is detected as the reduction of the positive signal which indicates P-TEFb template bound to Tat.

Drugs which can strongly inhibit or even prevent the interaction of Tat and P-TEFb template are potential candidates for further screenings to determine if they interfere with normal cellular processes. Preferably, inhibitors are small compounds suitable for use as anti-HIV drugs or compounds. The small compounds would bind (like allosteric effectors do) to regions of the Tat or P-TEFb that are not involved directly in enzymatic activity and this binding would inhibit the interaction between the two proteins.

Candidate drugs are examined, for example, for their ability to inhibit the normal interaction of P-TEFb with RNA polymerase II. The ideal candidate drug only inhibits or prevents the interaction of Tat and does not inhibit or prevent the normal interaction of P-TEFb with RNA polymerase II or any other normal cellular activities. Suitable screening methods include, but are not limited to, additional immunoassays, cell culture base assays, animal testing models and clinical trials.

EXAMPLE 11

Characterization of Human P-TEFb

Immunoprecipitation of PITALRE from HeLa extracts indicates that several other proteins are tightly associated with the kinase subunit even in the presence of 1 M NaCl and non-ionic detergents. Proteins of molecular masses, 87, 105, 133, 140 and 207 kDa are visible with silver staining, but the stoichiometry of these proteins is not known. There could also be additional proteins that do not stain well or that are hidden under the immunoglobulin bands present in the immunoprecipitates.

A. Characterization of the Two Potential Cyclin Subunits of Human P-TEFb.

Although northern analysis indicates that the intron containing mRNA is a minor species it is not known if the protein encoded becomes functionally associated with PITALRE. To examine the association of the proteins encoded by these potential cyclin subunit clones antibodies are made to each in rabbit (Pocono Rabbit Farm). These antibodies are used to probe western blots of PITALRE immunoprecipitates from HeLa cell extract. The recognition of proteins in PITALRE immunoprecipitates is strong evidence for a functional interaction. If the potential cyclin subunit antibodies recognize proteins associated with PITALRE, the size of these proteins is compared with the size of the proteins expressed in the baculovirus system. If there is a discrepancy between the size of the endogenous proteins and the recombinant proteins additional clones are obtained that encode a protein of appropriate size. Results indicate that 5' and 3' RACE products frequently have unusual sequences due to the presence or absence of intronic sequences and it is possible that the clones obtained so far may not have the correct amino- or carboxyl-terminal ends. However, this evidently does not negate their function or the ability of the skilled researcher to identify correct terminal sequences. The protein encoded by human HBL3 cDNA was co-expressed with PITALRE in a baculovirus system and produced an active heterodimeric kinase. The protein encoded by human cyclin HBL3 exhibited a mobility identical to the 87 kDa protein found in PITALRE immunoprecipitates. These results suggest that the protein subunits described herein are P-TEFb. Further confirmation is obtained by using antibodies to the cyclin subunit to probe PITALRE immunoprecipitates.

To determine if the identified cyclin protein is part of an active complex immunodepletions like those done with PITALRE (Example 6) are performed. If the ability to synthesize DRB-sensitive transcripts is eliminated from HeLa extracts by the antibodies a strong functional connection is made between the cyclin subunit and P-TEFb. At the same time antibodies against the identified cyclin subunit are used to carry out immunoprecipitation and the resulting pattern of proteins are compared to PITALRE immunoprecipitates. Besides PITALRE, it is important to determine what other proteins the two immunoprecipitates have in common. The current understanding of complexes containing PITALRE does not make clear if all the observed proteins are in a single complex or if perhaps there are several different PITALRE containing complexes. Using antibodies against another protein in the complex allows a better understanding of what proteins are in the complex with functionally active PITALRE.

B. Analysis of Complexes Containing PITALRE and a Cyclin Subunit of P-TEFb.

Since P-TEFb is a cyclin dependent kinase it is possible that it may associate with other proteins that regulate its activity. Many CDKs can be inhibited by small molecular mass proteins that bind to the cyclin/kinase pair (Morgan, 1995a; MacLachlan et al., 1995). If such an inhibitory protein binds to P-TEFb, the complex would be inactive and would be difficult to find with conventional assays that require activity. Armed with antibodies against several subunits of human P-TEFb different complexes containing PITALRE are examined to determine whether they have activity or not. HeLa nuclear extract are fractionated using conventional chromatographic methods and complexes containing PITALRE or the cyclin subunit are located by western blot. Initially, proteins in the extract are bound to phosphocellulose to remove most nucleic acid and the material eluted at 1 M KCl is applied to a Sepharose S200 column to effect a size separation. PITALRE and or cyclin containing complexes are identified and subjected to further purification. Immunoprecipitation is used to analyze the proteins associated with PITALRE at all stages of the purification. The column fractions and immunoprecipitates are examined for kinase activity and the column fractions are tested for their ability to function during Tat-transactivation when added back to PITALRE depleted extract. Both active and inactive complexes are identified by this method. Purification of the complexes with known properties allows identification of other potentially regulatory subunits through protein sequencing methods like those used in the cloning of the subunits of Drosophila P-TEFb.

C. Molecular Analysis of Human P-TEFb.

The availability of antibody and cDNA probes allows the assessment of expression patterns of P-TEFb. Some characterization of PITALRE has been carried out and it has been reported that PITALRE was localized to the nucleus and PITALRE mRNA was expressed ubiquitously over a variety of human tissues (Grana et al., 1994). In addition. PITALRE has been mapped to a region of chromosome 9 involved in certain types of cancer (Bullrich et al., 1995). The inventor's work indicates that mRNAs encoding both of the cyclin subunits that have been isolated are expressed in a similar manner to that seen for PITALRE. Northern blot analyses of tissues involved in the immune response are used to determine if cells that are normally infected with HIV preferentially express a specific cyclin subunit or a specific form of one the subunits.

Mapping of the cytogenic location of cyclin subunit(s) found to complex with PITALRE is used to determine if the areas map to other loci involved in similar types of cancer as found for PITALRE. Mapping is accomplished by using PCR primers that give specific products for human versus hamster DNA. Any correlations that are found are then useful for determining if there are genetic abnormalities in affected individuals.

D. Functional Analysis of P-TEFb.

An analysis of P-TEFb function in vivo is carried out using a co-transfection protocol with P-TEFb and an HIV-LTR reporter construct. The goal is to determine if over-expression of active P-TEFb causes an increase in Tat transactivation and to determine what regions of P-TEFb are required. Both HeLa and Jurkat cell lines that support modest or very high levels of Tat transactivation respectively are used. Expression of PITALRE has been shown to modestly stimulate Tat transactivation in several cell lines even though the others have found that expression of PITALRE does not increase dramatically the level of kinase activity found in PITALRE immunoprecipitates (Garriga et al., 1996a). This inability to increase the kinase activity of PITALRE is likely due to a limitation in the amount of the cyclin subunit(s) required for activity. In addition, the inventor and others (Garriga et al., 1996a) have not been able to get a large over-expression of PITALRE which suggests that the level of the kinase subunit may be regulated by a post-transcription mechanism. Co-expression of a cyclin subunit may allow for greater level of expressed proteins if the ratio of the kinase/cyclin pair is involved in regulating the level of the kinase. This can be studied by examining PITALRE levels during transient expression of a cyclin subunit in an induced PITALRE cell line. If higher level of the knockout kinase are observed, it may be possible to achieve much higher levels of P-TEFb in cells that have both kinase and cyclin subunits under the control of active promoters. This type of experiment may provide general information about the regulation of PITALRE levels in the cell. If the levels of the kinase knockout PITALRE protein are increased when the cyclin subunit is expressed then the effect of the potential dominant negative mutation on cell growth may be observed. If this is the case, the induction of the PITALRE kinase knockout in the presence of over-expressed cyclin subunit may be lethal to the cells.

To examine the effect of over-expression of P-TEFb on Tat transactivation, HeLa or Jurkat cells are co-transfected with constructs that express both subunits of P-TEFb and Tat along with an HIV-LTR reporter construct. The levels of both subunits of P-TEFb are compared before and after transfection to determine the level of over-expression. Measurement of reporter activity is made with and without Tat and with and without individual subunits of P-TEFb. If over-expression of P-TEFb causes a reasonable stimulation of Tat transactivation, constructs expressing mutant P-TEFb subunits are used to assess their effects. The kinase knockout mutation of PITALRE is studied to see if it will act as a dominant negative mutation. Most importantly, the requirement for the carboxyl-terminal domain of the cyclin subunit for Tat transactivation is examined. Effects of all interesting P-TEFb constructs on a Tat responsive reporter are compared to effects on other promoters, such as the complete CMV promoter, that use different activators. These in vivo studies should complement similarly designed in vitro experiments described below.

EXAMPLE 12

Examination of the Tat/P-TEFb Interaction.

An immobilized GST fusion protein containing an intact Tat activation domain is incubated with fractions around the elution point of PITALRE and extensively washed as was done in (see Example 6). The material bound to Tat is assayed for CTD kinase activity using RNA polymerase II as substrate (Marshall et al., 1996) and for the presence of PITALRE by immunoblotting. As was done before, negative controls are performed using Tat proteins with mutations that neutralize the activation domain. Any complex that fractionates with the ability to bind to Tat is monitored by immunoprecipitation with anti-PITALRE antibodies to identify subunits/cofactors that are needed for association with Tat. A PITALRE containing complex that binds to Tat may be purified in this manner and examined for its ability to support efficient Tat transactivation. For example, the recombinant PITALRE/human cyclin HBL1-1 and PITALRE/HBL3 complexes can be examined for their ability to interact with Tat and compared to the complexes derived from fractionation of HeLa nuclear proteins.

If a purified P-TEFb complex that interacts with Tat and recombinant PITALRE/cyclin complexes do not interact, the requirement of cofactors that do not co-purify with P-TEFb is likely. To find such cofactors an assay in which the association of recombinant PITALRE/cyclin complexes (rP-TEFb) with Tat is used to measure function and activity in the presence of fractions of HeLa nuclear extract. The association is monitored with either a CTD kinase assay or by immunoblot. Initially, the assay utilizes HeLa nuclear extract that was depleted of PITALRE in the presence of 1 M KCl. This type of extract should not be depleted of factors that interact ionically with PITALRE. An increase in the association of rP-TEFb with Tat in the presence of the depleted extract suggests the presence of cofactors. If such results are obtained, the association reactions are modified to learn if the cofactors interact with Tat or with rP-TEFb alone. First, immobilized Tat is incubated with the depleted extract. To determine if the cofactor(s) interact with Tat, the beads are washed and then incubated with rP-TEFb. If the affinity of the beads for P-TEFb increases then Tat associated cofactors are suggested. A similar experiment in which rP-TEFb is immobilized via its HIS-tag, incubated with the extract and then incubated with Tat shows if cofactor(s) associate with P-TEFb. In the latter experiment the binding of Tat is monitored by immunoblotting with anti-Tat antibodies. It is possible that some cofactors interact with both factors, but it is also possible that a cofactor interacts with just one factor causing a conformational change that enables that factor to associate with the other partner in the Tat/P-TEFb complex.

The simplest model for the function of TAR RNA is that it exerts its effect on transcription of the HIV-LTR due to its ultimate ability to recruit P-TEFb to the early elongation complex. Tat has been shown by a number of groups to bind to TAR (Fong et al., 1997; Aboul-ela et al., 1995; Neenhold and Rana, 1995; Rhim and Rice, 1994; Cullen, 1991) and P-TEFb or then unspecified CTD kinases have been shown to associate with Tat in vitro (Herrmann and Rice, 1993; Herrmann and Rice, 1995; Chun and Jeang, 1996) and in vivo (Yang et al., 1996). However, linkage between TAR and P-TEFb or any CTD kinase has not been made.

TAR RNA is produced in vitro using T7 polymerase and is included in various binding reactions like those described above. First, it is determined if the RNA has an effect on the efficiency of interaction of P-TEFb with Tat in the crude extract. TAR RNA is titrated into binding reactions that have otherwise been optimized for association of P-TEFb to Tat. Interaction efficiency is monitored by determining the fraction of PITALRE remaining in the extract after the Tat pull-down. The assay is then performed on any promising set of fractions identified from the binding studies above. It is possible that TAR RNA may disrupt the interaction of Tat with P-TEFb. Although at first this may seem inappropriate, it is important to note that Tat may be a component of the preinitiation complex and may not need to be recruited by TAR (Garcia-Martinez et al., 1997a). TAR may regulate the effect of Tat by disrupting the interaction between Tat and P-TEFb, thereby allowing P-TEFb to function. What ever the results, the development of models of Tat transactivation are greatly benefit from knowing the effect of TAR RNA on the Tat/P-TEFb interaction.

If the results indicate that TAR enhances the association of P-TEFb to Tat then an assay in which TAR RNA is immobilized to paramagnetic particles is used. Binding of P-TEFb to the beads dependent on the presence of Tat and crude extract or fractions generated from an extract is followed. The complexes are examined for their ability to increase the activity of associated P-TEFb. Specific activity of P-TEFb is monitored by a combination of western blotting, to determine relative amount of the factor, and CTD kinase assays, to measure the activity of the factor. If the results indicate that TAR disrupts the interaction of P-TEFb and Tat, that information is useful in interpreting the outcomes of the studies described below.

EXAMPLE 13

Elucidation of the Mechanism of Tat Transactivation

Progress on understanding the how Tat causes an increase in the number of polymerase molecules that synthesize full length HIV transcripts has been slow until now because of the lack of understanding of the elongation control process in general. Recent advancements in elongation control include the present identification of *Drosophila* P-TEFb as a CTD kinase (see also Marshall et al., 1996), the purification and characterization of *Drosophila* factor 2, an ATP dependent RNA polymerase II termination factor (Xie and Price, 1996), and the purification of a negative human elongation factor comprised of the homologues of the yeast SPT 4 and SPT5 proteins. The present identification of the kinase subunit of human P-TEFb and the requirement for P-TEFb in Tat transactivation makes it clear that studies on the mechanism of Tat transactivation should be focused on understanding the role of P-TEFb.

A. Association of Elongation Control Factors with the Transcriptional Machinery.

The association of known elongation control factors with transcription complexes on the HIV-LTR is studied to determine the effect of Tat on this association. The present immobilized template technology (see also Marshall et al., 1996; Xie and Price, 1996; Marshall and Price, 1992) and is used to determine if and when P-TEFb, factor 2, the SPT4/SPT5 complex, and other factors become associated with the transcription complex. Preinitiation complexes, early elongation complexes before TAR RNA is synthesized and elongation complexes containing TAR RNA are examined. The salt concentration used during washing steps and the exact transcription conditions used are important factors in these studies. The strategy outlined below is given as an example of the types of studies that are done.

The overall design of the association experiments is to form preinitiation complexes on an HIV-LTR template immobilized to paramagnetic beads, allow the polymerase to progress to the appropriate stage and then wash the complexes to remove non-associated proteins. Antibodies against the factors are used to probe for their presence in the isolated complexes. For this type of experiment to be successful a number of controls must be done. It is important to first determine the efficiency of initiation of preinitiation complexes because uninitiated polymerases would contribute to the signals obtained from immunoblotting of "elongation complexes". Although uninitiated polymerases could be eliminated with a 1 M salt wash, such a wash would also potentially disrupt factors in a potential elongation control particle. It cannot be assumed that a pulse of NTPs allows all preinitiation complexes to initiate and form early elongation complexes. In the *Drosophila* system the inclusion of $Mn^{++}$ instead of $Mg^{++}$ in the initiation phase increased the rate of initiation and, therefore, the fraction of polymerases that initiate. Even in the presence of $Mn^{++}$ less than half of the polymerases in preinitiation complexes initiated, as evidenced by resistance to a 1 M salt wash (Marshall et al., 1996). The initiation efficiency in a HeLa nuclear extract system was examined and found that $Mn^{++}$ does not stimulate the rate of initiation. This suggests that initiation is already quite efficient. To determine what fraction of polymerases initiate from the HIV-LTR in the presence and absence of Tat, immunoblotting with antibodies to RNA polymerase II is used. Preinitiation complexes are formed in the crude extract and then the complexes are washed extensively with buffer containing the highest salt possible that does not cause loss of polymerases that can initiate. These washed preinitiation complexes are the starting material for an experiment to determine the efficiency of initiation. The amount of RNA polymerase II in these complexes assayed by immunoblotting are compared to the amount after initiation and after washing with 1 M salt. The NTP concentrations, salt conditions and times to effect the greatest efficiency of initiation are varied as is practical. If the efficiency is greater than about 50% then the signals obtained by immunoblotting are interpretable.

Once good initiation conditions are are established then the conditions that allow the efficient formation of early elongation complexes containing nascent transcripts of between 10 and 30 nucleotides in length and complexes containing an intact TAR RNA stem and loop are determined. The shorter complexes would have made the transition from abortive initiation into elongation and, therefore, would have released contact with the promoter localized factors, but would not have synthesized TAR RNA. These conditions should be similar to those used to examine initiation from the HIV-LTR. To obtain the complexes with complete TAR RNA, limiting amounts of nucleotides are used to advance the polymerase to a set of positions that allow most complexes to have RNA in the 70 to 100 nucleotide range.

Alternatively, a second method to generate complexes with RNA of more uniform length is utilized such that the lactose (lac) repressor protein and a template containing the lac repressor binding site is positioned downstream of the TAR region to block elongation by the polymerase (Keen et al., 1996). The length of the RNA is monitored using incorporation of $\alpha$-$^{32}$P-CTP and initiation efficiency is checked as described above. If a significant number of complexes are terminating due to the action of factor 2, then antibodies are used against the newly cloned human factor to deplete the factor from extracts before assembly of the preinitiation complexes. Before this is done the effect of such depletion on Tat transactivation is examined.

After finding the appropriate conditions to efficiently generate the three types of complexes, immunoblotting studies are performed with all antibodies available for the factors potentially involved in elongation control. These include, antibodies against PITALRE and the cyclin subunit(s) of P-TEFb, human factor 2, SUPT4H (Chiang et al., 1996b) and SUPT5H (Chiang et al., 1996a), subunits of TFIIH including those in the CAK (Morgan, 1995b), and both subunits of TFIIF (Finkelstein et al., 1992). Tat is added at different times and its association with the complexes is monitored with antibodies (Brake et al., 1990). Initially, elongation complexes are generated in the presence of the extract and, therefore, in the presence of all factors. As the studies progress this is modified by washing the preinitiation complexes or early elongation complexes without TAR and then allowing the polymerases to advance to the next complex. This allows determination of what factors are lost from earlier complexes.

Although the simplest model for Tat action involves its binding to TAR and recruitment of P-TEFb, this model is complicated by several studies that indicate that Tat can associate with RNA polymerase II and can become part of the preinitiation complex (Garcia-Martinez et al., 1997a; Mavankal et al., 1996; Cujec et al., 1997). Using carefully controlled conditions, attempts are made to confirm that Tat associates with preinitiation complexes and extend the findings to other promoters such as the CMV promoter that is used as a control for all the experiments described above. Association of Tat with the preinitiation complex helps to explain why Tat has an effect on initiation, but does not explain the effect of Tat on elongation. It is possible that TAR RNA from an early elongation complex reaches back into the next preinitiation complex and affects the Tat RNA polymerase II interaction. It is also possible that Tat bound to TAR recruits an RNA polymerase II complex (holoenzyme) to the promoter. In either case the polymerase initiating under the influence of Tat might be more susceptible to the action of P-TEFb.

B. Functional Enhancement of P-TEFb Action by Tat.

It is clear from in vivo and in vitro studies that Tat has the ability to enhance the function of P-TEFb at the HIV-LTR. What is not clear is how this enhancement is accomplished. P-TEFb is not used only at the HIV-LTR, but rather is a cellular factor involved in elongation control at most promoters. Also the LTR does not absolutely require Tat to produce full length transcripts because if this were not the case mRNAs encoding Tat would not be produced.

One model consistent with most data is that the HIV-LTR is different compared to other promoters in that elongation complexes produced from the LTR are especially refractory to P-TEFb action. Tat may be required to eliminate a strong negative elongation potential imparted to polymerases that initiate from the HIV-LTR. This idea is supported by the effect of a number of P-TEFb inhibitors that blocked Tat transactivation. Although all of the inhibitors blocked Tat transactivation at lower concentrations than that needed to block activation by another activator on another promoter, at one log higher concentration all the inhibitors had cytotoxic effects, presumably due to inhibition of the normal function of P-TEFb. In transient transfection assays, increasing PITALRE concentration and presumably P-TEFb activity in a variety of cells was able to stimulate reporter constructs driven by a number of promoters with different activators.

While Tat transactivation on the HIV-LTR was dramatically stimulated, increasing PITALRE did not increase expression from the LTR in the absence of Tat. This supports the idea that the LTR is refractory to P-TEFb action and suggests that the increased sensitivity of Tat transactivation to the inhibitors might arise due to an increase in activity that counters the action of P-TEFb.

There are several possibilities for activities that might counter P-TEFb at the HIV-LTR One such activity might be the CTD phosphatase described by Dahmus (Dahmus, 1996; Chambers et al., 1995) and others (Chambers and Kane, 1996). If this is the case an amount of inhibitor that would only partially block P-TEFb might have a large effect on the function of the factor because of the balance of the two opposing activities. Another possibility is the FBI-1 protein (Pessler et al., 1997) that may be responsible for the function of the IST (inducer of short transcripts) element (Sheldon et al., 1993) found in the DNA around the start point of transcription of the HIV-LTR.

The negative activity of the HIV-LTR is first produced to compare to the CMV promoter with a co-transfection/reporter system in HeLa cells and then to determine the cause of the effect. Ultimately, it is determined if the IST element is involved by examining the sensitivity of the expression of a CAT reporter activity from promoter constructs with and without the element (Pendergrast and Hernandez, 1997; Sheldon et al., 1993). Cells are first transfected with the wildtype LTR reporter construct and either a Tat expression plasmid or a mock plasmid. The cells are plated into microtitre plate wells in duplicate and the dilutions of the compounds DRB or TRB in 100% DMSO are added into the wells to maintain a constant 1% DMSO. Cells are harvested and assayed for chloramphenicol acetyl transferase after 24 hours. General cytotoxicity assays are used to monitor cell death as described in Mancebo et al. Once the special sensitivity of the HIV-LTR is produced then the same assays using constructs in which the IST has been deleted are used. If the IST is what makes the LTR different from other promoters then the level of drug sensitivity decreases upon deletion of the element and the LTR minus IST looks more like a normal promoter. These experiments are carried out in HeLa cells that exhibit a low but reasonable level of Tat transactivation and in Jurkat cells that exhibit a much greater stimulation by Tat. If the IST element is the key for the uniqueness of the HIV-LTR then the FBI-1 protein characterized is a prime candidate for the factor responsible.

While the in vivo studies are underway the effect of the IST element is examined in vitro. Tat transactivation of the HIV-LTR is examined as in Example 6. First it is determined if the 50% inhibition point for the appearance of runoff from the LTR is different from that seen for other promoters such as the CMV promoter. If the difference is produced in vitro then LTR constructs are used with and without the IST element to probe for differences in the response to the inhibitors of P-TEFb.

C. Development of In vitro Assays that Allow Precise Determination of the Effect of Tat.

The study of Tat transactivation in vitro has been hampered by an inability to obtain significant stimulation of the elongation in a pulse chase assay designed to separate initiation from elongation. It has been the rule rather than the exception to use unusual conditions to obtain significant stimulation of DRB sensitive transcripts from the HIV-LTR in vitro. In some labs a 30 minute "presynthesis" step was used (Marciniak and Sharp, 1991) and in others the inclusion of citrate (Parada and Roeder, 1996) was needed to see significant Tat transactivation. The inventor has found that a 20 minute continuous labeling assay in which the NTP concentrations were lowered to 50 μM was sufficient to see a 12 fold stimulation.

The first step is to produce extracts from Jurkat cells, a B cell line that can support very high levels of Tat transactivation. The standard nuclear extract preparation described previously (Price et al., 1987) that has yielded very active extracts containing all the factors necessary for the efficient production of DRB-sensitive runoff transcripts is used. Cells are grown in suspension with high levels of fetal calf serum and are harvested in log growth. The extract is optimized for Tat transactivation with standard extract and template titrations as well as a condition search that includes titrations of mono- (KCl) and divalent ($Mg^{++}$ and $Zn^{++}$) cations. The inventor has found that the source of Tat is important. A Jurkat cell line stably expressing wildtype Tat and a Tat cys22gly mutation (Zauli et al., 1995) is also useful. Extracts made from these cells should have native Tat that is active as long as the activation domain has no mutations. The negative control for in vitro transcription reactions is to use the mutant extract normalized with the CMV promoter or the HIV-LTR template lacking the TAR element.

If Tat transactivation is found to be robust in the newly derived system, assays are used that allow more insight into the step or steps affected by Tat. A pulse chase reaction is used but otherwise the conditions are kept similar to the continuous labeling conditions that normally work. Pulse reactions are long at first and then are shortened. Care is taken to determine nascent transcript length so that it can be determined if nascent transcripts need to contain TAR RNA or if generation of TAR RNA during the chase is sufficient. The LTR construct containing the lac repressor block at +200 described above is used to generate elongation complexes containing TAR RNA during the pulse and then IPTG is added at various times during the chase to observe the kinetic parameters of functional TAT/TAR interaction.

Data is consistent with Tat having an effect on initiation that is manifest as an effect on elongation during the continuous labeling assay. It is possible that Tat affects reinitiation of other polymerase molecules at promoters just used. This hypothesis is examined by using a multiple round assay that allows counting of the number of polymerases that initiate from a single promoter during the course of the reaction. Basically, the lac repressor is used to block polymerases that have entered productive elongation and have progressed about 700 bp into the template. The second polymerase that initiates from the same promoter is stopped about 30 bp earlier due to steric interference with the existing blocked polymerase (Szentirmay and Sawadogo, 1993). The length of the 30 bp ladder indicates the number of polymerases that reinitiate. IPTG allows all appropriately blocked polymerases to run off the end of the template at 800 bp. The reinitiation assay can be run under identical conditions to the continuous labeling conditions that have been shown to give reasonable Tat transactivation. If evidence of reinitiation being stimulated by Tat is seen then it is conclusive and dictates a path of research designed to probe the reinitiation. If there is no evidence of reinitiation, but Tat is seen to work well, then reinitiation of transcription by Tat is ruled out as a major mechanism of Tat transactivation.

EXAMPLE 14

Tat Transactivation in Yeast

Both subunits of human P-TEFb are first transfected into yeast using a centromere plasmid with weak promoters driving the human cDNAs. The production of P-TEFb is followed with immunoblotting. It is first determined if human P-TEFb replaces the yeast CTD kinase, CTD K1, that has been recently demonstrated to be able to stimulate long transcripts in a HeLa extract system after inhibition of P-TEFb by DRB (Lee and Greenleaf, 1997; Sterner et al., 1995; Lee and Greenleaf, 1992). Yeast lacking expression of the kinase subunit, CTK 1, are viable but have a cold sensitive phenotype and other growth defects. It is next determined if human P-TEFb reverses these effects in a CTK 1 null. If P-TEFb causes more normal growth, it is possible that CTD K1 is the functional equivalent of P-TEFb in yeast. Yeast expressing human P-TEFb is transfected with a construct containing the sequences from +1 to +80 of the HIV-LTR coupled to a standard yeast promoter CYC1. The hybrid promoter is used to drive a β-galactosidase reporter. The effect of Tat is determined by including a Tat expression cassette in the β-galactosidase reporter construct. The yeast system is then used to examine the interaction between human P-TEFb and Tat.

Alternatively, if Tat transactivation is not attainable, the yeast system may still be used in examining the interaction between Tat and P-TEFb if the biochemical approach suggests that the two proteins interact. A two hybrid system is set up with a Gal 4-Tat fusion protein as bait. The human P-TEFb expression plasmid is modified such that the kinase carries a knockout mutation and the cyclin subunit has an activation domain attached at the carboxyl-terminus. The reporter containing Gal 4 binding sites should be activated by the P-TEFb expression plasmid. If so, then deletions of the large subunit are carried out to see if the interaction assayed by reporter activity is lost. These studies are compared to studies that examine the ability of truncated versions of P-TEFb to function in general elongation control in vitro and in Tat transactivation in vitro and in vivo.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aboul-ela, F., Karn, J., and Varani, G. (1995). The structure of the human immunodeficiency virus type-1 TAR RNA reveals principles of RNA recognition by Tat protein. Journal of Molecular Biology 253, 313–332.

Akoulitchev, Makela, Weinberg, and Reinherg, "Requirement for TFIIH kinase activity in transcription by RNA polymerase II," *Nature*, 377:557–560, 1995.

Allison, Wong, Fitzpatrick, Moyle, Ingles, *Molecular and Cellular Biology*, 8(1):321–329, 1988.

In: *Antibodies: A Laboratory Manual*, Cold Spring Harbor Laboratory, 1988.

Austin and Biggin, "In vitro transcription, Tfiih, Tfiie, Tfiif, Tfiid," *Proceedings of the National Academy of Sciences of the United States of America*, 93:5788–5792, 1996.

Ausubel, F. M., Brent, R., Kingston, R. E., Moore, D. D., Seidman, J. G., Smith, J. A., and Struhl, K. (1989). Current protocols in molecular biology (New York: Greene Publishing Associates and Wiley-Intersience). Bartolomei, Halden, Cullen, and Corden, *Molecular and Cellular Biology*, 8(1):330–339, 1988.

Baskaran, Dahmus, Wang, *Proc. Natl. Acad. Sci. USA*, 90:11167–11171, 1993.

Bender, Thompson, Kuehl, "Differential expression of c-myb mRNA in murine B lymphomas by a block to transcription elongation," *Science*, 237:1473–1476, 1987.

Bengal, Flores, Krauskopf, Reinberg, Aloni, "Role of the mammalian transcription factors IIF, IIS, and IIX during elongation by RNA polymerase II," *Mol. Cell. Biol.*, 11:1195–1206, 1991.

Bentley, "Regulation of transcriptional elongation by RNA polymerase II," *Curr. Opin. Genet. Dev*, 5:210–216, 1995.

Blau, Xiao, McCracken, O'Hare, Greenblatt, Bentley, "Three functional classes of transcriptional activation domains," *Molecular and Cellular Biology*, 16(5):2044–2055, 1996

Braddock, M., Thorbum, A. M., Kingsman, A. J., and Kingsman, S. M. (1991). Blocking of Tat-dependent HIV-1 RNA modification by an inhibitor of RNA polymerase II processivity. Nature 350, 439–441.

Bradsher, Jackson, Conaway, and Conaway, "RNA polymerase II transcription factor SIII. I. Identification, purification, and properties," *J. Biol. Chem.*, 268:25587–25593, 1993a.

Bradsher, Tan, McLaury, Conaway, Conaway, *J. Biol. Chem.*, 268:25594–25603, 1993b.

Brake, D. A., Goudsmit, J., Krone, W. J., Schammel, P., Appleby, N., Meloen, R. H., and Debouck, C. (1990). Characterization of murine monoclonal antibodies to the tat protein from human immunodeficiency virus type 1. Journal of Virology 64, 962–965. Brickey and Greenleaf, *Genetics*, 140:599–613, 1995.

Brent and Ptashne, *Cell*, 43:729–736, 1986

Brutlag et al., *CABIOS*, 6:237–245, 1990.

Bullrich, MacLachlan, Sang, Druck, Veronese, Allen, Chiorazzi, Koff, Heubner, Croce et al., "Chromosomal mapping of members of the cdc2 family of protein kinases, cdk3, cdk6, PISSLRE, and PITALRE, and a cdk inhibitor, p27Kip1, to regions involved in human cancer," *Cancer Research*, 55(6):1 199–1205, 1995.

Burton, Killeen, Sopta, Ortolan, Greenblatt, "RAP30/74: a general initiation factor that binds to RNA polymerase II," *Molecular and Cellular Biology*, 8(4):1602–1613, 1988.

Cadena and Dahmus, *J. Biol. Chem.*, 262(26):12468–12474, 1987.

Campbell, In: *Monoclonal Antibody Technology, Laboratory Techniques in Biochemistry and Molecular Biology*, Vol. 13, Burden and Von Knippenberg, Eds. pp. 75–83, Amsterdam, Elseview, 1984.

Chambers, Wang, Burton, Dahmus, *J. Biol. Chem.*, 270: 14962–14969, 1995.

Chambers, R. S. and Kane, C. M. (1996). Purification and characterization of an RNA polymerase II phosphatase from yeast. Journal of Biological Chemistry 271, 24498–24504.

Chen, Harless, Wright, and Kellems, "Identification and characterization of transcriptional arrest sites in exon 1 of the human adenosine deaminase gene," *Mol. Cell. Biol.*, 10:4555–4564, 1990.

Chen, Innis, Sun, Wright, Kellems, "Sequence requirements for transcriptional arrest in exon 1 of the human adenosine deaminase gene," *Mol. Cell. Biol.*, 11:6248–6256, 1991.

Chiang, P. W., Fogel, E., Jackson, C. L., Lieuallen, K., Lennon, G., Qu, X., Wang, SQ, and Kurnit, D. M. (1996a). Isolation, sequencing, and mapping of the human homologue of the yeast transcription factor, SPT5. Genomics 38, 421–424.

Chiang, P. W., Wang, S. Q., Smithivas, P., Song, W. J., Crombez, E., Akhtar, A., Im, R., Greenfield, J., Ramamoorthy, S., Van Keuren, M., Blackburn, C. C., Tsai, C. H., and Kurnit, D. M. (1996b). Isolation and characterization of the human and mouse homologues (SUPT4H and Supt4h) of the yeast SPT4 gene. Genomics 34, 368–375.

Chien, Bartel, Sternglanz, Fields, "The two-hybrid system: A method to identify and clone genes for proteins that interact with a protein of interest," *Proc. Natl. Acad. Sci. USA*, 88:9578–9582, 1991.

Chinsky, Maa, Ramamurthy, Kellems, *J. Biol. Chem.*, 264: 14561–14565, 1989.

Chodosh, Fire, Samuels, Sharp, *J. Biol. Chem.*, 264:2250–2257, 1989.

Chou and Fasman, "Conformational Parameters for Amino Acids in Helical, b-Sheet, and Random Coil Regions Calculated from Proteins," *Biochemistry*, 13(2):211–222, 1974b.

Chou and Fasman, "Empirical Predictions of Protein Conformation," *Ann. Rev. Biochem.*, 47:251–276, 1978b.

Chou and Fasman, "Prediction of b-Turns," *Biophys. J*, 26:367–384, 1979.

Chou and Fasman, "Prediction of Protein Conformation," *Biochemistry*, 13(2):222–245, 1974a.

Chou and Fasman, "Prediction of the Secondary Structure of Proteins from Their Amino Acid Sequence," *Adv. Enzymol. Relat. Areas Mol. Biol.*, 47:45–148, 1978a.

Chun, R. F. and Jeang, K. T. (1996). Requirements for RNA polymerase II carboxyl-terminal domain for transcription of human retroviruses, human T-cell lymphotrophic virus, and HIV-1. J. Biol. Chem. 271, 27888–27894.

Cisek and Corden, *Nature*, 339:679–684, 1989.

Cismowski, Laff, Solomon, and Reed, *Mol. Cell. Biol.*, 15:2983–2992, 1995.

Collart, Tourkine, Belin, Vassalli, Jeanteur, Blanchard, "c-fos Gene transcription in murine macrophages is modulated by a calcium-dependent block to elongation in intron 1," *Mol. Cell. Biol.*, 11:2826–2831, 1991.

Cujec, T. P., Cho, H., Maldonado, E., Meyer, J., Reinberg, D., and Peterlin, B. M. (1997). The human immunodeficiency virus transactivator Tat interacts with the RNA polymerase II holoenzyme. Mol. Cell. Biol. 17, 1817–1823.

Cullen, B. R. (1991). Regulation of HIV-1 gene expression. [Review]. FASEB Journal 5, 2361–2368.

Dahmus, "Phosphorylation of the C-terminal domain of RNA polymerase II," Biochim. Biophys. Acta *Gene Struct. Expression*, 1261:171–182, 1995.

Dahmus, "The role of multisite phosphorylation in the regulation of RNA polymerase II activity," [Review]. Progress in *Nucleic Acid Research and Molecular Biology*, 48:143–179, 1994.

Dahmus, M. E. (1996). Reversible phosphorylation of the c-terminal domain of RNA polymerase II. [review]. J. Biol. Chem. 271, 19009–19012.

Dignam, Lebovitz, Roeder, "Accurate transcription initiation by RNA polymerase II in a soluble extract from isolated mammalian nuclei," *Nucleic Acids Res.*, 11:1475–1489, 1983.

Dubois, Nguyen, Bellier, Bensaude, *J. Biol. Chem.*, 269: 13331–13336, 1994.

Durfee T et al., "The retinoblastoma protein associates with the protein phosphatase type 1 catalytic subunit," *Genes Dev.*, 7:555–569, 1993.

Dvir, Peterson, Knuth, Lu, Dynan, *Proc. Natl. Acad. Sci. USA*, 89:11920–11924, 1992.

Egyhazi, Ossoinak, Pigon, Holmgren, Lee, Greenleaf, *Chromosoma*, 104:422–433, 1996.

Feaver, Gileadi, Li, Kornberg, "CTD kinase associated with yeast RNA polymerase II initiation factor b," *Cell*, 67:1223–1230, 1991.

Feaver, Svejstrup, Henry, Kornberg, *Cell*, 79:1103–1109, 1994.

Fetrow and Bryant, "New Programs for Potein Tertiary Structure Prediction," *Biotechnology*, 11:479–483, 1993.

Fields and Song, "A novel genetic system to detect protein—protein interactions," *Nature*, 340:245–246, 1989.

Finkelstein, A., Kostrub, C. F., Li, J., Chavez, D. P., Wang, B. Q., Fang, S. M., Greenblatt, J., and Burton, Z. F. (1992). A cDNA encoding RAP74, a general initiation factor for transcription by RNA polymerase II. Nature 355, 464–467.

Flores, Lu, Reinberg, *J. Biol. Chem.*, 267:2786–2793, 1992.

Flores, Maldonado, Reinberg, "Factors involved in specific transcription by mammalian RNA polymerase II. Factors IIE and IIF independently interact with RNA polymerase II," *J. Biol. Chem.*, 264:8913–8921, 1989.

Fong, S. E., Smanik, P., Thais, T., Smith, M. C., and Jaskunas, S.R. (1997). Detection of specific human immunodeficiency virus type 1 tat-tar complexes in the presence of mild denaturing conditions. Journal of Virological Methods 66, 91–101.

Fraser, Sehgal, Darnell, *Proc. Natl. Acad. Sci. USA*, 76:2571–2575, 1979.

Frohman, In: PCR Protocols: *A Guide to Methods and Applications*, Academic Press, N.Y., 1990.

Garcia-Martinez, L. F., Ivanov, D., and Gaynor, R. B. (1997a). Association of Tat with purified HIV-1 and HIV-2 transcription preinitiation complexes. J. Biol. Chem. 272, 6951–6958.

Garcia-Martinez, L. F., Mavankal, G., Neveu, J. M., Lane, W. S., Ivanov, D., and Gaynor, R. B. (1997b). Purification of a Tat-associated kinase reveals a TFIIH complex that modulates HIV-1 transcription. EMBO J. 16, 2836–2850.

Garcia and Gaynor, "The human immunodeficiency virus type-1 long terminal repeat and its role in gene expression," [Review]. *Progress in Nucleic Acid Research and Molecular Biology*, 49:157–196, 1994.

Garriga, J., Mayol, X., and Grana, X. (1996a). The CDC2-related kinase PITALRE is the catalytic subunit of active multimeric protein complexes. Biochem. J. 319, 293–298.

Gefter et al., *Somatic Cell Genet.*, 3:231–236, 1977.

Goding, In: *Monoclonal Antibodies: Principles and Practice*, 2d ed., Orlando, Fla., Academic Press, 1986, pp. 60–61, 65–66, 71–74.

Gossen and Bujard, *Proc. Natl. Acad. Sci. USA*, 89:5547–5551, 1992.

Gossen et al., *Science*, 268:1766–1769, 1995.

Grana, De Luca, Sang, Fu, Claudio, Rosenblatt, Morgan, Giordano, "PITALRE, a nuclear CDC2-related protein kinase that phosphorylates the retinoblastoma protein in vitro", *Proc. Natl. Acad. Sci. USA*, 91:3834–3838, 1994.

Guo and Price, "Mechanism of DmS-II-mediated pause suppression by *Drosophila* RNA polymerase II," *J. Biol. Chem.*, 268:18762–18770, 1993.

Hair and Morgan, *Mol. Cell. Biol.I*, 13:7925–7934, 1993.

Harper, Adami, Wei, Keyomarsi, Elledge, "The p21 Cdk-interacting protein Cip1 is a potent inhibitor of GI cyclin-dependent kinases," *Cell*, 75:805–816, 1993.

Herrmann and Rice, "Lentivirus Tat proteins specifically associate with a cellular protein kinase, TAK, that hyperphosphorylates the carboxyl-terminal domain of the large subunit of RNA polymerase II: Candidate for a Tat cofactor," *J. Virol.*, 69:1612–1620, 1995.

Herrmann and Rice, "Specific interaction of the human immunodeficiency virus Tat proteins with a cellular protein kinase," *Virology*, 197:601–608, 1993.

Herrmann, Gold, Rice, "Viral transactivators specifically target distinct cellular protein kinases that phosphorylate the RNA polymerase II C-terminal domain," *Nucleic Acids Research*, 24(3):501–508, 1996.

Hopp, U.S. Pat. No. 4,554,101.

Irie, K., Nomoto, S., Miyajima, I., and Matsumoto, K. (1991). SGV1 encodes a CDC28/cdc2-related kinase required for a G alpha subunit-mediated adaptive response to pheromone in *S. cerevisiae*. Cell 65, 785–795.

Izban and Luse, "SII-facilitated transcript cleavage in RNA polymerase II complexes stalled early after initiation occurs in primarily dinucleotide increments." *J. Biol. Chem.* 268:12864–12873, 1993.

Jameson and Wolf, "The Antigenic Index: A Novel Algorithm for Predicting Antigenic Determinants," *Comput. Appl. Biosci.*, 4(1):181–186, 1988.

Johnston, *Microbiol. Rev.* 51:458–476, 1987).

Jones and Peterlin, "Control of RNA initiation and elongation at the HIV-1 promoter," [Review]. *Annual Review of Biochemistry*, 63:717–743, 1994.

Kang and Dahmus, "RNA polymerases IIA and 110 have distinct roles during transcription from the TATA-less murine dihydrofolate reductase promoter," *J. Biol. Chem.*, 268:25033–25040, 1993.

Karin and Hunter, *Curr. Biol.*, 5:747–757, 1995.

Kash, Innis, Jackson, Kellems, "Functional analysis of a stable transcription arrest site in the first intron of the murine adenosine deaminase gene," *Mol. Cell. Biol.*, 13:2718–2729, 1993.

Keegan, Gill, Ptashne, *Science*, 231:699–704, 1986.

Keen, N. J., Gait, M. J., and Karn, J. (1996). Human immunodeficiency virus type-1 Tat is an integral component of the activated transcription-elongation complex. Proc. Natl. Acad. Sci. USA 93, 2505–2510.

Kephart, Marshall, Price, "Stability of *Drosophila* RNA polymerase II elongation complexes in vitro," *Mol. Cell. Biol.*, 12:2067–2077, 1992.

Kephart, Wang, Burton, Price, "Functional analysis of *Drosophila* factor 5 (TFIIF), a general transcription factor," *J. Biol. Chem.*, 269:13536–13543, 1994.

Kerppola and Kane, *FASEB J*, 5:2833–2842, 1991.

Kessler, Ben-Asher, Aloni, "Elements modulating the block of transcription elongation at the adenovirus 2 attenuation site," *J. Biol. Chem.*, 264:9785–9790, 1989.

Kessler, Ben-Asher, Resnekov, Hatini, Bengal, Aloni, "A 21-base pair DNA fragment directs transcription attenuation within the simian virus 40 late leader," *J. Biol. Chem.*, 266:13019–13027, 1991.

Kim and Dahmus, *J. Biol. Chem.*, 264:3169–3176, 1989.

Kohler and Milstein, *Eur. J. Immunol.*, 6:511–519,1976.

Kohler and Milstein, *Nature*, 256:495–497, 1975.

Koleske and Young, *Trends Biochem. Sci.*, 20:113–116, 1995.

Kodak, *Nucleic Acids Res.*, 15:8125–8148, 1987.

Krauskopf, Ben-Asher, Aloni, "Minute virus of mice infection modifies cellular transcription elongation," *J. Virol.*, 68:2741–2745, 1994.

Krauskopf, Bengal, Aloni, *Mol. Cell. Biol.*, 11:3515–3521, 1991.

Krauskopf, Resnekov, Aloni, "A cis downstream element participates in regulation of in vitro transcription initiation from the P38 promoter of minute virus of mice," *J. Virol.*, 64:354–360, 1990.

Krumm, Hickey, and Groudine, "Promoter-proximal pausing of RNA polymerase II defines a general rate-limiting step after transcription initiation," *Genes and Development*, 9:559–572, 1995.

Krumm, Meulia, Brunvand, Groudine, *Genes Dev.*, 6:2201–2213, 1992.

Kyte, Doolittle, "A simple method for displaying the hydropathic character of a protein," J. Mol. Biol., 157(1): 105–132,1982.

Laspia, Rice, Mathews, "HIV-1 Tat protein increases transcriptional initiation and stabilizes elongation," *Cell*, 59:283–292, 1989.

Laub, Jakobovits, Aloni, *Proceedings of the National Academy of Sciences of the United States of America*, 77:3297–3301, 1980.

Lee and Greenleaf, "CTD kinase large subunit is encoded by CTK1, a gene required for normal growth of *Saccharomyces* cervisiae," *Gene Expression*, 1:149–167, 1992.

Lee and Greenleaf, *Proc. Natl. Acad. Sci. USA*, 86:3624–3628,1989.

Lee, J. M. and Greenleaf, A. L. (1997). Modulation of RNA polymerase II elongation efficiency by c-terminal heptapeptide repeat domain kinase I. J. Biol. Chem. 272, 10990–10993.

Li and Kornberg, *Proc. Natl. Acad. Sci. USA*, 91:2362–2366, 1994.

Liao, Zhang, Jeffery, Koleske, Thompson, Chao, Viljoen, Van Vuuren, Young, *Nature*, 374:193–196, 1995.

Lu, Zawel, Fisher, Egly, Reinberg, "Human general transcription factor IIH phosphorylates the C-terminal domain of RNA polymerase II," *Nature*, 358:641–645, 1992.

MacLachlan, T. K., Sang, N., and Giordano, A. (1995). Cyclins, cyclin-dependent kinases and cdk inhibitors: implications in cell cycle control and cancer. [Review] [235 refs]. Critical Reviews in Eukaryotic Gene Expression 5, 127–156.

Mäkelä, Parvin, Kim, Huber, Sharp, Weinberg, "A kinase-deficient transcription factor TFIIH is functional in basal and activated transcription," *Proc. Natl. Acad. Sci. USA*, 92:5174–5178, 1995.

Maldonado and Reinberg, "News on initiation and elongation of transcription by RNA polymerase II," *Curr. Opin. Cell Biol.*, 7:352–361, 1995.

Marciniak and Sharp, "HIV-1 Tat protein promotes formation of more-processive elongation complexes," *EMBO J*, 10:4189–4196, 1991.

Marshall and Price, "Control of formation of two distinct classes of RNA polymerase II elongation complexes," *Mol. Cell. Biol.,* 12:2078–2090, 1992.

Marshall and Price, "Purification of P-TEFb, a transcription factor required for the transition into productive elongation," *J. Biol. Chem.,* 270:12335–12338, 1995.

Marshall, N. F., Peng, J. M., Xie, Z., and Price, D. H. (1996). Control of RNA polymerase II elongation potential by a novel carboxyl-terminal domain kinase. J. Biol. Chem. 271, 27176–27183.

Mavankal, G., Ou, S. H. I., Oliver, H., Sigman, D., Gaynor, R. B., Transcription factors, and Gene expression (1996). Human immunodeficiency virus type 1 and 2 Tat proteins specifically interact with RNA polymerase II. Proc. Natl. Acad. Sci. USA 93, 2089–2094.

Mechti, Piechaczyk, Blanchard, Jeanteur, Lebleu, "Sequence requirements for premature transcription arrest within the first intron of the mouse c-fos gene," *Mol. Cell. Biol.,* 11:2832–2841, 1991.

Meulia, Krumm, Groudine, "Distinct properties of c-myc transcriptional elongation are revealed in *Xenopus* oocytes and mammalian cells and by template titration, 5,6-dichloro-1-b-D-ribofuranosylbenzimidazole (DRB), and promoter mutagenesis," *Mol. Cell. Biol.,* 13:5647–5658, 1993.

Middleton and Morgan, *Mol. Cell Biol.,* 10:727–735, 1990.

Miller, Asselin, Dufort, Yang, Gupta, Marcu, Nepveu, "A cis-acting element in the promoter region of the murine c-myc gene is necessary for transcriptional block," Mol. Cell. Biol., 9:5340–5349, 1989.

Morgan, Principles of CDK regulation, Nature 374:131–134, 1995.

Nakamura et al., In: *Enzyme Immunoassays: Heterogeneous and Homogeneous Systems,* Chapter 27, 1987.

Neenhold, H. R. and Rana, T. M. (1995). Major groove opening at the HIV-1 Tat binding site of TAR RNA evidenced by a rhodium probe. Biochemistry 34, 6303–6309.

Nonet, Sweetser, Young, *Cell,* 50:909–915, 1987.

O'Brien, Hardin, Greenleaf, Lis, *Nature,* 370:75–77, 1994.

Parada, C. A. and Roeder, R. G. (1996). Enhanced processivity of RNA polymerase II triggered by Tat-induced phosphorylation of its carboxy-terminal domain. Nature 384, 375–378.

Payne and Dahmus, "Partial purification and characterization of two distinct protein kinases that differentially phosphorylate the carboxyl-terminal domain of RNA polymerase subunit IIa," *J. Biol. Chem.,* 268:80–87, 1993.

Pendergrast, P. S. and Hernandez, N. (1997). RNA-targeted activators, but not DNA-targeted activators, repress the synthesis of short transcripts at the human immunodeficiency virus type 1 long terminal repeat. J. Virol. 71, 910–917.

Pessler, F., Pendergrast, P.S., and Hernandez, N. (1997). Purification and characterization of FBI-1, a cellular factor that binds to the human immunodeficiency virus type 1 inducer of short transcripts. Molecular & Cellular Biology 17, 3786–3798.

Peterson, Dvir, Anderson, Dynan, "DNA binding provides a signal for phosphorylation of the RNA polymerase II heptapeptide repeats," *Genes Dev.,* 6:426–438, 1992.

Price, Sluder, Greenleaf, "Dynamic interaction between a *Drosophila* transcription factor and RNA polymerase II," *Mol. Cell Biol.,* 9:1465–1475, 1989.

Price, Sluder, Greenleaf, "Fractionation of transcription factors for RNA polymerase II from *Drosophila* $K_c$ cell nuclear extracts," *J. Biol. Chem.,* 262:3244–3255, 1987.

Ramamurthy, Maa, Harless, Wright, Kellems, *Mol. Cell. Biol.,* 10:1484–1491, 1990.

Rasmussen and Lis, *J. Mol. Biol.,* 252:522–535, 1995.

Reddy and Reddy, "Differential binding of nuclear factors to the intron 1 sequences containing the transcriptional pause site correlates with c-myb expression," *Proc. Natl. Acad. Sci. USA,* 86:7326–7330, 1989.

Reinberg and Roeder, "Factors involved in specific transcription by mammalian RNA polymerase II. Transcription factor IIS stimulates elongation of RNA chains," *J. Biol. Chem.,* 262:3331–3337, 1987.

Reines, "Elongation factor-dependent transcript shortening by template-engaged RNA polymerase II," *J. Biol. Chem.,* 267:3795–3800, 1992.

*Remington's Pharmaceutical Sciences,* 15th Edition, 1035–1038 and 1570–1580.

Resnekov and Aloni, *Proc. Natl. Acad. Sci. USA,* 86:12–16, 1989.

Resnekov, Ben-Asher, Bengal, Choder, Hay, Kessler, Ragimov, Seiberg, Skolnik-David, and Aloni, "Transportation termination in animal viruses and cells," *Gene,* 72:91–104, 1988.

Resnitzky et al., *Mol. Cell. Biol.,* 14:1669–1679, 1994.

Rhim, H. and Rice, A. P. (1994). Functional significance of the dinucleotide bulge in stem-loop1 and stem-loop2 of HIV-2 TAR RNA. Virology 202, 202–211.

Rice, A. P. and Carlotti, F. (1990). Structural analysis of wild-type and mutant human immunodeficiency virus type 1 Tat proteins. J. Virol. 64, 6018–6026.

Roberts and Bentley, *EMBO J,* 11:1085–1093, 1992.

Rougvie and Lis, "Postinitiation transcriptional control in *Drosophila melanogaster,*" *Mol. Cell. Biol.,* 10:6041–6045, 1990.

Rougvie and Lis, "The RNA Polymerase II Molecule at the 5' End of the Uninduced hsp70 Gene of *D. Melanogaster* is Transcriptionally Engaged," *Cell,* 54:795–804, 1988.

Roy, Adamczewski, Seroz, Vermeulen, Tassan, Schaeffer, Nigg, Hoeijmakers, and Egly, *Cell,* 79:1093–1101, 1994.

Sambrook J, Fritsch E F, Maniatis, T, In: *Molecular cloning: A Laboratory Manual,* Cold Spring Harbor Press, Cold Spring Harbor, N.Y., 1989.

Sanchez-Pescador, Power, Barr, Steimer, Stempien, Brown-Shimer, Gee, Renard, Randolph, Levy et al., "Nucleotide sequence and expression of an AIDS-associated retrovirus (ARV-2)," *Science,* 227(4686):484–492, 1985.

Schneider-Schaulies, Schimpl, Wecker, *Eur. J. Immunol.,* 17:713–718, 1987.

Sehgal, Darnell, Tamm, *Cell,* 9:473–480, 1976.

Serizawa, Conaway, Conaway, "A carboxyl-terminal-domain kinase associated with RNA polymerase II transcription factor d from rat liver," *Proc. Natl. Acad. Sci. USA,* 89:7476–7480, 1992.

Serizawa, Mäkelä, Conaway, Conaway, Weinberg, Young, *Nature,* 374:280–282, 1995.

Sheldon, M., Ratnasabapathy, R., and Hernandez, N. (1993). Characterization of the inducer of short transcripts, a human immunodeficiency virus type 1 transcriptional element that activates the synthesis of short RNAs. Mol. Cell. Biol. 13, 1251–1263.

Shiekhattar, Mermelstein, Fisher, Drapkin, Dynlacht, Wessling, Morgan, and Reinberg, *Nature,* 374:283–287, 1995.

Shilatifard, Lane, Jackson, Conaway, Conaway, "An RNA polymerase II elongation factor encoded by the human ELL gene," *Science,* 271:1873–1876, 1996.

SivaRaman, Reines, Kane, "Purified elongation factor SII is sufficient to promote read-through by purified RNA polymerase II at specific termination sites in the human histone H3.3 gene," *J. Biol. Chem.*, 265:14554–14560, 1990.

Sluder, Greenleaf, Price, "Properties of a *Drosophila* RNA polymerase II elongation factor," J. Biol. Chem., 264: 8963–8969, 1989.

Spencer and Groudine, "Molecular analysis of the c-myc transcription elongation block: Implications for the generation of Burkitt's lymphoma," *Ann. NY Acad. Sci.*, 599:12–28, 1990a.

Spencer and Groudine, *Oncogene*, 5:777–786, 1990b.

Sterner, Lee, Hardin, Greenleaf, "The yeast carboxyl-terminal repeat domain kinase CTDK-I is a divergent cyclin—cyclin-dependent kinase complex," *Molecular and Cellular Biology*, 15:5716–5724, 1995.

Stone and Reinberg, *J. Biol. Chem.*, 267:6353–6360, 1992.

Strobl and Eick, "Hold back of RNA polymerase II at the transcription start site mediates down-regulation of c-myc in vivo," *EMBO J*, 11:3307–3314, 1992.

Szentirmay, M. N. and Sawadogo, M. (1993). Synthesis of reinitiated transcripts by mammalian RNA polymerase II is controlled by elongation factor SII. EMBO J. 12, 4677–4684.

Tamm and Kikuchi, *Proceedings of the National Academy of Sciences of the United States of America*, 76:5750–5754, 1979.

Tamm, Kikuchi, Darnell, Salditt-Georgeieff, *Biochemistry*, 19:2743–2748, 1980.

*Tet Expression Systems and Cell Lines* (July 1996), CLONTECHniques XI(3):2–5, 1996.

Thompson, Steinberg, Aronson, Burgess, *J. Biol. Chem.*, 264:11511–11520, 1989.

Valay, Simon, Dubois, Bensaude, Facca, Faye, *J. Mol. Biol.*, 249:535–544, 1995.

Venetianer, Dubois, Nguyen, Bellier, Seo, Bensaude, *Eur. J. Biochem.*, 233:83–92, 1995.

Wampler and Kadonaga, "Functional analysis of *Drosophila* transcription factor IIB," *Genes Dev.*, 6:1542–1552, 1992.

Wampler, Tyree, Kadonaga, "Fractionation of the general RNA polymerase II transcription factors from *Drosophila* embryos," *J. Biol. Chem.*, 265:21223–21231, 1990.

Weinberger, C. et al., *Science*, 228:740–742, 1985.

Wolf et al., "An Integrated Family of Amino Acid Sequence Analysis Programs," *Comput. Appl. Biosci.*, 4(1):187–191, 1988.

Wright and Bishop, "DNA sequences that mediate attenuation of transcription from the mouse protooncogene myc," *Proc. Natl. Acad. Sci. USA*, 86:505–509, 1989.

Wright, "Regulation of eukaryotic gene expression by transcriptional attenuation," *Molecular Biology of the Cell*, 4:661–668, 1993.

Xie and Price, "Purification of an RNA polymerase II transcript release factor from *Drosophila*," *J. Biol. Chem.*, 271:11043–11046, 1996.

Yang, Herrmann, Price, "The human immunodeficiency virus Tat proteins specifically associate with TAK in vivo and require the carboxy-terminal domain of RNA polymerase II for function," *Journal of Virology*, 70:4576–4584, 1996.

Yankulov, K., Blau, J., Purton, T., Roberts, S., Bentley, "Transcriptional elongation by RNA polymerase II is stimulated by transactivators," *Cell*, 77:749–759, 1994.

Yankulov, Pandes, McCracken, Bouchard, Bentley, "TFIIH functions in regulating transcriptional elongation by RNA polymerase II in *Xenopus* oocytes," *Molecular and Cellular Biology*, 16:3291–3299, 1996.

Yankulov, Yamashita, Roy, Egly, Bentley, "The transcriptional elongation inhibitor 5,6-dichloro-1-β-D-ribofuranosylbenzimidazole inhibits transcription factor IIH-associated protein kinase," *J. Biol. Chem.*, 270:23922–23925, 1995.

Yue, Favot, Dunn, Cassady, Hume, "Expression of mRNA encoding the macrophage colony-stimulating factor receptor (c-fins) is controlled by a constitutive promoter and tissue-specific transcription elongation," *Mol. Cell. Biol.*, 13:3191–3201, 1993.

Zandomeni, Zandomeni, Shugar, Weinmann, *J. Biol. Chem.*, 261:3414–3419, 1986.

Zauli, G., Gibellini, D., Caputo, A., Bassini, A., Negrini, M., Monne, M., Mazzoni, M., and Capitani, S. (1995). The human immunodeficiency virus type-1 Tat protein upregulates Bcl-2 gene expression in Jurkat T-cell lines and primary peripheral blood mononuclear cells. Blood 86, 3823–3834.

Zehring, Lee, Weeks, Jokerst, and Greenleaf, *Proc. Natl. Acad. Sci. USA*, 85:3698–3702, 1988.

Zhou and Sharp, *EMBO Journal*, 14:321–328, 1995.

What is claimed is:

1. An isolated nucleic acid molecule comprising a nucleic acid sequence that encodes a polypeptide having the amino acid sequence of SEQ ID NO:2.

2. An isolated nucleic acid consisting of a nucleic acid that encodes a polypeptide consisting of the amino acid sequence of SEQ ID NO:4, a nucleic acid that encodes a polypeptide consisting of the amino acid sequence of SEQ ID NO:45, a nucleic acid that encodes a polypeptide consisting of the amino acid sequence of SEQ ID NO:47, or a nucleic acid that encodes a polypeptide consisting of the amino acid sequence of SEQ ID NO:50.

3. The isolated nucleic acid molecule of claim 1, comprising a nucleic acid sequence that has the nucleotide sequence from position 115 to position 1327 of SEQ ID NO:1.

4. An isolated fragment of the isolated nucleic acid of claim 2, wherein said fragment encodes at least 16 contiguous amino acids of SEQ ID NO:4, at least 20 contiguous amino acids of SEQ ID NO:45, at least 20 contiguous amino acids of SEQ ID NO:47 or at least 125 contiguous amino acids of SEQ ID NO:50.

5. The isolated fragment of claim 4, wherein said fragment encodes at least 25 contiguous amino acids of SEQ ID NO:4, SEQ ID NO:45 or SEQ ID NO:47.

6. The isolated fragment of claim 5, wherein said fragment encodes at least about 30 contiguous amino acids of SEQ ID NO:4, SEQ ID NO:45 or SEQ ID NO:47.

7. The isolated fragment of claim 6, wherein said fragment encodes at least about 40 contiguous amino acids of SEQ ID NO:4, SEQ ID NO:45 or SEQ ID NO:47.

8. The isolated fragment of claim 7, wherein said fragment encodes at least about 50 contiguous amino acids of SEQ ID NO:4, SEQ ID NO:45 or SEQ ID NO:47.

9. The isolated fragment of claim 8, wherein said fragment encodes at least about 60 contiguous amino acids of SEQ ID NO:4, SEQ ID NO:45 or SEQ ID NO:47.

10. The isolated fragment of claim 9, wherein said fragment encodes at least about 70 contiguous amino acids of SEQ ID NO:4, SEQ ID NO:45 or SEQ ID NO:47.

11. The isolated fragment of claim 10, wherein said fragment encodes at least about 80 contiguous amino acids of SEQ ID NO:4, SEQ ID NO:45 or SEQ ID NO:47.

12. The isolated fragment of claim 11, wherein said fragment encodes at least about 90 contiguous amino acids of SEQ ID NO:4, SEQ ID NO:45 or SEQ ID NO:47.

13. The isolated fragment of claim 12, wherein said fragment encodes at least about 100 contiguous amino acids of SEQ ID NO:4, SEQ ID NO:45 or SEQ ID NO:47.

14. The isolated fragment of claim 4, wherein said fragment encodes at least 125 contiguous amino acids of SEQ ID NO:4, SEQ ID NO:45, SEQ ID NO:47 or SEQ ID NO:50.

15. The isolated fragment of claim 4, wherein said fragment encodes at least about 150 contiguous amino acids of SEQ ID NO:4, SEQ ID NO:45, SEQ ID NO:47 or SEQ ID NO:50.

16. The isolated fragment of claim 4, wherein said fragment encodes at least about 200 contiguous amino acids of SEQ ID NO:4, SEQ ID NO:45, SEQ ID NO:47 or SEQ ID NO:50.

17. An isolated nucleic acid molecule comprising a nucleic acid sequence that encodes a polypeptide having the amino acid sequence of SEQ ID NO:4, SEQ ID NO:45, SEQ ID NO:47 or SEQ ID NO:50.

18. The isolated nucleic acid molecule of claim 17, comprising a nucleic acid sequence that encodes a polypeptide having the amino acid sequence of SEQ ID NO:4.

19. The isolated nucleic acid molecule of claim 17, comprising a nucleic acid sequence that encodes a polypeptide having the amino acid sequence of SEQ ID NO:45.

20. The isolated nucleic acid molecule of claim 17, comprising a nucleic acid sequence that encodes a polypeptide having the amino acid sequence of SEQ ID NO:47.

21. The isolated nucleic acid molecule of claim 17, comprising a nucleic acid sequence that encodes a polypeptide having the amino acid sequence of SEQ ID NO:50.

22. The isolated nucleic acid fragment of claim 4 operatively linked to a promoter.

23. A vector comprising the fragment of claim 4.

24. The vector of claim 23, comprised within a recombinant host cell.

25. An isolated nucleic acid molecule encoding a fusion protein, wherein said isolated nucleic acid molecule comprises the fragment of claim 4 and a second nucleic acid coding region and wherein said isolated nucleic acid molecule encodes said fusion protein.

26. An isolated nucleic acid molecule comprising a nucleic acid sequence that encodes a P-TEFb large subunit protein, wherein said P-TEFb large subunit protein binds to a P-TEFb kinase subunit protein having the sequence of SEQ ID NO:2 or SEQ ID NO:6 to form a P-TEFb enzyme complex that promotes transcription elongation and wherein said nucleic acid molecule comprises the nucleotide sequence of SEQ ID NO:44.

27. An isolated nucleic acid molecule comprising a nucleic acid sequence that encodes a P-TEFb large subunit protein, wherein said P-TEFb large subunit protein binds to a P-TEFb kinase subunit protein having the sequence of SEQ ID NO:2 or SEQ ID NO:6 to form a P-TEFb enzyme complex that promotes transcription elongation and wherein said nucleic acid molecule comprises the nucleotide sequence of SEQ ID NO:46.

28. An isolated nucleic acid molecule comprising a nucleic acid sequence that encodes a P-TEFb large subunit protein, wherein said P-TEFb large subunit protein binds to a P-TEFb kinase subunit protein having the sequence of SEQ ID NO:2 or SEQ ID NO:6 to form a P-TEFb enzyme complex that promotes transcription elongation and wherein said nucleic acid molecule comprises the nucleotide sequence of SEQ ID NO:49.

29. An isolated nucleic acid molecule comprising the nucleotide sequence of SEQ ID NO:44, SEQ ID NO:46 or SEQ ID NO:49.

30. The isolated nucleic acid molecule of claim 29, wherein the nucleic acid molecule is up to about 10,000 basepairs in length.

31. The isolated nucleic acid molecule of claim 30, wherein the nucleic acid molecule is up to about 5,000 basepairs in length.

32. An isolated nucleic acid molecule comprising:
(a) a first nucleic acid sequence that encodes a P-TEFb small subunit protein that has kinase activity and binds to a P-TEFb large subunit protein of SEQ ID NO:4, SEQ ID NO:45, SEQ ID NO:47 or SEQ ID NO:50 to form a P-TEFb enzyme complex that promotes transcription elongation, wherein said P-TEFb small subunit protein has the amino acid sequence of SEQ ID NO:2 or SEQ ID NO:6; and
(b) a second nucleic acid sequence that encodes a P-TEFb large subunit protein that binds to a P-TEFb kinase subunit protein of SEQ ID NO:2 or SEQ ID NO:6 to form a P-TEFb enzyme complex that promotes transcription elongation, wherein said P-TEFb large subunit protein has the amino acid sequence set forth in SEQ ID NO:4, SEQ ID NO:45, SEQ ID NO:47 or SEQ ID NO:50.

33. The isolated nucleic acid molecule of claim 32, wherein said first nucleic acid sequence encodes a polypeptide having the amino acid sequence of SEQ ID NO:6.

34. The isolated nucleic acid molecule of claim 32, wherein said second nucleic acid sequence encodes a polypeptide that has the amino acid sequence of SEQ ID NO:45, SEQ ID NO:47 or SEQ ID. NO:50.

35. The isolated nucleic acid molecule of claim 34, wherein said second nucleic acid sequence has the nucleotide sequence of SEQ ID NO:44, SEQ ID NO:46 or SEQ ID NO:49.

36. The isolated nucleic acid molecule of claim 32, wherein said first nucleic acid sequence has the nucleotide sequence of SEQ ID NO:5 and wherein said second nucleic acid sequence has the nucleotide sequence of SEQ ID NO:44, SEQ ID NO:46 or SEQ ID NO:49.

37. One or more expression units comprising:
(a) a first isolated expression unit comprising, under the transcriptional control of a promoter, a first nucleic acid sequence that encodes a P-TEFb small subunit protein that has kinase activity and binds to a P-TEFb large subunit protein of SEQ ID NO:4, SEQ ID NO:45, SEQ ID NO:47 or SEQ ID NO:50 to form a P-TEFb enzyme complex that promotes transcription elongation, wherein said P-TEFb small subunit protein has the amino acid sequence of SEQ ID NO:2 or SEQ ID NO:6; and
(b) a second isolated expression unit comprising, under the transcriptional control of a promoter, a second nucleic acid sequence that encodes a P-TEFb large subunit protein that binds to a P-TEFb kinase subunit protein of SEQ ID NO:2 or SEQ ID NO:6 to form a P-TEFb enzyme complex that promotes transcription elongation, wherein said P-TEFb large subunit protein has the amino acid sequence of SEQ ID NO:4, SEQ ID NO:45, SEQ ID NO:47 or SEQ ID NO:50.

38. The one or more expression units of claim 37, wherein said first expression unit comprises a first nucleic acid sequence that encodes a P-TEFb small subunit protein that has kinase activity and binds to a P-TEFb large subunit protein of SEQ ID NO:4, SEQ ID NO:45, SEQ ID NO:47 or SEQ ID NO:50 to form a P-TEFb enzyme complex that promotes transcription elongation, wherein said first nucleic acid sequence has the nucleotide sequence of SEQ ID NO:5.

39. The one or more expression units of claim 37, wherein said second expression unit comprises a second nucleic acid sequence that encodes a P-TEFb large subunit protein that binds to a P-TEFb kinase subunit protein of SEQ ID NO:2 or SEQ ID NO:6 to form a P-TEFb enzyme complex that promotes transcription elongation, wherein said P-TEFb large subunit protein has the amino acid sequence of SEQ ID NO:4.

40. The one or more expression units of claim 37, wherein said second expression unit comprises a second nucleic acid sequence that encodes a P-TEFb large subunit protein that binds to a P-TEFb kinase subunit protein of SEQ ID NO:2 or SEQ ID NO:6 to form a P-TEFb enzyme complex that promotes transcription elongation, wherein said P-TEFb large subunit protein has the amino acid sequence of SEQ ID NO:45.

41. The one or more expression units of claim 37, wherein said second expression unit comprises a second nucleic acid sequence that encodes a P-TEFb large subunit protein that binds to a P-TEFb kinase subunit protein of SEQ ID NO:2 or SEQ ID NO:6 to form a P-TEFb enzyme complex that promotes transcription elongation, wherein said P-TEFb large subunit protein has the amino acid sequence of SEQ ID NO:47.

42. The one or more expression units of claim 37, wherein said second expression unit comprises a second nucleic acid sequence that encodes a P-TEFb large subunit protein that binds to a P-TEFb kinase subunit protein of SEQ ID NO:2 or SEQ ID NO:6 to form a P-TEFb enzyme complex that promotes transcription elongation, wherein said P-TEFb large subunit protein has the amino acid sequence of SEQ ID NO:50.

43. The one or more expression units of claim 37, wherein said second expression unit comprises a second nucleic acid sequence that has the nucleotide sequence of SEQ ID NO:44.

44. The one or more expression units of claim 37, wherein said second expression unit comprises a second nucleic acid sequence that has the nucleotide sequence of SEQ ID NO:46.

45. The one or more expression units of claim 37, wherein said second expression unit comprises a second nucleic acid sequence that has the nucleotide sequence of SEQ ID NO:49.

46. The one or more expression units of claim 37, wherein said first and said second expression units are comprised in a single expression vector.

47. The one or more expression units of claim 37, wherein said first and said second expression units are each comprised in a separate expression vector.

48. The one or more expression units of claim 37, wherein said one or more expression units are comprised within a recombinant host cell.

49. A recombinant host cell comprising the isolated nucleic acid molecule in accordance with claim 1, claim 2 or claim 32, or comprising an isolated fragment of an isolated nucleic acid in accordance with claim 4.

50. The recombinant host cell of claim 49, wherein said cell is a prokaryotic host cell.

51. The recombinant host cell of claim 49, wherein said cell is a eukaryotic host cell.

52. The recombinant host cell of claim 51, wherein said cell is a mammalian host cell.

53. The recombinant host cell of claim 49, wherein said cell further comprises an HIV Tat protein.

54. A recombinant host cell that comprises the isolated fragment of an isolated nucleic acid molecule in accordance with claim 4.

55. A recombinant host cell that comprises the isolated nucleic acid molecule in accordance with claim 1.

56. A recombinant host cell that comprises the isolated nucleic acid molecule in accordance with claim 2.

57. A recombinant host cell that comprises the isolated nucleic acid molecule in accordance with claim 32.

58. A recombinant host cell that comprises one or more expression units in accordance with claim 37.

59. The recombinant host cell of claim 58, wherein said cell is a prokaryotic host cell.

60. The recombinant host cell of claim 58, wherein said cell is a eukaryotic host cell.

61. The recombinant host cell of claim 60, wherein said cell is a mammalian host cell.

62. The recombinant host cell of claim 58, wherein said cell further comprises an HIV Tat protein.

63. The recombinant host cell of claim 58, wherein said one or more expression units are comprised in a single expression vector.

64. The recombinant host cell of claim 58, wherein said one or more expression units are each comprised in a separate expression vector.

65. An isolated nucleic acid molecule comprising the nucleotide sequence of SEQ ID NO:44.

66. An isolated nucleic acid molecule comprising the nucleotide sequence of SEQ ID NO:46.

67. An isolated nucleic acid molecule comprising the nucleotide sequence of SEQ ID NO:49.

* * * * *

SEQUENCE LISTING (1) GENERAL INFORMATION:

(iii) NUMBER OF SEQUENCES: 68

(2) INFORMATION FOR SEQ ID NO: 1:

(i) SEQUENCE CHARACTERISTICS:
      (A) LENGTH: 1457 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 115..1326

(xi) SEQUENCE DESCRIPTION: SEQ ID NO: 1:

```
-continued

TGTTGAGTCA ACAGCTGTAG ATACACCAAT TGTTGCCGAT TTCTTTCTTT TCGACTGTCG           60

GCTTCTCGCG AAACTGTGAT TGTGAAAATT GTACAAATAG AGGCAAATTT AACC ATG           117
                                                            Met
                                                             1

GCG CAC ATG TCC CAC ATG CTC CAG CAG CCT TCG GGG TCG ACG CCC TCC           165
Ala His Met Ser His Met Leu Gln Gln Pro Ser Gly Ser Thr Pro Ser
              5                  10                  15

AAC GTG GGC TCC AGC TCA TCG CGC ACG ATG TCC CTG ATG GAG AAA CAA           213
Asn Val Gly Ser Ser Ser Ser Arg Thr Met Ser Leu Met Glu Lys Gln
             20                  25                  30

AAG TAC ATC GAG GAC TAC GAC TTT CCC TAC TGC GAC GAG AGC AAC AAA           261
Lys Tyr Ile Glu Asp Tyr Asp Phe Pro Tyr Cys Asp Glu Ser Asn Lys
         35                  40                  45

TAC GAA AAG GTG GCG AAA ATT GGC CAA GGC ACC TTC GGA GAG GTT TTT           309
Tyr Glu Lys Val Ala Lys Ile Gly Gln Gly Thr Phe Gly Glu Val Phe
 50                  55                  60                  65

AAG GCT CGC GAG AAA AAG GGC AAC AAG AAG TTT GTG GCC ATG AAG AAG           357
Lys Ala Arg Glu Lys Lys Gly Asn Lys Lys Phe Val Ala Met Lys Lys
                 70                  75                  80

GTG CTG ATG GAC AAC GAA AAG GAG GGC TTT CCC ATC ACG GCT CTG CGA           405
Val Leu Met Asp Asn Glu Lys Glu Gly Phe Pro Ile Thr Ala Leu Arg
             85                  90                  95

GAG ATC CGC ATC CTG CAG CTG CTA AAG CAC GAG AAC GTG GTG AAT CTG           453
Glu Ile Arg Ile Leu Gln Leu Leu Lys His Glu Asn Val Val Asn Leu
         100                 105                 110

ATC GAG ATC TGC CGC ACC AAG GCC ACC GCC ACG AAT GGT TAC AGA TCC           501
Ile Glu Ile Cys Arg Thr Lys Ala Thr Ala Thr Asn Gly Tyr Arg Ser
     115                 120                 125

ACC TTC TAT TTG GTC TTT GAT TTC TGC GAA CAC GAT TTG GCA GGT CTT           549
Thr Phe Tyr Leu Val Phe Asp Phe Cys Glu His Asp Leu Ala Gly Leu
130                 135                 140                 145

CTG TCC AAC ATG AAC GTC AAG TTC AGT CTG GGC GAG ATT AAG AAG GTT           597
Leu Ser Asn Met Asn Val Lys Phe Ser Leu Gly Glu Ile Lys Lys Val
                 150                 155                 160

ATG CAG CAG CTT TTA AAC GGT TTG TAT TAC ATC CAC AGC AAC AAG ATC           645
Met Gln Gln Leu Leu Asn Gly Leu Tyr Tyr Ile His Ser Asn Lys Ile
             165                 170                 175

CTG CAC CGA GAC ATG AAA GCT GCC AAC GTG CTG ATT ACC AAG CAT GGC           693
Leu His Arg Asp Met Lys Ala Ala Asn Val Leu Ile Thr Lys His Gly
         180                 185                 190

ATC TTA AAG CTG GCT GAC TTT GGC TTG GCC CGT GCT TTT AGC ATT CCA           741
Ile Leu Lys Leu Ala Asp Phe Gly Leu Ala Arg Ala Phe Ser Ile Pro
     195                 200                 205

AAG AAC GAG AGT AAG AAT CGC TAT ACC AAT CGC GTA GTA ACC TTG TGG           789
Lys Asn Glu Ser Lys Asn Arg Tyr Thr Asn Arg Val Val Thr Leu Trp
210                 215                 220                 225

TAC CGG CCG CCT GAG CTG CTA CTT GGT GAC CGC AAC TAT GGT CCA CCC           837
Tyr Arg Pro Pro Glu Leu Leu Leu Gly Asp Arg Asn Tyr Gly Pro Pro
                 230                 235                 240

GTG GAC ATG TGG GGA GCC GGC TGC ATA ATG GCC GAG ATG TGG ACA CGC           885
Val Asp Met Trp Gly Ala Gly Cys Ile Met Ala Glu Met Trp Thr Arg
             245                 250                 255

TCG CCC ATC ATG CAA GGC AAT ACG GAG CAG CAG CAG TTA ACC TTT ATT           933
Ser Pro Ile Met Gln Gly Asn Thr Glu Gln Gln Gln Leu Thr Phe Ile
         260                 265                 270

TCG CAG CTA TGC GGC TCC TTT ACG CCG GAC GTG TGG CCG GGA GTG GAG           981
Ser Gln Leu Cys Gly Ser Phe Thr Pro Asp Val Trp Pro Gly Val Glu
     275                 280                 285

GAG CTG GAG CTG TAC AAA TCC ATC GAG CTG CCA AAG AAC CAG AAG CGT          1029
```

```
Glu Leu Glu Leu Tyr Lys Ser Ile Glu Leu Pro Lys Asn Gln Lys Arg
290                 295                 300                 305

CGA GTC AAG GAG CGC CTG CGT CCG TAT GTC AAG GAT CAA ACC GGC TGT      1077
Arg Val Lys Glu Arg Leu Arg Pro Tyr Val Lys Asp Gln Thr Gly Cys
                    310                 315                 320

GAT CTA TTG GAC AAA TTG CTG ACC CTT GAT CCC AAG AAA CGC ATC GAT      1125
Asp Leu Leu Asp Lys Leu Leu Thr Leu Asp Pro Lys Lys Arg Ile Asp
                325                 330                 335

GCG GAC ACA GCT CTG AAT CAC GAC TTC TTC TGG ACG GAT CCC ATG CCC      1173
Ala Asp Thr Ala Leu Asn His Asp Phe Phe Trp Thr Asp Pro Met Pro
                340                 345                 350

AGC GAC TTG AGC AAG ATG CTG TCC CAG CAC CTG CAG AGC ATG TTC GAG      1221
Ser Asp Leu Ser Lys Met Leu Ser Gln His Leu Gln Ser Met Phe Glu
                355                 360                 365

TAC CTG GCG CAG CCA CGC CGC AGC AAC CAG ATG CGC AAC TAT CAC CAG      1269
Tyr Leu Ala Gln Pro Arg Arg Ser Asn Gln Met Arg Asn Tyr His Gln
370                 375                 380                 385

CAA CTG ACC ACC ATG AAC CAG AAG CCC CAG GAC AAC AGT ATG ATT GAC      1317
Gln Leu Thr Thr Met Asn Gln Lys Pro Gln Asp Asn Ser Met Ile Asp
                390                 395                 400

CGG GTT TGG TAGACTGCCA GAGGTGTACG CACCCGACTA ATAGTTTCTC               1366
Arg Val Trp

ACCTTCAACT AGCGTTAGGT TATTAGGTTA GTGTACAATA AAAATATTGG CATTTGCATT    1426

AGCGCTTGCT CCAAATATAA AAAAAAAAAA A                                   1457

(2) INFORMATION FOR SEQ ID NO: 2:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala His Met Ser His Met Leu Gln Gln Pro Ser Gly Ser Thr Pro
1               5                   10                  15

Ser Asn Val Gly Ser Ser Ser Arg Thr Met Ser Leu Met Glu Lys
            20                  25                  30

Gln Lys Tyr Ile Glu Asp Tyr Asp Phe Pro Tyr Cys Asp Glu Ser Asn
            35                  40                  45

Lys Tyr Glu Lys Val Ala Lys Ile Gly Gln Gly Thr Phe Gly Glu Val
        50                  55                  60

Phe Lys Ala Arg Glu Lys Lys Gly Asn Lys Lys Phe Val Ala Met Lys
65                  70                  75                  80

Lys Val Leu Met Asp Asn Glu Lys Glu Gly Phe Pro Ile Thr Ala Leu
                85                  90                  95

Arg Glu Ile Arg Ile Leu Gln Leu Leu Lys His Glu Asn Val Val Asn
                100                 105                 110

Leu Ile Glu Ile Cys Arg Thr Lys Ala Thr Ala Thr Asn Gly Tyr Arg
            115                 120                 125

Ser Thr Phe Tyr Leu Val Phe Asp Phe Cys Glu His Asp Leu Ala Gly
            130                 135                 140

Leu Leu Ser Asn Met Asn Val Lys Phe Ser Leu Gly Glu Ile Lys Lys
145                 150                 155                 160

Val Met Gln Gln Leu Leu Asn Gly Leu Tyr Tyr Ile His Ser Asn Lys
                165                 170                 175
```

```
Ile Leu His Arg Asp Met Lys Ala Ala Asn Val Leu Ile Thr Lys His
            180                 185                 190

Gly Ile Leu Lys Leu Ala Asp Phe Gly Leu Ala Arg Ala Phe Ser Ile
        195                 200                 205

Pro Lys Asn Glu Ser Lys Asn Arg Tyr Thr Asn Arg Val Val Thr Leu
    210                 215                 220

Trp Tyr Arg Pro Pro Glu Leu Leu Gly Asp Arg Asn Tyr Gly Pro
225                 230                 235                 240

Pro Val Asp Met Trp Ala Gly Cys Ile Met Ala Glu Met Trp Thr
                245                 250                 255

Arg Ser Pro Ile Met Gln Gly Asn Thr Glu Gln Gln Leu Thr Phe
                260                 265                 270

Ile Ser Gln Leu Cys Gly Ser Phe Thr Pro Asp Val Trp Pro Gly Val
        275                 280                 285

Glu Glu Leu Glu Leu Tyr Lys Ser Ile Glu Leu Pro Lys Asn Gln Lys
    290                 295                 300

Arg Arg Val Lys Glu Arg Leu Arg Pro Tyr Val Lys Asp Gln Thr Gly
305                 310                 315                 320

Cys Asp Leu Leu Asp Lys Leu Leu Thr Leu Asp Pro Lys Lys Arg Ile
                325                 330                 335

Asp Ala Asp Thr Ala Leu Asn His Asp Phe Phe Trp Thr Asp Pro Met
                340                 345                 350

Pro Ser Asp Leu Ser Lys Met Leu Ser Gln His Leu Gln Ser Met Phe
    355                 360                 365

Glu Tyr Leu Ala Gln Pro Arg Arg Ser Asn Gln Met Arg Asn Tyr His
    370                 375                 380

Gln Gln Leu Thr Thr Met Asn Gln Lys Pro Gln Asp Asn Ser Met Ile
385                 390                 395                 400

Asp Arg Val Trp
```

(2) INFORMATION FOR SEQ ID NO: 3:

(i) SEQUENCE CHARACTERISTICS:
        (A) LENGTH: 4328 base pairs
        (B) TYPE: nucleic acid
        (C) STRANDEDNESS: single
        (D) TOPOLOGY: linear (xi) SEQUENCE DESCRIPTION: SEQ ID NO: 3:

```
CAGCCCTGCC GACGGCCATA CTTGAAAATA CATTTTTTTC TGCAAAGTTT GTCATTGTCA      60

CTGTGTGAAT GGAATCTGTG ATGTGTTGTG GAATTAAAAA CGTCAAGTAA CAACCCGTA     120

ATGGTTAAAG TGCACGGCGA AAGCAGTGCG AATAACTATG AATTGATACA AAAGTTGCAT    180

AACACGTCGC CTGGTGTCGC GGTTAGTGTG TTTTTCGTCT CGTTTCGTTT CCGCCGCAGT    240

CGCAGTTTCC AAAAAACCTC ACCACACCAT ACCATCTCCA CCACGCACAC ACACACACAA    300

ACAAACACGC AGAGACGCGG CGGCGGAAAA AGTGTGCGGA CCGCGGATTT AACCCCTCGT    360

TCCAAACCCA AATTGGAGTC TCCCAAAAAC AGCGAAATAT CGAGTGTGGC TTAGCCGATG    420

TGCCGTGCGA TCCCCACTGC CCCTTCCGTA CCGCTGCCAC CCCCGCCACA GCAGCAACGC    480

ACACGGATAC GGACACAGAC ACCAATACCA GCGCACTCAA GCACGGCCGA CAAAGAAAGA    540

GCGCTCTCCC TTCCTCTTTG TACAGTTAGT TCCTACAGCT GAATCAGCCA AAAGAAATTA    600

CTAGGTCCAT TCCGAGGCGC AGTTTGCATG TGAAACGGAG GTCCCCGCAT AACCACGCGG    660

AACCCGAAAT TCCAGATCCC CATCTCCGCT GCACGGATAA AGGAAACATA CAACCATGAG    720
```

-continued

| | |
|---|---|
| TCTCCTAGCC ACGCCAATGC CCCAGGCGGC CACCGCCTCA TCTTCTTCAT CCGCCTCCGC | 780 |
| GGCCGCCTCG GCCAGCGGGA TTCCAATCAC CGCCAACAAC AACCTGCCTT TCGAGAAGGA | 840 |
| CAAGATCTGG TACTTCAGCA ACGATCAGCT GGCCAATTTG CCAAGCAGAA GATGCGGCAT | 900 |
| CAAGGGCGAC GATGAGCTGC AGTACCGCCA GATGACCGCC TATCTGATAC AGGAAATGGG | 960 |
| TCAGCGTCTG CAGGTGTCCC AACTGTGCAT CAACACGGCC ATTGTGTACA TGCATCGGTT | 1020 |
| CTACGCCTTT CACTCCTTCA CCCACTTTCA TCGCAACTCC ATGGCGTCGG CGAGCCTCTT | 1080 |
| CTTGGCCGCC AAGGTAGAAG AGCAACCGCG GAAGCTGGAG CATGTTATTC GGGCCGCCAA | 1140 |
| CAAGTGCCTG CCGCCGACCA CCGAGCAGAA TTACGCCGAA CTCGCCCAGG AGCTTGTGTT | 1200 |
| CAACGAGAAC GTGCTCCTGC AGACGCTGGG CTTCGATGTG CCATCGATC ATCCGCACAC | 1260 |
| GCATGTGGTG CGCACCTGCC AGCTGGTCAA AGCATGCAAG GATCTGGCGC AGACATCGTA | 1320 |
| CTTCTTGGCC TCGAACAGCC TGCATCTGAC CTCGATGTGC CTCCAATATC GCCCCACGGT | 1380 |
| CGTAGCCTGT TTCTGCATTT ACCTAGCCTG CAAGTGGTCC CGATGGGAGA TCCCCCAGTC | 1440 |
| GACCGAGGGC AAGCACTGGT TCTACTATGT GGACAAGACG GTCTCGCTGG ATTTGCTAAA | 1500 |
| GCAGCTGACA GATGAGTTCA TCGCTATCTA TGAGAAGAGC CCGGCCCGTC TGAAGTCTAA | 1560 |
| GCTTAACTCG ATCAAGGCGA TCGCCCAGGG AGCCAGCAAT CGGACAGCTA ACAGCAAGGA | 1620 |
| CAAACCAAAG GAGGACTGGA AGATCACCGA GATGATGAAG GGCTACCACT CAAACATCAC | 1680 |
| GACACCACCA GAGCTGTTAA ACGGCAACGA CAGCCGGGAT CGGGACCGAG ATCGTGAACG | 1740 |
| GGAGAGAGAG CGGGAACGGG ATCCGTCGTC ACTACTGCCG CCACCGGCTA TGGTGCCGCA | 1800 |
| GCAAAGACGA CAGGATGGTG GACATCAGCG CTCGTCCTCA GTGAGCGGAG TGCCAGGCAG | 1860 |
| CAGCTCTTCG TCGTCTTCCT CCAGTCACAA GATGCCAAAT TACCCTGGTG GCATGCCGCC | 1920 |
| CGAAGCTCAT CCGGATCACA AGTCAAAGCA GCCGGGCTAT AACAATCGAA TGCCCTCAAG | 1980 |
| TCACCAGCGT AGTAGTAGCA GTGGACTCGG TTCCTCGGGA AGTGGCAGCC AGCACAGCAG | 2040 |
| CTCATCCTCG TCGTCTTCAA GCCAGCAGCC TGGCCGACCG TCTATGCCCG TGGACTATCA | 2100 |
| CAAATCCTCT CGCGGCATGC CGCCGGTAGG CGTGGGCATG CCACCTCACG GCAGCCACAA | 2160 |
| GATGACTTCG GGCTCCAAGC CTCAACAGCC GCAGCAGCAG CCGGTCCCAC ATCCATCCGC | 2220 |
| CTCTAATTCC TCTGCATCGG GCATGTCCTC CAAGGATAAA TCCCAGAGCA ACAAAATGTA | 2280 |
| TCCGAACGCA CCGCCGCCAT ACAGTAATAG TGCCCCTCAA AACCCGCTGA TGTCGCGTGG | 2340 |
| TGGATATCCA GGCGCTAGCA ATGGATCCCA GCCCCCGCCT CCCGCCGGAT ACGGCGGCCA | 2400 |
| TCGCAGCAAA TCCGGCTCCA CCGTCCATGG CATGCCGCAT TTCGAGCAGC AATTGCCCTA | 2460 |
| TTCCCAGAGC CAGAGCTACG GCCACATGCA GCAGCAGCCA GTGCCTCAGT CTCAGCAGCA | 2520 |
| ACAGATGCCT CCGGAGGCAT CCCAGCACTC GTTGCAGTCC AAGAACTCGC TCTTCAGTCC | 2580 |
| AGAGTGGCCA GACATTAAAA AGGAGCCCAT GTCGCAGTCG CAACCACAGC TTTTTAACGG | 2640 |
| TTTGCTACCC CCTCCTGCGC CTCCCGGCCA CGATTACAAG CTAAATAGCC ATCCGCGCGA | 2700 |
| CAAAGAAAGT CCCAAGAAAG AGCGACTAAC GCCAACCAAA AAGGATAAGC ACCGTCCTGT | 2760 |
| AATGCCCCCA ATGGGCAGTG GGAACAGTTC CTCCGGCTCG GGATCATCAA AGCCGATGCT | 2820 |
| ACCGCCTCAC AAGAAGCAGA TACCCCATGG CGGGGACCTG TTGACCAATC CTGGAGAGAG | 2880 |
| TGGAAGCCTA AAACGGCCCA ACGAGATCTC GGGAAGTCAG TATGGACTAA ATAAGCTGGA | 2940 |
| TGAAATAGAT AACAGTAATA TGCCTCGAGA AAAGCTTCGC AAGCTGGACA CTACAACTGG | 3000 |
| ACTACCAACT TATCCGAATT ATGAGGAGAA ACACACGCCT CTGAATATGT CCAACGGAAT | 3060 |
| CGAGACAACG CCGGATCTGG TGCGCAGTTT GCTAAAGGAG AGTCTGTGTC CATCGAACGC | 3120 |

-continued

```
TTCGCTCCTG AAACCGGATG CCTTGACTAT GCCTGGCCTG AAACCACCGG CCGAACTACT    3180

TGAGCCCATG CCCGCACCAG CGACAATCAA GAAAGAACAG GGAATAACTC CGATGACCAG    3240

TTTGGCTAGT GGGCCCGCAC CCATGGATTT GGAAGTACCC ACTAAACAGG CCGGAGAGAT    3300

TAAGGAGGAA AGCAGCAGCA AGTCCGAAAA GAAAAAGAAG AAGGATAAAC ACAAACACAA    3360

GGAGAAGGAC AAGTCCAAGG ACAAGACGGA AAAGGAGGAG CGTAAGAAGC ACAAGAGGGA    3420

CAAGCAGAAG GATCGTAGCG GCAGCGGTGG CAGCAAGGAC AGTTCTCTTC CCAATGAGCC    3480

TCTGAAGATG GTTATCAAGA ATCCCAACGG CAGCCTGCAG GCCGGTGCGT CAGCTCCCAT    3540

TAAACTTAAG ATCAGCAAAA ATAAGGTTGA ACCCAATAAC TACTCTGCAG CGGCGGGTCT    3600

GCCTGGCGCA ATCGGATATG GCTTGCCTCC AACTACGGCT ACCACCACAT CCGCTTCGAT    3660

CGGAGCAGCT GCTCCTGTTC TGCCTCCTTA TGGTGCCGGC GGTGGTGGCT ACAGCTCATC    3720

GGGCGGCAGC AGTTCCGGTG GCAGCAGCAA GAAAAAGCAC AGCGATCGTG ACCGCGACAA    3780

GGAGAGCAAA AAGAATAAGA GCCAAGACTA CGCGAAGTAC AATGGCGCTG GTGGCGGCAT    3840

CTTTAATCCC CTTGGCGGTG CTGGCGCCGC ACCCAATATG TCTGGAGGAA TGGGCGCCCC    3900

CATGTCTACT GCTGTACCAC CATCCATGCT GTTGGCGCCC ACCGGTGCAG TACCACCCTC    3960

TGCCGCTGGG CTGGCACCGC CTCCCATGCC CGTCTACAAC AAGAAGTAGT GGTAGCGGTC    4020

AGAGGGTTAT TCTTAAGTCG TACGTTTTGA TATATGTATA GAACCTCAGT AAGTCCGATT    4080

GTAGTATAGT TGTTAGGATT GTTAGTGAGA TGCATTATTG ATTTTAGTTA AGCACATAGA    4140

TAAAACTCCA AATTGGAAGT GAAACCGGAT GCGCAGATCG AAGAAGAATG GAAGTAGATG    4200

TCGCGATGGG GCTGGACGTA AAAGCAGTAC TCAAATCGCG AAAACTTTTG TACAGCATTA    4260

ATTAGTTTAT AACTATAATA AATAGCATAC ATATAAGCCC AAAAAAAAAA AAAAAAAAAA    4320

AAAAAAAA                                                             4328
```

(2) INFORMATION FOR SEQ ID NO: 4:

(i) SEQUENCE CHARACTERISTICS:
        (A) LENGTH: 1097 amino acids
        (B) TYPE: amino acid
        (C) STRANDEDNESS: <Unknown>
        (D) TOPOLOGY: linear (xi) SEQUENCE DESCRIPTION: SEQ ID NO: 4:

```
Met Ser Leu Leu Ala Thr Pro Met Pro Gln Ala Ala Thr Ala Ser Ser
 1               5                  10                  15

Ser Ser Ser Ala Ser Ala Ala Ala Ser Ala Ser Gly Ile Pro Ile Thr
            20                  25                  30

Ala Asn Asn Asn Leu Pro Phe Glu Lys Asp Lys Ile Trp Tyr Phe Ser
        35                  40                  45

Asn Asp Gln Leu Ala Asn Leu Pro Ser Arg Arg Cys Gly Ile Lys Gly
    50                  55                  60

Asp Asp Glu Leu Gln Tyr Arg Gln Met Thr Ala Tyr Leu Ile Gln Glu
65                  70                  75                  80

Met Gly Gln Arg Leu Gln Val Ser Gln Leu Cys Ile Asn Thr Ala Ile
                85                  90                  95

Val Tyr Met His Arg Phe Tyr Ala Phe His Ser Phe Thr His Phe His
                100                 105                 110

Arg Asn Ser Met Ala Ser Ala Ser Leu Phe Leu Ala Ala Lys Val Glu
            115                 120                 125

Glu Gln Pro Arg Lys Leu Glu His Val Ile Arg Ala Ala Asn Lys Cys
```

-continued

```
            130                 135                 140
Leu Pro Pro Thr Thr Glu Gln Asn Tyr Ala Glu Leu Ala Gln Glu Leu
145                 150                 155                 160

Val Phe Asn Glu Asn Val Leu Leu Gln Thr Leu Gly Phe Asp Val Ala
                165                 170                 175

Ile Asp His Pro His Thr His Val Val Arg Thr Cys Gln Leu Val Lys
                180                 185                 190

Ala Cys Lys Asp Leu Ala Gln Thr Ser Tyr Phe Leu Ala Ser Asn Ser
                195                 200                 205

Leu His Leu Thr Ser Met Cys Leu Gln Tyr Arg Pro Thr Val Val Ala
210                 215                 220

Cys Phe Cys Ile Tyr Leu Ala Cys Lys Trp Ser Arg Trp Glu Ile Pro
225                 230                 235                 240

Gln Ser Thr Glu Gly Lys His Trp Phe Tyr Val Asp Lys Thr Val
                245                 250                 255

Ser Leu Asp Leu Leu Lys Gln Leu Thr Asp Glu Phe Ile Ala Ile Tyr
                260                 265                 270

Glu Lys Ser Pro Ala Arg Leu Lys Ser Lys Leu Asn Ser Ile Lys Ala
                275                 280                 285

Ile Ala Gln Gly Ala Ser Asn Arg Thr Ala Asn Ser Lys Asp Lys Pro
290                 295                 300

Lys Glu Asp Trp Lys Ile Thr Glu Met Met Lys Gly Tyr His Ser Asn
305                 310                 315                 320

Ile Thr Thr Pro Pro Glu Leu Leu Asn Gly Asn Asp Ser Arg Asp Arg
                325                 330                 335

Asp Arg Asp Arg Glu Arg Glu Arg Glu Arg Asp Pro Ser Ser
                340                 345                 350

Leu Leu Pro Pro Pro Ala Met Val Pro Gln Gln Arg Gln Asp Gly
                355                 360                 365

Gly His Gln Arg Ser Ser Val Ser Gly Val Pro Gly Ser Ser Ser
                370                 375                 380

Ser Ser Ser Ser Ser Ser His Lys Met Pro Asn Tyr Pro Gly Gly Met
385                 390                 395                 400

Pro Pro Glu Ala His Pro Asp His Lys Ser Lys Gln Pro Gly Tyr Asn
                405                 410                 415

Asn Arg Met Pro Ser Ser His Gln Arg Ser Ser Ser Gly Leu Gly
                420                 425                 430

Ser Ser Gly Ser Gly Ser Gln His Ser Ser Ser Ser Ser Ser
                435                 440                 445

Ser Gln Gln Pro Gly Arg Pro Ser Met Pro Val Asp Tyr His Lys Ser
450                 455                 460

Ser Arg Gly Met Pro Pro Val Gly Val Gly Met Pro Pro His Gly Ser
465                 470                 475                 480

His Lys Met Thr Ser Gly Ser Lys Pro Gln Gln Pro Gln Gln Gln Pro
                485                 490                 495

Val Pro His Pro Ser Ala Ser Asn Ser Ser Ala Ser Gly Met Ser Ser
                500                 505                 510

Lys Asp Lys Ser Gln Ser Asn Lys Met Tyr Pro Asn Ala Pro Pro Pro
                515                 520                 525

Tyr Ser Asn Ser Ala Pro Gln Asn Pro Leu Met Ser Arg Gly Gly Tyr
                530                 535                 540

Pro Gly Ala Ser Asn Gly Ser Gln Pro Pro Pro Ala Gly Tyr Gly
545                 550                 555                 560
```

-continued

```
Gly His Arg Ser Lys Ser Gly Ser Thr Val His Gly Met Pro His Phe
            565                 570                 575

Glu Gln Gln Leu Pro Tyr Ser Gln Ser Gln Ser Tyr Gly His Met Gln
        580                 585                 590

Gln Gln Pro Val Pro Gln Ser Gln Gln Gln Met Pro Pro Glu Ala
    595                 600                 605

Ser Gln His Ser Leu Gln Ser Lys Asn Ser Leu Phe Ser Pro Glu Trp
610                 615                 620

Pro Asp Ile Lys Lys Glu Pro Met Ser Gln Ser Gln Pro Gln Leu Phe
625                 630                 635                 640

Asn Gly Leu Leu Pro Pro Ala Pro Pro Gly His Asp Tyr Lys Leu
            645                 650                 655

Asn Ser His Pro Arg Asp Lys Glu Ser Pro Lys Lys Glu Arg Leu Thr
            660                 665                 670

Pro Thr Lys Lys Asp Lys His Arg Pro Val Met Pro Met Gly Ser
        675                 680                 685

Gly Asn Ser Ser Ser Gly Ser Gly Ser Ser Lys Pro Met Leu Pro Pro
    690                 695                 700

His Lys Lys Gln Ile Pro His Gly Gly Asp Leu Leu Thr Asn Pro Gly
705                 710                 715                 720

Glu Ser Gly Ser Leu Lys Arg Pro Asn Glu Ile Ser Gly Ser Gln Tyr
            725                 730                 735

Gly Leu Asn Lys Leu Asp Glu Ile Asp Asn Ser Asn Met Pro Arg Glu
        740                 745                 750

Lys Leu Arg Lys Leu Asp Thr Thr Thr Gly Leu Pro Thr Tyr Pro Asn
    755                 760                 765

Tyr Glu Glu Lys His Thr Pro Leu Asn Met Ser Asn Gly Ile Glu Thr
770                 775                 780

Thr Pro Asp Leu Val Arg Ser Leu Leu Lys Glu Ser Leu Cys Pro Ser
785                 790                 795                 800

Asn Ala Ser Leu Leu Lys Pro Asp Ala Leu Thr Met Pro Gly Leu Lys
            805                 810                 815

Pro Pro Ala Glu Leu Leu Glu Pro Met Pro Ala Pro Ala Thr Ile Lys
        820                 825                 830

Lys Glu Gln Gly Ile Thr Pro Met Thr Ser Leu Ala Ser Gly Pro Ala
    835                 840                 845

Pro Met Asp Leu Glu Val Pro Thr Lys Gln Ala Gly Glu Ile Lys Glu
850                 855                 860

Glu Ser Ser Ser Lys Ser Glu Lys Lys Lys Lys Asp Lys His Lys
865                 870                 875                 880

His Lys Glu Lys Asp Lys Ser Lys Asp Lys Thr Glu Lys Glu Arg
            885                 890                 895

Lys Lys His Lys Arg Asp Lys Gln Lys Asp Arg Ser Gly Ser Gly Gly
        900                 905                 910

Ser Lys Asp Ser Ser Leu Pro Asn Glu Pro Leu Lys Met Val Ile Lys
    915                 920                 925

Asn Pro Asn Gly Ser Leu Gln Ala Gly Ala Ser Ala Pro Ile Lys Leu
930                 935                 940

Lys Ile Ser Lys Asn Lys Val Glu Pro Asn Asn Tyr Ser Ala Ala Ala
945                 950                 955                 960

Gly Leu Pro Gly Ala Ile Gly Tyr Gly Leu Pro Pro Thr Thr Ala Thr
            965                 970                 975
```

-continued

```
Thr Thr Ser Ala Ser Ile Gly Ala Ala Ala Pro Val Leu Pro Pro Tyr
            980             985             990
Gly Ala Gly Gly Gly Tyr Ser Ser Gly Gly Ser Ser Ser Gly
        995             1000            1005
Gly Ser Ser Lys Lys His Ser Asp Arg Asp Arg Asp Lys Glu Ser
1010            1015            1020
Lys Lys Asn Lys Ser Gln Asp Tyr Ala Lys Tyr Asn Gly Ala Gly Gly
1025            1030            1035            1040
Gly Ile Phe Asn Pro Leu Gly Gly Ala Gly Ala Ala Pro Asn Met Ser
            1045            1050            1055
Gly Gly Met Gly Ala Pro Met Ser Thr Ala Val Pro Pro Ser Met Leu
            1060            1065            1070
Leu Ala Pro Thr Gly Ala Val Pro Pro Ser Ala Ala Gly Leu Ala Pro
            1075            1080            1085
Pro Pro Met Pro Val Tyr Asn Lys Lys
            1090            1095
```

(2) INFORMATION FOR SEQ ID NO: 5:

(i) SEQUENCE CHARACTERISTICS:
        (A) LENGTH: 1119 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1116

(xi) SEQUENCE DESCRIPTION: SEQ ID NO: 5:

```
ATG GCA AAG CAG TAC GAC TCG GTG GAG TGC CCT TTT TGT GAT GAA GTT        48
Met Ala Lys Gln Tyr Asp Ser Val Glu Cys Pro Phe Cys Asp Glu Val
  1               5                  10                  15

TCC AAA TAC GAG AAG CTC GCC AAG ATC GGC CAA GGC ACC TTC GGG GAG        96
Ser Lys Tyr Glu Lys Leu Ala Lys Ile Gly Gln Gly Thr Phe Gly Glu
             20                  25                  30

GTG TTC AAG GCC AGG CAC CGC AAG ACC GGC CAG AAG GTG GCT CTG AAG       144
Val Phe Lys Ala Arg His Arg Lys Thr Gly Gln Lys Val Ala Leu Lys
         35                  40                  45

AAG GTG CTG ATG GAA AAC GAG AAG GAG GGG TTC CCC ATT ACA GCC TTG       192
Lys Val Leu Met Glu Asn Glu Lys Glu Gly Phe Pro Ile Thr Ala Leu
 50                  55                  60

CGG GAG ATC AAG ATC CTT CAG CTT CTA AAA CAC GAG AAT GTG GTC AAC       240
Arg Glu Ile Lys Ile Leu Gln Leu Leu Lys His Glu Asn Val Val Asn
 65                  70                  75                  80

TTG ATT GAG ATT TGT CGA ACC AAA GCT TCC CCC TAT AAC CGC TGC AAG       288
Leu Ile Glu Ile Cys Arg Thr Lys Ala Ser Pro Tyr Asn Arg Cys Lys
                 85                  90                  95

GGT AGT ATA TAC CTG GTG TTC GAC TTC TGC GAG CAT GAC CTT GCT GGG       336
Gly Ser Ile Tyr Leu Val Phe Asp Phe Cys Glu His Asp Leu Ala Gly
            100                 105                 110

CTG TTG AGC AAT GTT TTG GTC AAG TTC ACG CTG TCT GAG ATC AAG AGG       384
Leu Leu Ser Asn Val Leu Val Lys Phe Thr Leu Ser Glu Ile Lys Arg
        115                 120                 125

GTG ATG CAG ATG CTG CTT AAC GGC CTC TAC TAC ATC CAC AGA AAC AAG       432
Val Met Gln Met Leu Leu Asn Gly Leu Tyr Tyr Ile His Arg Asn Lys
    130                 135                 140

ATC CTG CAT AGG GAC ATG AAG GCT GCT AAT GTG CTT ATC ACT CGT GAT       480
Ile Leu His Arg Asp Met Lys Ala Ala Asn Val Leu Ile Thr Arg Asp
145                 150                 155                 160
```

```
GGG GTC CTG AAG CTG GCA GAC TTT GGG CTG GCC CGG GCC TTC AGC CTG       528
Gly Val Leu Lys Leu Ala Asp Phe Gly Leu Ala Arg Ala Phe Ser Leu
            165                 170                 175

GCC AAG AAC AGC CAG CCC AAC CGC TAC ACC AAC CGT GTG GTG ACA CTC       576
Ala Lys Asn Ser Gln Pro Asn Arg Tyr Thr Asn Arg Val Val Thr Leu
            180                 185                 190

TGG TAC CGG CCC CCG GAG CTG TTG CTC GGG GAG CGG GAC TAC GGC CCC       624
Trp Tyr Arg Pro Pro Glu Leu Leu Leu Gly Glu Arg Asp Tyr Gly Pro
            195                 200                 205

CCC ATT GAC CTG TGG GGT GCT GGG TGC ATC ATG GCA GAG ATG TGG ACC       672
Pro Ile Asp Leu Trp Gly Ala Gly Cys Ile Met Ala Glu Met Trp Thr
            210                 215                 220

CGC AGC CCC ATC ATG CAG GGC AAC ACG GAG CAG CAC CAA CTC GCC CTC       720
Arg Ser Pro Ile Met Gln Gly Asn Thr Glu Gln His Gln Leu Ala Leu
225                 230                 235                 240

ATC AGT CAG CTC TGC GGC TCC ATC ACC CCT GAG GTG TGG CCA AAC GTG       768
Ile Ser Gln Leu Cys Gly Ser Ile Thr Pro Glu Val Trp Pro Asn Val
            245                 250                 255

GAC AAC TAT GAG CTG TAC GAA AAG CTG GAG CTG GTC AAG GGC CAG AAG       816
Asp Asn Tyr Glu Leu Tyr Glu Lys Leu Glu Leu Val Lys Gly Gln Lys
            260                 265                 270

CGG AAG GTG AAG GAC AGG CTG AAG GCC TAT GTG CGT GAC CCA TAC GCA       864
Arg Lys Val Lys Asp Arg Leu Lys Ala Tyr Val Arg Asp Pro Tyr Ala
            275                 280                 285

CTG GAC CTC ATC GAC AAG CTG CTG GTG CTG GAC CCT GCC CAG CGC ATC       912
Leu Asp Leu Ile Asp Lys Leu Leu Val Leu Asp Pro Ala Gln Arg Ile
            290                 295                 300

GAC AGC GAT GAC GCC CTC AAC CAC GAC TTC TTC TGG TCC GAC CCC ATG       960
Asp Ser Asp Asp Ala Leu Asn His Asp Phe Phe Trp Ser Asp Pro Met
305                 310                 315                 320

CCC TCC GAC CTC AAG GGC ATG CTC TCC ACC CAC CTG ACG TCC ATG TTC      1008
Pro Ser Asp Leu Lys Gly Met Leu Ser Thr His Leu Thr Ser Met Phe
            325                 330                 335

GAG TAC TTG GCA CCA CCG CGC CGG AAG GGC AGC CAG ATC ACC CAG CAG      1056
Glu Tyr Leu Ala Pro Pro Arg Arg Lys Gly Ser Gln Ile Thr Gln Gln
            340                 345                 350

TCC ACC AAC CAG AGT CGC AAT CCC GCC ACC ACC AAC CAG ACG GAG TTT      1104
Ser Thr Asn Gln Ser Arg Asn Pro Ala Thr Thr Asn Gln Thr Glu Phe
            355                 360                 365

GAG CGC GTC TTC TGA                                                   1119
Glu Arg Val Phe
    370
```

(2) INFORMATION FOR SEQ ID NO: 6:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Ala Lys Gln Tyr Asp Ser Val Glu Cys Pro Phe Cys Asp Glu Val
1               5                   10                  15

Ser Lys Tyr Glu Lys Leu Ala Lys Ile Gly Gln Gly Thr Phe Gly Glu
            20                  25                  30

Val Phe Lys Ala Arg His Arg Lys Thr Gly Gln Lys Val Ala Leu Lys
            35                  40                  45

Lys Val Leu Met Glu Asn Glu Lys Glu Gly Phe Pro Ile Thr Ala Leu
            50                  55                  60
```

```
Arg Glu Ile Lys Ile Leu Gln Leu Leu Lys His Glu Asn Val Val Asn
 65                  70                  75                  80

Leu Ile Glu Ile Cys Arg Thr Lys Ala Ser Pro Tyr Asn Arg Cys Lys
                 85                  90                  95

Gly Ser Ile Tyr Leu Val Phe Asp Phe Cys Glu His Asp Leu Ala Gly
            100                 105                 110

Leu Leu Ser Asn Val Leu Val Lys Phe Thr Leu Ser Glu Ile Lys Arg
        115                 120                 125

Val Met Gln Met Leu Leu Asn Gly Leu Tyr Tyr Ile His Arg Asn Lys
    130                 135                 140

Ile Leu His Arg Asp Met Lys Ala Ala Asn Val Leu Ile Thr Arg Asp
145                 150                 155                 160

Gly Val Leu Lys Leu Ala Asp Phe Gly Leu Ala Arg Ala Phe Ser Leu
                165                 170                 175

Ala Lys Asn Ser Gln Pro Asn Arg Tyr Thr Asn Arg Val Val Thr Leu
            180                 185                 190

Trp Tyr Arg Pro Pro Glu Leu Leu Gly Glu Arg Asp Tyr Gly Pro
        195                 200                 205

Pro Ile Asp Leu Trp Gly Ala Gly Cys Ile Met Ala Glu Met Trp Thr
210                 215                 220

Arg Ser Pro Ile Met Gln Gly Asn Thr Glu Gln His Gln Leu Ala Leu
225                 230                 235                 240

Ile Ser Gln Leu Cys Gly Ser Ile Thr Pro Glu Val Trp Pro Asn Val
                245                 250                 255

Asp Asn Tyr Glu Leu Tyr Glu Lys Leu Glu Leu Val Lys Gly Gln Lys
            260                 265                 270

Arg Lys Val Lys Asp Arg Leu Lys Ala Tyr Val Arg Asp Pro Tyr Ala
        275                 280                 285

Leu Asp Leu Ile Asp Lys Leu Leu Val Leu Asp Pro Ala Gln Arg Ile
    290                 295                 300

Asp Ser Asp Asp Ala Leu Asn His Asp Phe Phe Trp Ser Asp Pro Met
305                 310                 315                 320

Pro Ser Asp Leu Lys Gly Met Leu Ser Thr His Leu Thr Ser Met Phe
                325                 330                 335

Glu Tyr Leu Ala Pro Pro Arg Arg Lys Gly Ser Gln Ile Thr Gln Gln
            340                 345                 350

Ser Thr Asn Gln Ser Arg Asn Pro Ala Thr Thr Asn Gln Thr Glu Phe
        355                 360                 365

Glu Arg Val Phe
370

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 7:

ACGAATTCCA CACAATCCAA AGATC                                    25

(2) INFORMATION FOR SEQ ID NO: 8:

(i) SEQUENCE CHARACTERISTICS:
        (A) LENGTH: 26 base pairs
```

(B) TYPE: nucleic acid
            (C) STRANDEDNESS: single
            (D) TOPOLOGY: linear (xi) SEQUENCE DESCRIPTION: SEQ ID NO: 8:

CAGAATTCCT ATTGCCGATC CCCAGA                                                        26

(2) INFORMATION FOR SEQ ID NO: 9:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: one-of(8, 14)
            (D) OTHER INFORMATION: /mod_base= OTHER
                /note= "N = A or C or G or T"

(ix) FEATURE:
            (A) NAME/KEY: modified_base
            (B) LOCATION: 12
            (D) OTHER INFORMATION: /mod_base= OTHER
                /note= "Y = C or T"

(ix) FEATURE:
            (A) NAME/KEY: modified_base
            (B) LOCATION: one-of(17, 20)
            (D) OTHER INFORMATION: /mod_base= OTHER
                /note= "R = A or G"

(xi) SEQUENCE DESCRIPTION: SEQ ID NO: 9:

GGAATTCNAT GYTNCARCAR CC                                                            22

(2) INFORMATION FOR SEQ ID NO: 10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: one-of(13, 16, 19, 22, 25)
            (D) OTHER INFORMATION: /mod_base= OTHER
                /note= "R = A or G"

(xi) SEQUENCE DESCRIPTION: SEQ ID NO: 10:

AACTGCAGTC CARAARAART CRTGRTT                                                       27

(2) INFORMATION FOR SEQ ID NO: 11:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 11:

TGTCAAGGAT CAAACCGGCT GTGAT                                                         25

(2) INFORMATION FOR SEQ ID NO: 12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 12:

CGAATTCCAA GAAACGCATC GATGC                                    25

(2) INFORMATION FOR SEQ ID NO: 13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 13:

AGACCTGCCA AATCGTGT                                            18

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 14:

AGAAGGTGGA TCTGTAACCA TTCGT                                    25

(2) INFORMATION FOR SEQ ID NO: 15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 15:

GGAATTCAGA TCTCGATCAG ATTCA                                    25

(2) INFORMATION FOR SEQ ID NO: 16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 16:

TTACTACTCG AGCTACCAAA CCCGGTC                                  27

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 17:

TAAGCAAGCT TCTATGGCGC ACATGTCC                                 28

(2) INFORMATION FOR SEQ ID NO: 18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 18:

TTACTACTCG AGCTACCAAA CCCGGTC                                                    27

(2) INFORMATION FOR SEQ ID NO: 19:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: one-of(13, 16, 22)
            (D) OTHER INFORMATION: /mod_base= OTHER
                /note= "Y = C or T"

(ix) FEATURE:
            (A) NAME/KEY: modified_base
            (B) LOCATION: 17
            (D) OTHER INFORMATION: /mod_base= OTHER
                /note= "W = A or T"

(ix) FEATURE:
            (A) NAME/KEY: modified_base
            (B) LOCATION: 18
            (D) OTHER INFORMATION: /mod_base= OTHER
                /note= "S = C or G"

(ix) FEATURE:
            (A) NAME/KEY: modified_base
            (B) LOCATION: 19
            (D) OTHER INFORMATION: /mod_base= OTHER
                /note= "N = A or C or G or T"

(xi) SEQUENCE DESCRIPTION: SEQ ID NO: 19:

GGAATTCTGG TAYTTYWSNA AYGA                                                       24

(2) INFORMATION FOR SEQ ID NO: 20:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 11
            (D) OTHER INFORMATION: /mod_base= OTHER
                /note= "Y = C or T"

(ix) FEATURE:
            (A) NAME/KEY: modified_base
            (B) LOCATION: 14
            (D) OTHER INFORMATION: /mod_base= OTHER
                /note= "R = A or G"

(ix) FEATURE:
            (A) NAME/KEY: modified_base
            (B) LOCATION: one-of(17, 20)
            (D) OTHER INFORMATION: /mod_base= OTHER
                /note= "N = A or C or G or T"

(xi) SEQUENCE DESCRIPTION: SEQ ID NO: 20:

CGGGATCCTG YTCRAANGGN GGCAT                                                      25

(2) INFORMATION FOR SEQ ID NO: 21:

(i) SEQUENCE CHARACTERISTICS:
            (A) LENGTH: 24 base pairs
            (B) TYPE: nucleic acid
            (C) STRANDEDNESS: single

```
            (D) TOPOLOGY: linear (ix) FEATURE:
            (A) NAME/KEY: modified_base
            (B) LOCATION: one-of(11, 14, 20)
            (D) OTHER INFORMATION: /mod_base= OTHER
                /note= "N = A or C or G or T"

(ix) FEATURE:
            (A) NAME/KEY: modified_base
            (B) LOCATION: 23
            (D) OTHER INFORMATION: /mod_base= OTHER
                /note= "R = A or G"

(xi) SEQUENCE DESCRIPTION: SEQ ID NO: 21:

CGGGATCCAA NGGNGGCATN CCRT                                              24

(2) INFORMATION FOR SEQ ID NO: 22:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 22:

ATCACGACAC CACCAGAGCT GTTA                                              24

(2) INFORMATION FOR SEQ ID NO: 23:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 23:

CGAATTCAGA TCGTGAACGG GA                                                22

(2) INFORMATION FOR SEQ ID NO: 24:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO: 24:

CGAATTCAGG CGCTAGCAAT G                                                 21

(2) INFORMATION FOR SEQ ID NO: 25:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 25:

GAAAGGCGTA GAACCGA                                                      17

(2) INFORMATION FOR SEQ ID NO: 26:

(i) SEQUENCE CHARACTERISTICS:
            (A) LENGTH: 26 base pairs
            (B) TYPE: nucleic acid
            (C) STRANDEDNESS: single
            (D) TOPOLOGY: linear
```

-continued (xi) SEQUENCE DESCRIPTION: SEQ ID NO: 26:

GCTGACCCAT TTCCTGTATC AGATAG                                         26

(2) INFORMATION FOR SEQ ID NO: 27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 27:

GGAATTCTTC TGCTTGGCGA AT                                             22

(2) INFORMATION FOR SEQ ID NO: 28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 28:

GGGAATTCGA GGTTCTATAC ATAT                                           24

(2) INFORMATION FOR SEQ ID NO: 29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 29:

CTGTGTGAAT GGAATCTGTG ATGTG                                          25

(2) INFORMATION FOR SEQ ID NO: 30:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 30:

TATCCCGGGT CATATGAGTC TCCTAGCC                                       28

(2) INFORMATION FOR SEQ ID NO: 31:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 31:

Met Leu Gln Gln Pro Ser Gly Ser Thr Pro Ser Asn Val
1               5                   10

(2) INFORMATION FOR SEQ ID NO: 32:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (xi) SEQUENCE DESCRIPTION: SEQ ID NO: 32:

Ala Asp Thr Ala Leu Asn His Asp Phe Phe Trp Thr Asp Pro Met Pro
 1               5                  10                  15
Ser (2) INFORMATION FOR SEQ ID NO: 33:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (xi) SEQUENCE DESCRIPTION: SEQ ID NO: 33:

Met Leu Gln Gln Pro
 1               5

(2) INFORMATION FOR SEQ ID NO: 34:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (xi) SEQUENCE DESCRIPTION: SEQ ID NO: 34:

Asn His Asp Phe Phe Trp Thr
 1               5

(2) INFORMATION FOR SEQ ID NO: 35:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (xi) SEQUENCE DESCRIPTION: SEQ ID NO: 35:

Ser Pro Glu Trp Pro Asp Ile
 1               5

(2) INFORMATION FOR SEQ ID NO: 36:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 36:

Trp Tyr Phe Ser Asn Asp Gln Leu Ala Asn Ser Pro Ser Arg
 1               5                  10

(2) INFORMATION FOR SEQ ID NO: 37:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 37:

Thr Val His Gly Met Pro Pro Phe Glu Gln Gln Leu Pro Tyr
 1               5                  10

(2) INFORMATION FOR SEQ ID NO: 38:

```
    (i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (xi) SEQUENCE DESCRIPTION: SEQ ID NO: 38:

Trp Tyr Phe Ser Asn Asp
 1               5

(2) INFORMATION FOR SEQ ID NO: 39:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (xi) SEQUENCE DESCRIPTION: SEQ ID NO: 39:

Met Pro Pro Phe Glu Gln
 1               5

(2) INFORMATION FOR SEQ ID NO: 40:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (xi) SEQUENCE DESCRIPTION: SEQ ID NO: 40:

His Gly Met Pro Pro Phe
 1               5

(2) INFORMATION FOR SEQ ID NO: 41:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 41:

GCAGGATCCA GAATTCCATA TGGCAAAGCA GTACGACTCG G                   41

(2) INFORMATION FOR SEQ ID NO: 42:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 42:

CAGTACTCGA GTTATCAGAA GACGCGCTCA AAC                             33

(2) INFORMATION FOR SEQ ID NO: 43:

(i) SEQUENCE CHARACTERISTICS:
        (A) LENGTH: 4528 base pairs
        (B) TYPE: nucleic acid
        (C) STRANDEDNESS: single
        (D) TOPOLOGY: linear (xi) SEQUENCE DESCRIPTION: SEQ ID NO: 43:

GGGGGGGGGG GGGTGAATGA AGGAGCGGGC GGAGGAGGAA TTGTCATGGC GTCGGGCCGT  60
```

-continued

```
GGAGCTTCTT CTCGCTGGTT CTTTACTCGG GAACAGCTGG AGAACACGCC GAGCCGCCGC      120

TGCGGAGTGG AGGCGGATAA AGAGCTCTCG TGCCGCCAGC AGGCGGCCAA CCTCATCCAG      180

GAGATGGGAC AGCGTCTCAA TGTCTCTCAG CTTACAATAA ACACTGCGAT TGTTTATATG      240

CACAGGTTTT ATATGCACCA TTCTTTCACC AAATTCAACA AAAATATAAT ATCGTCTACT      300

GCATTATTTT TGGCTGCAAA AGTGGAAGAA CAGGCTCGAA AACTTGAACA TGTTATCAAA      360

GTAGCACATG CTTGTCTTCA TCCTCTAGAG CCACTGCTGG ATACTAAATG TGATGCTTAC      420

CTTCAACAGA CTCAAGAACT GGTTATACTT GAAACCATAA TGCTACAAAC TCTAGGTTTT      480

GAGATCACCA TTGAACACCC ACACACAGAT GTGGTGAAAT GTACCCAGTT AGTAAGAGCA      540

AGCAAGGATT TGGCACAGAC ATCCTATTTC ATGGCTACCA ACAGTCTGCA TCTTACAACC      600

TTCTGTCTTC AGTACAAACC AACAGTGATA GCATGTGTAT GCATTCATTT GGCTTGCAAA      660

TGGTCCAATT GGGAGATCCC TGTATCAACT GATGGAAAGC ATTGGTGGGA ATATGTGGAT      720

CCTACAGTTA CTCTAGAATT ATTAGATGAG CTAACACATG AGTTTCTACA AATATTGGAG      780

AAAACGCCTA ATAGGTTGAA GAAGATTCGA ACTGGAGGG CTAATCAGGC AGCTAGGAAA       840

CCAAAAGTAG ATGGACAGGT ATCAGAGACA CCACTTCTTG GTTCATCTTT GGTCCAGAAT      900

TCCATTTTAG TAGATAGTGT CACTGGTGTG CCTACAAACC CAAGTTTTCA GAAACCATCT      960

ACATCAGCAT TCCCTGCGCC AGTACCTCTA AATTCAGGAA ATATTTCTGT TCAAGCAGC     1020

CATACATCTG ATAATTTGTC AATGCTAGCA ACAGGAATGC CAAGTACTTC ATACGGTTTA    1080

TCATCACACC AGGAATGGCC TCAACATCAA GACTCAGCAA GGACAGAACA GCTATATTCA    1140

CAGAAACAGG AGACATCTTT GTCTGGTAGC CAGTACAACA TCAACTTCCA GCAGGGACCT    1200

TCTATATCAC TGCATTCAGG ATTACATCAC AGACCTGACA AAATTTCAGA TCATTCTTCT    1260

GTTAAGCAAG AATATACTCA TAAAGCAGGG AGCAGTAAAC ACCATGGGCC AATTTCCACT    1320

ACTCCAGGAA TAATTCCTCA GAAAATGTCT TTAGATAAAT ATAGAGAAAA GCGTAAACTA    1380

GAAACTCTTG ATCTCGATGT AAGGGATCAT TATATAGCTG CCCAGGTAGA ACAGCAGCAC    1440

AAACAAGGGC AGTCACAGGC AGCCAGCAGC AGTTCTGTTA CTTCTCCCAT TAAAATGAAA    1500

ATACCTATCG CAAATACTGA AAAATACATG GCAGATAAAA AGGAAAAGAG TGGGTCACTG    1560

AAATTACGGA TTCCAATACC ACCCACTGAT AAAAGCGCCA GTAAAGAAGA ACTGAAAATG    1620

AAAATAAAAG TTTCTTCTTC AGAAAGACAC AGCTCTTCTG ATGAAGGCAG TGGGAAAAGC    1680

AAACATTCAA GCCCACATAT TAGCAGAGAC CATAAGGAGA AGCACAAGGA GCATCCTTCA    1740

AGCCGCCACC ACACCAGCAG CCACAAGCAT TCCCACTCGC ATAGTGGCAG CAGCAGCGGT    1800

GGCAGTAAAC ACAGTGCCGA CGGAATACCA CCCACTGTTC TGAGGAGTCC TGTTGGCCTG    1860

AGCAGTGATG GCATTTCCTC TAGCTCCAGC TCTTCAAGGA AGAGGCTGCA TGTCAATGAT    1920

GCATCTCACA ACCACCACTC CAAAATGAGC AAAAGTTCCA AAAGTTCAGG TGGGCTACGG    1980

ACATCTCAGC ACCTCGTGAA ACTGGACAAG AAGCCAGTGG AGACCAACGG TCCTGATGCC    2040

AATCACGAGT ACAGTACAAG CAGCCAGCAT ATGGACTACA AGACACATT CGACATGCTG     2100

GACTCACTGT TAAGTGCCCA AGGAATGAAC ATGTAATAAT TTGTTTAGGT CAATTTTTCC    2160

TTTACTTTTT TAATTTAAAA ATTGTTAGAA TGGAAAAATT CCTTCTGATC TAGCAGTGGT    2220

AACCCCTGCT GTTGCTGCCA CTGCTTCAAT ATTTGTAAGT GCTACTTTAT TCTTCATTCT    2280

GAAAAGAAGA GATTATAGTA ACAAGTCTT TATCTCCACA TATGATAGTG TTATAAAATAC     2340

TGTAAAGGCA TGGAAGGTGC AAAACTCAGT ATTTCTACAA TTGCAGCTAA GAACATTAGG    2400

ATGAATGGCT GGCTGCTTCT AGGAATATAA GATGCCTCAA GCATTCATTA TTTATGATTT    2460
```

```
GAATACTGTA GCTATTTTTT GTTGCTTGGC TTTTGAATGA GTGTAAATTG TTTTCTTTTG    2520

TGTATTTATA CTTGTATGTA TGATTTGCAT GTTTCAATGA TAAAGGGATA AAACAGTATA    2580

CTGACAACTG TTTACAAGAA AGTGGAGAAA ATGTACTACA TTTTGTATGT TTAGATATTA    2640

CCGTAAATAC TCAGGATTGG AGCTGCTTGT AAGTATAACA ATATACAGAA TACTTTATTT    2700

TATCTTGTCA GAGTTCCATC ACTATCTAAA ACAAAGGTGC AATTTTTTAT GTTAACCTTA    2760

AATCTAGCCC TTACTGGAAG CCACTGATAG GGACATTCAC TACCAGATGT GTGCAGTGCA    2820

GCAGATGGTC ATATAACACT GTGAGGCACT GAATTTTGCC TTCAGAGGTT CTGACCAGAT    2880

TGGCTGCTGA ATAGCCCCT AACTTTCTGA AGGCTTGAAG AGGAAAAAAT AAAGTTTACA     2940

TACTCTTGAT GGAAGTGCAT TTAAATGTTT GTTGGCTTGT TGCAGTTCTA TGAAACAGAG    3000

CTGTTAATAA TGGTTATGTG GATTACTGTG ATTTGAAAAC TAAATTCACA ATAACTTACC    3060

TAGTAGAGAT TTAGTGAGTT GTTTCCTTTA AAGAATTTTA CACTACATAT TTTAATAGTA    3120

AACAGGGTCA CTTTCCTTTA GCATTCAGAA TGACACCATA TTCTTAAATA TACTCCTTCC    3180

CTGAAGCGTG TTTGTGTGTG ATGCCATATT TCTTTTTCAG GTAAATGTAG TCTTCCTTAT    3240

AAAAATGAAA TTAAACCTAT GCTCTCAATT CTTTTATATT CTAACAATAA ATAAAAAAGA    3300

AAAGATTACT GACTGTGCAT TGTACCTGTA TTTATAGTTT ATGGTTATCA GAAGCTCTGT    3360

AAGAAAGAAA AGGTCAGCTC CCAGGCAAAC CAGTAGTGGA GGTTTTACAT TTGTTTGCAC    3420

ATCTCAGTAT ATTTCTGTTG AGGTAAAGTT TGCACAGTCA TCTGACTTCT GATCAAGCAT    3480

TAGATTTTAA CTTGTTTAGA TTTTGTCTTA AACACCAGTA ATATGGCTCT TGTTTATCAG    3540

CTAATCTTGA ATTTATTCTG TGGTAAATCT TTTGAGTTGC TGAGTATATT TGAGATTGAT    3600

TGGATTCAAC CTCTTGTTGA ACTGAAAACT TAATTTTTTC TCTGTATTTT TGTTACAAAG    3660

CCACTGATAC GTGCACAATT GTAATTAAGT ATGTTGCAGT TGTAAATATT AGAGTTTAAT    3720

CTCATGCTCT ACCTTTATTT AGCAATTACC TAATTTGCCA GTAGCTTTAT AATTTTTAAA    3780

GATAATTGTT CATTATTTTG TCAATGTTAT TTGAACTTGG GGTACTTAGG AGCCTCTTTG    3840

TAGGGACTGT GCCTAGGTAG CATGTCCTAA CATTTGTTCT GGTCTTGCAT AACTTCAGTA    3900

TCTTTGTCAT TATATGTAAC TTTGTTGCTC TGTATGGCAT AATATTGTAT CCATAAACAT    3960

GGTAATTTTG ATACAGTTAT ACTTTTACAG TGGTACATAA TCCAAGGACT AGTATAGAAT    4020

TAAGCTGAGT GCAAGATGAG GGAGGGAAGG GCTTTCTTGG TAATTTAGAT GTGAAACCTC    4080

TACAGAGCTA TCATGTAAAA ACTACATGAG GTGGTTGTGC TACTGTATAA TTGGGGGTGA    4140

TAATACCAGG AATTTTAATA AGATTTTGTA AAGAATATCC AGAAAGTAG TGAACTTATT     4200

TTCAGTAGGC ATAGAAAACA ATGTGAATAT TTAAGGTCTG TGACTATAGT TAAACTTCAC    4260

TAAGAATTTG CAGAATTGTT TTGAGATGTG TGAATAAAGG TAATTTTATT GAATCTTCAT    4320

TGGTGCTAAT GTTGGACAGT TAAAAAGATA GCTAGTGTAT ATTGTTATGG GTCAGTACTT    4380

ATTAGTACTT CCAAAATTGA ATTTGAAATG CTATGTATTC ACTTTTCACT CTGTAAATGT    4440

AATTCTTTAC AATGACTTTA TTTATTAAAG GGCAGCCAGT TGTCATTTGT AAAAAAAAA    4500

AAAAAAAAAA AAAGCGGCCG CTGAATTC                                     4528
```

(2) INFORMATION FOR SEQ ID NO: 44:

(i) SEQUENCE CHARACTERISTICS:
        (A) LENGTH: 2091 base pairs
        (B) TYPE: nucleic acid
        (C) STRANDEDNESS: single
        (D) TOPOLOGY: linear (xi) SEQUENCE DESCRIPTION: SEQ ID NO: 44:

```
ATGGCGTCGG GCCGTGGAGC TTCTTCTCGC TGGTTCTTTA CTCGGGAACA GCTGGAGAAC      60
ACGCCGAGCC GCCGCTGCGG AGTGGAGGCG GATAAAGAGC TCTCGTGCCG CCAGCAGGCG     120
GCCAACCTCA TCCAGGAGAT GGGACAGCGT CTCAATGTCT CTCAGCTTAC AATAAACACT     180
GCGATTGTTT ATATGCACAG GTTTTATATG CACCATTCTT TCACCAAATT CAACAAAAAT     240
ATAATATCGT CTACTGCATT ATTTTTGGCT GCAAAAGTGG AAGAACAGGC TCGAAAACTT     300
GAACATGTTA TCAAAGTAGC ACATGCTTGT CTTCATCCTC TAGAGCCACT GCTGGATACT     360
AAATGTGATG CTTACCTTCA ACAGACTCAA GAACTGGTTA TACTTGAAAC CATAATGCTA     420
CAAACTCTAG GTTTTGAGAT CACCATTGAA CACCCACACA CAGATGTGGT GAAATGTACC     480
CAGTTAGTAA GAGCAAGCAA GGATTTGGCA CAGACATCCT ATTTCATGGC TACCAACAGT     540
CTGCATCTTA CAACCTTCTG TCTTCAGTAC AAACCAACAG TGATAGCATG TGTATGCATT     600
CATTTGGCTT GCAAATGGTC CAATTGGGAG ATCCCTGTAT CAACTGATGG AAAGCATTGG     660
TGGGAATATG TGGATCCTAC AGTTACTCTA GAATTATTAG ATGAGCTAAC ACATGAGTTT     720
CTACAAATAT GGAGAAAAC GCCTAATAGG TTGAAGAAGA TTCGAAACTG GAGGGCTAAT     780
CAGGCAGCTA GGAAACCAAA AGTAGATGGA CAGGTATCAG AGACACCACT TCTTGGTTCA     840
TCTTTGGTCC AGAATTCCAT TTTAGTAGAT AGTGTCACTG GTGTGCCTAC AAACCCAAGT     900
TTTCAGAAAC CATCTACATC AGCATTCCCT GCGCCAGTAC CTCTAAATTC AGGAAATATT     960
TCTGTTCAAG ACAGCCATAC ATCTGATAAT TTGTCAATGC TAGCAACAGG AATGCCAAGT    1020
ACTTCATACG GTTTATCATC ACACCAGGAA TGGCCTCAAC ATCAAGACTC AGCAAGGACA    1080
GAACAGCTAT ATTCACAGAA ACAGGAGACA TCTTTGTCTG GTAGCCAGTA CAACATCAAC    1140
TTCCAGCAGG GACCTTCTAT ATCACTGCAT TCAGGATTAC ATCACAGACC TGACAAAATT    1200
TCAGATCATT CTTCTGTTAA GCAAGAATAT ACTCATAAAG CAGGGAGCAG TAAACACCAT    1260
GGGCCAATTT CCACTACTCC AGGAATAATT CCTCAGAAAA TGTCTTTAGA TAAATATAGA    1320
GAAAAGCGTA AACTAGAAAC TCTTGATCTC GATGTAAGGG ATCATTATAT AGCTGCCCAG    1380
GTAGAACAGC AGCACAAACA AGGGCAGTCA CAGGCAGCCA GCAGCAGTTC TGTTACTTCT    1440
CCCATTAAAA TGAAAATACC TATCGCAAAT ACTGAAAAAT ACATGGCAGA TAAAAAGGAA    1500
AAGAGTGGGT CACTGAAATT ACGGATTCCA ATACCACCCA CTGATAAAAG CGCCAGTAAA    1560
GAAGAACTGA AAATGAAAAT AAAAGTTTCT TCTTCAGAAA GACACAGCTC TTCTGATGAA    1620
GGCAGTGGGA AAAGCAAACA TTCAAGCCCA CATATTAGCA GAGACCATAA GGAGAAGCAC    1680
AAGGAGCATC CTTCAAGCCG CCACCACACC AGCAGCCACA AGCATTCCCA CTCGCATAGT    1740
GGCAGCAGCA GCGGTGGCAG TAAACACAGT GCCGACGGAA TACCACCCAC TGTTCTGAGG    1800
AGTCCTGTTG GCCTGAGCAG TGATGGCATT TCCTCTAGCT CCAGCTCTTC AAGGAAGAGG    1860
CTGCATGTCA ATGATGCATC TCACAACCAC CACTCCAAAA TGAGCAAAAG TTCCAAAAGT    1920
TCAGGTGGGC TACGGACATC TCAGCACCTC GTGAAACTGG ACAAGAAGCC AGTGGAGACC    1980
AACGGTCCTG ATGCCAATCA CGAGTACAGT ACAAGCAGCC AGCATATGGA CTACAAAGAC    2040
ACATTCGACA TGCTGGACTC ACTGTTAAGT GCCCAAGGAA TGAACATGTA A            2091
```

(2) INFORMATION FOR SEQ ID NO: 45:

(i) SEQUENCE CHARACTERISTICS:
(A) LENGTH: 696 amino acids
(B) TYPE: amino acid

```
      (C) STRANDEDNESS: <Unknown>
      (D) TOPOLOGY: linear (xi) SEQUENCE DESCRIPTION: SEQ ID NO: 45:

Met Ala Ser Gly Arg Gly Ala Ser Ser Arg Trp Phe Phe Thr Arg Glu
 1               5                  10                  15

Gln Leu Glu Asn Thr Pro Ser Arg Arg Cys Gly Val Glu Ala Asp Lys
             20                  25                  30

Glu Leu Ser Cys Arg Gln Gln Ala Ala Asn Leu Ile Gln Glu Met Gly
         35                  40                  45

Gln Arg Leu Asn Val Ser Gln Leu Thr Ile Asn Thr Ala Ile Val Tyr
     50                  55                  60

Met His Arg Phe Tyr Met His His Ser Phe Thr Lys Phe Asn Lys Asn
 65                  70                  75                  80

Ile Ile Ser Ser Thr Ala Leu Phe Leu Ala Ala Lys Val Glu Glu Gln
                 85                  90                  95

Ala Arg Lys Leu Glu His Val Ile Lys Val Ala His Ala Cys Leu His
            100                 105                 110

Pro Leu Glu Pro Leu Leu Asp Thr Lys Cys Asp Ala Tyr Leu Gln Gln
        115                 120                 125

Thr Gln Glu Leu Val Ile Leu Glu Thr Ile Met Leu Gln Thr Leu Gly
    130                 135                 140

Phe Glu Ile Thr Ile Glu His Pro His Thr Asp Val Val Lys Cys Thr
145                 150                 155                 160

Gln Leu Val Arg Ala Ser Lys Asp Leu Ala Gln Thr Ser Tyr Phe Met
                165                 170                 175

Ala Thr Asn Ser Leu His Leu Thr Thr Phe Cys Leu Gln Tyr Lys Pro
            180                 185                 190

Thr Val Ile Ala Cys Val Cys Ile His Leu Ala Cys Lys Trp Ser Asn
        195                 200                 205

Trp Glu Ile Pro Val Ser Thr Asp Gly Lys His Trp Trp Glu Tyr Val
    210                 215                 220

Asp Pro Thr Val Thr Leu Glu Leu Leu Asp Glu Leu Thr His Glu Phe
225                 230                 235                 240

Leu Gln Ile Leu Glu Lys Thr Pro Asn Arg Leu Lys Lys Ile Arg Asn
                245                 250                 255

Trp Arg Ala Asn Gln Ala Ala Arg Lys Pro Lys Val Asp Gly Gln Val
            260                 265                 270

Ser Glu Thr Pro Leu Leu Gly Ser Ser Leu Val Gln Asn Ser Ile Leu
        275                 280                 285

Val Asp Ser Val Thr Gly Val Pro Thr Asn Pro Ser Phe Gln Lys Pro
    290                 295                 300

Ser Thr Ser Ala Phe Pro Ala Pro Val Pro Leu Asn Ser Gly Asn Ile
305                 310                 315                 320

Ser Val Gln Asp Ser His Thr Ser Asp Asn Leu Ser Met Leu Ala Thr
                325                 330                 335

Gly Met Pro Ser Thr Ser Tyr Gly Leu Ser Ser His Gln Glu Trp Pro
            340                 345                 350

Gln His Gln Asp Ser Ala Arg Thr Glu Gln Leu Tyr Ser Gln Lys Gln
        355                 360                 365

Glu Thr Ser Leu Ser Gly Ser Gln Tyr Asn Ile Asn Phe Gln Gln Gly
    370                 375                 380

Pro Ser Ile Ser Leu His Ser Gly Leu His His Arg Pro Asp Lys Ile
385                 390                 395                 400
```

```
Ser Asp His Ser Ser Val Lys Gln Glu Tyr Thr His Lys Ala Gly Ser
                405                 410                 415

Ser Lys His His Gly Pro Ile Ser Thr Thr Pro Gly Ile Ile Pro Gln
                420                 425                 430

Lys Met Ser Leu Asp Lys Tyr Arg Glu Lys Arg Lys Leu Glu Thr Leu
                435                 440                 445

Asp Leu Asp Val Arg Asp His Tyr Ile Ala Ala Gln Val Glu Gln Gln
            450                 455                 460

His Lys Gln Gly Gln Ser Gln Ala Ala Ser Ser Ser Val Thr Ser
465                 470                 475                 480

Pro Ile Lys Met Lys Ile Pro Ile Ala Asn Thr Glu Lys Tyr Met Ala
                485                 490                 495

Asp Lys Lys Glu Lys Ser Gly Ser Leu Lys Leu Arg Ile Pro Ile Pro
                500                 505                 510

Pro Thr Asp Lys Ser Ala Ser Lys Glu Glu Leu Lys Met Lys Ile Lys
            515                 520                 525

Val Ser Ser Ser Glu Arg His Ser Ser Ser Asp Glu Gly Ser Gly Lys
            530                 535                 540

Ser Lys His Ser Ser Pro His Ile Ser Arg Asp His Lys Glu Lys His
545                 550                 555                 560

Lys Glu His Pro Ser Ser Arg His His Thr Ser Ser His Lys His Ser
                565                 570                 575

His Ser His Ser Gly Ser Ser Gly Gly Ser Lys His Ser Ala Asp
            580                 585                 590

Gly Ile Pro Pro Thr Val Leu Arg Ser Pro Val Gly Leu Ser Ser Asp
                595                 600                 605

Gly Ile Ser Ser Ser Ser Ser Ser Arg Lys Arg Leu His Val Asn
            610                 615                 620

Asp Ala Ser His Asn His His Ser Lys Met Ser Lys Ser Ser Lys Ser
625                 630                 635                 640

Ser Gly Gly Leu Arg Thr Ser Gln His Leu Val Lys Leu Asp Lys Lys
                645                 650                 655

Pro Val Glu Thr Asn Gly Pro Asp Ala Asn His Glu Tyr Ser Thr Ser
                660                 665                 670

Ser Gln His Met Asp Tyr Lys Asp Thr Phe Asp Met Leu Asp Ser Leu
            675                 680                 685

Leu Ser Ala Gln Gly Met Asn Met
690                 695
```

(2) INFORMATION FOR SEQ ID NO: 46:

(i) SEQUENCE CHARACTERISTICS:
        (A) LENGTH: 2190 base pairs
        (B) TYPE: nucleic acid
        (C) STRANDEDNESS: single
        (D) TOPOLOGY: linear (xi) SEQUENCE DESCRIPTION: SEQ ID NO: 46:

```
ATGGCGTCGG GCCGTGGAGC TTCTTCTCGC TGGTTCTTTA CTCGGGAACA GCTGGAGAAC      60

ACGCCGAGCC GCCGCTGCGG AGTGGAGGCG GATAAAGAGC TCTCGTGCCG CCAGCAGGCG     120

GCCAACCTCA TCCAGGAGAT GGGACAGCGT CTCAATGTCT CTCAGCTTAC AATAAACACT     180

GCGATTGTTT ATATGCACAG GTTTTATATG CACCATTCTT TCACCAAATT CAACAAAAAT     240

ATAATATCGT CTACTGCATT ATTTTTGGCT GCAAAAGTGG AAGAACAGGC TCGAAAACTT     300
```

-continued

```
GAACATGTTA TCAAAGTAGC ACATGCTTGT CTTCATCCTC TAGAGCCACT GCTGGATACT      360

AAATGTGATG CTTACCTTCA ACAGACTCAA GAACTGGTTA TACTTGAAAC CATAATGCTA      420

CAAACTCTAG GTTTTGAGAT CACCATTGAA CACCCACACA CAGATGTGGT GAAATGTACC      480

CAGTTAGTAA GAGCAAGCAA GGATTTGGCA CAGACATCCT ATTTCATGGC TACCAACAGT      540

CTGCATCTTA CAACCTTCTG TCTTCAGTAC AAACCAACAG TGATAGCATG TGTATGCATT      600

CATTTGGCTT GCAAATGGTC CAATTGGGAG ATCCCTGTAT CAACTGATGG AAAGCATTGG      660

TGGGAATATG TGGATCCTAC AGTTACTCTA GAATTATTAG ATGAGCTAAC ACATGAGTTT      720

CTACAAATAT TGGAGAAAAC GCCTAATAGG TTGAAGAAGA TTCGAAACTG GAGGGCTAAT      780

CAGGCAGCTA GGAAACCAAA AGTAGATGGA CAGGTATCAG AGACACCACT TCTTGGTTCA      840

TCTTTGGTCC AGAATTCCAT TTTAGTAGAT AGTGTCACTG GTGTGCCTAC AAACCCAAGT      900

TTTCAGAAAC CATCTACATC AGCATTCCCT GCGCCAGTAC CTCTAAATTC AGGAAATATT      960

TCTGTTCAAG ACAGCCATAC ATCTGATAAT TTGTCAATGC TAGCAACAGG AATGCCAAGT     1020

ACTTCATACG GTTTATCATC ACACCAGGAA TGGCCTCAAC ATCAAGACTC AGCAAGGACA     1080

GAACAGCTAT ATTCACAGAA ACAGGAGACA TCTTTGTCTG GTAGCCAGTA CAACATCAAC     1140

TTCCAGCAGG GACCTTCTAT ATCACTGCAT TCAGGATTAC ATCACAGACC TGACAAAATT     1200

TCAGATCATT CTTCTGTTAA GCAGGAATAT ACTCATAAAG CAGGGAGCAG TAAACACCAT     1260

GGGCCAATTT CCACTACTCC AGGAATAATT CCTCAGAAAA TGTCTTTAGA TAAATATAGA     1320

GAAAAGCGTA AACTAGAAAC TCTTGATCTC GATGTAAGGG ATCATTATAT AGCTGCCCAG     1380

GTAGAACAGC AGCACAAACA AGGGCAGTCA CAGGCAGCCA GCAGCAGTTC TGTTACTTCT     1440

CCCATTAAAA TGAAAATACC TATCGCAAAT ACTGAAAAAT ACATGGCAGA TAAAAAGGAA     1500

AAGAGTGGGT CACTGAAATT ACGGATTCCA ATACCACCCA CTGATAAAAG CGCCAGTAAA     1560

GAAGAACTGA AAATGAAAAT AAAAGTTTCT TCTTCAGAAA GACACAGCTC TTCTGATGAA     1620

GGCAGTGGGA AAAGCAAACA TTCAAGCCCA CATATTAGCA GAGACCATAA GGAGAAGCAC     1680

AAGGAGCATC CTTCAAGCCG CCACCACACC AGCAGCCACA AGCATTCCCA CTCGCATAGT     1740

GGCAGCAGCA GCGGTGGCAG TAAACACAGT GCCGACGGAA TACCACCCAC TGTTCTGAGG     1800

AGTCCTGTTG GCCTGAGCAG TGATGGCATT TCCTCTAGCT CCAGCTCTTC AAGGAAGAGG     1860

CTGCATGTCA ATGATGCATC TCACAACCAC CACTCCAAAA TGAGCAAAAG TTCCAAAAGT     1920

TCAGGTAGTT CATCTAGTTC TTCCTCCTCT GTTAAGCAGT ATATATCCTC TCACAACTCT     1980

GTTTTTAACC ATCCCTTACC CCTCCTCCCC TGTCACATAC CAGGTGGGCT ACGGACATCT     2040

CTGCACCTCG TGAAACTGGA CAAGAAGCCA GTGGAGACCA ACGGTCCTGA TGCCAATCAC     2100

GAGTACAGTA CAAGCAGCCA GCATATGGAC TACAAAGACA CATTCGACAT GCTGGACTCA     2160

CTGTTAAGTG CCCAAGGAAT GAACATGTAA                                     2190
```

(2) INFORMATION FOR SEQ ID NO: 47:

(i) SEQUENCE CHARACTERISTICS:
        (A) LENGTH: 729 amino acids
        (B) TYPE: amino acid
        (C) STRANDEDNESS: <Unknown>
        (D) TOPOLOGY: linear (xi) SEQUENCE DESCRIPTION: SEQ ID NO: 47:

```
Met Ala Ser Gly Arg Gly Ala Ser Ser Arg Trp Phe Phe Thr Arg Glu
 1               5                  10                  15

Gln Leu Glu Asn Thr Pro Ser Arg Arg Cys Gly Val Glu Ala Asp Lys
```

-continued

```
                20                  25                  30
Glu Leu Ser Cys Arg Gln Gln Ala Ala Asn Leu Ile Gln Glu Met Gly
            35                  40                  45
Gln Arg Leu Asn Val Ser Gln Leu Thr Ile Asn Thr Ala Ile Val Tyr
        50                  55                  60
Met His Arg Phe Tyr Met His His Ser Phe Thr Lys Phe Asn Lys Asn
 65                  70                  75                  80
Ile Ile Ser Ser Thr Ala Leu Phe Leu Ala Ala Lys Val Glu Glu Gln
                85                  90                  95
Ala Arg Lys Leu Glu His Val Ile Lys Val Ala His Ala Cys Leu His
            100                 105                 110
Pro Leu Glu Pro Leu Leu Asp Thr Lys Cys Asp Ala Tyr Leu Gln Gln
        115                 120                 125
Thr Gln Glu Leu Val Ile Leu Glu Thr Ile Met Leu Gln Thr Leu Gly
    130                 135                 140
Phe Glu Ile Thr Ile Glu His Pro His Thr Asp Val Val Lys Cys Thr
145                 150                 155                 160
Gln Leu Val Arg Ala Ser Lys Asp Leu Ala Gln Thr Ser Tyr Phe Met
                165                 170                 175
Ala Thr Asn Ser Leu His Leu Thr Thr Phe Cys Leu Gln Tyr Lys Pro
            180                 185                 190
Thr Val Ile Ala Cys Val Cys Ile His Leu Ala Cys Lys Trp Ser Asn
        195                 200                 205
Trp Glu Ile Pro Val Ser Thr Asp Gly Lys His Trp Trp Glu Tyr Val
    210                 215                 220
Asp Pro Thr Val Thr Leu Glu Leu Leu Asp Glu Leu Thr His Glu Phe
225                 230                 235                 240
Leu Gln Ile Leu Glu Lys Thr Pro Asn Arg Leu Lys Lys Ile Arg Asn
                245                 250                 255
Trp Arg Ala Asn Gln Ala Ala Arg Lys Pro Lys Val Asp Gly Gln Val
            260                 265                 270
Ser Glu Thr Pro Leu Leu Gly Ser Ser Leu Val Gln Asn Ser Ile Leu
        275                 280                 285
Val Asp Ser Val Thr Gly Val Pro Thr Asn Pro Ser Phe Gln Lys Pro
    290                 295                 300
Ser Thr Ser Ala Phe Pro Ala Pro Val Pro Leu Asn Ser Gly Asn Ile
305                 310                 315                 320
Ser Val Gln Asp Ser His Thr Ser Asp Asn Leu Ser Met Leu Ala Thr
                325                 330                 335
Gly Met Pro Ser Thr Ser Tyr Gly Leu Ser Ser His Gln Glu Trp Pro
            340                 345                 350
Gln His Gln Asp Ser Ala Arg Thr Glu Gln Leu Tyr Ser Gln Lys Gln
        355                 360                 365
Glu Thr Ser Leu Ser Gly Ser Gln Tyr Asn Ile Asn Phe Gln Gln Gly
    370                 375                 380
Pro Ser Ile Ser Leu His Ser Gly Leu His His Arg Pro Asp Lys Ile
385                 390                 395                 400
Ser Asp His Ser Ser Val Lys Gln Glu Tyr Thr His Lys Ala Gly Ser
                405                 410                 415
Ser Lys His His Gly Pro Ile Ser Thr Thr Pro Gly Ile Ile Pro Gln
            420                 425                 430
Lys Met Ser Leu Asp Lys Tyr Arg Glu Lys Arg Lys Leu Glu Thr Leu
        435                 440                 445
```

```
Asp Leu Asp Val Arg Asp His Tyr Ile Ala Ala Gln Val Glu Gln Gln
        450                 455                 460
His Lys Gln Gly Gln Ser Gln Ala Ala Ser Ser Ser Val Thr Ser
465                 470                 475                 480
Pro Ile Lys Met Lys Ile Pro Ile Ala Asn Thr Glu Lys Tyr Met Ala
                485                 490                 495
Asp Lys Lys Glu Lys Ser Gly Ser Leu Lys Leu Arg Ile Pro Ile Pro
                500                 505                 510
Pro Thr Asp Lys Ser Ala Ser Lys Glu Glu Leu Lys Met Lys Ile Lys
            515                 520                 525
Val Ser Ser Ser Glu Arg His Ser Ser Ser Asp Glu Gly Ser Gly Lys
        530                 535                 540
Ser Lys His Ser Ser Pro His Ile Ser Arg Asp His Lys Glu Lys His
545                 550                 555                 560
Lys Glu His Pro Ser Ser Arg His His Thr Ser Ser His Lys His Ser
                565                 570                 575
His Ser His Ser Gly Ser Ser Ser Gly Gly Ser Lys His Ser Ala Asp
            580                 585                 590
Gly Ile Pro Pro Thr Val Leu Arg Ser Pro Val Gly Leu Ser Ser Asp
        595                 600                 605
Gly Ile Ser Ser Ser Ser Ser Ser Arg Lys Arg Leu His Val Asn
    610                 615                 620
Asp Ala Ser His Asn His His Ser Lys Met Ser Lys Ser Ser Lys Ser
625                 630                 635                 640
Ser Gly Ser Ser Ser Ser Ser Ser Ser Val Lys Gln Tyr Ile Ser
                645                 650                 655
Ser His Asn Ser Val Phe Asn His Pro Leu Pro Leu Leu Pro Cys His
                660                 665                 670
Ile Pro Gly Gly Leu Arg Thr Ser Gln His Leu Val Lys Leu Asp Lys
            675                 680                 685
Lys Pro Val Glu Thr Asn Gly Pro Asp Ala Asn His Glu Tyr Ser Thr
        690                 695                 700
Ser Ser Gln His Met Asp Tyr Lys Asp Thr Phe Asp Met Leu Asp Ser
705                 710                 715                 720
Leu Leu Ser Ala Gln Gly Met Asn Met
                725

(2) INFORMATION FOR SEQ ID NO: 48:

(i) SEQUENCE CHARACTERISTICS:
        (A) LENGTH: 2360 base pairs
        (B) TYPE: nucleic acid
        (C) STRANDEDNESS: single
        (D) TOPOLOGY: linear (xi) SEQUENCE DESCRIPTION: SEQ ID NO: 48:

GGAAGTGCCT GCAACCTTCG CCGCTGCCTT CTGGTTGAAG CACTATGGAG GGAGAGAGGA      60

AGAACAACAA CAAACGGTGG TATTTCACTC GAGAACAGCT GGAAAATAGC CCATCCCGTC    120

GTTTTGGCGT GGACCCAGAT AAAGAACTTT CTTATCGCCA GCAGGCGGCC AATCTGCTTC    180

AGGACATGGG GCAGCGTCTT AACGTCTCAC AATTGACTAT CAACACTGCT ATAGTATACA    240

TGCATCGATT CTACATGATT CAGTCCTTCA CACGGTTCCC TGGAAATTCT GTGGCTCCAG    300

CAGCCTTGTT TCTAGCAGCT AAAGTGGAGG AGCAGCCCAA AAAATTGGAA CATGTCATCA    360

AGGTAGCACA TACTTGTCTC CATCCTCAGG AATCCCTTCC TGATACTAGA AGTGAGGCTT    420
```

-continued

```
ATTTGCAACA AGTTCAAGAT CTGGTCATTT TAGAAAGCAT AATTTTGCAG ACTTTAGGCT      480

TTGAACTAAC AATTGATCAC CCACATACTC ATGTAGTAAA GTGCACTCAA CTTGTTCGAG      540

CAAGCAAGGA CTTAGCACAG ACTTCTTACT TCATGGCAAC AACAGCCTG CATTTGACCA       600

CATTTAGCCT GCAGTACACA CCTCCTGTGG TGGCCTGTGT CTGCATTCAC CTGGCTTGCA      660

AGTGGTCCAA TTGGGAGATC CCAGTCTCAA CTGACGGGAA GCACTGGTGG GAGTATGTTG      720

ACGCCACTGT GACCTTGGAA CTTTTAGATG AACTGACACA TGAGTTTCTA CAGATTTTGG      780

AGAAAACTCC CAACAGGCTC AAACGCATTT GGAATTGGAG GGCATGCGAG GCTGCCAAGA      840

AAACAAAAGC AGATGACCGA GGAACAGATG AAAAGACTTC AGAGCAGACA ATCCTCAATA      900

TGATTTCCCA GAGCTCTTCA GACACAACCA TTGCAGGTTT AATGAGCATG TCAACTTCTA      960

CCACAAGTGC AGTGCCTTCC CTGCCAGTCT CCGAAGAGTC ATCCAGCAAC TTAACCAGTG     1020

TGGAGATGTT GCCGGGCAAG CGTTGGCTGT CCTCCCAACC TTCTTTCAAA CTAGAACCTA     1080

CTCAGGGTCA TCGGACTAGT GAGAATTTAG CACTTACAGG AGTTGATCAT TCCTTACCAC     1140

AGGATGGTTC AAATGCATTT ATTTCCCAGA AGCAGAATAG TAAGAGTGTG CCATCAGCTA     1200

AAGTGTCACT GAAAGAATAC CGCGCGAAGC ATGCAGAAGA ATTGGCTGCC CAGAAGAGGC     1260

AACTGGAGAA CATGGAAGCC AATGTGAAGT CACAATATGC ATATGCTGCC CAGAATCTCC     1320

TTTCTCATCA TGATAGCCAT TCTTCAGTCA TTCTAAAAAT GCCCATAGAG GGTTCAGAAA     1380

ACCCCGAGCG GCCTTTTCTG GAAAAGGCTG ACAAAACAGC TCTCAAAATG AGAATCCCAG     1440

TGGCAGGTGG AGATAAAGCT GCGTCTTCAA AACCAGAGGA GATAAAAATG CGCATAAAAG     1500

TCCATGCTGC AGCTGATAAG CACAATTCTG TAGAGGACAG TGTTACAAAG AGCCGAGAGC     1560

ACAAAGAAGA GCGCAAGACT CACCCATCTA ATCATCATCA TCATCATAAT CACCCACTCAC    1620

ACAAGCACTC TCATTCCCAA CTTCCAGTTG GTACTGGGAA CAAACGTCCT GGTGATCCAA     1680

AACATAGTAG CCAGACAAGC AACTTAGCAC ATAAAACCTA TAGCTTGTCT AGTTCTTTTT     1740

CCTCTTCCAG TTCTACTCGT AAAAGGGGAC CCTCTGAAGA GACTGGAGGG GCTGTGTTTG     1800

ATCATCCAGC CAAGATTGCC AAGAGTACTA AATCCTCTTC CCTAAATTTC TCCTTCCCTT     1860

CACTTCCTAC AATGGGTCAG ATGCCTGGGC ATAGCTCAGA CACAAGTGGC CTTTCCTTTT     1920

CACAGCCCAG CTGTAAAACT CGTGTCCCTC ATTCGAAACT GGATAAAGGG CCCACTGGGG     1980

CCAATGGTCA CAACACGACC CAGACAATAG ACTATCAAGA CACTGTGAAT ATGCTTCACT     2040

CCCTGCTCAG TGCCCAGGGT GTTCAGCCCA CTCAGCCCAC TGCATTTGAA TTTGTTCGTC     2100

CTTATAGTGA CTATCTGAAT CCTCGGTCTG GTGGAATCTC CTCGAGATCT GGCAATACAG     2160

ACAAACCCCG GCCACCACCT CTGCCATCAG AACCTCCTCC ACCACTTCCA CCCCTTCCTA     2220

AGTAAAAAAA GAAAAGAAG AGGAGAAAAA AACTTCTTTA AAAAACACA TAATTTTTCT      2280

TTTTTTTTG GGGAAAAAAA AATTTTTTTT AAAATTTTTT CCCCAAGGGA CGGGGGAAAA      2340

TTTTATTTTT AAAATTTTTT                                                 2360
```

(2) INFORMATION FOR SEQ ID NO: 49:

(i) SEQUENCE CHARACTERISTICS:
        (A) LENGTH: 2181 base pairs
        (B) TYPE: nucleic acid
        (C) STRANDEDNESS: single
        (D) TOPOLOGY: linear (xi) SEQUENCE DESCRIPTION: SEQ ID NO: 49:

```
ATGGAGGGAG AGAGGAAGAA CAACAACAAA CGGTGGTATT TCACTCGAGA ACAGCTGGAA       60
```

```
AATAGCCCAT CCCGTCGTTT TGGCGTGGAC CCAGATAAAG AACTTTCTTA TCGCCAGCAG      120

GCGGCCAATC TGCTTCAGGA CATGGGGCAG CGTCTTAACG TCTCACAATT GACTATCAAC      180

ACTGCTATAG TATACATGCA TCGATTCTAC ATGATTCAGT CCTTCACACG GTTCCCTGGA      240

AATTCTGTGG CTCCAGCAGC CTTGTTTCTA GCAGCTAAAG TGGAGGAGCA GCCCAAAAAA      300

TTGGAACATG TCATCAAGGT AGCACATACT TGTCTCCATC CTCAGGAATC CCTTCCTGAT      360

ACTAGAAGTG AGGCTTATTT GCAACAAGTT CAAGATCTGG TCATTTTAGA AAGCATAATT      420

TTGCAGACTT TAGGCTTTGA ACTAACAATT GATCACCCAC ATACTCATGT AGTAAAGTGC      480

ACTCAACTTG TTCGAGCAAG CAAGGACTTA GCACAGACTT CTTACTTCAT GGCAACCAAC      540

AGCCTGCATT TGACCACATT TAGCCTGCAG TACACACCTC CTGTGGTGGC CTGTGTCTGC      600

ATTCACCTGG CTTGCAAGTG GTCCAATTGG GAGATCCCAG TCTCAACTGA CGGGAAGCAC      660

TGGTGGGAGT ATGTTGACGC CACTGTGACC TTGGAACTTT TAGATGAACT GACACATGAG      720

TTTCTACAGA TTTTGGAGAA AACTCCCAAC AGGCTCAAAC GCATTTGGAA TTGGAGGGCA      780

TGCGAGGCTG CCAAGAAAAC AAAAGCAGAT GACCGAGGAA CAGATGAAAA GACTTCAGAG      840

CAGACAATCC TCAATATGAT TTCCCAGAGC TCTTCAGACA CAACCATTGC AGGTTTAATG      900

AGCATGTCAA CTTCTACCAC AAGTGCAGTG CCTTCCCTGC CAGTCTCCGA AGAGTCATCC      960

AGCAACTTAA CCAGTGTGGA GATGTTGCCG GGCAAGCGTT GGCTGTCCTC CCAACCTTCT     1020

TTCAAACTAG AACCTACTCA GGGTCATCGG ACTAGTGAGA ATTTAGCACT TACAGGAGTT     1080

GATCATTCCT TACCACAGGA TGGTTCAAAT GCATTTATTT CCCAGAAGCA GAATAGTAAG     1140

AGTGTGCCAT CAGCTAAAGT GTCACTGAAA GAATACCGCG CGAAGCATGC AGAAGAATTG     1200

GCTGCCCAGA AGAGGCAACT GGAGAACATG GAAGCCAATG TGAAGTCACA ATATGCATAT     1260

GCTGCCCAGA ATCTCCTTTC TCATCATGAT AGCCATTCTT CAGTCATTCT AAAAATGCCC     1320

ATAGAGGGTT CAGAAAACCC CGAGCGGCCT TTTCTGGAAA AGGCTGACAA AACAGCTCTC     1380

AAAATGAGAA TCCCAGTGGC AGGTGGAGAT AAAGCTGCGT CTTCAAAACC AGAGGAGATA     1440

AAAATGCGCA TAAAGTCCA TGCTGCAGCT GATAAGCACA ATTCTGTAGA GGACAGTGTT     1500

ACAAAGAGCC GAGAGCACAA AGAAGAGCGC AAGACTCACC CATCTAATCA TCATCATCAT     1560

CATAATCACC ACTCACACAA GCACTCTCAT TCCCAACTTC CAGTTGGTAC TGGGAACAAA     1620

CGTCCTGGTG ATCCAAAACA TAGTAGCCAG ACAAGCAACT TAGCACATAA AACCTATAGC     1680

TTGTCTAGTT CTTTTTCCTC TTCCAGTTCT ACTCGTAAAA GGGGACCCTC TGAAGAGACT     1740

GGAGGGGCTG TGTTTGATCA TCCAGCCAAG ATTGCCAAGA GTACTAAATC CTCTTCCCTA     1800

AATTTCTCCT TCCCTTCACT TCCTACAATG GGTCAGATGC CTGGGCATAG CTCAGACACA     1860

AGTGGCCTTT CCTTTTCACA GCCCAGCTGT AAAACTCGTG TCCCTCATTC GAAACTGGAT     1920

AAAGGGCCCA CTGGGGCCAA TGGTCACAAC ACGACCCAGA CAATAGACTA TCAAGACACT     1980

GTGAATATGC TTCACTCCCT GCTCAGTGCC CAGGGTGTTC AGCCCACTCA GCCCACTGCA     2040

TTTGAATTTG TTCGTCCTTA TAGTGACTAT CTGAATCCTC GGTCTGGTGG AATCTCCTCG     2100

AGATCTGGCA ATACAGACAA ACCCCGGCCA CCACCTCTGC CATCAGAACC TCCTCCACCA     2160

CTTCCACCCC TTCCTAAGTA A                                               2181
```

(2) INFORMATION FOR SEQ ID NO: 50:

(i) SEQUENCE CHARACTERISTICS:
        (A) LENGTH: 726 amino acids
        (B) TYPE: amino acid

```
            (C) STRANDEDNESS: <Unknown>
            (D) TOPOLOGY: linear (xi) SEQUENCE DESCRIPTION: SEQ ID NO: 50:

Met Glu Gly Glu Arg Lys Asn Asn Lys Arg Trp Tyr Phe Thr Arg
 1               5                  10                  15

Glu Gln Leu Glu Asn Ser Pro Ser Arg Arg Phe Gly Val Asp Pro Asp
             20                  25                  30

Lys Glu Leu Ser Tyr Arg Gln Gln Ala Ala Asn Leu Leu Gln Asp Met
         35                  40                  45

Gly Gln Arg Leu Asn Val Ser Gln Leu Thr Ile Asn Thr Ala Ile Val
 50                  55                  60

Tyr Met His Arg Phe Tyr Met Ile Gln Ser Phe Thr Arg Phe Pro Gly
 65                  70                  75                  80

Asn Ser Val Ala Pro Ala Ala Leu Phe Leu Ala Ala Lys Val Glu Glu
                 85                  90                  95

Gln Pro Lys Lys Leu Glu His Val Ile Lys Val Ala His Thr Cys Leu
            100                 105                 110

His Pro Gln Glu Ser Leu Pro Asp Thr Arg Ser Glu Ala Tyr Leu Gln
        115                 120                 125

Gln Val Gln Asp Leu Val Ile Leu Glu Ser Ile Ile Leu Gln Thr Leu
    130                 135                 140

Gly Phe Glu Leu Thr Ile Asp His Pro His Thr His Val Val Lys Cys
145                 150                 155                 160

Thr Gln Leu Val Arg Ala Ser Lys Asp Leu Ala Gln Thr Ser Tyr Phe
                165                 170                 175

Met Ala Thr Asn Ser Leu His Leu Thr Thr Phe Ser Leu Gln Tyr Thr
            180                 185                 190

Pro Pro Val Val Ala Cys Val Cys Ile His Leu Ala Cys Lys Trp Ser
        195                 200                 205

Asn Trp Glu Ile Pro Val Ser Thr Asp Gly Lys His Trp Trp Glu Tyr
    210                 215                 220

Val Asp Ala Thr Val Thr Leu Glu Leu Leu Asp Glu Leu Thr His Glu
225                 230                 235                 240

Phe Leu Gln Ile Leu Glu Lys Thr Pro Asn Arg Leu Lys Arg Ile Trp
                245                 250                 255

Asn Trp Arg Ala Cys Glu Ala Ala Lys Lys Thr Lys Ala Asp Asp Arg
            260                 265                 270

Gly Thr Asp Glu Lys Thr Ser Glu Gln Thr Ile Leu Asn Met Ile Ser
        275                 280                 285

Gln Ser Ser Ser Asp Thr Thr Ile Ala Gly Leu Met Ser Met Ser Thr
    290                 295                 300

Ser Thr Thr Ser Ala Val Pro Ser Leu Pro Val Ser Glu Glu Ser Ser
305                 310                 315                 320

Ser Asn Leu Thr Ser Val Glu Met Leu Pro Gly Lys Arg Trp Leu Ser
                325                 330                 335

Ser Gln Pro Ser Phe Lys Leu Glu Pro Thr Gln Gly His Arg Thr Ser
            340                 345                 350

Glu Asn Leu Ala Leu Thr Gly Val Asp His Ser Leu Pro Gln Asp Gly
        355                 360                 365

Ser Asn Ala Phe Ile Ser Gln Lys Gln Asn Ser Lys Ser Val Pro Ser
    370                 375                 380

Ala Lys Val Ser Leu Lys Glu Tyr Arg Ala Lys His Ala Glu Glu Leu
385                 390                 395                 400
```

```
Ala Ala Gln Lys Arg Gln Leu Glu Asn Met Glu Ala Asn Val Lys Ser
            405                 410                 415

Gln Tyr Ala Tyr Ala Ala Gln Asn Leu Leu Ser His His Asp Ser His
        420                 425                 430

Ser Ser Val Ile Leu Lys Met Pro Ile Glu Gly Ser Glu Asn Pro Glu
        435                 440                 445

Arg Pro Phe Leu Glu Lys Ala Asp Lys Thr Ala Leu Lys Met Arg Ile
    450                 455                 460

Pro Val Ala Gly Gly Asp Lys Ala Ala Ser Ser Lys Pro Glu Glu Ile
465                 470                 475                 480

Lys Met Arg Ile Lys Val His Ala Ala Ala Asp Lys His Asn Ser Val
                485                 490                 495

Glu Asp Ser Val Thr Lys Ser Arg Glu His Lys Glu Glu Arg Lys Thr
                500                 505                 510

His Pro Ser Asn His His His His Asn His His Ser His Lys His
            515                 520                 525

Ser His Ser Gln Leu Pro Val Gly Thr Gly Asn Lys Arg Pro Gly Asp
530                 535                 540

Pro Lys His Ser Ser Gln Thr Ser Asn Leu Ala His Lys Thr Tyr Ser
545                 550                 555                 560

Leu Ser Ser Ser Phe Ser Ser Ser Ser Thr Arg Lys Arg Gly Pro
                565                 570                 575

Ser Glu Glu Thr Gly Gly Ala Val Phe Asp His Pro Ala Lys Ile Ala
                580                 585                 590

Lys Ser Thr Lys Ser Ser Ser Leu Asn Phe Ser Phe Pro Ser Leu Pro
                595                 600                 605

Thr Met Gly Gln Met Pro Gly His Ser Ser Asp Thr Ser Gly Leu Ser
            610                 615                 620

Phe Ser Gln Pro Ser Cys Lys Thr Arg Val Pro His Ser Lys Leu Asp
625                 630                 635                 640

Lys Gly Pro Thr Gly Ala Asn Gly His Asn Thr Thr Gln Thr Ile Asp
                645                 650                 655

Tyr Gln Asp Thr Val Asn Met Leu His Ser Leu Leu Ser Ala Gln Gly
                660                 665                 670

Val Gln Pro Thr Gln Pro Thr Ala Phe Glu Phe Val Arg Pro Tyr Ser
            675                 680                 685

Asp Tyr Leu Asn Pro Arg Ser Gly Gly Ile Ser Ser Arg Ser Gly Asn
    690                 695                 700

Thr Asp Lys Pro Arg Pro Pro Leu Pro Ser Glu Pro Pro Pro
705                 710                 715                 720

Leu Pro Pro Leu Pro Lys
                725

(2) INFORMATION FOR SEQ ID NO: 51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 51:

TTCCCACCAA TGCTTTCC                                                    18

(2) INFORMATION FOR SEQ ID NO: 52:
```

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 52:

CCATCAGTTG ATACAGGGAT CT                                            22

(2) INFORMATION FOR SEQ ID NO: 53:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 53:

GGAATTCAGA AGGTTGTAAG ATGC                                          24

(2) INFORMATION FOR SEQ ID NO: 54:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 54:

ACACACAGAT GTGGTGAAAT GTACCCA                                       27

(2) INFORMATION FOR SEQ ID NO: 55:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 55:

GCATCTTACA ACCTTCTG                                                 18

(2) INFORMATION FOR SEQ ID NO: 56:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO: 56:

GGAATTCATG GAAAGCATTG GTGGGAAT                                      28

(2) INFORMATION FOR SEQ ID NO: 57:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 57:

CCTCCACTAC TGGTTTGCCT GG                                            22

(2) INFORMATION FOR SEQ ID NO: 58:

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 58:

GGACTAGTAT AAATATGGCG TCGGGCCGTG                                         30

(2) INFORMATION FOR SEQ ID NO: 59:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 59:

GGAGATCTTA CATGTTCATT CCTTGGG                                            27

(2) INFORMATION FOR SEQ ID NO: 60:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 60:

GGAGACAAGT ATGTGCTACC TTGATGACA                                          29

(2) INFORMATION FOR SEQ ID NO: 61:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 61:

GGAATTCGGG CTGCTCCTCC ACTTTAG                                            27

(2) INFORMATION FOR SEQ ID NO: 62:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 62:

GGAATTCGCT GCTGGAGCCA CAGAA                                              25

(2) INFORMATION FOR SEQ ID NO: 63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 63:

GTGTCACTGA AAGAATACCG                                                    20

(2) INFORMATION FOR SEQ ID NO: 64:

(i) SEQUENCE CHARACTERISTICS:
```

(A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 64:

GGAATTCAGG TGGAGATAAA GCTGC                                               25

(2) INFORMATION FOR SEQ ID NO: 65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 65:

GCTCTAGATA AATATGGAGG GAGAGAGGAA                                          30

(2) INFORMATION FOR SEQ ID NO: 66:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 66:

GGAATTCTTA CTTAGGAAGG GGTGGAAGTG                                          30

(2) INFORMATION FOR SEQ ID NO: 67:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO: 67:

GGAATTCTTA CTTAGGAAGG GGTGGAAGTG GTGGAGGAGG TTAC                          44

(2) INFORMATION FOR SEQ ID NO: 68:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: linear (xi) SEQUENCE DESCRIPTION: SEQ ID NO: 68:

Ala Cys Ser Tyr Ser Pro Thr Ser Pro Ser Tyr Ser Pro Thr Ser Pro
 1               5                  10                  15

Ser Tyr Ser Pro Thr Ser Pro Ser Lys Lys
            20                  25